(12) United States Patent
Flynn et al.

(10) Patent No.: US 9,382,228 B2
(45) Date of Patent: Jul. 5, 2016

(54) N-ACYL-N'-(PYRIDIN-2-YL) UREAS AND ANALOGS EXHIBITING ANTI-CANCER AND ANTI-PROLIFERATIVE ACTIVITIES

(71) Applicant: Deciphera Pharmaceuticals, LLC, Lawrence, KS (US)

(72) Inventors: Daniel L. Flynn, Lawrence, KS (US); Timothy Malcolm Caldwell, Fishers, IN (US); Michael D. Kaufman, Lawrence, KS (US); William C. Patt, Lawrence, KS (US); Thiwanka Samarakoon, Quincy, MA (US); Lakshminarayana Vogeti, Arlington, MA (US); Karen M. Yates, Fishers, IN (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 0 days.

(21) Appl. No.: 14/214,185

(22) Filed: Mar. 14, 2014

(65) Prior Publication Data

US 2014/0275080 A1    Sep. 18, 2014

Related U.S. Application Data

(60) Provisional application No. 61/789,971, filed on Mar. 15, 2013.

(51) Int. Cl.
| | | |
|---|---|---|
| *C07D 213/65* | (2006.01) | |
| *C07D 401/14* | (2006.01) | |
| *C07D 405/14* | (2006.01) | |
| *C07D 413/14* | (2006.01) | |
| *C07D 417/14* | (2006.01) | |

(52) U.S. Cl.
CPC ............ *C07D 401/14* (2013.01); *C07D 405/14* (2013.01); *C07D 413/14* (2013.01); *C07D 417/14* (2013.01)

(58) Field of Classification Search
CPC .......................... C07D 213/65; C07D 401/04
USPC .......................................... 546/256; 514/333
See application file for complete search history.

(56) References Cited

U.S. PATENT DOCUMENTS

| | | | |
|---|---|---|---|
| 8,278,331 B2 * | 10/2012 | Flynn et al. ................... | 514/333 |
| 2008/0214544 A1 | 9/2008 | Bellon et al. | |
| 2008/0255155 A1 | 10/2008 | Raeppel et al. | |
| 2010/0120806 A1 | 5/2010 | Flynn et al. | |

OTHER PUBLICATIONS

Dorwald, Side Reactions in Organic Synthesis, 2005, Wiley: VCH Weinheim Preface, pp. 1-15 & Chapter 8, pp. 279-308.*
International Search Report from corresponding International Application No. PCT/US2014/029664 dated Nov. 6, 2014.

* cited by examiner

*Primary Examiner* — Patricia L Morris
(74) *Attorney, Agent, or Firm* — Cooley LLP

(57) ABSTRACT

Described are compounds of Formula I

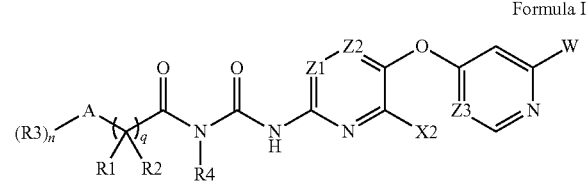

Formula I which find utility in the treatment of cancer, autoimmune diseases and metabolic bone disorders through inhibition of c-FMS (CSF-1R), c-KIT, and/or PDGFR kinases. These compounds also find utility in the treatment of other mammalian diseases mediated by c-FMS, c-KIT, or PDGFR kinases.

43 Claims, No Drawings

SEQUENCE LISTING

<160> NUMBER OF SEQ ID NOS: 3

<210> SEQ ID NO 1
<211> LENGTH: 435
<212> TYPE: PRT
<213> ORGANISM: Homo sapiens

<400> SEQUENCE: 1

```
Tyr Lys Tyr Lys Gln Lys Pro Lys Tyr Gln Val Arg Trp Lys Ile Ile
1               5                   10                  15

Glu Ser Tyr Glu Gly Asn Ser Tyr Thr Phe Ile Asp Pro Thr Gln Leu
            20                  25                  30

Pro Tyr Asn Glu Lys Trp Glu Phe Pro Arg Asn Asn Leu Gln Phe Gly
        35                  40                  45

Lys Thr Leu Gly Ala Gly Ala Phe Gly Lys Val Val Glu Ala Thr Ala
    50                  55                  60

Phe Gly Leu Gly Lys Glu Asp Ala Val Leu Lys Val Ala Val Lys Met
65                  70                  75                  80

Leu Lys Ser Thr Ala His Ala Asp Glu Lys Glu Ala Leu Met Ser Glu
                85                  90                  95

Leu Lys Ile Met Ser His Leu Gly Gln His Glu Asn Ile Val Asn Leu
            100                 105                 110

Leu Gly Ala Cys Thr His Gly Gly Pro Val Leu Val Ile Thr Glu Tyr
        115                 120                 125

Cys Cys Tyr Gly Asp Leu Leu Asn Phe Leu Arg Arg Lys Ala Glu Ala
    130                 135                 140

Met Leu Gly Pro Ser Leu Ser Pro Gly Gln Asp Pro Glu Gly Gly Val
145                 150                 155                 160

Asp Tyr Lys Asn Ile His Leu Glu Lys Lys Tyr Val Arg Arg Asp Ser
                165                 170                 175

Gly Phe Ser Ser Gln Gly Val Asp Thr Tyr Val Glu Met Arg Pro Val
            180                 185                 190

Ser Thr Ser Ser Asn Asp Ser Phe Ser Glu Gln Asp Leu Asp Lys Glu
        195                 200                 205

Asp Gly Arg Pro Leu Glu Leu Arg Asp Leu Leu His Phe Ser Ser Gln
    210                 215                 220

Val Ala Gln Gly Met Ala Phe Leu Ala Ser Lys Asn Cys Ile His Arg
225                 230                 235                 240

Asp Val Ala Ala Arg Asn Val Leu Leu Thr Asn Gly His Val Ala Lys
                245                 250                 255
```

-continued

```
Ile Gly Asp Phe Gly Leu Ala Arg Asp Ile Met Asn Asp Ser Asn Tyr
            260                 265                 270

Ile Val Lys Gly Asn Ala Arg Leu Pro Val Lys Trp Met Ala Pro Glu
        275                 280                 285

Ser Ile Phe Asp Cys Val Tyr Thr Val Gln Ser Asp Val Trp Ser Tyr
    290                 295                 300

Gly Ile Leu Leu Trp Glu Ile Phe Ser Leu Gly Leu Asn Pro Tyr Pro
305                 310                 315                 320

Gly Ile Leu Val Asn Ser Lys Phe Tyr Lys Leu Val Lys Asp Gly Tyr
                325                 330                 335

Gln Met Ala Gln Pro Ala Phe Ala Pro Lys Asn Ile Tyr Ser Ile Met
            340                 345                 350

Gln Ala Cys Trp Ala Leu Glu Pro Thr His Arg Pro Thr Phe Gln Gln
        355                 360                 365

Ile Cys Ser Phe Leu Gln Glu Gln Ala Gln Glu Asp Arg Arg Glu Arg
    370                 375                 380

Asp Tyr Thr Asn Leu Pro Ser Ser Arg Ser Gly Gly Ser Gly Ser
385                 390                 395                 400

Ser Ser Ser Glu Leu Glu Glu Glu Ser Ser Ser Glu His Leu Thr Cys
                405                 410                 415

Cys Glu Gln Gly Asp Ile Ala Gln Pro Leu Leu Gln Pro Asn Asn Tyr
            420                 425                 430

Gln Phe Cys
        435

<210> SEQ ID NO 2
<211> LENGTH: 676
<212> TYPE: PRT
<213> ORGANISM: Artificial Sequence
<220> FEATURE:
<223> OTHER INFORMATION: uKit with N-terminal GST fusion

<400> SEQUENCE: 2

Leu Gly Tyr Trp Lys Ile Lys Gly Leu Val Gln Pro Thr Arg Leu Leu
1               5                   10                  15

Leu Glu Tyr Leu Glu Glu Lys Tyr Glu Glu His Leu Tyr Glu Arg Asp
            20                  25                  30

Glu Gly Asp Lys Trp Arg Asn Lys Lys Phe Glu Leu Gly Leu Glu Phe
        35                  40                  45

Pro Asn Leu Pro Tyr Tyr Ile Asp Gly Asp Val Lys Leu Thr Gln Ser
    50                  55                  60

Met Ala Ile Ile Arg Tyr Ile Ala Asp Lys His Asn Met Leu Gly Gly
65                  70                  75                  80

Cys Pro Lys Glu Arg Ala Glu Ile Ser Met Leu Glu Gly Ala Val Asp
                85                  90                  95

Ile Arg Tyr Gly Val Ser Arg Ile Ala Tyr Ser Lys Asp Phe Glu Thr
            100                 105                 110

Leu Lys Val Asp Phe Leu Ser Lys Leu Pro Glu Met Leu Lys Met Phe
        115                 120                 125

Glu Asp Arg Leu Cys His Lys Thr Tyr Leu Asn Gly Asp His Val Thr
    130                 135                 140

His Pro Asp Phe Met Leu Tyr Asp Ala Leu Asp Val Val Leu Tyr Met
145                 150                 155                 160

Asp Pro Met Cys Leu Asp Ala Phe Pro Lys Leu Val Cys Phe Lys Lys
                165                 170                 175
```

Arg Ile Glu Ala Ile Pro Gln Ile Asp Lys Tyr Leu Lys Ser Ser Lys
            180                 185                 190

Tyr Ile Trp Pro Leu Gln Gly Trp Gln Ala Thr Phe Gly Gly Gly Asp
        195                 200                 205

His Pro Pro Lys Ser Asp Leu Val Pro Arg His Asn Gln Thr Ser Leu
    210                 215                 220

Tyr Lys Lys Ala Gly Ser Ala Ala Val Leu Glu Glu Asn Leu Tyr
225                 230                 235                 240

Phe Gln Gly Thr Tyr Lys Tyr Leu Gln Lys Pro Met Tyr Glu Val Gln
                245                 250                 255

Trp Lys Val Val Glu Glu Ile Asn Gly Asn Asn Tyr Val Tyr Ile Asp
            260                 265                 270

Pro Thr Gln Leu Pro Tyr Asp His Lys Trp Glu Phe Pro Arg Asn Arg
        275                 280                 285

Leu Ser Phe Gly Lys Thr Leu Gly Ala Gly Ala Phe Gly Lys Val Val
    290                 295                 300

Glu Ala Thr Ala Tyr Gly Leu Ile Lys Ser Asp Ala Ala Met Thr Val
305                 310                 315                 320

Ala Val Lys Met Leu Lys Pro Ser Ala His Leu Thr Glu Arg Glu Ala
                325                 330                 335

Leu Met Ser Glu Leu Lys Val Leu Ser Tyr Leu Gly Asn His Met Asn
            340                 345                 350

Ile Val Asn Leu Leu Gly Ala Cys Thr Ile Gly Gly Pro Thr Leu Val
        355                 360                 365

Ile Thr Glu Tyr Cys Cys Tyr Gly Asp Leu Leu Asn Phe Leu Arg Arg
    370                 375                 380

Lys Arg Asp Ser Phe Ile Cys Ser Lys Gln Glu Asp His Ala Glu Ala
385                 390                 395                 400

Ala Leu Tyr Lys Asn Leu Leu His Ser Lys Glu Ser Ser Cys Ser Asp
                405                 410                 415

Ser Thr Asn Glu Tyr Met Asp Met Lys Pro Gly Val Ser Tyr Val Val
            420                 425                 430

Pro Thr Lys Ala Asp Lys Arg Arg Ser Val Arg Ile Gly Ser Tyr Ile
        435                 440                 445

Glu Arg Asp Val Thr Pro Ala Ile Met Glu Asp Asp Glu Leu Ala Leu
450                 455                 460

Asp Leu Glu Asp Leu Leu Ser Phe Ser Tyr Gln Val Ala Lys Gly Met
465                 470                 475                 480

Ala Phe Leu Ala Ser Lys Asn Cys Ile His Arg Asp Leu Ala Ala Arg
                485                 490                 495

Asn Ile Leu Leu Thr His Gly Arg Ile Thr Lys Ile Cys Asp Phe Gly
            500                 505                 510

Leu Ala Arg Asp Ile Lys Asn Asp Ser Asn Tyr Val Val Lys Gly Asn
        515                 520                 525

Ala Arg Leu Pro Val Lys Trp Met Ala Pro Glu Ser Ile Phe Asn Cys
    530                 535                 540

Val Tyr Thr Phe Glu Ser Asp Val Trp Ser Tyr Gly Ile Phe Leu Trp
545                 550                 555                 560

Glu Leu Phe Ser Leu Gly Ser Ser Pro Tyr Pro Gly Met Pro Val Asp
                565                 570                 575

Ser Lys Phe Tyr Lys Met Ile Lys Glu Gly Phe Arg Met Leu Ser Pro
            580                 585                 590

Glu His Ala Pro Ala Glu Met Tyr Asp Ile Met Lys Thr Cys Trp Asp

```
            595                 600                 605
Ala Asp Pro Leu Lys Arg Pro Thr Phe Lys Gln Ile Val Gln Leu Ile
        610                 615                 620

Glu Lys Gln Ile Ser Glu Ser Thr Asn His Ile Tyr Ser Asn Leu Ala
625                 630                 635                 640

Asn Cys Ser Pro Asn Arg Gln Lys Pro Val Asp His Ser Val Arg
                645                 650                 655

Ile Asn Ser Val Gly Ser Thr Ala Ser Ser Gln Pro Leu Leu Val
                660                 665                 670

His Asp Val
        675

<210> SEQ ID NO 3
<211> LENGTH: 550
<212> TYPE: PRT
<213> ORGANISM: Homo sapiens

<400> SEQUENCE: 3

Gln Lys Lys Pro Arg Tyr Glu Ile Arg Trp Lys Val Ile Glu Ser Val
1               5                   10                  15

Ser Ser Asp Gly His Glu Tyr Ile Tyr Val Asp Pro Met Gln Leu Pro
                20                  25                  30

Tyr Asp Ser Thr Trp Glu Leu Pro Arg Asp Gln Leu Val Leu Gly Arg
            35                  40                  45

Thr Leu Gly Ser Gly Ala Phe Gly Gln Val Val Glu Ala Thr Ala His
    50                  55                  60

Gly Leu Ser His Ser Gln Ala Thr Met Lys Val Ala Val Lys Met Leu
65                  70                  75                  80

Lys Ser Thr Ala Arg Ser Ser Glu Lys Gln Ala Leu Met Ser Glu Leu
                85                  90                  95

Lys Ile Met Ser His Leu Gly Pro His Leu Asn Val Val Asn Leu Leu
            100                 105                 110

Gly Ala Cys Thr Lys Gly Gly Pro Ile Tyr Ile Ile Thr Glu Tyr Cys
        115                 120                 125

Arg Tyr Gly Asp Leu Val Asp Tyr Leu His Arg Asn Lys His Thr Phe
    130                 135                 140

Leu Gln His His Ser Asp Lys Arg Arg Pro Pro Ser Ala Glu Leu Tyr
145                 150                 155                 160

Ser Asn Ala Leu Pro Val Gly Leu Pro Leu Pro Ser His Val Ser Leu
                165                 170                 175

Thr Gly Glu Ser Asp Gly Gly Tyr Met Asp Met Ser Lys Asp Glu Ser
            180                 185                 190

Val Asp Tyr Val Pro Met Leu Asp Met Lys Gly Asp Val Lys Tyr Ala
    195                 200                 205

Asp Ile Glu Ser Ser Asn Tyr Met Ala Pro Tyr Asp Asn Tyr Val Pro
210                 215                 220

Ser Ala Pro Glu Arg Thr Cys Arg Ala Thr Leu Ile Asn Glu Ser Pro
225                 230                 235                 240

Val Leu Ser Tyr Met Asp Leu Val Gly Phe Ser Tyr Gln Val Ala Asn
                245                 250                 255

Gly Met Glu Phe Leu Ala Ser Lys Asn Cys Val His Arg Asp Leu Ala
            260                 265                 270

Ala Arg Asn Val Leu Ile Cys Glu Gly Lys Leu Val Lys Ile Cys Asp
        275                 280                 285
```

```
Phe Gly Leu Ala Arg Asp Ile Met Arg Asp Ser Asn Tyr Ile Ser Lys
    290                 295                 300

Gly Ser Thr Phe Leu Pro Leu Lys Trp Met Ala Pro Glu Ser Ile Phe
305             310                 315                 320

Asn Ser Leu Tyr Thr Thr Leu Ser Asp Val Trp Ser Phe Gly Ile Leu
                325                 330                 335

Leu Trp Glu Ile Phe Thr Leu Gly Gly Thr Pro Tyr Pro Glu Leu Pro
            340                 345                 350

Met Asn Glu Gln Phe Tyr Asn Ala Ile Lys Arg Gly Tyr Arg Met Ala
        355                 360                 365

Gln Pro Ala His Ala Ser Asp Glu Ile Tyr Glu Ile Met Gln Lys Cys
    370                 375                 380

Trp Glu Glu Lys Phe Glu Ile Arg Pro Pro Phe Ser Gln Leu Val Leu
385             390                 395                 400

Leu Leu Glu Arg Leu Leu Gly Glu Gly Tyr Lys Lys Lys Tyr Gln Gln
            405                 410                 415

Val Asp Glu Glu Phe Leu Arg Ser Asp His Pro Ala Ile Leu Arg Ser
            420                 425                 430

Gln Ala Arg Leu Pro Gly Phe His Gly Leu Arg Ser Pro Leu Asp Thr
        435                 440                 445

Ser Ser Val Leu Tyr Thr Ala Val Gln Pro Asn Glu Gly Asp Asn Asp
    450                 455                 460

Tyr Ile Ile Pro Leu Pro Asp Pro Lys Pro Glu Val Ala Asp Glu Gly
465             470                 475                 480

Pro Leu Glu Gly Ser Pro Ser Leu Ala Ser Ser Thr Leu Asn Glu Val
            485                 490                 495

Asn Thr Ser Ser Thr Ile Ser Cys Asp Ser Pro Leu Glu Pro Gln Asp
            500                 505                 510

Glu Pro Glu Pro Glu Pro Gln Leu Glu Leu Gln Val Glu Pro Glu Pro
        515                 520                 525

Glu Leu Glu Gln Leu Pro Asp Ser Gly Cys Pro Ala Pro Arg Ala Glu
    530                 535                 540

Ala Glu Asp Ser Phe Leu
545             550
```

N-ACYL-N'-(PYRIDIN-2-YL) UREAS AND ANALOGS EXHIBITING ANTI-CANCER AND ANTI-PROLIFERATIVE ACTIVITIES

PRIORITY

This application claims the benefit of U.S. Provisional Application No. 61/789,971, filed Mar. 15, 2013. The entire disclosure of this application is relied on and incorporated into this application by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DECP_063_01US_SeqList_ST25.txt, date recorded: Mar. 15, 2014, file size 18 kilobytes).

FIELD OF THE INVENTION

Disclosed are compounds which find utility in the treatment of cancer, autoimmune diseases and metabolic bone disorders through inhibition of c-FMS (CSF-1R), c-KIT, and/or PDGFR kinases. These compounds also find utility in the treatment of other mammalian diseases mediated by c-FMS, c-KIT, or PDGFR kinases.

BACKGROUND OF THE INVENTION

Autoimmune diseases, including autoimmune arthritis, represent significant human diseases of high morbidity and prevalence. Rheumatoid arthritis affects ~0.6% of the world population (Firestein, G. S., Nature (2003) 423: 356). While the adaptive immune response, involving generation of autoantibodies which react with tissue antigen, is involved in the etiology and initial propagation of these diseases (Edwards, J. C. et al, New England Journal of Medicine (2004) 350: 2572; Genovese, M. C. et al, New England Journal of Medicine (2005) 353: 1114), the chronic manifestations of tissue and joint damage are mediated in large part by cellular events mediated by the innate immune response (Firestein, G. S., Nature (2003) 423: 356; Paniagua, R. T. et al, Arthritis Research & Therapy (2010) 12: R32). Contributing cell types from the innate immune response which mediate chronic tissue damage include fibroblast-like synoviocytes, macrophages, mast cells, and osteoclasts.

Kinases represent a protein family that play critical roles in mammalian cell function, including cell proliferation, survival, motility, response to growth factors, and secretion of cytokines and other proinflammatory, proangiogenic, and immunomodulatory substances. Thus, elucidation of kinases which mediate these events in fibroblast-like synoviocytes, macrophages, mast cells, and osteoclasts represents a rational approach to new therapies for the treatment of autoimmune diseases.

Imatinib is a marketed kinase inhibitor for the treatment of the cancer chronic myelogenous leukemia (CML, Druker, B. J. et al, New England Journal of Medicine (2001) 344: 1031) and for the treatment of gastrointestinal stromal tumors (GIST, Demetri, G. D., et al, New England Journal of Medicine (2002) 347: 472). Imatinib has also shown benefit in cancer patients co-presenting with autoimmune diseases such as rheumatoid arthritis (Ihara, M. K. et al, Clinical Rheumatology (2003) 22: 362; Eklund, K. K. and Joensuu, H., Ann Medicine (2003) 35: 362; Ames, P. R. et al, Journal of Rheumatology (2008) 35: 1682). The kinases inhibited by imatinib which confer its efficacy in the treatment of CML and GIST are BCR-ABL kinase and c-KIT kinase, respectively. Beyond these two kinases, other kinases inhibited by imatinib include c-FMS, PDGFR-alpha, and PDGFR-beta (Dewer, A. L. et al, Blood (2005) 105: 3127; Fabian, M. A. et al, Nature Biotechnology (2005) 23: 329).

Recent research disclosures have identified c-FMS kinase to be associated with activation of synovial macrophages, PDGFR kinase to be associated with activation of fibroblast-like synoviocytes, and c-KIT kinase to be associated with activation of mast cells (Paniagua, R. T., et al Journal of Clinical Investigation (2006) 116: 2633). c-FMS kinase has also been associated with the proliferation and differentiation of monocytes into macrophages and osteoclasts, which are recruited to mediate joint damage in rheumatoid arthritis (Paniagua, R. T. et al, Arthritis Research & Therapy (2010) 12: R32; Yao, Z. et al, Journal of Biological Chemistry (2006) 281: 11846; Patel, S, and Player, M. R. Current Topics in Medicinal Chemistry (2009) 9: 599; Pixley, F. J. et al, Trends in Cell Biology (2004) 14: 628).

In recent years, the importance of the tumor microenvironment in cancer motility, invasion, and metastasis has become more clearly defined. Specifically, the role of tumor-associated macrophages (TAMs) in tumor progression has been studied. These host (stromal) macrophages are recruited to tumor sites or to pre-metastatic niches to modify the tumor environment and render that environment more conducive to tumor motility, invasion and metastasis. These TAMs are known to express c-FMS receptor tyrosine kinase (also known as CSF-1R) on their surfaces and to rely on signaling through this kinase by binding to the activating ligands CSF-1 (also known as macrophase colony stimulating factor, or M-CSF) and interleukin-34 (IL-34). Activation of this c-FMS/M-CSF (CSF1-R/CSF-1) signaling axis stimulates monocyte proliferation, differentiation into tumor associated macrophages, and promotion of macrophage cell survival. By stimulating the TAM component of the tumor microenvironment, c-FMS kinase activation is associated with tumor cell migration, invasion, and metastasis (J. Condeelis and J. W. Pollard, Cell (2006) 124: 263; S. Patel and M. R. Player, Current Topics in Medicinal Chemistry (2009) 9: 599). Ablation of CSF-1, the ligand for c-FMS kinase, in mice reduced tumor progression and significantly reduced metastasis in a murine model of breast cancer; whereas overexpression of CSF-1 accelerated metastasis in this model (E. Y. Lin et al, Journal of Experimental Medicine (2001) 193: 727). Furthermore, an interaction between tumor cells and macrophages has been described, wherein macrophage secretion of the tumor growth factor EGF and tumor cell secretion of CSF-1 establish a paracrine loop that promotes tumor migration and invasiveness. This paracrine loop was blocked by administration of an antibody to the c-FMS kinase (J. Wyckoff et al, Cancer Research (2004) 64: 7022). Correlative clinical data have also shown that overexpression of CSF-1 in tumors is a predictor of poor prognosis (R. D. Leek and A. L. Harris, Journal of Mammary Gland Biology Neoplasia (2002) 7: 177; E. Y. Lin et al, Journal of Mammary Gland Biology Neoplasia (2002) 7: 147). c-FMS kinase activation is also required for osteoclast differentiation and activation. Its involvement in mediating bone metastases of various cancers, including breast and prostate cancers, has been reported (S. Patel and M. R. Player, Current Topics in Medicinal Chemistry (2009) 9: 599). High plasma concentrations of CSF-1 have been reported in bone metastatic prostate cancer, implicating activation of osteoclast c-FMS kinase in prostate cancer bone metastases (H. Ide, et al, Human Cell (2008) 21:1).

c-FMS inhibitors have been reported to reduce radiographic bone lesions when evaluated in models of metastatic bone disease (C. L. Manthey, et al, Molecular Cancer Therapy (2009) 8: 3151; H. Ohno et al, Mol. Cancer. Therapy (2006) 5: 2634). M-CSF-mediated activation of both LYVE-1+ and LYVE1-macrophages also mediates pathological angiogenesis and lymphangiogenesis in murine models of cancer, and blockade of c-FMS signaling resulted in suppression of tumor angiogenesis/lymphangiogenesis (Y. Kubota et al., Journal of Experimental Medicine (2009) 206: 1089). Administration of a CSF-1R inhibitor blocked the recruitment of bone marrow derived TAMs and also bone marrow derived monocytic myeloid-derived suppressor cells (MDSCs) to tumor sites; this blockade led to a significant decrease in tumor angiogenesis and when combined with anti-VEGFR-2 therapy synergistically suppressed tumor growth (S. J. Priceman, et al. Blood (2010) 115: 1461). Irradiation of glioblastoma tumors in mice was shown to cause a temporary decrease in tumor size only to be followed by a rebound tumor vasculogenesis mediated by the recruitment of bone marrow derived monocytes expressing CD11b and F4/80 surface antigens (M. Kioi et al, Journal of Clinical Investigation (2010) 120: 694). CD11b+ and F4/80+ monocytes are also known to express functional c-FMS receptors. Hence, blockade of tumor infiltrating c-FMS+ bone marrow derived monocytes by the use of c-FMS kinase inhibitors offers the potential to prevent tumor rebound vasculogenesis and glioblastoma tumor progression. CSF-1R blockade has also been shown to reverse immunotolerance mechanisms in an immunocompetent murine breast cancer model and promote the appearance of anti-tumor immune programs by upregulating CD8+ T-cell-mediated tumor suppression. Restoration of an anti-tumor immune program was mechanistically linked to c-FMS inhibitor blockade of TAM-mediated Programmed Death Ligand-1 (PDL-1) immunotolerance (D. G. DeNardo, et al. Cancer Discovery (2011) 1: OF52).

Hence, small molecule inhibitors of c-FMS kinase, c-KIT kinase, or PDGFR kinases provide a rational approach to new therapies for the treatment of autoimmune diseases, and to particularly block the chronic tissue destruction mediated by the innate immune system. Inhibition of c-FMS kinase also provides a rational approach to new therapies for the treatment of cancers, especially for the treatment of cancer invasiveness, cancer angiogenesis or vasculogenesis, cancer metastasis, cancer immunotolerance, and for the treatment of cancers prone to bone metastases.

There is a need to provide kinase inhibitors which selectively inhibit kinases causative of the chronic tissue destruction in autoimmune disease (c-FMS, c-KIT, PDGFR), without inhibiting other kinases targeted by marketed cancer therapeutics (ABL, BCR-ABL, KDR, SRC, LCK, LYN, FGFR and other kinases). The present invention discloses novel inhibitors that inhibit c-FMS, c-KIT, and/or PDGFR kinases for the treatment of autoimmune diseases which also exhibit selectivity by not potently inhibiting other kinases including ABL, BCR-ABL, KDR, SRC, LCK, LYN, FGFR, MET and other kinases. The inhibitors of the present invention also find utility in the treatment of other mammalian diseases, including human diseases, mediated by c-FMS, c-KIT, or PDGFR kinases.

Such diseases include, without limitation, cancers, autoimmune diseases, and bone resorptive diseases.

SUMMARY OF THE INVENTION

In one aspect, compounds of the Formula I are described:

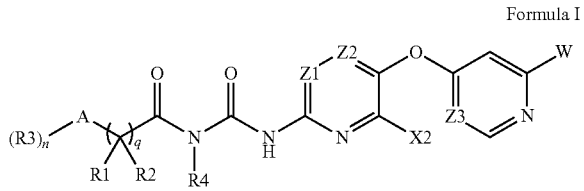

Formula I or pharmaceutically acceptable salts, enantiomers, stereoisomers, or tautomers thereof, wherein A is taken from the group consisting of C1-C6 alkyl, deutero-C1-C6 alkyl wherein the alkyl chain is partially or completely deuterated, branched C3-C8alkyl, fluoroC1-C6alkyl wherein the alkyl is fully or partially fluorinated, C3-C8-carbocyclyl, C6-C12 spirobicycloalkyl, adamantyl, bicyclo[2.2.1]heptanyl, bicyclo[2.2.2]octyl, or a 4-8 membered heterocyclic ring, and wherein each A moiety may be further substituted with one, two, or three R3 moieties;

W is a C5-C6heteroaryl or phenyl, and wherein each W is optionally substituted by one, two, or three R5;

each X1 and X2 and X3 are individually and independently hydrogen, C1-C6 alkyl, or fluoro-C1-C6 alkyl wherein the alkyl chain is partially or completely fluorinated;

Z is CX3 or N;

Z2 is CX1 or N;

Z3 is CH or N;

each R1 and R2 is individually and independently H, C1-C6 alkyl, fluoroC1-C6alkyl wherein the alkyl is fully or partially fluorinated, hydroxyl, C1-C6 alkoxy, fluoroC1-C6alkoxy wherein the alkyl group is fully or partially fluorinated, or cyano;

each R3 is individually and independently H, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano;

each R4 is individually and independently hydrogen, C1-C6 alkyl, or branched C3-C8 alkyl;

each R5 is individually and independently hydrogen, C1-C6 alkyl, deutero-C1-C6 alkyl wherein the alkyl chain is partially or completely deuterated, branched C3-C8 alkyl, halogen, cyano, fluoro-C1-C6 alkyl wherein the alkyl chain is partially or completely fluorinated, —(CH$_2$)$_m$—C(O)NR8(R9), —(CH$_2$)$_m$—C(O)—R6, —(CH$_2$)$_m$—C(O)R7, —(CH$_2$)$_m$—CN, —(CH$_2$)$_m$—OR8, —(CH$_2$)$_m$—NR8(R9), or —(CH$_2$)$_m$—R7, wherein each alkyl or alkylene is optionally substituted with one or two C1-C6 alkyl;

Each R6 is individually and independently hydrogen, C1-C6 alkyl, branched C3-C8 alkyl, C3-C8 cycloalkyl, —(CH$_2$)$_m$—CN, —(CH$_2$)$_m$—OR8, —(CH$_2$)$_m$—NR8(R9), or —(CH$_2$)$_m$—R7, wherein each alkyl or alkylene is optionally substituted with one or two C1-C6 alkyl;

each R7 is independently and individually selected from the group consisting of

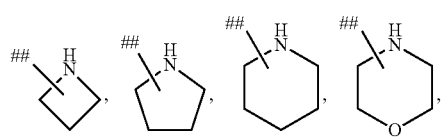

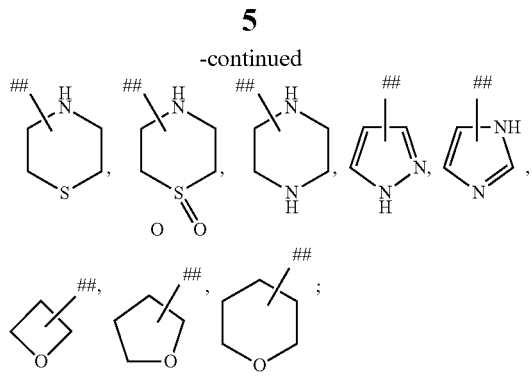

and wherein the symbol (##) is the point of attachment to respective R5 or R6 moieties containing a R7 moiety;

each R7 is optionally substituted with —(R10)$_p$;

each R8 and R9 is individually and independently H, C1-C6 alkyl, fluoro-C1-C6 alkyl wherein the alkyl chain is partially or completely fluorinated, or branched C3-C8 alkyl;

each R10 is individually and independently C1-C6 alkyl, —(CH$_2$)$_m$—CN, —(CH$_2$)$_m$—OR3, —(CH$_2$)$_m$—NR8(R9), or —(CH$_2$)$_m$—C(O)—R6, wherein each alkyl or alkylene is optionally substituted with one or two C1-C6 alkyl;

each m is individually and independently 0, 1, 2, or 3;
each n is individually and independently 0, 1, 2, or 3;
each p is 0, 1, 2, or 3;
each q is 0, 1, 2, or 3;
and with the proviso that only one of Z1 and Z2 is N.

In one embodiment of Formula I, A is C1-C6alkyl.

In one embodiment of Formula I, A is branched C3-C8alkyl.

In one embodiment of Formula I, A is fluoroC1-C6alkyl wherein the alkyl is fully or partially fluorinated.

In one embodiment of Formula I, A is C3-C8carbocyclyl.

In one embodiment of Formula I, A is a 4-8 membered heterocyclic ring.

In one embodiment of Formula I, W is selected from the group consisting of pyrazolyl, imidazolyl, isoxazolyl, oxazolyl, thiazolyl, triazolyl, pyridinyl, and phenyl.

In one embodiment of Formula I, W pyrazolyl.
In one embodiment of Formula I, W is imidazolyl.
In one embodiment of Formula I, W is isoxazolyl.
In one embodiment of Formula I, W is oxazolyl.
In one embodiment of Formula I, W is thiazolyl.
In one embodiment of Formula I, W is triazolyl.
In one embodiment of Formula I, W is pyridinyl.
In one embodiment of Formula I, W is phenyl.

In one embodiment of Formula I, Z1 is CX3, Z2 is CX1, and X1, X2 and X3 are each individually and independently hydrogen, C1-C6 alkyl, or fluoro-C1-C6 alkyl wherein the alkyl chain is partially or completely fluorinated.

In one embodiment of Formula I, Z1 is CX3, Z2 is CX1, and X1, X2 and X3 are each individually and independently hydrogen or C1-C6 alkyl.

In one embodiment of Formula I, Z1 is CX3, Z2 is CX1, X3 is H, and X1 and X2 are each individually and independently hydrogen or C1-C6 alkyl.

In one embodiment of Formula I, Z1 is CX3, Z2 is CX1, X3 is H, and one of X1 and X2 is hydrogen and the other is C1-C6alkyl.

In one embodiment of Formula I, Z1 is CX3, Z2 is CX1, and X1, X2 and X3 are hydrogen.

In one embodiment of Formula I, Z1 is N, Z2 is CX1, and X1 and X2 are each individually and independently hydrogen, C1-C6 alkyl, or fluoro-C1-C6 alkyl wherein the alkyl chain is partially or completely fluorinated.

In one embodiment of Formula I, Z1 is N, Z2 is CX1, and X1 and X2 are each individually and independently hydrogen or C1-C6 alkyl.

In one embodiment of Formula I, Z1 is N, Z2 is CX1, and one of X1 and X2 is hydrogen and the other is C1-C6alkyl.

In one embodiment of Formula I, Z1 is N, Z2 is CX1, and X1 and X2 are hydrogen.

In one embodiment of Formula I, Z1 is CX3, Z2 is N, and X2 and X3 are each individually and independently hydrogen, C1-C6 alkyl, or fluoro-C1-C6 alkyl wherein the alkyl chain is partially or completely fluorinated.

In one embodiment of Formula I, Z1 is CX3, Z2 is N, and X2 and X3 are each individually and independently hydrogen or C1-C6 alkyl.

In one embodiment of Formula I, Z1 is CX3, Z2 is N, X3 is H, and X2 is hydrogen or C1-C6 alkyl.

In one embodiment of Formula I, Z1 is CX3, Z2 is N, and X2 and X3 are hydrogen.

In one embodiment of Formula I, Z3 is CH.
In one embodiment of Formula I, Z3 is N.

In one embodiment of Formula I, each R1 and R2 is individually and independently H or C1-C6 alkyl.

In one embodiment of Formula I, each R1 and R2 is H.

In one embodiment of Formula I, each R3 is individually and independently C1-C6alkyl, hydrogen, C1-C6alkoxy, or fluoro-C1-C6 alkyl wherein the alkyl chain is partially or completely fluorinated.

In one embodiment of Formula I, each R3 is individually and independently C1-C6alkyl.

In one embodiment of Formula I, each R3 is individually and independently hydrogen.

In one embodiment of Formula I, each R3 is individually and independently C1-C6alkoxy.

In one embodiment of Formula I, R4 is hydrogen.

In one embodiment of Formula I, R4 is C1-C6 alkyl or branched C3-C8 alkyl.

In one embodiment of Formula I, q is 0, 1, 2, or 3.
In one embodiment of Formula I, q is 0, 1, or 2.
In one embodiment of Formula I, q is 0 or 1.
In one embodiment of Formula I, q is 0.
In one embodiment of Formula I, q is 1.
In one embodiment of Formula I, n is 0, 1, 2, or 3.
In one embodiment of Formula I, n is 0, 1, or 2.
In one embodiment of Formula I is a compound wherein.
In one embodiment of Formula I, n is 0.
In one embodiment of Formula I, n is 1.

In another embodiment, the compound of Formula I is a compound of Formula Ia

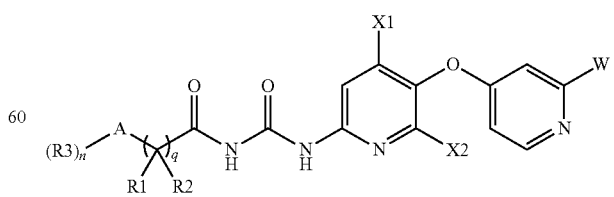

Formula Ia wherein A, X1, X2, R1, R2, R3, W, n and q are as broadly defined above; or a pharmaceutically acceptable salt, enantiomer, stereoisomer, or tautomer thereof.

In one embodiment of Formula Ia, A is C1-C6alkyl.

In one embodiment of Formula Ia, A is branched C3-C8alkyl.

In one embodiment of Formula Ia, A is fluoroC1-C6alkyl wherein the alkyl is fully or partially fluorinated.

In one embodiment of Formula Ia, A is C3-C8carbocyclyl.

In one embodiment of Formula Ia, A is a 4-8 membered heterocyclic ring.

In one embodiment of Formula Ia, W is selected from the group consisting of pyrazolyl, imidazolyl, isoxazolyl, oxazolyl, thiazolyl, triazolyl, pyridinyl, and phenyl.

In one embodiment of Formula Ia, W pyrazolyl.

In one embodiment of Formula Ia, W is imidazolyl.

In one embodiment, of Formula Ia, W is isoxazolyl.

In one embodiment of Formula Ia, W is oxazolyl.

In one embodiment of Formula Ia, W is thiazolyl.

In one embodiment of Formula Ia, W is triazolyl.

In one embodiment of Formula Ia, W is pyridinyl.

In one embodiment of Formula Ia, W is phenyl.

In one embodiment of Formula Ia, X1 and X2 are individually and independently hydrogen, C1-C6 alkyl, or fluoro-C1-C6 alkyl wherein the alkyl chain is partially or completely fluorinated.

In one embodiment of Formula Ia, X1 and X2 are individually and independently hydrogen or C1-C6 alkyl.

In one embodiment of Formula Ia, one of X1 and X2 is hydrogen and the other is C1-C6alkyl.

In one embodiment of Formula Ia, X1 and X2 are hydrogen.

In one embodiment of Formula Ia, each R1 and R2 is individually and independently H or C1-C6 alkyl.

In one embodiment of Formula Ia, each R1 and R2 is H.

In one embodiment of Formula Ia, each R3 is individually and independently C1-C6alkyl, hydrogen, C1-C6alkoxy, or fluoro-C1-C6 alkyl wherein the alkyl chain is partially or completely fluorinated.

In one embodiment of Formula Ia, each R3 is individually and independently C1-C6alkyl.

In one embodiment of Formula Ia, each R3 is individually and independently hydrogen.

In one embodiment of Formula Ia, each R3 is individually and independently fluoro-C1-C6 alkyl wherein the alkyl chain is partially or completely fluorinated.

In one embodiment of Formula Ia, R3 is C1-C6 alkoxy.

In one embodiment of Formula Ia, q is 0, 1, 2, or 3.

In one embodiment of Formula Ia, q is 0, 1, or 2.

In one embodiment of Formula Ia, q is 0 or 1.

In one embodiment of Formula Ia. q is 0.

In one embodiment of Formula Ia, q is 1.

In one embodiment of Formula Ia, n is 0, 1, 2, or 3.

In one embodiment of Formula Ia, n is 0, 1, or 2.

In one embodiment of Formula Ia, n is 0 or 1.

In one embodiment of Formula Ia, n is 0.

In one embodiment of Formula Ia n is 1.

In another embodiment, the compound of Formula I is a compound of Formula Ib

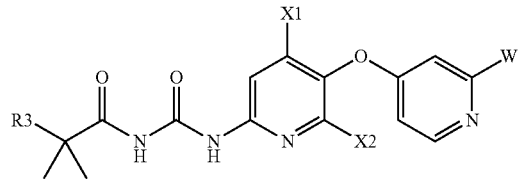

Formula Ib wherein R3, X1, X2 and W are as broadly defined above; or a pharmaceutically acceptable salt, enantiomer, stereoisomer, or tautomer thereof.

In one embodiment of Formula Ib, R3 is C1-C6alkyl, hydrogen or C1-C6alkoxy.

In one embodiment of Formula Ib, R3 is C1-C6alkyl.

In one embodiment of Formula Ib, R3 is methyl.

In one embodiment of Formula Ib, R3 is hydrogen.

In one embodiment of Formula Ib, R3 is C1-C6alkoxy.

In one embodiment of Formula Ib, R3 is methoxy.

In one embodiment of Formula Ib, R3 is ethoxy.

In one embodiment of Formula Ib, W is selected from the group consisting of pyrazolyl, imidazolyl, isoxazolyl, oxazolyl, thiazolyl, triazolyl, pyridinyl, and phenyl.

In one embodiment of Formula Ib, W pyrazolyl.

In one embodiment of Formula Ib, W is imidazolyl.

In one embodiment of Formula Ib, W is isoxazolyl.

In one embodiment of Formula Ib, W is oxazolyl.

In one embodiment of Formula Ib, W is thiazolyl.

In one embodiment of Formula Ib, W is triazolyl.

In one embodiment of Formula Ib, W is pyridinyl.

In one embodiment of Formula Ib, W is phenyl.

In one embodiment of Formula Ib, X1 and X2 are individually and independently hydrogen, C1-C6 alkyl, or fluoro-C1-C6 alkyl wherein the alkyl chain is partially or completely fluorinated.

In one embodiment of Formula Ib, X1 and X2 are individually and independently hydrogen or C1-C6 alkyl.

In one embodiment of Formula Ib, X1 and X2 are hydrogen.

In one embodiment of Formula Ib, one of X1 and X2 is hydrogen and the other is C1-C6alkyl.

In one embodiment of Formula Ib, X1 is hydrogen and X2 is C1-C6alkyl.

In one embodiment of Formula Ib, X1 is hydrogen and X2 is methyl.

In one embodiment of Formula Ib, X1 is C1-C6alkyl and X2 is hydrogen.

In one embodiment of Formula Ib, X1 is methyl and X2 is hydrogen.

In one embodiment of Formula Ib, R3 is methyl, hydrogen or methoxy and X1 and X2 are individually and independently hydrogen or methyl.

In one embodiment of Formula Ib, R3 is methyl, hydrogen or methoxy and X1 and X2 are individually and independently hydrogen or methyl, and W is pyrazolyl.

In one embodiment of Formula Ib, R3 is methyl, hydrogen or methoxy and X1 and X2 are individually and independently hydrogen or methyl, and W is imidazolyl.

In one embodiment of Formula Ib, R3 is methyl, hydrogen or methoxy and X1 and X2 are individually and independently hydrogen or methyl, and W is isoxazolyl.

In one embodiment of Formula Ib, R3 is methyl, hydrogen or methoxy and X1 and X2 are individually and independently hydrogen or methyl, and W is oxazolyl.

In one embodiment of Formula Ib, R3 is methyl, hydrogen or methoxy and X1 and X2 are individually and independently hydrogen or methyl, and W is thiazolyl.

In one embodiment of Formula Ib, R3 is methyl, hydrogen or methoxy and X1 and X2 are individually and independently hydrogen or methyl, and W is pyridinyl.

In one embodiment of Formula Ib, R3 is methyl, hydrogen or methoxy and X1 and X2 are individually and independently hydrogen or methyl, and W is phenyl.

In one embodiment, the compound of Formula I is a compound of Formula Ic

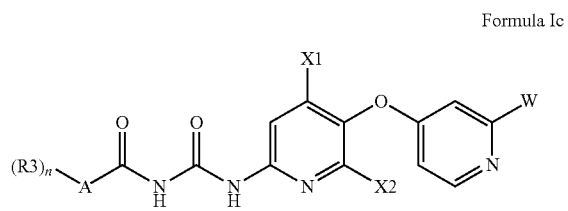

Formula Ic wherein A is C3-C8 carbocyclyl and R3, X1, X2, W and n are as broadly defined above; or a pharmaceutically acceptable salt, enantiomer, stereoisomer, or tautomer thereof.

In one embodiment of Formula Ic, A is cyclopropyl.
In one embodiment of Formula Ic, A is cyclobutyl.
In one embodiment of Formula Ic, A is cyclopentyl.
In one embodiment of Formula Ic, A is cyclohexyl.
In one embodiment of Formula Ic, each R3 is individually and independently C1-C6alkyl, hydrogen, C1-C6alkoxy, or fluoro-C1-C6 alkyl wherein the alkyl chain is partially or completely fluorinated.

In one embodiment of Formula Ic is a compound wherein: each R3 is individually and independently C1-C6alkyl.

In one embodiment of Formula Ic, n is 0, 1, or 2.
In one embodiment of Formula Ic, n is 0 or 1.
In one embodiment of Formula Ic, n is 0.
In one embodiment of Formula Ic, n is 1.
In one embodiment of Formula Ic, n is 1 and R3 is methyl.
In one embodiment of Formula Ic, n is 1 and R3 is hydrogen.
In one embodiment of Formula Ic, n is 1 and R3 is C1-C6alkoxy.
In one embodiment of Formula Ic, n is 1 and R3 is methoxy.
In one embodiment of Formula Ic, n is 1 and R3 is ethoxy.
In one embodiment of Formula Ic, n is 1 and R3 is fluoro-C1-C6 alkyl wherein the alkyl chain is partially or completely fluorinated.
In one embodiment of Formula Ic, n is 1 and R3 is trifluoromethyl.
In one embodiment of Formula Ic, W is selected from the group consisting of pyrazolyl, imidazolyl, isoxazolyl, oxazolyl, thiazolyl, triazolyl, pyridinyl, and phenyl.
In one embodiment of Formula Ic, W pyrazolyl.
In one embodiment of Formula Ic, W is imidazolyl.
In one embodiment of Formula Ic, W is isoxazolyl.
In one embodiment of Formula Ic, W is oxazolyl.
In one embodiment of Formula Ic, W is thiazolyl.
In one embodiment of Formula Ic, W is triazolyl.
In one embodiment of Formula Ic, W is pyridinyl.
In one embodiment of Formula Ic, W is phenyl.
In one embodiment of Formula Ic, X1 and X2 are individually and independently hydrogen, C1-C6 alkyl, or fluoro-C1-C6 alkyl wherein the alkyl chain is partially or completely fluorinated; or a pharmaceutically acceptable salt, enantiomer, stereoisomer, or tautomer thereof.

In one embodiment of Formula Ic, X1 and X2 are individually and independently hydrogen or C1-C6 alkyl.
In one embodiment of Formula Ic, X1 and X2 are hydrogen.
In one embodiment of Formula Ic, one of X1 and X2 is hydrogen and the other is C1-C6alkyl.
In one embodiment of Formula Ic, X1 is hydrogen and X2 is C1-C6alkyl.
In one embodiment of Formula Ic, X1 is hydrogen and X2 is methyl.
In one embodiment of Formula Ic, X1 is C1-C6alkyl and X2 is hydrogen.
In one embodiment of Formula Ic, X1 is methyl and X2 is hydrogen.

In one embodiment, the compound of Formula I is a compound of Formula Id

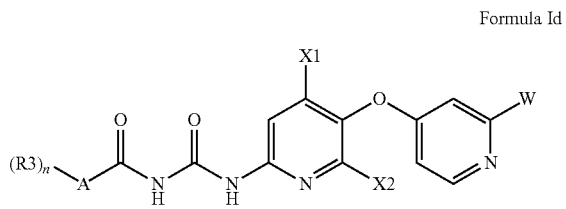

Formula Id wherein A is a 4-8 membered heterocyclic ring and R3, X1, X2, W and n are as broadly defined above; or a pharmaceutically acceptable salt, enantiomer, stereoisomer, or tautomer thereof.

In one embodiment of Formula Id, A is tetrahydrofuranyl.
In one embodiment of Formula Id, A is tetrahydropyranyl.
In one embodiment of Formula Id, A is oxetanyl.
In one embodiment of Formula Id, each R3 is individually and independently C1-C6alkyl, hydrogen, C1-C6alkoxy, or fluoro-C1-C6 alkyl wherein the alkyl chain is partially or completely fluorinated.
In one embodiment of Formula Id, each R3 is individually and independently C1-C6alkyl.
In one embodiment of Formula Id, n is 0, 1, or 2.
In one embodiment of Formula Id, n is 0 or 1.
In one embodiment of Formula Id, n is 0.
In one embodiment of Formula Id, n is 1.
In one embodiment of Formula Id, n is 1 and R3 is methyl.
In one embodiment of Formula Id, n is 1 and R3 is hydrogen.
In one embodiment of Formula Id, n is 1 and R3 is C1-C6alkoxy.
In one embodiment of Formula Id, n is 1 and R3 is methoxy.
In one embodiment of Formula Id, n is 1 and R3 is ethoxy.
In one embodiment of Formula Id, n is 1 and R3 is fluoro-C1-C6 alkyl wherein the alkyl chain is partially or completely fluorinated.
In one embodiment of Formula Id, n is 1 and R3 is trifluoromethyl.
In one embodiment of Formula Id, W is selected from the group consisting of pyrazolyl, imidazolyl, isoxazolyl, oxazolyl, thiazolyl, triazolyl, pyridinyl, and phenyl.
In one embodiment of Formula Id, W pyrazolyl.
In one embodiment of Formula Id, W is imidazolyl.
In one embodiment of Formula Id, W is isoxazolyl.
In one embodiment of Formula Id, W is oxazolyl.
In one embodiment of Formula Id, W is thiazolyl.

In one embodiment of Formula Id, W is triazolyl.
In one embodiment of Formula Id, W is pyridinyl.
In one embodiment of Formula Id, W is phenyl.

In one embodiment of Formula Id, X1 and X2 are individually and independently hydrogen, C1-C6 alkyl, or fluoro-C1-C6 alkyl wherein the alkyl chain is partially or completely fluorinated.

In one embodiment of Formula Id, X1 and X2 are individually and independently hydrogen or C1-C6 alkyl.

In one embodiment of Formula Id, X1 and X2 are hydrogen.

In one embodiment of Formula Id, one of X1 and X2 is hydrogen and the other is C1-C6alkyl.

In one embodiment of Formula Id, X1 is hydrogen and X2 is C1-C6alkyl.

In one embodiment of Formula Id, X1 is hydrogen and X2 is methyl.

In one embodiment of Formula Id, X1 is C1-C6alkyl and X2 is hydrogen.

In one embodiment of Formula Id, X1 is methyl and X2 is hydrogen.

In some embodiments, the invention comprises a compound selected from the group consisting of trans-3-fluoro-3-methyl-N-((5-((2-(1-methyl-1H-pyrazol-4-yl)pyridin-4-yl)oxy)pyridin-2-yl)carbamoyl)cyclobutanecarboxamide, 3,3-dimethyl-N-((5-((2-(1-methyl-1H-pyrazol-4-yl)pyridin-4-yl)oxy)pyridin-2-yl)carbamoyl)cyclobutanecarboxamide, N-((5-((2-(1-methyl-1H-pyrazol-4-yl)pyridin-4-yl)oxy)pyridin-2-yl)carbamoyl)-3-(1-(trifluoromethyl)cyclopropyl)propanamide, N-((5-((2-(1-methyl-1H-pyrazol-4-yl)pyridin-4-yl)oxy)pyridin-2-yl)carbamoyl)-2-(tetrahydro-2H-pyran-4-yl)acetamide, 3,3-dimethyl-N-((5-((6-(1-methyl-1H-pyrazol-4-yl)pyrimidin-4-yl)oxy)pyridin-2-yl)carbamoyl)cyclobutanecarboxamide, N-((6-methyl-5-((2-(1-methyl-1H-pyrazol-4-yl)pyridin-4-yl)oxy)pyridin-2-yl)carbamoyl)pivalamide, N-((6-methyl-5-((2-(1-methyl-1H-pyrazol-4-yl)pyridin-4-yl)oxy)pyridin-2-yl)carbamoyl)propionamide, N-((6-methyl-5-((2-(1-methyl-1H-pyrazol-4-yl)pyridin-4-yl)oxy)pyridin-2-yl)carbamoyl)-2-(tetrahydro-2H-pyran-4-yl)acetamide, trans-4-methyl-N-((6-methyl-5-((2-(1-methyl-1H-pyrazol-4-yl)pyridin-4-yl)oxy)pyridin-2-yl)carbamoyl)cyclohexanecarboxamide, N-((6-methyl-5-((2-(1-methyl-1H-pyrazol-4-yl)pyridin-4-yl)oxy)pyridin-2-yl)carbamoyl)tetrahydrofuran-3-carboxamide, N-((6-methyl-5-((2-(1-methyl-1H-pyrazol-4-yl)pyridin-4-yl)oxy)pyridin-2-yl)carbamoyl)-3-(1-(trifluoromethyl)cyclopropyl)propanamide, 4,4-difluoro-N-((6-methyl-5-((2-(1-methyl-1H-pyrazol-4-yl)pyridin-4-yl)oxy)pyridin-2-yl)carbamoyl)cyclohexanecarboxamide, 3,3-dimethyl-N-((6-methyl-5-((2-(1-methyl-1H-pyrazol-4-yl)pyridin-4-yl)oxy)pyridin-2-yl)carbamoyl)cyclobutanecarboxamide, 3,3-dimethyl-N-((6-methyl-5-((2-(3-methylisoxazol-5-yl)pyridin-4-yl)oxy)pyridin-2-yl)carbamoyl)cyclobutanecarboxamide, N-((6-methyl-5-((2-(1-methyl-1H-pyrazol-4-yl)pyridin-4-yl)oxy)pyridin-2-yl)carbamoyl)-3-oxocyclobutanecarboxamide, N-((6-methyl-5-((2-(1-methyl-1H-pyrazol-4-yl)pyridin-4-yl)oxy)pyridin-2-yl)carbamoyl)cyclohexanecarboxamide, N-((6-methyl-5-((2-(1-methyl-1H-pyrazol-4-yl)pyridin-4-yl)oxy)pyridin-2-yl)carbamoyl)tetrahydro-2H-pyran-4-carboxamide, N-((6-methyl-5-((2-(1-methyl-1H-pyrazol-4-yl)pyridin-4-yl)oxy)pyridin-2-yl)carbamoyl)cyclobutanecarboxamide, N-((6-methyl-5-((2-(1-methyl-1H-pyrazol-4-yl)pyridin-4-yl)oxy)pyridin-2-yl)carbamoyl)cyclopentanecarboxamide, 2-methoxy-N-((6-methyl-5-((2-(1-methyl-1H-pyrazol-4-yl)pyridin-4-yl)oxy)pyridin-2-yl)carbamoyl)acetamide, 2-methoxy-N-((5-((2-(1-methyl-1H-pyrazol-4-yl)pyridin-4-yl)oxy)pyridin-2-yl)carbamoyl)acetamide, 3,3-difluoro-N-((6-methyl-5-((2-(1-methyl-1H-pyrazol-4-yl)pyridin-4-yl)oxy)pyridin-2-yl)carbamoyl)cyclobutanecarboxamide, N-((6-methyl-5-((2-(1-methyl-1H-pyrazol-4-yl)pyridin-4-yl)oxy)pyridin-2-yl)carbamoyl)isobutyramide, N-((5-((2-(1-methyl-1H-pyrazol-4-yl)pyridin-4-yl)oxy)pyridin-2-yl)carbamoyl)isobutyramide, 4-methoxy-N-((6-methyl-5-((2-(1-methyl-1H-pyrazol-4-yl)pyridin-4-yl)oxy)pyridin-2-yl)carbamoyl)butanamide, N-((5-((2-(1-methyl-1H-pyrazol-4-yl)pyridin-4-yl)oxy)pyridin-2-yl)carbamoyl)pivalamide, 1-cyano-N-((5-((2-(1-methyl-1H-pyrazol-4-yl)pyridin-4-yl)oxy)pyridin-2-yl)carbamoyl)cyclopropanecarboxamide, 1-cyano-N-((6-methyl-5-((2-(1-methyl-1H-pyrazol-4-yl)pyridin-4-yl)oxy)pyridin-2-yl)carbamoyl)cyclopropanecarboxamide, 2-cyano-2-methyl-N-((6-methyl-5-((2-(1-methyl-1H-pyrazol-4-yl)pyridin-4-yl)oxy)pyridin-2-yl)carbamoyl)propanamide, 2-cyano-2-methyl-N-((5-((2-(1-methyl-1H-pyrazol-4-yl)pyridin-4-yl)oxy)pyridin-2-yl)carbamoyl)propanamide, N-((5-((2-(1-methyl-1H-pyrazol-4-yl)pyridin-4-yl)oxy)pyridin-2-yl)carbamoyl)spiro[3.3]heptane-2-carboxamide, N-((6-methyl-5-((2-(1-methyl-1H-pyrazol-4-yl)pyridin-4-yl)oxy)pyridin-2-yl)carbamoyl)spiro[3.3]heptane-2-carboxamide, N-((5-((2-(1-methyl-1H-pyrazol-4-yl)pyridin-4-yl)oxy)pyridin-2-yl)carbamoyl)-1-(trifluoromethyl)cyclopropanecarboxamide, N-((6-methyl-5-((2-(1-methyl-1H-pyrazol-4-yl)pyridin-4-yl)oxy)pyridin-2-yl)carbamoyl)-1-(trifluoromethyl)cyclopropanecarboxamide, 3,3,3-trifluoro-2,2-dimethyl-N-((5-((2-(1-methyl-1H-pyrazol-4-yl)pyridin-4-yl)oxy)pyridin-2-yl)carbamoyl)propanamide, 3,3,3-trifluoro-2,2-dimethyl-N-((6-methyl-5-((2-(1-methyl-1H-pyrazol-4-yl)pyridin-4-yl)oxy)pyridin-2-yl)carbamoyl)propanamide, N-((6-methyl-5-((2-(1-methyl-1H-pyrazol-4-yl)pyridin-4-yl)oxy)pyridin-2-yl)carbamoyl)adamantane-1-carboxamide, N-((5-((2-(1-methyl-1H-pyrazol-4-yl)pyridin-4-yl)oxy)pyridin-2-yl)carbamoyl)adamantane-1-carboxamide, N-((6-methyl-5-((6'-methyl-[2,3'-bipyridin]-4-yl)oxy)pyridin-2-yl)carbamoyl)pivalamide, N-((5-((2-(1-(trideuteromethyl)-1H-pyrazol-4-yl)pyridin-4-yl)oxy)pyridin-2-yl)carbamoyl)isobutyramide, N-((6-methyl-5-((2-(1-(trideuteromethyl)-1H-pyrazol-4-yl)pyridin-4-yl)oxy)pyridin-2-yl)carbamoyl)isobutyramide, N-((6-methyl-5-((2-(1-(trideuteromethyl)-1H-pyrazol-4-yl)pyridin-4-yl)oxy)pyridin-2-yl)carbamoyl)pivalamide, trans-N-((6-methyl-5-((2-(1-methyl-1H-pyrazol-4-yl)pyridin-4-yl)oxy)pyridin-2-yl)carbamoyl)-4-(trifluoromethyl)cyclohexanecarboxamide, N-((6-methyl-5-((2-(1-(trideuteromethyl)-1H-pyrazol-4-yl)pyridin-4-yl)oxy)pyridin-2-yl)carbamoyl)tetrahydrofuran-3-carboxamide, trans-N-((5-((2-(1-methyl-1H-pyrazol-4-yl)pyridin-4-yl)oxy)pyridin-2-yl)carbamoyl)-4-(trifluoromethyl)cyclohexanecarboxamide, 2-cyclohexyl-N-((6-methyl-5-((2-(1-methyl-1H-pyrazol-4-yl)pyridin-4-yl)oxy)pyridin-2-yl)carbamoyl)acetamide, 4,4,4-trifluoro-3,3-dimethyl-N-((6-methyl-5-((2-(1-methyl-1H-pyrazol-4-yl)pyridin-4-yl)oxy)pyridin-2-yl)carbamoyl)butanamide, 4,4,4-trifluoro-3,3-dimethyl-N-((5-((2-(1-methyl-1H-pyrazol-4-yl)pyridin-4-yl)oxy)pyridin-2-yl)carbamoyl)butanamide, N-((5-((2-(1-methyl-1H-pyrazol-4-yl)pyridin-4-yl)oxy)pyridin-2-yl)carbamoyl)-2-(4-methylpiperazin-1-yl)acetamide, N-((6-methyl-5-((2-(1-methyl-1H-pyrazol-4-yl)pyridin-4-yl)oxy)pyridin-2-yl)carbamoyl)-2-(4-methylpiperazin-1-yl)acetamide, N-((5-((2-(1-methyl-1H-pyrazol-4-yl)pyridin-4-yl)oxy)pyridin-2-yl)carbamoyl)cyclopropanecarboxamide, 1-methyl-N-((5-((2-(1-methyl-1H-pyrazol-4-yl)pyridin-4-yl)oxy)pyridin-2-yl)carbamoyl)cyclopropanecarboxamide, N-((6-methyl-5-((2-(1-methyl-1H-pyrazol-4-yl)pyridin-4-yl)oxy)pyridin-2-yl)carbamoyl)cyclopropanecarboxamide, 1-methyl-N-((6-methyl-5-((2-

(1-methyl-1H-pyrazol-4-yl)pyridin-4-yl)oxy)pyridin-2-yl)carbamoyl)cyclopropanecarboxamide, 2-methoxy-2-methyl-N-((5-((2-(1-methyl-1H-pyrazol-4-yl)pyridin-4-yl)oxy)pyridin-2-yl)carbamoyl)propanamide, N-((6-methyl-5-((2'-methyl-[2,4'-bipyridin]-4-yl)oxy)pyridin-2-yl)carbamoyl)pivalamide, 3-methyl-N-((5-((2-(1-methyl-1H-pyrazol-4-yl)pyridin-4-yl)oxy)pyridin-2-yl)carbamoyl)oxetane-3-carboxamide, 2-methoxy-2-methyl-N-((6-methyl-5-((2-(1-methyl-1H-pyrazol-4-yl)pyridin-4-yl)oxy)pyridin-2-yl)carbamoyl)propanamide, N-((6-methyl-5-((2-(1-methyl-1H-pyrazol-4-yl)pyridin-4-yl)oxy)pyridin-2-yl)carbamoyl)-4-(trifluoromethoxy)butanamide, N-((5-((2-(1-ethyl-1H-pyrazol-4-yl)pyridin-4-yl)oxy)-6-methylpyridin-2-yl)carbamoyl)pivalamide, N-((5-((2-(1-ethyl-1H-pyrazol-4-yl)pyridin-4-yl)oxy)-6-methylpyridin-2-yl)carbamoyl)isobutyramide, 2-(bicyclo[2.2.1]heptan-2-yl)-N-((5-((2-(1-methyl-1H-pyrazol-4-yl)pyridin-4-yl)oxy)pyridin-2-yl)carbamoyl)acetamide, 2,2-dimethyl-N-((5-((2-(1-methyl-1H-pyrazol-4-yl)pyridin-4-yl)oxy)pyridin-2-yl)carbamoyl)butanamide, N-((5-((2-(1-methyl-1H-pyrazol-4-yl)pyridin-4-yl)oxy)pyridin-2-yl)carbamoyl)bicyclo[2.2.1]heptane-2-carboxamide, N-((5-((2-(1-methyl-1H-pyrazol-4-yl)pyridin-4-yl)oxy)pyridin-2-yl)carbamoyl)cyclopentanecarboxamide, N-((5-((2-(1-methyl-1H-pyrazol-4-yl)pyridin-4-yl)oxy)pyridin-2-yl)carbamoyl)tetrahydrofuran-3-carboxamide, N-((5-((2-(1-methyl-1H-pyrazol-4-yl)pyridin-4-yl)oxy)pyridin-2-yl)carbamoyl)cyclohexanecarboxamide, N-((5-((2-(1-methyl-1H-pyrazol-4-yl)pyridin-4-yl)oxy)pyridin-2-yl)carbamoyl)tetrahydro-2H-pyran-4-carboxamide, 2,2-dimethyl-N-((6-methyl-5-((2-(1-methyl-1H-pyrazol-4-yl)pyridin-4-yl)oxy)pyridin-2-yl)carbamoyl)butanamide, N-((5-((2-(2-methylthiazol-5-yl)pyridin-4-yl)oxy)pyridin-2-yl)carbamoyl)pivalamide, N-((6-methyl-5-((6'-methyl-[2,3'-bipyridin]-4-yl)oxy)pyridin-2-yl)carbamoyl)isobutyramide, 2-methoxy-2-methyl-N-((5-((6'-methyl-[2,3'-bipyridin]-4-yl)oxy)pyridin-2-yl)carbamoyl)propanamide, N-((5-((6'-methyl-[2,3'-bipyridin]-4-yl)oxy)pyridin-2-yl)carbamoyl)pivalamide, N-((5-((2-(1-methyl-1H-pyrazol-4-yl)pyridin-4-yl)oxy)pyridin-2-yl)carbamoyl)bicyclo[2.2.2]octane-2-carboxamide, N-((5-((2-(4-(1-methylpiperidin-4-yl)phenyl)pyridin-4-yl)oxy)pyridin-2-yl)carbamoyl)isobutyramide, N-((6-methyl-5-((2-(3-methylisoxazol-5-yl)pyridin-4-yl)oxy)pyridin-2-yl)carbamoyl)pivalamide, 1-methoxy-N-((5-((2-(1-methyl-1H-pyrazol-4-yl)pyridin-4-yl)oxy)pyridin-2-yl)carbamoyl)cyclopropanecarboxamide, 1-methoxy-N-((6-methyl-5-((2-(1-methyl-1H-pyrazol-4-yl)pyridin-4-yl)oxy)pyridin-2-yl)carbamoyl)cyclopropanecarboxamide, N-((6-methyl-5-((2'-methyl-[2,4'-bipyridin]-4-yl)oxy)pyridin-2-yl)carbamoyl)isobutyramide, N-((5-((2'-methyl-[2,4'-bipyridin]-4-yl)oxy)pyridin-2-yl)carbamoyl)pivalamide, N-((6-ethyl-5-((2-(1-methyl-1H-pyrazol-4-yl)pyridin-4-yl)oxy)pyridin-2-yl)carbamoyl)pivalamide, N-((5-((2-(1-methyl-1H-pyrazol-4-yl)pyridin-4-yl)oxy)-6-(trifluoromethyl)pyridin-2-yl)carbamoyl)isobutyramide, N-((6-ethyl-5-((2-(1-methyl-1H-pyrazol-4-yl)pyridin-4-yl)oxy)pyridin-2-yl)carbamoyl)tetrahydro-2H-pyran-4-carboxamide, N-((4-methyl-5-((2-(1-methyl-1H-pyrazol-4-yl)pyridin-4-yl)oxy)pyridin-2-yl)carbamoyl)pivalamide, N-((5-((2'-methyl-[2,4'-bipyridin]-4-yl)oxy)pyridin-2-yl)carbamoyl)tetrahydrofuran-3-carboxamide, N-((6-methyl-5-((2-(2-methylthiazol-5-yl)pyridin-4-yl)oxy)pyridin-2-yl)carbamoyl)pivalamide, 1-methyl-N-((5-((2-(1-methyl-1H-pyrazol-4-yl)pyridin-4-yl)oxy)pyridin-2-yl)carbamoyl)cyclobutanecarboxamide, N-((4-methyl-5-((2-(1-methyl-1H-pyrazol-4-yl)pyridin-4-yl)oxy)pyridin-2-yl)carbamoyl)isobutyramide, N-((5-((6'-methyl-[2,3'-bipyridin]-4-yl)oxy)pyridin-2-yl)carbamoyl)tetrahydrofuran-3-carboxamide, N-((5-((2-(pyrimidin-5-yl)pyridin-4-yl)oxy)pyridin-2-yl)carbamoyl)pivalamide, 2-methoxy-2-methyl-N-((4-methyl-5-((2-(1-methyl-1H-pyrazol-4-yl)pyridin-4-yl)oxy)pyridin-2-yl)carbamoyl)propanamide, 1-methyl-N-((6-methyl-5-((2-(1-methyl-1H-pyrazol-4-yl)pyridin-4-yl)oxy)pyridin-2-yl)carbamoyl)cyclobutanecarboxamide, N-((5-((2-(oxazol-5-yl)pyridin-4-yl)oxy)pyridin-2-yl)carbamoyl)pivalamide, N-((5-((6'-(trifluoromethyl)-[2,3'-bipyridin]-4-yl)oxy)pyridin-2-yl)carbamoyl)pivalamide, N-((5-((2'-(trifluoromethyl)-[2,4'-bipyridin]-4-yl)oxy)pyridin-2-yl)carbamoyl)pivalamide, N-((6-methyl-5-((2'-morpholino-[2,4'-bipyridin]-4-yl)oxy)pyridin-2-yl)carbamoyl)isobutyramide, 2-methoxy-2-methyl-N-((6-methyl-5-((6'-methyl-[2,3'-bipyridin]-4-yl)oxy)pyridin-2-yl)carbamoyl)propanamide, N-((5-((2-(2-methylthiazol-5-yl)pyridin-4-yl)oxy)pyridin-2-yl)carbamoyl)propionamide, N-((5-((2-(4-methyl-1H-imidazol-1-yl)pyridin-4-yl)oxy)pyridin-2-yl)carbamoyl)pivalamide, N-((6-methyl-5-((6'-methyl-[2,3'-bipyridin]-4-yl)oxy)pyridin-2-yl)carbamoyl)cyclopentanecarboxamide, N-((5-((2-(1-methyl-1H-pyrazol-4-yl)pyridin-4-yl)oxy)pyridin-2-yl)carbamoyl)-1-(trifluoromethyl)cyclobutanecarboxamide, N-((6-methyl-5-((2-(1-methyl-1H-pyrazol-4-yl)pyridin-4-yl)oxy)pyridin-2-yl)carbamoyl)-1-(trifluoromethyl)cyclobutanecarboxamide, N-((5-((6'-methyl-[2,3'-bipyridin]-4-yl)oxy)pyridin-2-yl)carbamoyl)tetrahydro-2H-pyran-4-carboxamide, N-((5-((2-(1-methyl-1H-imidazol-4-yl)pyridin-4-yl)oxy)pyridin-2-yl)carbamoyl)pivalamide, N-((5-((6'-(methylamino)-[2,3'-bipyridin]-4-yl)oxy)pyridin-2-yl)carbamoyl)pivalamide, N-((5-((6'-amino-[2,3'-bipyridin]-4-yl)oxy)pyridin-2-yl)carbamoyl)pivalamide, N-((5-((6'-cyano-[2,3'-bipyridin]-4-yl)oxy)-6-methylpyridin-2-yl)carbamoyl)pivalamide, N-((5-((6'-methyl-[2,3'-bipyridin]-4-yl)oxy)pyridin-2-yl)carbamoyl)propionamide, N-((6-methyl-5-((2-(4-(1-methylpiperidin-4-yl)phenyl)pyridin-4-yl)oxy)pyridin-2-yl)carbamoyl)pivalamide, N-((5-((6'-cyano-[2,3'-bipyridin]-4-yl)oxy)-6-methylpyridin-2-yl)carbamoyl)-2-methoxy-2-methylpropanamide, N-((5-((2-(1-methyl-1H-pyrazol-4-yl)pyridin-4-yl)oxy)pyridin-2-yl)carbamoyl)-7-oxabicyclo[2.2.1]heptane-2-carboxamide, 3-methyl-N-((6-methyl-5-((2-(1-methyl-1H-pyrazol-4-yl)pyridin-4-yl)oxy)pyridin-2-yl)carbamoyl)oxetane-3-carboxamide, 2-methoxy-2-methyl-N-((6-methyl-5-((2-(2-methylthiazol-5-yl)pyridin-4-yl)oxy)pyridin-2-yl)carbamoyl)propanamide, 1-methyl-N-((5-((6'-methyl-[2,3'-bipyridin]-4-yl)oxy)pyridin-2-yl)carbamoyl)cyclopropanecarboxamide, N-((5-((2-(2-methylthiazol-5-yl)pyridin-4-yl)oxy)pyridin-2-yl)carbamoyl)tetrahydrofuran-3-carboxamide, N-((4,6-dimethyl-5-((2-(1-methyl-1H-pyrazol-4-yl)pyridin-4-yl)oxy)pyridin-2-yl)carbamoyl)pivalamide, N-((4,6-dimethyl-5-((2-(1-methyl-1H-pyrazol-4-yl)pyridin-4-yl)oxy)pyridin-2-yl)carbamoyl)tetrahydro-2H-pyran-4-carboxamide, N-((6-methyl-5-((2-(4-(4-methylpiperazin-1-yl)phenyl)pyridin-4-yl)oxy)pyridin-2-yl)carbamoyl)pivalamide, 2-methoxy-2-methyl-N-((5-((2-(2-methylthiazol-5-yl)pyridin-A-yl)oxy)pyridin-2-yl)carbamoyl)propanamide, 2-methoxy-2-methyl-N-((6-methyl-5-((2'-methyl-[2,4'-bipyridin]-4-yl)oxy)pyridin-2-yl)carbamoyl)propanamide, 1-methyl-N-((5-((2-(2-methylthiazol-5-yl)pyridin-4-yl)oxy)pyridin-2-yl)carbamoyl)cyclopropanecarboxamide, 1-methoxy-N-((6-methyl-5-((2-(2-methylthiazol-5-yl)pyridin-4-yl)oxy)pyridin-2-yl)carbamoyl)cyclopropanecarboxamide, 2-ethoxy-2-methyl-N-((5-((2-(1-methyl-1H-pyrazol-4-yl)pyridin-4-yl)oxy)pyridin-2-yl)carbamoyl)propanamide, 2-ethoxy-2-methyl-N-((5-((2-(2-methylthiazol-5-yl)pyridin-4-yl)oxy)pyridin-2-yl)carbamoyl)propanamide, N-((5-

((2-(thiazol-5-yl)pyridin-4-yl)oxy)pyridin-2-yl)carbamoyl) pivalamide, 1-methoxy-N-((5-((6'-methyl-[2,3'-bipyridin]-4-yl)oxy)pyridin-2-yl)carbamoyl) cyclopropanecarboxamide, 2-ethoxy-2-methyl-N-((6-methyl-5-((2-(1-methyl-1H-pyrazol-4-yl)pyridin-4-yl)oxy)pyridin-2-yl)carbamoyl)propanamide, N-((5-((2-(4-methyl-1H-imidazol-1-yl)pyridin-4-yl)oxy)pyridin-2-yl)carbamoyl)propionamide, N-((6-methyl-5-((2-(2-methylthiazol-5-yl)pyridin-4-yl)oxy)pyridin-2-yl)carbamoyl)tetrahydro-2H-pyran-4-carboxamide, 2-methoxy-2-methyl-N-((5-((2-(4-methyl-1H-imidazol-1-yl)pyridin-4-yl)oxy)pyridin-2-yl)carbamoyl)propanamide, N-((6-methyl-5-((2-(thiazol-5-yl)pyridin-4-yl)oxy)pyridin-2-yl)carbamoyl)pivalamide, 2-methoxy-2-methyl-N-((5-((2-(1-methyl-1H-imidazol-4-yl)pyridin-4-yl)oxy)pyridin-2-yl)carbamoyl)propanamide, 2-methoxy-2-methyl-N-((6-methyl-5-((2-(4-(1-methylpiperidin-4-yl)phenyl)pyridin-4-yl)oxy)pyridin-2-yl)carbamoyl)propanamide, N-((6-methyl-5-((2-(4-methyl-1H-imidazol-1-yl)pyridin-4-yl)oxy)pyridin-2-yl)carbamoyl)isobutyramide, 1-methyl-N-((6-methyl-5-((2-(4-methyl-1H-imidazol-1-yl)pyridin-4-yl)oxy)pyridin-2-yl)carbamoyl)cyclopropanecarboxamide, N-((6 methyl-5-((2-(4-methyl-1H-imidazol-1-yl)pyridin-4-yl)oxy)pyridin-2-yl)carbamoyl)tetrahydrofuran-3-carboxamide, N-((6-methyl-5-((2-(4-methyl-1H-imidazol-1-yl)pyridin-4-yl)oxy)pyridin-2-yl)carbamoyl)-7-oxabicyclo exo-[2.2.1]heptane-2-carboxamide, N-((5-((2-(1-methyl-1H-imidazol-4-yl)pyridin-4-yl)oxy)pyridin-2-yl)carbamoyl)propionamide, N-((5-((2-(1,2-dimethyl-1H-imidazol-5-yl)pyridin-4-yl)oxy)pyridin-2-yl)carbamoyl)-2-methoxy-2-methylpropanamide, N-((4,6-dimethyl-5-((2-(1-methyl-1H-pyrazol-4-yl)pyridin-4-yl)oxy)pyridin-2-yl)carbamoyl)-2-methoxy-2-methylpropanamide, N-((6-ethyl-5-((2-(1-methyl-1H-pyrazol-4-yl)pyridin-4-yl)oxy)pyridin-2-yl)carbamoyl)-1-methoxycyclopropanecarboxamide, N-((6-methyl-5-((2-(4-methyl-1H-imidazol-1-yl)pyridin-4-yl)oxy)pyridin-2-yl)carbamoyl)tetrahydro-2H-pyran-4-carboxamide, 1-methoxy-N-((5-((2-(4-methyl-1H-imidazol-1-yl)pyridin-4-yl)oxy)pyridin-2-yl)carbamoyl) cyclopropanecarboxamide, 1-methoxy-N-((6-methyl-5-((2-(4-(1-methylpiperidin-4-yl)phenyl)pyridin-4-yl)oxy)pyridin-2-yl)carbamoyl)cyclopropanecarboxamide, 1-methoxy-N-((5-((2-(1-methyl-1H-imidazol-4-yl)pyridin-4-yl)oxy)pyridin-2-yl)carbamoyl)cyclopropanecarboxamide, 2-methoxy-2-methyl-N-((6-methyl-5-((2-(3-methylisoxazol-5-yl)pyridin-4-yl)oxy)pyridin-2-yl)carbamoyl)propanamide, 1-methyl-N-((6-methyl-5-((2-(4-methyl-1H-imidazol-1-yl)pyridin-4-yl)oxy)pyridin-2-yl)carbamoyl)cyclobutanecarboxamide, N-((4-methyl-5-((2-(4-methyl-1H-imidazol-1-yl)pyridin-4-yl)oxy)pyridin-2-yl)carbamoyl)pivalamide, 1-methoxy-N-((5-((2-(2-methylthiazol-5-yl)pyridin-A-yl)oxy)pyridin-2-yl)carbamoyl)cyclopentanecarboxamide, 1-methoxy-N-((6-methyl-5-((2-(1-methyl-1H-pyrazol-4-yl)pyridin-4-yl)oxy)pyridin-2-yl)carbamoyl)cyclopentanecarboxamide, N-((5-((2-(2-methyloxazol-5-yl)pyridin-4-yl)oxy)pyridin-2-yl)carbamoyl)pivalamide, 4-methyl-N-((6-methyl-5-((2-(1-methyl-1H-pyrazol-4-yl)pyridin-4-yl)oxy)pyridin-2-yl)carbamoyl)tetrahydro-2H-pyran-4-carboxamide, 1-methoxy-N-((5-((2-(1-methyl-1H-pyrazol-4-yl)pyridin-4-yl)oxy)pyridin-2-yl)carbamoyl)cyclopentanecarboxamide, 1-methoxy-N-((5-((2-(4-methyl-1H-imidazol-1-yl)pyridin-4-yl)oxy)pyridin-2-yl)carbamoyl)cyclopentanecarboxamide, 1-methoxy-N-((5-((2-(2-methylthiazol-5-yl)pyridin-4-yl)oxy)pyridin-2-yl)carbamoyl)cyclopropanecarboxamide, N-((5-((2-(2-methylthiazol-5-yl)pyridin-4-yl)oxy)pyridin-2-yl)carbamoyl)tetrahydro-2H-pyran-4-carboxamide, 4-methyl-N-((5-((2-(4-methyl-1H-imidazol-1-yl)pyridin-4-yl)oxy)pyridin-2-yl)carbamoyl)tetrahydro-2H-pyran-4-carboxamide, 4-methyl-N-((5-((2-(2-methylthiazol-5-yl)pyridin-4-yl)oxy)pyridin-2-yl)carbamoyl)tetrahydro-2H-pyran-4-carboxamide, 2-methoxy-2-methyl-N-((5-((2-(2-methyloxazol-5-yl)pyridin-1-yl)oxy)pyridin-2-yl)carbamoyl)propanamide, 2-methoxy-2-methyl-N-((5-((2'-methyl-[2,4'-bipyridin]-4-yl)oxy)pyridin-2-yl)carbamoyl)propanamide, 2-ethoxy-2-methyl-N-((5-((2'-methyl-[2,4'-bipyridin]-4-yl)oxy)pyridin-2-yl)carbamoyl)propanamide, 1-methoxy-N-((4-methyl-5-((2-(4-methyl-1H-imidazol-1-yl)pyridin-4-yl)oxy)pyridin-2-yl)carbamoyl)cyclopentanecarboxamide, 4-methyl-N-((5-((2-(2-methyloxazol-5-yl)pyridin-4-yl)oxy)pyridin-2-yl)carbamoyl)tetrahydro-2H-pyran-4-carboxamide, 2-methoxy-2-methyl-N-((4-methyl-5-((2-(4-methyl-1H-imidazol-1-yl)pyridin-4-yl)oxy)pyridin-2-yl)carbamoyl)propanamide, N-((4,6-dimethyl-5-((2-(1-methyl-1H-pyrazol-4-yl)pyridin-4-yl)oxy)pyridin-2-yl)carbamoyl)-4-methyltetrahydro-2H-pyran-4-carboxamide, 1-methoxy-N-((6-methyl-5-((2-(3-methylisoxazol-5-yl)pyridin-4-yl)oxy)pyridin-2-yl)carbamoyl)cyclopentanecarboxamide, N-((6-ethyl-5-((2-(1-methyl-1H-pyrazol-4-yl)pyridin-4-yl)oxy)pyridin-2-yl)carbamoyl)-4-methyltetrahydro-2H-pyran-4-carboxamide, 1-methoxy-N-((5-((2'-methyl-[2,4'-bipyridin]-4-yl)oxy)pyridin-2-yl)carbamoyl)cyclopentanecarboxamide, N-((5-((2-(2-isopropyl-1H-imidazol-4-yl)pyridin-4-yl)oxy)pyridin-2-yl)carbamoyl)pivalamide, N-((5-((2-(1-ethyl-1H-pyrazol-4-yl)pyridin-4-yl)oxy)pyridin-2-yl)carbamoyl)-2-methoxy-2-methylpropanamide, N-((5-((2-(1H-1,2,3-triazol-4-yl)pyridin-4-yl)oxy)-6-methylpyridin-2-yl)carbamoyl) pivalamide, N-((5-((2-(1-allyl-1H-pyrazol-4-yl)pyridin-4-yl)oxy)pyridin-2-yl)carbamoyl)-2-methoxy-2-methylpropanamide, N-((5-((2-(2-isopropyl-1H-imidazol-5-yl)pyridin-4-yl)oxy)pyridin-2-yl)carbamoyl)-2-methoxy-2-methylpropanamide, N-((5-((2-(1-methyl-1H-pyrazol-4-yl)pyridin-4-yl)oxy)pyrimidin-2-yl)carbamoyl)pivalamide, 4-methyl-N-((5-((2-(1-methyl-1H-pyrazol-4-yl)pyridin-4-yl)oxy)pyridin-2-yl)carbamoyl)tetrahydro-2H-pyran-4-carboxamide, N-((5-((2-(1-ethyl-2-isopropyl-1H-imidazol-5-yl)pyridin-4-yl)oxy)pyridin-2-yl)carbamoyl)pivalamide, and N-((5-((2-(1-methyl-1H-pyrazol-4-yl)pyridin-4-yl)oxy)pyrazin-2-yl)carbamoyl)pivalamide, or a pharmaceutically acceptable salt, enantiomer, stereoisomer, or tautomer thereof.

In certain embodiments, the invention comprises a method of treating mammalian disease wherein the disease etiology or progression is at least partially mediated by the kinase activity of c-FMS, PDGFR-β, or c-KIT kinases, wherein the kinase is a wildtype form, a mutant oncogenic form, an aberrant fusion protein form or a polymorph thereof, the method comprising administering to a mammal in need thereof an effective amount of a compound of formula I.

In other embodiments, the present invention comprises a pharmaceutical composition, comprising a compound of formula I and a pharmaceutically acceptable carrier.

In certain embodiments, the composition comprises an additive selected from adjuvants, excipients, diluents, or stabilizers.

In some embodiments, the invention includes a method of treating cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia, the method comprising administering to a patient in need thereof an effective amount of a compound of formula I.

In some embodiments, the invention includes a method of treating glioblastomas, breast cancers, pancreatic cancers, metastasis of primary tumor sites, or cancers that are metastatic to bone, the method comprising administering to a patient in need thereof an effective amount of a compound of formula I.

In certain embodiments of the present methods, the compound is administered orally, parenterally, by inhalation, or subcutaneously.

In some embodiments, the invention provides the use of a compound of Formula I, or a pharmaceutically acceptable salt thereof, in the treatment of cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia, the method comprising administering to a patient in need thereof an effective amount of a compound of formula I.

In some embodiments, the invention provides the use of a compound of Formula I, or a pharmaceutically acceptable salt thereof, in the treatment of glioblastomas, breast cancers, pancreatic cancers, metastasis of primary tumor sites, or cancers that are metastatic to bone, the method comprising administering to a patient in need thereof an effective amount of a compound of formula I.

In some embodiments, the invention provides for the use of a compound of Formula I, or a pharmaceutically acceptable salt thereof, for the manufacture of a medicament for the treatment of cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia.

In certain embodiments, the invention provides for the use of a compound of Formula I, or a pharmaceutically acceptable salt thereof, for the manufacture of a medicament for the treatment of glioblastomas, breast cancers, pancreatic cancers, metastasis of primary tumor sites, or cancers that are metastatic to bone.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, and pharmaceutically acceptable salts. Thus, the terms "compound", "compounds", "test compound" or "test compounds" as used in this disclosure refer to the compounds of this disclosure and any and all possible isomers, stereoisomers, enantiomers, diastereomers, tautomers, and pharmaceutically acceptable salts thereof.

DEFINITIONS

The term "alkyl" as used herein refers to a straight chain alkyl, wherein alkyl chain length is indicated by a range of numbers. In exemplary embodiments, "alkyl" refers to an alkyl chain as defined above containing 1, 2, 3, 4, 5, or 6 carbons (i.e., C1-C6 alkyl). Examples of an alkyl group include, but are not limited to, methyl, ethyl, propyl, butyl, pentyl, and hexyl.

The term "branched alkyl" as used herein refers to an alkyl chain wherein a branching point in the chain exists, and the total number of carbons in the chain is indicated by a range of numbers. In exemplary embodiments, "branched alkyl" refers to an alkyl chain as defined above containing from 3, 4, 5, 6, 7, or 8 carbons (i.e., branched C3-C8 alkyl). Examples of a branched alkyl group include, but are not limited to, iso-propyl, iso-butyl, secondary-butyl, and tertiary-butyl, 2-pentyl, 3-pentyl, 2-hexyl, and 3-hexyl.

The term "alkoxy" as used herein refers to —O—(alkyl), wherein "alkyl" is as defined above.

The term "branched alkoxy" as used herein refers to —O-(branched alkyl), wherein "branched alkyl" is as defined above.

The term "alkylene" as used herein refers to an alkyl moiety interposed between two other atoms. In exemplary embodiments, "alkylene" refers to an alkyl moiety as defined above containing 1, 2, or 3 carbons. Examples of an alkylene group include, but are not limited to —CH$_2$—, —CH$_2$CH$_2$—, and —CH$_2$CH$_2$CH$_2$—. In exemplary embodiments, alkylene groups are branched.

The term "alkynyl" as used herein refers to a carbon chain containing one carbon-carbon triple bond. In exemplary embodiments, "alkynyl" refers to a carbon chain as described above containing 2 or 3 carbons (i.e., C2-C3 alkynyl). Examples of an alkynyl group include, but are not limited to, ethyne and propyne.

The term "aryl" as used herein refers to a cyclic hydrocarbon, where the ring is characterized by delocalized π electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or ring atoms (i.e., C6-C10 aryl). Examples of an aryl group include, but are not limited to, benzene, naphthalene, tetralin, indene, and indane.

The term "cycloalkyl" or "carbocyclyl" as used herein refers to a monocyclic saturated carbon ring, wherein the number of ring atoms is indicated by a range of numbers. In exemplary embodiments, "cycloalkyl" or "carbocyclyl" refers to a carbon ring as defined above containing 3, 4, 5, 6, 7, or 8 ring atoms (i.e., C3-C8 cycloalkyl). Examples of a cycloalkyl group include, but are not limited to, cyclopropyl, cyclobutyl, cyclopentyl, cyclohexyl, cycloheptyl, and cyclooctyl.

The term "halogen" or "halo" as used herein refers to fluorine, chlorine, bromine, and iodine.

The term "heterocycle" or "heterocyclyl" as used herein refers to a cyclic hydrocarbon, wherein at least one of the ring atoms is an O, N, or S, wherein the number of ring atoms is indicated by a range of numbers. Heterocyclyl moieties as defined herein have C or N bonding hands through which the heterocyclyl ring is connected to an adjacent moiety. For example, in some embodiments, a ring N atom from the heterocyclyl is the bonding atom of the heterocylic moiety. In exemplary embodiments, "heterocyclyl" refers to a mono- or bi-cyclic hydrocarbon containing 4, 5, 6, 7 or 8 ring atoms (i.e., C4-C8 heterocyclyl). Examples of a heterocycle group include, but are not limited to, aziridine, oxirane, thiirane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, dioxane, and 7-oxabicyclo[2.2.1]heptane.

The term "heteroaryl" as used herein refers to a cyclic hydrocarbon, where at least one of the ring atoms is an O, N, or S, the ring is characterized by delocalized π electrons (aromaticity) shared among the ring members, and wherein the number of ring atoms is indicated by a range of numbers. Heteroaryl moieties as defined herein have C or N bonding hands through which the heteroaryl ring is connected to an adjacent moiety. For example, in some embodiments, a ring N atom from the heteroaryl is the bonding atom of the heteroaryl moiety. In exemplary embodiments, "heteroaryl" refers to a cyclic hydrocarbon as described above containing 5 or 6 ring atoms (i.e., C5-C6 heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "spirobicycloalkyl" refers to a bicyclic saturated carbon ring system in which the two rings are connected through just one atom. Spirobicycloalkyl rings are taken from, but not limited to spiro[2.2]pentanyl, spiro[2.3]hexanyl, spiro[2.4]heptanyl, spiro[3.3]heptanyl, spiro[2.5]octanyl, spiro[3.4]octanyl, spiro[2.6]nonanyl, spiro[3.5]nonanyl, spiro[4.4]nonanyl, spiro[2.7]decanyl, spiro[3.6]decanyl, spiro[4.5]decanyl, spiro[3.7]undecanyl, spiro[4.6]undecanyl, spiro[5.5]undecanyl, spiro[4.7]dodecanyl, and spiro[5.6]dodecanyl.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "salts" as used herein embraces pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer," "administering, or "administration" as used herein refer to either directly administering a compound or pharmaceutically acceptable salt of the compound or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The terms "isolated" and "purified" as used herein refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the terms "patient" or "subject" include, without limitation, a human or an animal. Exemplary animals include, but are not limited to, mammals such as mouse, rat, guinea pig, dog, feline, horse, cow, pig, monkey, chimpanzee, baboon, or rhesus monkey.

The terms "treatment," "treat," and "treating," are meant to include the full spectrum of intervention for the cancer from which the patient is suffering, such as administration of the active compound to alleviate, slow or reverse one or more of the symptoms and to delay progression of the cancer even if the cancer is not actually eliminated. Treating can be curing, improving, or at least partially ameliorating the disorder.

Structural, chemical and stereochemical definitions are broadly taken from IUPAC recommendations, and more specifically from Glossary of Terms used in Physical Organic Chemistry (IUPAC Recommendations 1994) as summarized by Miller, P. *Pure Appl. Chem.* 1994, 66, pp. 1077-1184 and Basic Terminology of Stereochemistry (IUPAC Recommendations 1996) as summarized by Moss, G. P. *Pure Appl. Chem.* 1996, 68, pp. 2193-2222.

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

The term "tautomer" as used herein refers to compounds produced by the phenomenon wherein a proton of one atom of a molecule shifts to another atom. See March, Advanced Organic Chemistry: Reactions, Mechanisms and Structures, 4th Ed., John Wiley & Sons, pp. 69-74 (1992). Tautomerism is defined as isomerism of the general form

where the isomers (called tautomers) are readily interconvertible; the atoms connecting the groups X, Y and Z are typically any of C, H, O, or S, and G is a group which becomes an electrofuge or nucleofuge during isomerization. The most common case, when the electrofuge is $H^+$, is also known as "prototropy." Tautomers are defined as isomers that arise from tautomerism, independent of whether the isomers are isolable.

The exemplified compounds of the present invention are preferably formulated as a pharmaceutical composition using a pharmaceutically acceptable carrier and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 19$^{th}$ ed., Mack Publishing Co., 1995).

The compounds of Formula I, or a pharmaceutically acceptable salt thereof, may be prepared by a variety of procedures known in the art, as well as those described below. The specific synthetic steps may be combined in different ways to prepare the Formula I compounds, or a pharmaceutically acceptable salt thereof.

The compounds employed as initial starting materials in the synthesis of the compounds of Formula Ia are well known and, to the extent not commercially available, are readily synthesized using specific references provided, by standard procedures commonly employed by those of ordinary skill in the art, or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

ChemDraw version 10 or 12 (CambridgeSoft Corporation, Cambridge, Mass.) was used to name the structures of intermediates and exemplified compounds.

The following abbreviations are used in this disclosure and have the following definitions: "ADP" is adenosine diphosphate, "ATP" is adenosine triphosphate, "conc." is concentrated, "CDI" is 1,1'-carbonyldiimidazole, "DBU" is 1,8-diazabicyclo[5.4.0]undec-7-ene, "DCE" is 1,2-dichloroethane, "DCM" is dichloromethane, "DIEA" is N,N-diisopropylethylamine, "DMA" is N,N-dimethylacetamide, "DMAP" is 4-(dimethylamino)pyridine, "DMF" is N,N-dimethylformamide, "DPPF" is 1,1'-bis(diphenylphosphino)ferrocene, "DMSO" is dimethylsulfoxide, "DPPA" is diphenylphosphryl azide, "EDC" is N-(3-dimethylaminopropyl)-N'-ethylcarbodiimide hydrochloride, "ESI" is electrospray ionization, "Et$_2$O" is diethylether, "EtOAc" is ethyl acetate, "EtOH" is ethanol, "GST" is glutathione S-transferase, "h" is hour or hours, "Hex" is hexane, "HOBT" is 1-hydroxybenzotriazole, "IC$_{50}$" is half maximal inhibitory concentration, "IPA" refers to isopropyl alcohol, "LiHMDS" is lithium bis(trimethylsilyl)amide, "MeCN" is acetonitrile, "MeOH" is methanol, "Me$_4$tBuXPhos" is di-tert-butyl(2',4',6'-triisopropyl-3,4,5,6-tetramethyl-[1,1'-biphenyl]-2-yl)phosphine, "MHz" is megahertz, "min" is minute or minutes, "MS" is mass spectrometry, "MTBE" is methyl tert-butyl ether, "NADH" is nicotinamide adenine dinucleotide, "NBS" is N-bromosuccinimide, "NMR" is nuclear magnetic resonance, "PBS" is phosphate buffered saline, "Pd/C" is palladium on carbon, "Pd(OAc)$_2$" is palladium(II) acetate, "Pd$_2$(dba)$_3$" is tris(dibenzylideneacetone)dipalladium(0), "Pd (PPh₃)₂Cl₂" is dichlorobis(triphenylphosphine)palladium(II) "Pd(PPh₃)₄" is tetrakis(triphenylphosphine)palladium (0), "pet ether" is petroleum ether, "prep-HPLC" is preparative high performance liquid chromatography, "prep-TLC" is preparative thin layer chromatography, "RT" is room temperature which is also known as "ambient temp," which will be understood to consist of a range of normal laboratory temperatures ranging from 15-25° C., "satd." is saturated, "t-butyl-X-Phos" is 2-di-tert-butylphosphino-2',4',6'-triisopropylbiphenyl, "TBAF" is tetrabutylammonium fluoride, "TBTU" is O-benzotriazole-1-yl-N,N,N',N'-tetramethyluronium tetrafluoroborate, "TEA" is triethylamine, "TFA" is trifluoroacetic acid, "THF" is tetrahydrofuran, "Tris" is tris(hydroxymethyl)aminomethane, "Xantphos" is 4,5-bis(diphenylphosphino)-9,9-dimethylxanthene, and "X-Phos" is 2-dicyclohexylphosphino-2',4',6'-triisopropylbiphenyl.

General Chemistry

The compounds of Formula I are prepared by the general synthetic methods illustrated in the schemes below and the accompanying examples. Suitable reaction conditions for the steps of these schemes are well known in the art and appropriate substitutions of solvents and co-reagents are within the skill of the art. Those skilled in the art will understand that synthetic intermediates may be isolated and/or purified by well known techniques as needed or desired, and that it will be possible to use various intermediates directly in subsequent synthetic steps with little or no purification. Furthermore, those skilled in the art will appreciate that in some instances, the order in which moieties are introduced is not critical. The particular order of steps required to produce the compounds of Formula I is dependent upon the particular compound being synthesized, the starting compound, and the relative lability of the substituted moieties, as is well appreciated by the ordinary skilled chemist. All substituents, unless otherwise indicated, are as broadly defined above.

The compounds of Formula I may contain —NH or —OH moieties at the R1, R2, R3 and W positions. It will be understood by those skilled in the art that in some instances it may be advantageous to use an amine or hydroxyl protecting group during synthesis to temporarily mask one or more —NH or —OH moieties. Said protecting group can be removed from any subsequent intermediate leading to the synthesis of compound 1, using standard conditions that effect removal of said protecting group, said conditions of which will be familiar to those skilled in the art. When not specified in a scheme, it will be understood by those skilled in the art that the R1, R2, R3 and W moieties represented in the schemes below may optionally contain standard amino or hydroxyl protecting groups that can be removed at any opportune time in the synthetic sequence.

Compounds 1 of the invention can be prepared as illustrated in Scheme 1. In one embodiment, N-acylisocyantes of formula 3 are reacted with amine 5, typically in the presence of a base such as triethylamine or pyridine, to provide compound 1 (R4=H). Isocyanate 3 is prepared from acid chloride 2 by reaction with silver cyanate, or alternately from amide 6 (R4=H) by reaction with oxalyl chloride. If not commercially available, 2 and 6 can readily be prepared from acid 4 by standard methods. In another embodiment, compound 1 (R4=H) can be prepared by reaction of N-acyl carbamate 7 with amine 5 in the presence of a base, for example N-methylpyrrolidine, typically at elevated temperature, for example 50-80° C. Carbamate 7 is prepared from amide 6 (R4=H) by treatment with a strong base, for example lithium bis(trimethylsilyl)amide, and quenching of the resultant anion with isopropenyl chloroformate to provide 2. In another embodiment, compound 1 (R4≠H) is prepared by reaction of carbonyl chloride 8 (R4≠H) with general amine 5. Intermediate 8 is prepared from amide 6 (R4≠H) by reaction with phosgene or the like. Those skilled in the art will appreciate that intermediates of scheme 1 may be isolated or may be generated and used in situ.

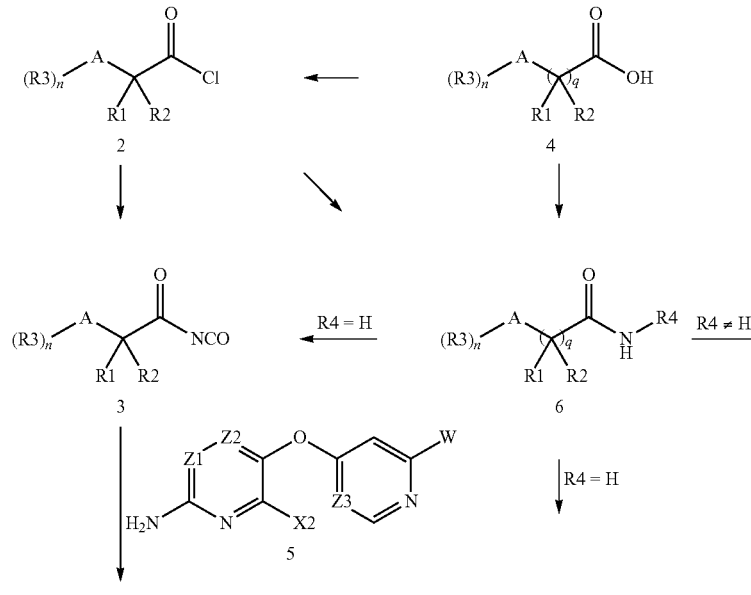

Scheme 1

-continued

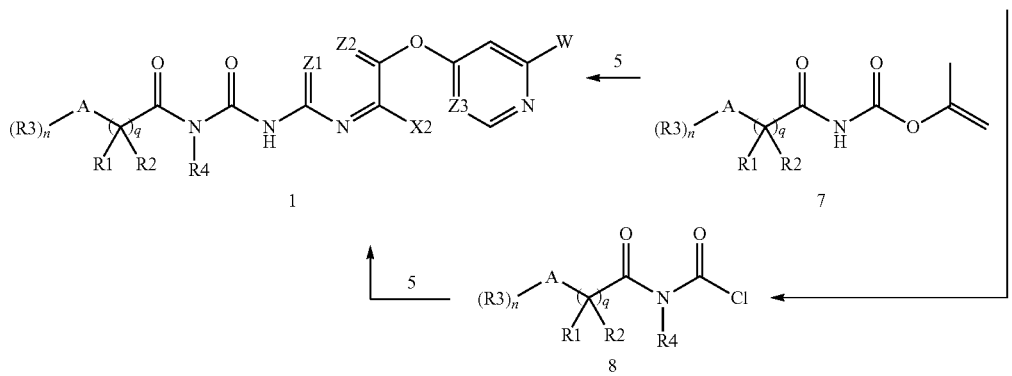

Scheme 2 illustrates an alternative preparation of compounds of formula 1 by the reaction of intermediate 10 with M-W (11) wherein W is an aryl or heteroaryl moiety and M is a boronic acid, boronate ester, trialkylstannyl moiety, or other moiety capable of transferring a W-moiety in a transition metal-catalyzed cross coupling reaction. Conditions for the transformation of 10 to 1 are dependent on the nature of the W-moiety, but generally include the use of palladium catalysts, for example $Pd(PPh_3)_4$ or $Pd_2(dba)_3$, optionally in the presence of additional ligands, for example Xantphos. General conditions to accomplish this transformation (including Suzuki coupling and Stille coupling) are well known to those skilled in the art. Intermediate 10 is readily available from the reaction of intermediate 9 with isocyanate 3 or carbamate 2, as described above in Scheme 1.

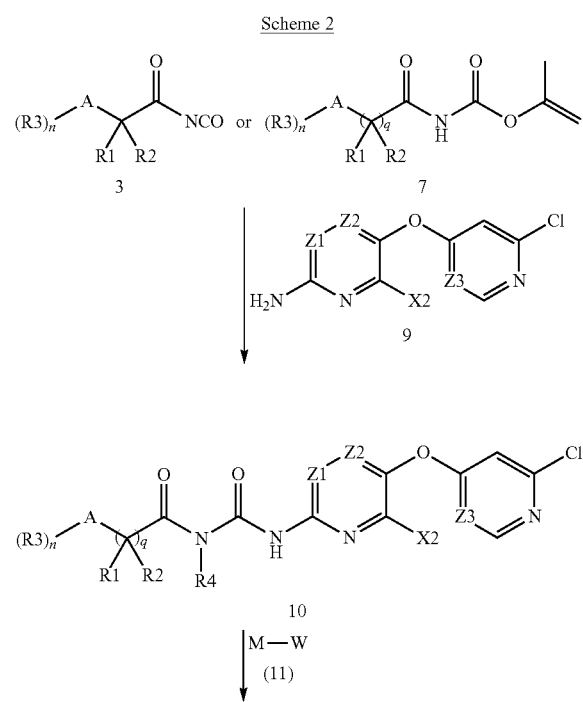

-continued

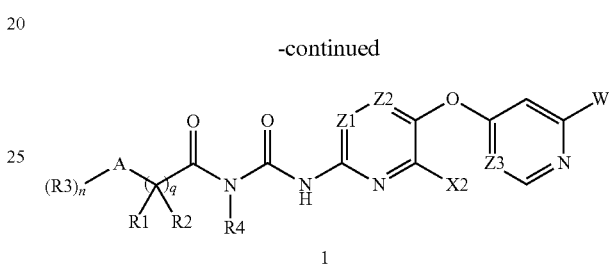

General amines 5 and 9 can be synthesized according to methods commonly known to those skilled in the art as illustrated in Scheme 3. In one embodiment, amine 9 can be prepared directly from the reaction of 12 with dichloride 13. Suitable conditions include combining 12, 13 and potassium tert-butoxide and heating in a solvent, for example dimethylacetamide, and heating said mixture at a temp of 80-120° C. In another embodiment, amine 9 can be prepared from nitro compound 16 by reduction under standard conditions, for example by treatment with zinc dust in the presence of ammonium chloride or by hydrogenation over Raney nickel. Nitro compound 16 is in turn prepared from the reaction of 15 with compound 14, wherein Y is a halide. Suitable conditions to effect said transformation include combining 15 and 14 with a base, for example potassium carbonate, and heating said mixture at a temp of 80-120° C. in a solvent such as dimethylformamide to effect ether formation. In another embodiment, nitro 16 is obtained by the reaction of 18 with dichloride 13. In one embodiment, by analogy to Scheme 2, further conversion of 9 to 5 is effected by reaction of 9 with reagent M-W (11), wherein M is trialkylstannyl or a boronic acid or boronate ester. Conditions for the transformation of 9 to 5 are dependent on the nature of the W-moiety, but generally include the use of palladium catalysts, as further illustrated in the accompanying examples. In another embodiment, intermediate 16 can first be transformed to intermediate 17. Further reduction of the nitro group of 17 provides general amine 5.

Scheme 3

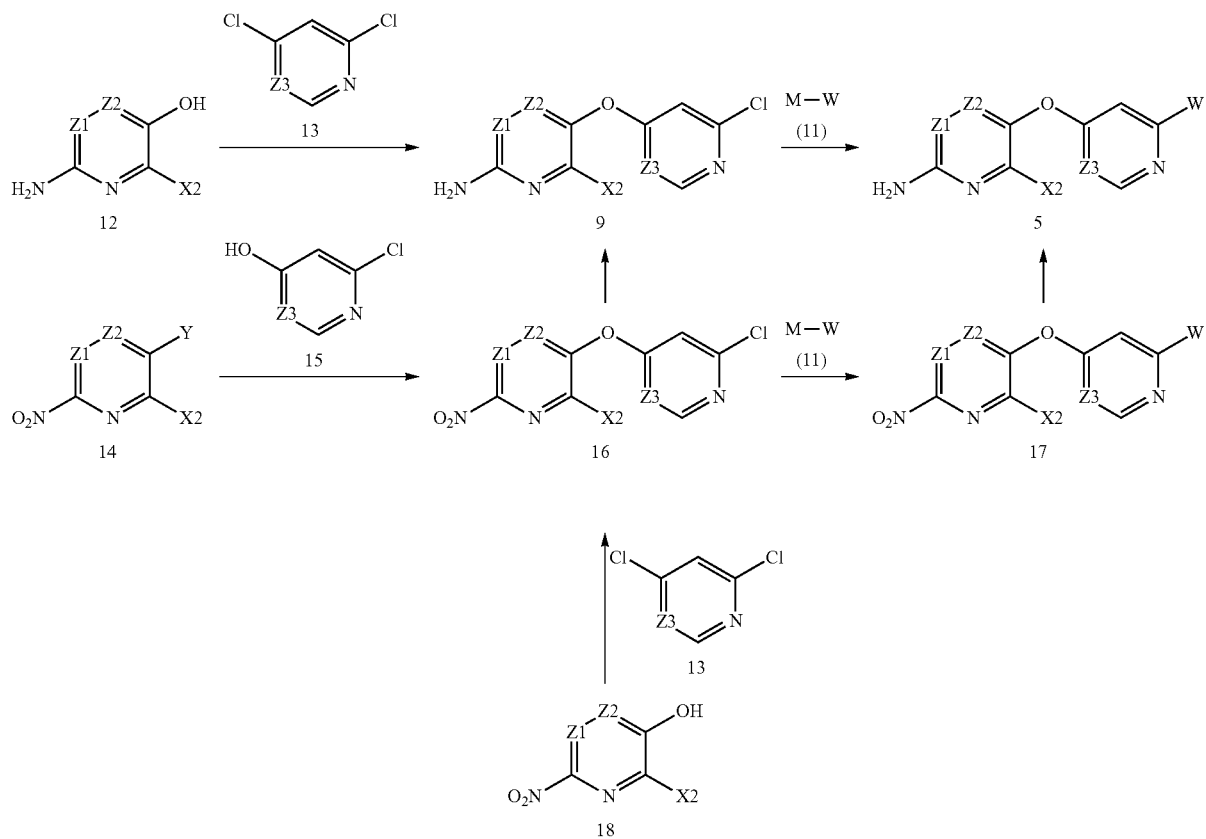

Scheme 4 illustrates the synthesis of amine 25, a variant of general amine 5 wherein W is isoxazol-5-yl. Reaction of amine 9 to with trimethylsilylacetylene (19) in the presence of a palladium catalyst affords 20. Removal of the trimethylsilyl group affords 21. Conversion of 21 to isoxazole 2 is accomplished by [3+2]cycloaddition with the reagent derived from oxime 24, N-chlorosuccinimide, and triethylamine. Alternately, amine 25 can be prepared by reduction of the nitro moiety of 26, in turn available by a similar sequence of reactions commencing with nitro-chloride 16.

Scheme 4

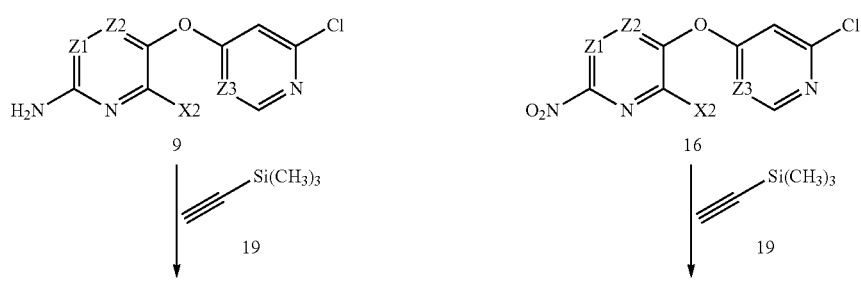

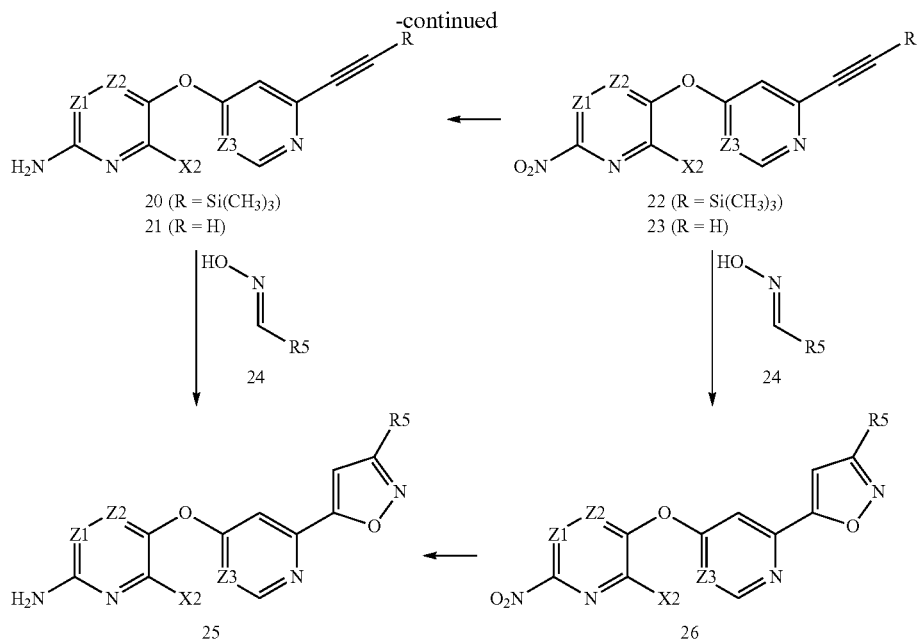

Using the synthetic procedures and methods described herein and methods known to those skilled in the art, the following compounds were made: trans-3-fluoro-3-methyl-N-((5-((2-(1-methyl-1H-pyrazol-4-yl)pyridin-4-yl)oxy)pyridin-2-yl)carbamoyl)cyclobutanecarboxamide, 3,3-dimethyl-N-((5-((2-(1-methyl-1H-pyrazol-4-yl)pyridin-4-yl)oxy)pyridin-2-yl)carbamoyl)cyclobutanecarboxamide, N-((5-((2-(1-methyl-1H-pyrazol-4-yl)pyridin-4-yl)oxy)pyridin-2-yl)carbamoyl)-3-(1-(trifluoromethyl)cyclopropyl)propanamide, N-((5-((2-(1-methyl-1H-pyrazol-4-yl)pyridin-4-yl)oxy)pyridin-2-yl)carbamoyl)-2-(tetrahydro-2H-pyran-4-yl)acetamide, 3,3-dimethyl-N-((5-((6-(1-methyl-1H-pyrazol-4-yl)pyrimidin-4-yl)oxy)pyridin-2-yl)carbamoyl)cyclobutanecarboxamide, N-((6-methyl-5-((2-(1-methyl-1H-pyrazol-4-yl)pyridin-4-yl)oxy)pyridin-2-yl)carbamoyl)pivalamide, N-((6-methyl-5-((2-(1-methyl-1H-pyrazol-4-yl)pyridin-4-yl)oxy)pyridin-2-yl)carbamoyl)propionamide, N-((6-methyl-5-((2-(1-methyl-1H-pyrazol-4-yl)pyridin-4-yl)oxy)pyridin-2-yl)carbamoyl)-2-(tetrahydro-2H-pyran-4-yl)acetamide, trans-4-methyl-N-((6-methyl-5-((2-(1-methyl-1H-pyrazol-4-yl)pyridin-4-yl)oxy)pyridin-2-yl)carbamoyl)cyclohexanecarboxamide, N-((6-methyl-5-((2-(1-methyl-1H-pyrazol-4-yl)pyridin-4-yl)oxy)pyridin-2-yl)carbamoyl)tetrahydrofuran-3-carboxamide, N-((6-methyl-5-((2-(1-methyl-1H-pyrazol-4-yl)pyridin-4-yl)oxy)pyridin-2-yl)carbamoyl)-3-(1-(trifluoromethyl)cyclopropyl)propanamide, 4,4-difluoro-N-((6-methyl-5-((2-(1-methyl-1H-pyrazol-4-yl)pyridin-4-yl)oxy)pyridin-2-yl)carbamoyl)cyclohexanecarboxamide, 3,3-dimethyl-N-((6-methyl-5-((2-(1-methyl-1H-pyrazol-4-yl)pyridin-4-yl)oxy)pyridin-2-yl)carbamoyl)cyclobutanecarboxamide, 3,3-dimethyl-N-((6-methyl-5-((2-(3-methylisoxazol-5-yl)pyridin-4-yl)oxy)pyridin-2-yl)carbamoyl)cyclobutanecarboxamide, N-((6-methyl-5-((2-(1-methyl-1H-pyrazol-4-yl)pyridin-4-yl)oxy)pyridin-2-yl)carbamoyl)-3-oxocyclobutanecarboxamide, N-((6-methyl-5-((2-(1-methyl-1H-pyrazol-4-yl)pyridin-4-yl)oxy)pyridin-2-yl)carbamoyl)cyclohexanecarboxamide, N-((6-methyl-5-((2-(1-methyl-1H-pyrazol-4-yl)pyridin-4-yl)oxy)pyridin-2-yl)carbamoyl)tetrahydro-2H-pyran-4-carboxamide, N-((6-methyl-5-((2-(1-methyl-1H-pyrazol-4-yl)pyridin-4-yl)oxy)pyridin-2-yl)carbamoyl)cyclobutanecarboxamide, N-((6-methyl-5-((2-(1-methyl-1H-pyrazol-4-yl)pyridin-4-yl)oxy)pyridin-2-yl)carbamoyl)cyclopentanecarboxamide, 2-methoxy-N-((6-methyl-5-((2-(1-methyl-1H-pyrazol-4-yl)pyridin-4-yl)oxy)pyridin-2-yl)carbamoyl)acetamide, 2-methoxy-N-((5-((2-(1-methyl-1H-pyrazol-4-yl)pyridin-4-yl)oxy)pyridin-2-yl)carbamoyl)acetamide, 3,3-difluoro-N-((6-methyl-5-((2-(1-methyl-1H-pyrazol-4-yl)pyridin-4-yl)oxy)pyridin-2-yl)carbamoyl)cyclobutanecarboxamide, N-((6-methyl-5-((2-(1-methyl-1H-pyrazol-4-yl)pyridin-4-yl)oxy)pyridin-2-yl)carbamoyl)isobutyramide, N-((5-((2-(1-methyl-1H-pyrazol-4-yl)pyridin-4-yl)oxy)pyridin-2-yl)carbamoyl)isobutyramide, 4-methoxy-N-((6-methyl-5-((2-(1-methyl-1H-pyrazol-4-yl)pyridin-4-yl)oxy)pyridin-2-yl)carbamoyl)butanamide, N-((5-((2-(1-methyl-1H-pyrazol-4-yl)pyridin-4-yl)oxy)pyridin-2-yl)carbamoyl)pivalamide, 1-cyano-N-((5-((2-(1-methyl-1H-pyrazol-4-yl)pyridin-4-yl)oxy)pyridin-2-yl)carbamoyl)cyclopropanecarboxamide, 1-cyano-N-((6-methyl-5-((2-(1-methyl-1H-pyrazol-4-yl)pyridin-4-yl)oxy)pyridin-2-yl)carbamoyl)cyclopropanecarboxamide, 2-cyano-2-methyl-N-((6-methyl-5-((2-(1-methyl-1H-pyrazol-4-yl)pyridin-4-yl)oxy)pyridin-2-yl)carbamoyl)propanamide, 2-cyano-2-methyl-N-((5-((2-(1-methyl-1H-pyrazol-4-yl)pyridin-4-yl)oxy)pyridin-2-yl)carbamoyl)propanamide, N-((5-((2-(1-methyl-1H-pyrazol-4-yl)pyridin-4-yl)oxy)pyridin-2-yl)carbamoyl)spiro[3.3]heptane-2-carboxamide, N-((6-methyl-5-((2-(1-methyl-1H-pyrazol-4-yl)pyridin-4-yl)oxy)pyridin-2-yl)carbamoyl)spiro[3.3]heptane-2-carboxamide, N-((5-((2-(1-methyl-1H-pyrazol-4-yl)pyridin-4-yl)oxy)pyridin-2-yl)carbamoyl)-1-(trifluoromethyl)cyclopropanecarboxamide, N-((6-methyl-5-((2-(1-methyl-1H-pyrazol-4-yl)pyridin-4-yl)oxy)pyridin-2-yl)carbamoyl)-1-(trifluoromethyl)cyclopropanecarboxamide, 3,3,3-trifluoro-2,2-dimethyl-N-((5-((2-(1-methyl-1H-pyrazol-4-yl)pyridin-4-yl)oxy)pyridin-2-yl)carbamoyl)propanamide, 3,3,3-trifluoro-2,2-dimethyl-N-((6-methyl-5-((2-(1-methyl-1H-pyrazol-4-yl)pyridin-4-yl)oxy)pyridin-2-yl)carbamoyl)propanamide, N-((6-methyl-5-((2-(1-methyl-1H-pyrazol-4-yl)pyridin-4-yl)oxy)pyridin-2-yl)carbamoyl)adamantane-1- carboxamide, N-((5-((2-(1-methyl-1H-pyrazol-4-yl)pyridin-4-yl)oxy)pyridin-2-yl)carbamoyl)adamantane-1-carboxamide, N-((6-methyl-5-((6'-methyl-[2,3'-bipyridin]-4-yl)oxy)pyridin-2-yl)carbamoyl)pivalamide, N-((5-((2-(1-(trideuteromethyl)-1H-pyrazol-4-yl)pyridin-4-yl)oxy)pyridin-2-yl)carbamoyl)isobutyramide, N-((6-methyl-5-((2-(1-(trideuteromethyl)-1H-pyrazol-4-yl)pyridin-4-yl)oxy)pyridin-2-yl)carbamoyl)isobutyramide, N-((6-methyl-5-((2-(1-(trideuteromethyl)-1H-pyrazol-4-yl)pyridin-4-yl)oxy)pyridin-2-yl)carbamoyl)pivalamide, trans-N-((6-methyl-5-((2-(1-methyl-1H-pyrazol-4-yl)pyridin-4-yl)oxy)pyridin-2-yl)carbamoyl)-4-(trifluoromethyl)cyclohexanecarboxamide, N-((6-methyl-5-((2-(1-(trideuteromethyl)-1H-pyrazol-4-yl)pyridin-4-yl)oxy)pyridin-2-yl)carbamoyl)tetrahydrofuran-3-carboxamide, trans-N-((5-((2-(1-methyl-1H-pyrazol-4-yl)pyridin-4-yl)oxy)pyridin-2-yl)carbamoyl)-4(trifluoromethyl)cyclohexanecarboxamide, 2-cyclohexyl-N-((6-methyl-5-((2-(1-methyl-1H-pyrazol-4-yl)pyridin-4-yl)oxy)pyridin-2-yl)carbamoyl)acetamide, 4,4,4-trifluoro-3,3-dimethyl-N-((6-methyl-5-((2-(1-methyl-1H-pyrazol-4-yl)pyridin-4-yl)oxy)pyridin-2-yl)carbamoyl)butanamide, 4,4,4-trifluoro-3,3-dimethyl-N-((5-((2-(1-methyl-1H-pyrazol-4-yl)pyridin-4-yl)oxy)pyridin-2-yl)carbamoyl)butanamide, N-((5-((2-(1-methyl-1H-pyrazol-4-yl)pyridin-4-yl)oxy)pyridin-2-yl)carbamoyl)-2-(4-methylpiperazin-1-yl)acetamide, N-((6-methyl-5-((2-(1-methyl-1H-pyrazol-4-yl)pyridin-4-yl)oxy)pyridin-2-yl)carbamoyl)-2-(4-methylpiperazin-1-yl)acetamide, N-((5-((2-(1-methyl-1H-pyrazol-4-yl)pyridin-4-yl)oxy)pyridin-2-yl)carbamoyl)cyclopropanecarboxamide, 1-methyl-N-((5-((2-(1-methyl-1H-pyrazol-4-yl)pyridin-4-yl)oxy)pyridin-2-yl)carbamoyl)cyclopropanecarboxamide, N-((6-methyl-5-((2-(1-methyl-1H-pyrazol-4-yl)pyridin-4-yl)oxy)pyridin-2-yl)carbamoyl)cyclopropanecarboxamide, 1-methyl-N-((6-methyl-5-((2-(1-methyl-1H-pyrazol-4-yl)pyridin-4-yl)oxy)pyridin-2-yl)carbamoyl)cyclopropanecarboxamide, 2-methoxy-2-methyl-N-((5-((2-(1-methyl-1H-pyrazol-4-yl)pyridin-4-yl)oxy)pyridin-2-yl)carbamoyl)propanamide, N-((6-methyl-5-((2'-methyl-[2,4'-bipyridin]-4-yl)oxy)pyridin-2-yl)carbamoyl)pivalamide, 3-methyl-N-((5-((2-(1-methyl-1H-pyrazol-4-yl)pyridin-4-yl)oxy)pyridin-2-yl)carbamoyl)oxetane-3-carboxamide, 2-methoxy-2-methyl-N-((6-methyl-5-((2-(1-methyl-1H-pyrazol-4-yl)pyridin-4-yl)oxy)pyridin-2-yl)carbamoyl)propanamide, N-((6-methyl-5-((2-(1-methyl-1H-pyrazol-4-yl)pyridin-4-yl)oxy)pyridin-2-yl)carbamoyl)-4-(trifluoromethoxy)butanamide, N-((5-((2-(1-ethyl-1H-pyrazol-4-yl)pyridin-4-yl)oxy)-6-methylpyridin-2-yl)carbamoyl)pivalamide, N-((5-((2-(1-ethyl-1H-pyrazol-4-yl)pyridin-4-yl)oxy)-6-methylpyridin-2-yl)carbamoyl)isobutyramide, 2-(bicyclo[2.2.1]heptan-2-yl)-N-((5-((2-(1-methyl-1H-pyrazol-4-yl)pyridin-4-yl)oxy)pyridin-2-yl)carbamoyl)acetamide, 2,2-dimethyl-N-((5-((2-(1-methyl-1H-pyrazol-4-yl)pyridin-4-yl)oxy)pyridin-2-yl)carbamoyl)butanamide, N-((5-((2-(1-methyl-1H-pyrazol-4-yl)pyridin-4-yl)oxy)pyridin-2-yl)carbamoyl)bicyclo[2.2.1]heptane-2-carboxamide, N-((5-((2-(1-methyl-1H-pyrazol-4-yl)pyridin-4-yl)oxy)pyridin-2-yl)carbamoyl)cyclopentanecarboxamide, N-((5-((2-(1-methyl-1H-pyrazol-4-yl)pyridin-4-yl)oxy)pyridin-2-yl)carbamoyl)tetrahydrofuran-3-carboxamide, N-((5-((2-(1-methyl-1H-pyrazol-4-yl)pyridin-4-yl)oxy)pyridin-2-yl)carbamoyl)cyclohexanecarboxamide, N-((5-((2-(1-methyl-1H-pyrazol-4-yl)pyridin-4-yl)oxy)pyridin-2-yl)carbamoyl)tetrahydro-2H-pyran-4-carboxamide, 2,2-dimethyl-N-((6-methyl-5-((2-(1-methyl-1H-pyrazol-4-yl)pyridin-4-yl)oxy)pyridin-2-yl)carbamoyl)butanamide, N-((5-((2-(2-methylthiazol-5-yl)pyridin-4-yl)oxy)pyridin-2-yl)carbamoyl)pivalamide, N-((6-methyl-5-((6'-methyl-[2,3'-bipyridin]-4-yl)oxy)pyridin-2-yl)carbamoyl)isobutyramide, 2-methoxy-2-methyl-N-((5-((6'-methyl-[2,3'-bipyridin]-4-yl)oxy)pyridin-2-yl)carbamoyl)propanamide, N-((5-((6'-methyl-[2,3'-bipyridin]-4-yl)oxy)pyridin-2-yl)carbamoyl)pivalamide, N-((5-((2-(1-methyl-1H-pyrazol-4-yl)pyridin-4-yl)oxy)pyridin-2-yl)carbamoyl)bicyclo[2.2.2]octane-2-carboxamide, N-((5-((2-(4-(1-methylpiperidin-4-yl)phenyl)pyridin-4-yl)oxy)pyridin-2-yl)carbamoyl)isobutyramide, N-((6-methyl-5-((2-(3-methylisoxazol-5-yl)pyridin-4-yl)oxy)pyridin-2-yl)carbamoyl)pivalamide, 1-methoxy-N-((5-((2-(1-methyl-1H-pyrazol-4-yl)pyridin-4-yl)oxy)pyridin-2-yl)carbamoyl)cyclopropanecarboxamide, 1-methoxy-N-((6-methyl-5-((2-(1-methyl-1H-pyrazol-4-yl)pyridin-4-yl)oxy)pyridin-2-yl)carbamoyl)cyclopropanecarboxamide, N-((6-methyl-5-((2'-methyl-[2,4'-bipyridin]-4-yl)oxy)pyridin-2-yl)carbamoyl)isobutyramide, N-((5-((2'-methyl-[2,4'-bipyridin]-4-yl)oxy)pyridin-2-yl)carbamoyl)pivalamide, N-((6-ethyl-5-((2-(1-methyl-1H-pyrazol-4-yl)pyridin-4-yl)oxy)pyridin-2-yl)carbamoyl)pivalamide, N-((5-((2-(1-methyl-1H-pyrazol-4-yl)pyridin-4-yl)oxy)-6-(trifluoromethyl)pyridin-2-yl)carbamoyl)isobutyramide, N-((6-ethyl-5-((2-(1-methyl-1H-pyrazol-4-yl)pyridin-4-yl)oxy)pyridin-2-yl)carbamoyl)tetrahydro-2H-pyran-4-carboxamide, N-((4-methyl-5-((2-(1-methyl-1H-pyrazol-4-yl)pyridin-4-yl)oxy)pyridin-2-yl)carbamoyl)pivalamide, N-((5-((2'-methyl-[2,4'-bipyridin]-4-yl)oxy)pyridin-2-yl)carbamoyl)tetrahydrofuran-3-carboxamide, N-((6-methyl-5-((2-(2-methylthiazol-5-yl)pyridin-4-yl)oxy)pyridin-2-yl)carbamoyl)pivalamide, 1-methyl-N-((5-((2-(1-methyl-1H-pyrazol-4-yl)pyridin-4-yl)oxy)pyridin-2-yl)carbamoyl)cyclobutanecarboxamide, N-((4-methyl-5-((2-(1-methyl-1H-pyrazol-4-yl)pyridin-4-yl)oxy)pyridin-2-yl)carbamoyl)isobutyramide, N-((5-((6'-methyl-[2,3'-bipyridin]-4-yl)oxy)pyridin-2-yl)carbamoyl)tetrahydrofuran-3-carboxamide, N-((5-((2-(pyrimidin-5-yl)pyridin-4-yl)oxy)pyridin-2-yl)carbamoyl)pivalamide, 2-methoxy-2-methyl-N-((4-methyl-5-((2-(1-methyl-1H-pyrazol-4-yl)pyridin-4-yl)oxy)pyridin-2-yl)carbamoyl)propanamide, 1-methyl-N-((6-methyl-5-((2-(1-methyl-1H-pyrazol-4-yl)pyridin-4-yl)oxy)pyridin-2-yl)carbamoyl)cyclobutanecarboxamide, N-((5-((2-(oxazol-5-yl)pyridin-4-yl)oxy)pyridin-2-yl)carbamoyl)pivalamide, N-((5-((6'-(trifluoromethyl)-[2,3'-bipyridin]-4-yl)oxy)pyridin-2-yl)carbamoyl)pivalamide, N-((5-((2'-(trifluoromethyl)-[2,4'-bipyridin]-4-yl)oxy)pyridin-2-yl)carbamoyl)pivalamide, N-((6-methyl-5-((2'-morpholino-[2,4'-bipyridin]-4-yl)oxy)pyridin-2-yl)carbamoyl)isobutyramide, 2-methoxy-2-methyl-N-((6-methyl-5-((6'-methyl-[2,3'-bipyridin]-4-yl)oxy)pyridin-2-yl)carbamoyl)propanamide, N-((5-((2-(2-methylthiazol-5-yl)pyridin-4-yl)oxy)pyridin-2-yl)carbamoyl)propionamide, N-((5-((2-(4-methyl-1H-imidazol-1-yl)pyridin-4-yl)oxy)pyridin-2-yl)carbamoyl)pivalamide, N-((6-methyl-5-((6'-methyl-[2,3'-bipyridin]-4-yl)oxy)pyridin-2-yl)carbamoyl)cyclopentanecarboxamide, N-((5-((2-(1-methyl-1H-pyrazol-4-yl)pyridin-4-yl)oxy)pyridin-2-yl)carbamoyl)-1-(trifluoromethyl)cyclobutanecarboxamide, N-((6-methyl-5-((2-(1-methyl-1H-pyrazol-4-yl)pyridin-4-yl)oxy)pyridin-2-yl)carbamoyl)-1-(trifluoromethyl)cyclobutanecarboxamide, N-((5-((6'-methyl-[2,3'-bipyridin]-4-yl)oxy)pyridin-2-yl)carbamoyl)tetrahydro-2H-pyran-4-carboxamide, N-((5-((2-(1-methyl-1H-imidazol-4-yl)pyridin-4-yl)oxy)pyridin-2-yl)carbamoyl)pivalamide, N-((5-((6'-(methylamino)-[2,3'-bipyridin]-4-yl)oxy)pyridin-2-yl)carbamoyl)pivalamide, N-((5-((6'-amino-[2,3'-bipyridin]-4-yl)oxy)pyridin-2-yl)carbamoyl)pivalamide, N-((5-((6'-cyano-[2,3'-bipyridin]-4-yl)oxy)-6-methylpyridin-2-yl)carbamoyl)pivalamide, N-((5-

((6'-methyl-[2,3'-bipyridin]-4-yl)oxy)pyridin-2-yl)carbamoyl)propionamide, N-((6-methyl-5-((2-(4-(1-methylpiperidin-4-yl)phenyl)pyridin-4-yl)oxy)pyridin-2-yl)carbamoyl)pivalamide, N-((5-((6'-cyano-[2,3'-bipyridin]-4-yl)oxy)-6-methylpyridin-2-yl)carbamoyl)-2-methoxy-2-methylpropanamide, N-((5-((2-(1-methyl-1H-pyrazol-4-yl)pyridin-4-yl)oxy)pyridin-2-yl)carbamoyl)-7-oxabicyclo[2.2.1]heptane-2-carboxamide, 3-methyl-N-((6-methyl-5-((2-(1-methyl-1H-pyrazol-4-yl)pyridin-4-yl)oxy)pyridin-2-yl)carbamoyl)oxetane-3-carboxamide, 2-methoxy-2-methyl-N-((6-methyl-5-((2-(2-methylthiazol-5-yl)pyridin-4-yl)oxy)pyridin-2-yl)carbamoyl)propanamide, 1-methyl-N-((5-((6'-methyl-[2,3'-bipyridin]-4-yl)oxy)pyridin-2-yl)carbamoyl)cyclopropanecarboxamide, N-((5-((2-(2-methylthiazol-5-yl)pyridin-4-yl)oxy)pyridin-2-yl)carbamoyl)tetrahydrofuran-3-carboxamide, N-((4,6-dimethyl-5-((2-(1-methyl-1H-pyrazol-4-yl)pyridin-4-yl)oxy)pyridin-2-yl)carbamoyl)pivalamide, N-((4,6-dimethyl-5-((2-(1-methyl-1H-pyrazol-4-yl)pyridin-4-yl)oxy)pyridin-2-yl)carbamoyl)tetrahydro-2H-pyran-4-carboxamide, N-((6-methyl-5-((2-(4-(4-methylpiperazin-1-yl)phenyl)pyridin-4-yl)oxy)pyridin-2-yl)carbamoyl)pivalamide, 2-methoxy-2-methyl-N-((5-((2-(2-methylthiazol-5-yl)pyridin-A-yl)oxy)pyridin-2-yl)carbamoyl)propanamide, 2-methoxy-2-methyl-N-((6-methyl-5-((2'-methyl-[2,4'-bipyridin]-4-yl)oxy)pyridin-2-yl)carbamoyl)propanamide, 1-methyl-N-((5-((2-(2-methylthiazol-5-yl)pyridin-4-yl)oxy)pyridin-2-yl)carbamoyl)cyclopropanecarboxamide, 1-methoxy-N-((6-methyl-5-((2-(2-methylthiazol-5-yl)pyridin-4-yl)oxy)pyridin-2-yl)carbamoyl)cyclopropanecarboxamide, 2-ethoxy-2-methyl-N-((5-((2-(1-methyl-1H-pyrazol-4-yl)pyridin-4-yl)oxy)pyridin-2-yl)carbamoyl)propanamide, 2-ethoxy-2-methyl-N-((5-((2-(2-methylthiazol-5-yl)pyridin-4-yl)oxy)pyridin-2-yl)carbamoyl)propanamide, N-((5-((2-(thiazol-5-yl)pyridin-4-yl)oxy)pyridin-2-yl)carbamoyl)pivalamide, 1-methoxy-N-((5-((6'-methyl-[2,3'-bipyridin]-4-yl)oxy)pyridin-2-yl)carbamoyl)cyclopropanecarboxamide, 2-ethoxy-2-methyl-N-((6-methyl-5-((2-(1-methyl-1H-pyrazol-4-yl)pyridin-4-yl)oxy)pyridin-2-yl)carbamoyl)propanamide, N-((5-((2-(4-methyl-1H-imidazol-1-yl)pyridin-4-yl)oxy)pyridin-2-yl)carbamoyl)propionamide, N-((6-methyl-5-((2-(2-methylthiazol-5-yl)pyridin-4-yl)oxy)pyridin-2-yl)carbamoyl)tetrahydro-2H-pyran-4-carboxamide, 2-methoxy-2-methyl-N-((5-((2-(4-methyl-1H-imidazol-1-yl)pyridin-4-yl)oxy)pyridin-2-yl)carbamoyl)propanamide, N-((6-methyl-5-((2-(thiazol-5-yl)pyridin-4-yl)oxy)pyridin-2-yl)carbamoyl)pivalamide, 2-methoxy-2-methyl-N-((5-((2-(1-methyl-1H-imidazol-4-yl)pyridin-4-yl)oxy)pyridin-2-yl)carbamoyl)propanamide, 2-methoxy-2-methyl-N-((6-methyl-5-((2-(4-(1-methylpiperidin-4-yl)phenyl)pyridin-4-yl)oxy)pyridin-2-yl)carbamoyl)propanamide, N-((6-methyl-5-((2-(4-methyl-1H-imidazol-1-yl)pyridin-4-yl)oxy)pyridin-2-yl)carbamoyl)isobutyramide, 1-methyl-N-((6-methyl-5-((2-(4-methyl-1H-imidazol-1-yl)pyridin-4-yl)oxy)pyridin-2-yl)carbamoyl)cyclopropanecarboxamide, N-((6 methyl-5-((2-(4-methyl-1H-imidazol-1-yl)pyridin-4-yl)oxy)pyridin-2-yl)carbamoyl)tetrahydrofuran-3-carboxamide, N-((6-methyl-5-((2-(4-methyl-1H-imidazol-1-yl)pyridin-4-yl)oxy)pyridin-2-yl)carbamoyl)-7-oxabicyclo exo-[2.2.1]heptane-2-carboxamide, N-((5-((2-(1-methyl-1H-imidazol-4-yl)pyridin-4-yl)oxy)pyridin-2-yl)carbamoyl)propionamide, N-((5-((2-(1,2-dimethyl-1H-imidazol-5-yl)pyridin-4-yl)oxy)pyridin-2-yl)carbamoyl)-2-methoxy-2-methylpropanamide, N-((4,6-dimethyl-5-((2-(1-methyl-1H-pyrazol-4-yl)pyridin-4-yl)oxy)pyridin-2-yl)carbamoyl)-2-methoxy-2-methylpropanamide, N-((6-ethyl-5-((2-(1-methyl-1H-pyrazol-4-yl)pyridin-4-yl)oxy)pyridin-2-yl)carbamoyl)-1-methoxycyclopropanecarboxamide, N-((6-methyl-5-((2-(4-methyl-1H-imidazol-1-yl)pyridin-4-yl)oxy)pyridin-2-yl)carbamoyl)tetrahydro-2H-pyran-4-carboxamide, 1-methoxy-N-((5-((2-(4-methyl-1H-imidazol-1-yl)pyridin-4-yl)oxy)pyridin-2-yl)carbamoyl)cyclopropanecarboxamide, 1-methoxy-N-((6-methyl-5-((2-(4-(1-methylpiperidin-4-yl)phenyl)pyridin-4-yl)oxy)pyridin-2-yl)carbamoyl)cyclopropanecarboxamide, 1-methoxy-N-((5-((2-(1-methyl-1H-imidazol-4-yl)pyridin-4-yl)oxy)pyridin-2-yl)carbamoyl)cyclopropanecarboxamide, 2-methoxy-2-methyl-N-((6-methyl-5-((2-(3-methylisoxazol-5-yl)pyridin-4-yl)oxy)pyridin-2-yl)carbamoyl)propanamide, 1-methyl-N-((6-methyl-5-((2-(4-methyl-1H-imidazol-1-yl)pyridin-4-yl)oxy)pyridin-2-yl)carbamoyl)cyclobutanecarboxamide, N-((4-methyl-5-((2-(4-methyl-1H-imidazol-1-yl)pyridin-4-yl)oxy)pyridin-2-yl)carbamoyl)pivalamide, 1-methoxy-N-((5-((2-(2-methylthiazol-5-yl)pyridin-A-yl)oxy)pyridin-2-yl)carbamoyl)cyclopentanecarboxamide, 1-methoxy-N-((6-methyl-5-((2-(1-methyl-1H-pyrazol-4-yl)pyridin-4-yl)oxy)pyridin-2-yl)carbamoyl)cyclopentanecarboxamide, N-((5-((2-(2-methyloxazol-5-yl)pyridin-4-yl)oxy)pyridin-2-yl)carbamoyl)pivalamide, 4-methyl-N-((6-methyl-5-((2-(1-methyl-1H-pyrazol-4-yl)pyridin-4-yl)oxy)pyridin-2-yl)carbamoyl)tetrahydro-2H-pyran-4-carboxamide, 1-methoxy-N-((5-((2-(1-methyl-1H-pyrazol-4-yl)pyridin-4-yl)oxy)pyridin-2-yl)carbamoyl)cyclopentanecarboxamide, 1-methoxy-N-((5-((2-(4-methyl-1H-imidazol-1-yl)pyridin-4-yl)oxy)pyridin-2-yl)carbamoyl)cyclopentanecarboxamide, 1-methoxy-N-((5-((2-(2-methylthiazol-5-yl)pyridin-4-yl)oxy)pyridin-2-yl)carbamoyl)cyclopropanecarboxamide, N-((5-((2-(2-methylthiazol-5-yl)pyridin-4-yl)oxy)pyridin-2-yl)carbamoyl)tetrahydro-2H-pyran-4-carboxamide, 4-methyl-N-((5-((2-(4-methyl-1H-imidazol-1-yl)pyridin-4-yl)oxy)pyridin-2-yl)carbamoyl)tetrahydro-2H-pyran-4-carboxamide, 4-methyl-N-((5-((2-(2-methylthiazol-5-yl)pyridin-4-yl)oxy)pyridin-2-yl)carbamoyl)tetrahydro-2H-pyran-4-carboxamide, 2-methoxy-2-methyl-N-((5-((2-(2-methyloxazol-5-yl)pyridin-4-yl)oxy)pyridin-2-yl)carbamoyl)propanamide, 2-methoxy-2-methyl-N-((5-((2'-methyl-[2,4'-bipyridin]-4-yl)oxy)pyridin-2-yl)carbamoyl)propanamide, 2-ethoxy-2-methyl-N-((5-((2'-methyl-[2,4'-bipyridin]-4-yl)oxy)pyridin-2-yl)carbamoyl)propanamide, 1-methoxy-N-((4-methyl-5-((2-(4-methyl-1H-imidazol-1-yl)pyridin-4-yl)oxy)pyridin-2-yl)carbamoyl)cyclopentanecarboxamide, 4-methyl-N-((5-((2-(2-methyloxazol-5-yl)pyridin-4-yl)oxy)pyridin-2-yl)carbamoyl)tetrahydro-2H-pyran-4-carboxamide, 2-methoxy-2-methyl-N-((4-methyl-5-((2-(4-methyl-1H-imidazol-1-yl)pyridin-4-yl)oxy)pyridin-2-yl)carbamoyl)propanamide, N-((4,6-dimethyl-5-((2-(1-methyl-1H-pyrazol-4-yl)pyridin-4-yl)oxy)pyridin-2-yl)carbamoyl)-4-methyltetrahydro-2H-pyran-4-carboxamide, 1-methoxy-N-((6-methyl-5-((2-(3-methylisoxazol-5-yl)pyridin-4-yl)oxy)pyridin-2-yl)carbamoyl)cyclopentanecarboxamide, N-((6-ethyl-5-((2-(1-methyl-1H-pyrazol-4-yl)pyridin-4-yl)oxy)pyridin-2-yl)carbamoyl)-4-methyltetrahydro-2H-pyran-4-carboxamide, 1-methoxy-N-((5-((2'-methyl-[2,4'-bipyridin]-4-yl)oxy)pyridin-2-yl)carbamoyl)cyclopentanecarboxamide, N-((5-((2-(2-isopropyl-1H-imidazol-4-yl)pyridin-4-yl)oxy)pyridin-2-yl)carbamoyl)pivalamide, N-((5-((2-(1-ethyl-1H-pyrazol-4-yl)pyridin-4-yl)oxy)pyridin-2-yl)carbamoyl)-2-methoxy-2-methylpropanamide, N-((5-((2-(1H-1,2,3-triazol-4-yl)pyridin-4-yl)oxy)-6-methylpyridin-2-yl)carbamoyl)pivalamide, N-((5-((2-(1-allyl-1H-pyrazol-4-yl)pyridin-4-yl)oxy)pyridin-2-yl)carbamoyl)-2-methoxy-2- methylpropanamide, N-((5-((2-(2-isopropyl-1H-imidazol-5-yl)pyridin-4-yl)oxy)pyridin-2-yl)carbamoyl)-2-methoxy-2-methylpropanamide, N-((5-((2-(1-methyl-1H-pyrazol-4-yl)pyridin-4-yl)oxy)pyrimidin-2-yl)carbamoyl)pivalamide, 4-methyl-N-((5-((2-(1-methyl-1H-pyrazol-4-yl)pyridin-4-yl)oxy)pyridin-2-yl)carbamoyl)tetrahydro-2H-pyran-4-carboxamide, N-((5-((2-(1-ethyl-2-isopropyl-1H-imidazol-5-yl)pyridin-4-yl)oxy)pyridin-2-yl)carbamoyl)pivalamide, and N-((5-((2-(1-methyl-1H-pyrazol-4-yl)pyridin-4-yl)oxy)pyrazin-2-yl)carbamoyl)pivalamide.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

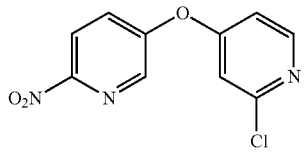 [SMILES: O=[N+]([O-])c1ccc(Oc2ccnc(Cl)c2)cn1]

Example A1

A solution of 5-bromo-2-nitropyridine (15 g, 73.9 mmol) in DMF (300 mL) was sparged with Ar, treated with $Cs_2CO_3$ (48.2 g, 148 mmol) and 2-chloro-4-hydroxypyridine (10.53 g, 81 mmol), sparged again with Ar and heated at 85° C. overnight. The mixture was cooled to RT, filtered through a bed of silica gel, washed thoroughly with EtOAc, and the filtrate treated with 5% LiCl and stirred overnight. The layers were separated, the aqueous layer extracted with additional EtOAc (4×) and the combined organics were dried over $Na_2SO_4$ and concentrated to dryness. The residue was dissolved in EtOAc, treated with 5% LiCl, stirred for 1 h, the layers separated and the aqueous layer extracted with EtOAc (3×). The combined organics were dried over $Na_2SO_4$, concentrated to dryness and purified via silica gel chromatography (EtOAc/Hex). The material was suspended in MTBE, sonicated and the resulting solid collected via filtration to afford 2-chloro-4-((6-nitropyridin-3-yl)oxy)pyridine (6.06 g, 33%). $^1$H NMR (400 MHz, DMSO-$d_6$): δ 8.62 (d, J=2.4, 1H), 8.43-8.39 (m, 2H), 8.06 (dd, J=8.8, 2.8 Hz, 1H), 7.36 (d, J=2.0 Hz, 1H), 7.23 (dd, J=5.6, 2.0 Hz, 1H); MS (ESI) m/z: 252.0 (M+H+).

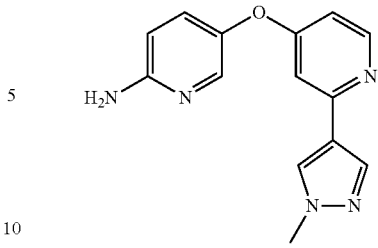

Example A2

A suspension of Example A1 (14.38 g, 57.1 mmol), 1-methyl-4-(4,4,5,5-tetramethyl-1,3,2-dioxaborolan-2-yl)-1H-pyrazole (13.08 g, 62.9 mmol) and $Cs_2CO_3$ (55.9 g, 171 mmol) in DMF (150 mL) was sparged with Ar, treated with tetrakis(triphenylphosphine)palladium (0) [Pd(PPh$_3$)$_4$](6.60 g, 5.71 mmol), sparged again with Ar and heated at 90° C. overnight. The mixture was cooled to RT, the solids removed via filtration through diatomaceous earth, washed with EtOAc and the filtrate concentrated to near-dryness. The residue was treated with EtOAc, washed with 5% LiCl (1×) and the aqueous layer back-extracted with EtOAc (4×). The combined organics were dried over $Na_2SO_4$, concentrated to dryness and purified via silica gel chromatography (MeOH/DCM) to afford 2-(1-methyl-1H-pyrazol-4-yl)-4-((6-nitropyridin-3-yl)oxy)pyridine (12.28 g, 72%). $^1$H NMR (400 MHz, DMSO-$d_6$): δ 8.59 (d, J=2.8 Hz, 1H), 8.49 (d, J=5.6 Hz, 1H), 8.41 (d, J=8.9 Hz, 1H), 8.29 (s, 1H), 8.00 (d, J=0.7 Hz, 1H), 7.97 (dd, J=8.9, 2.8 Hz, 1H), 7.44 (d, J=2.4 Hz, 1H), 6.97 (dd, J=5.6, 2.4 Hz, 1H), 3.85 (s, 3H); MS (ESI) m/z: 298.1 (M+H+).

A mixture of 2-(1-methyl-1H-pyrazol-4-yl)-4-((6-nitropyridin-3-yl)oxy)pyridine (11.88 g, 40.0 mmol) and NH$_4$Cl (22.4 g, 419 mmol) in EtOH (200 mL) and water (200 mL) was treated portion-wise with iron powder (22.4 g, 401 mmol), stirred for 0.5 h, treated with additional NH$_4$Cl (22.4 g, 419 mmol) and iron powder (22.4 g, 401 mmol) and stirred at RT for 3 h. The solids were removed via filtration through diatomaceous earth and washed with EtOAc and DCM. The filtrate was washed with water, the aqueous layer back-extracted with DCM (4×) and the combined organics were dried over $Na_2SO_4$, concentrated to dryness and purified via silica gel chromatography (MeOH/DCM) to afford 5-((2-(1-methyl-1H-pyrazol-4-yl)pyridin-4-yl)oxy)pyridin-2-amine (6.4 g, 60%). MS (ESI) m/z: 268.1 (M+H+).

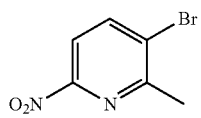

Example A3

A 0° C. solution of sulfuric acid (125 mL) was treated drop-wise with $H_2O_2$ (30%, 63.1 mL, 2058 mmol), stirred for 15 min, treated drop-wise with a cold solution of 6-amino-3-bromo-2-picoline (35 g, 187 mmol) in sulfuric acid (125 mL), allowed to warm to RT and stirred for 4 h. The mixture was poured onto ice (1.2 kg) and the resulting solid collected via filtration, dissolved in DCM, washed with brine, dried over $Na_2SO_4$ and concentrated to dryness. The aqueous filtrate and washes were combined, extracted with DCM (2×) and the combined organics were dried over Na₂SO₄, concentrated to dryness, purified via silica gel chromatography (EtOAc/Hex) and combined with the above-isolated solid to afford 3-bromo-2-methyl-6-nitropyridine (25.59 g, 63%). MS (ESI) m/z: 218.9 (M+H⁺).

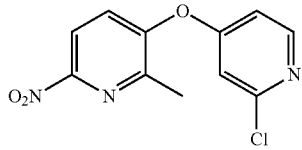 [SMILES: Cc1nc([N+](=O)[O-])ccc1Oc1ccnc(Cl)c1]

Example A4

A solution of Example A3 (25.59 g, 118 mmol), K₂CO₃ (48.9 g, 354 mmol) and 2-chloro-4-hydroxy-pyridine (30.6 g, 236 mmol) in DMF (160 mL) was sparged with Ar, heated at 100° C. overnight, then cooled to RT. The mixture was treated with water and EtOAc, the solids removed via filtration through diatomaceous earth and washed with water, EtOAc, then DCM. The aqueous filtrate was extracted with EtOAc (2×) and the organic extracts were combined with the organic filtrates, washed with water, then brine, dried over Na₂SO₄ and concentrated to dryness. The residue was treated with MTBE, sonicated and the resulting solid collected via filtration to afford 3-((2-chloropyridin-4-yl)oxy)-2-methyl-6-nitropyridine (17.16 g, 55%). ¹H NMR (400 MHz, DMSO-d₆): δ 8.38 (d, J=5.7 Hz, 1H), 8.25 (d, J=8.7 Hz, 1H), 7.95 (d, J=8.7 Hz, 1H), 7.29 (d, J=2.3 Hz, 1H), 7.16 (dd, J=5.7, 2.3 Hz, 1H), 2.46 (s, 3H); MS (ESI) m/z: 266.0 (M+H⁺).

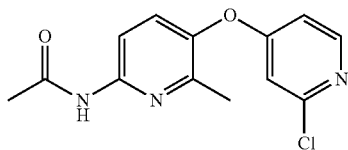 [SMILES: CC(=O)Nc1ccc(Oc2ccnc(Cl)c2)c(C)n1]

Example A5

A solution of 3-hydroxy-2-methylpyridine (20.0 g, 183 mmol) and Na₂CO₃ (38.8 g, 367 mmol) in H₂O (320 mL) and MeOH (200 mL) was treated with I₂ (46.5 g, 183 mmol) and stirred at RT for 1 h. The mixture was acidified with HCl (2 M), extracted with EtOAc (2×) and the combined organics were washed with brine, dried over Na₂SO₄ and concentrated to dryness. The material was suspended in 1:1 EtOAc/Hex, sonicated and the solid collected via filtration and dried. The filtrate was concentrated to dryness, treated with DCM, the solid collected via filtration and combined with the first solid to afford 6-iodo-2-methylpyridin-3-ol (20.5 g, 48%). MS (ESI) m/z: 236.0 (M+H⁺).

A mixture of 6-iodo-2-methylpyridin-3-ol (6.8 g, 28.9 mmol), 2,4-dichloro pyridine (8.56 g, 57.9 mmol) and K₂CO₃ (4.00 g, 28.9 mmol) in DMA (50 mL) was heated at 110° C. for 16 h under argon. The mixture was cooled to RT, treated with H₂O, extracted with EtOAc (2×) and the combined organics were washed with H₂O, then brine, dried over Na₂SO₄, concentrated to dryness and purified via silica gel chromatography (EtOAc/Hex) to afford 3-((2-chloropyridin-4-yl)oxy)-6-iodo-2-methylpyridine (7.35 g, 73%) as a white solid. MS (ESI) m/z: 346.9 (M+H⁺).

A solution of 3-((2-chloropyridin-4-yl)oxy)-6-iodo-2-methylpyridine (8.5 g, 24.53 mmol) in dioxane (100 mL) was sparged with argon, treated with acetamide (5.07 g, 86 mmol), Cs₂CO₃ (11.99 g, 36.8 mmol), X-Phos (0.585 g, 1.226 mmol) and Pd₂(dba)₃ (1.123 g, 1.226 mmol) and heated at 83° C. for 16 h. The mixture was cooled to RT, treated with EtOAc, solids removed via filtration through diatomaceous earth, rinsed well with EtOAc, and the filtrate washed with H₂O, then brine, dried over Na₂SO₄, concentrated to dryness and purified via silica gel chromatography (EtOAc/Hex) to afford N-(5-((2-chloropyridin-4-yl)oxy)-6-methylpyridin-2-yl)acetamide (3.8 g, 56%) as an off-white solid. MS (ESI) m/z: 278.0 (M+H⁺).

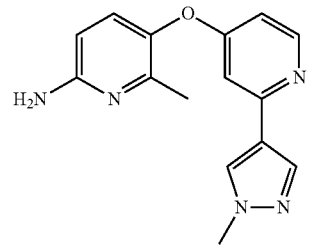 [SMILES: Cc1nc(N)ccc1Oc1ccnc(-c2cnn(C)c2)c1]

Example A6

Method 1: A solution of Example A5 (3.83 g, 13.79 mmol) in dioxane (50 mL) was sparged with argon, treated with a solution of K₂CO₃ (3.81 g, 27.6 mmol) in H₂O (10 mL), 1-methyl-4-(4,4,5,5-tetramethyl-1,3,2-dioxaborolan-2-yl)-1H-pyrazole (3.44 g, 16.55 mmol) and Pd(PPh₃)₄ (0.637 g, 0.552 mmol) and heated at 80° C. for 16 h. The mixture was cooled to RT, treated with H₂O, extracted with EtOAc (2×) and the combined organics washed with H₂O, then brine, dried over Na₂SO₄ and concentrated to dryness. The material was suspended in 3:2 EtOAc/Hex, sonicated and the resulting solid collected via filtration and dried. The filtrate was concentrated to dryness, purified via silica gel chromatography (MeOH/DCM) and combined with the isolated solid to afford N-(6-methyl-5-((2-(1-methyl-1H-pyrazol-4-yl)pyridin-4-yl)oxy)pyridin-2-yl)acetamide (3.88 g, 87%) as a white solid. ¹H NMR (400 MHz, DMSO-d₆): δ 10.60 (s, 1H), 8.34 (d, J=5.7 Hz, 1H), 8.25 (s, 1H), 8.01 (d, J=8.8 Hz, 1H), 7.95 (s, 1H), 7.57 (d, J=8.8 Hz, 1H), 7.17 (d, J=2.4 Hz, 1H), 6.58 (dd, J=5.7, 2.4 Hz, 1H), 3.84 (s, 3H), 2.25 (s, 3H), 2.08 (s, 3H); MS (ESI) m/z: 324.1 (M+H⁺).

A solution of N-(6-methyl-5-((2-(1-methyl-1H-pyrazol-4-yl)pyridin-4-yl)oxy)pyridin-2-yl)acetamide (3.88 g, 12.00 mmol) in THF (30 mL) was treated with 2M HCl (30 mL, 60 mmol), heated at 65° C. for 6 h, cooled to RT and concentrated to dryness. The mixture was treated with H₂O, neutralized with solid NaHCO₃, extracted with EtOAc (2×) and the combined organics were washed with brine, dried over Na₂SO₄ and concentrated to dryness. The material was suspended in 3:2 EtOAc/Hex, sonicated and the resulting solid collected via filtration and dried to afford 6-methyl-5-((2-(1-methyl-1H-pyrazol-4-yl)pyridin-4-yl)oxy)pyridin-2-amine (3.1 g, 92%) as a white solid. MS (ESI) m/z: 282.1 (M+H⁺).

Method 2: A mixture of Example A8 (4.42 g, 18.76 mmol), 1-methyl-4-(4,4,5,5-tetramethyl-1,3,2-dioxaborolan-2-yl)-1H-pyrazole (5.07 g, 24.38 mmol), and K₂CO₃ in dioxane (60 mL) and water (15 mL) was sparged with Ar, treated with Pd(PPh$_3$)$_4$ (1.084 g, 0.938 mmol), sparged with Ar again and heated at 90° C. for 6 h. The reaction was cooled to RT, treated with saturated brine, and extracted with EtOAc (3×). The organics were dried over Na$_2$SO$_4$ and concentrated to dryness. The residue was treated with EtOAc (30 mL) and briefly sonicated. The solids were collected by filtration, washed with EtOAc (10 mL) and dried under vacuum to obtain the product (4.15 g, 79% yield) of suitable NMR purity. This material (4.15 g, 14.75 mmol) was dissolved in THF (300 mL) and MeOH (15 mL) and treated with thiol-modified silica gel (1.2 mmol thiol/g, 4.92 g, 5.90 mmol). The mixture was stirred at RT for 4 h, filtered through a pad of diatomaceous earth and washed with EtOAc (300 mL) and THF (400 mL). The filtrate was concentrated to dryness. The residue was treated with EtOAc (30 mL) and the solid was collected by filtration, washed with EtOAc and dried under vacuum at 80° C. to obtain 5-((2-(1-methyl-1H-pyrazol-4-yl)pyridin-4-yl)oxy)pyridin-2-amine (3.6 g, 87% yield). $^1$H NMR (400 MHz, DMSO-d$_6$): δ 8.30 (d, J=5.7 Hz, 1H), 8.22 (s, 1H), 7.93 (d, J=0.7 Hz, 1H), 7.17 (d, J=8.7 Hz, 1H), 7.10 (d, J=2.4 Hz, 1H), 6.49 (dd, J=5.7, 2.4 Hz, 1H), 6.34 (d, J=8.7 Hz, 1H), 5.93 (s, 2H), 3.84 (s, 3H), 2.06 (s, 3H); MS (ESI) m/z: 282.1 (M+H$^+$).

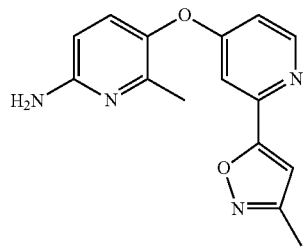 [SMILES: Cc1cc(-c2cc(Oc3ccc(N)nc3C)ccn2)on1]

Example A7

A solution of Example A5 (0.35 g, 1.260 mmol) in DMF (5 mL) was sparged with argon, treated with TEA (1 mL) trimethylsilylacetylene (0.531 mL, 3.78 mmol), copper(I) iodide (0.024 g, 0.126 mmol) and dichlorobis(triphenylphosphine) palladium(II) [Pd(PPh$_3$)$_2$Cl$_2$](0.088 g, 0.126 mmol) and heated at 75° C. under argon for 16 h. The mixture was cooled to RT, treated with EtOAc, solids removed via filtration through diatomaceous earth, rinsed well with EtOAc and H$_2$O and the layers of the filtrate separated. The aqueous layer was extracted with EtOAc (1×) and the combined organics were washed with brine, dried over Na$_2$SO$_4$ and concentrated to dryness. The resulting material was dissolved in MeOH (20 mL), treated with K$_2$CO$_3$ (300 mg) and stirred at RT for 1 h. The mixture was concentrated to dryness, treated with EtOAc, sonicated, the solids removed via filtration through diatomaceous earth, rinsed well with EtOAc and the filtrate concentrated to dryness and purified via silica gel chromatography (EtOAc/Hex) to afford N-(5-((2-ethynylpyridin-4-yl)oxy)-6-methylpyridin-2-yl)acetamide (102 mg, 30%) as a light red solid. $^1$H NMR (400 MHz, DMSO-d$_6$): δ 10.62 (s, 1H); 8.40 (d, J=5.8 Hz, 1H); 8.01 (d, J=8.8 Hz, 1H); 7.60 (d, J=6.0 Hz, 1H); 7.04 (d, J=2.5 Hz, 1H); 6.89 (dd, J=5.8, 2.6 Hz, 1H); 4.34 (s, 1H); 2.22 (s, 3H); 2.07 (s, 3H); MS (ESI) m/z: 268.1 (M+H$^+$).

A solution of N-chlorosuccinimide (0.153 g, 1.145 mmol) in DMF (1 mL) was treated with acetaldoxime (0.068 g, 1.145 mmol), stirred at RT for 30 min, then added to a solution of N-(5-((2-ethynylpyridin-4-yl)oxy)-6-methylpyridin-2-yl)acetamide (0.102 g, 0.382 mmol) and TEA (0.5 mL) in DMF (1 mL) and heated at 60° C. for 1 h. The mixture was cooled to RT, treated with H$_2$O, extracted with EtOAc (2×) and the combined organics were washed with H$_2$O, then brine, dried over Na$_2$SO$_4$, concentrated to dryness and purified via silica gel chromatography (MeOH/DCM) to afford N-(6-methyl-5-((2-(3-methylisoxazol-5-yl)pyridin-4-yl)oxy)pyridin-2-yl) acetamide (110 mg, 89%) as a white solid. $^1$H NMR (400 MHz, DMSO-d$_6$): δ 10.64 (s, 1H), 8.55 (d, J=5.7 Hz, 1H), 8.03 (d, J=8.8 Hz, 1H), 7.64 (d, J=8.8 Hz, 1H), 7.35 (d, J=2.5 Hz, 1H), 6.96 (m, 2H), 2.28 (s, 3H), 2.25 (s, 3H), 2.08 (s, 3H); MS (ESI) m/z: 325.1 (M+H$^+$).

A mixture of N-(6-methyl-5-((2-(3-methylisoxazol-5-yl)pyridin-4-yl)oxy)pyridin-2-yl)acetamide (0.11 g, 0.339 mmol) and 2M HCl (1.696 mL, 3.39 mmol) in THF (3 mL) was heated at 60° C. for 4 h. The mixture was cooled to RT, treated with EtOAc and H$_2$O, neutralized with NaHCO$_3$, the layers separated and the aqueous layer extracted with EtOAc (1×). The combined organics were washed with brine, dried over Na$_2$SO$_4$ and concentrated to dryness to afford 6-methyl-5-((2-(3-methylisoxazol-5-yl)pyridin-4-yl)oxy)pyridin-2-amine (90 mg, 94%) as a white solid. $^1$H NMR (400 MHz, DMSO-d$_6$): δ 8.51 (d, J=5.7 Hz, 1H); 7.26 (d, J=2.5 Hz, 1H); 7.22 (d, J=8.7 Hz, 1H); 6.95 (s, 1H); 6.89 (dd, J=5.7, 2.5 Hz, 1H); 6.36 (d, J=8.7 Hz, 1H); 6.00 (s, 2H); 2.28 (s, 3H); 2.06 (s, 3H); MS (ESI) m/z: 283.1 (M+H$^+$).

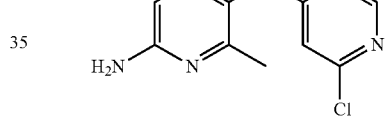

Example A8

Method 1: A solution of Example A4 (1 g, 3.76 mmol) in EtOH (37.6 mL) was treated with tin(II) chloride dihydrate (4.25 g, 18.82 mmol) and stirred at 80° C. for 30 h. The mixture was cooled to RT, treated slowly with satd. NaHCO$_3$ (5 mL), stirred for several minutes and filtered through diatomaceous earth. The filtrate was dried over Na$_2$SO$_4$ and concentrated to dryness to afford crude 5-((2-chloropyridin-4-yl)oxy)-6-methylpyridin-2-amine (645 mg, 73%) as an orange solid which was used without further purification. MS (ESI) m/z: 236.1 (M+H$^+$).

Method 2: Example A4 (5.0 g, 18.82 mmol) and ammonium chloride (30.2 g, 565 mmol) were suspended in a mixture of MeOH:THF (1:1, 100 mL). Zinc powder (12.31 g, 188 mmol) was added portionwise over 10 min and then the mixture was stirred at RT overnight. The reaction mixture was diluted with EtOAc (500 mL) and filtered. The filtrate was concentrated in vacuo and the residue was purified by silica gel chromatography to obtain 5-((2-chloropyridin-4-yl)oxy)-6-methylpyridin-2-amine (3.72 g, 84%). $^1$H NMR (400 MHz, DMSO-d$_6$): δ 8.24 (d, J=5.7 Hz, 1H), 7.20 (d, J=8.7 Hz, 1H), 6.89 (d, J=2.2 Hz, 1H), 6.85 (dd, J=5.8, 2.3 Hz, 1H), 6.35 (d, J=8.7 Hz, 1H), 6.02 (s, 2H), 2.05 (s, 3H); MS (ESI) m/z: 236.1 (M+H$^+$).

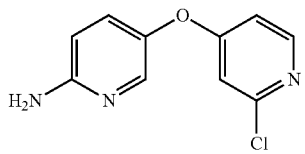

Example A9

A solution of Example A1 (20.00 g, 79 mmol) in MeOH (40 mL) was hydrogenated in presence of Raney Nickel (2.00 g, 34.1 mmol) at 40 psi for 3 h. The catalyst was removed via filtration, rinsed with MeOH and the filtrate concentrated to dryness to afford 5-((2-chloropyridin-4-yl)oxy)pyridin-2-amine (18.52 g, 105%) as a brown solid. MS (ESI) m/z: 222.0 (M+H$^+$).

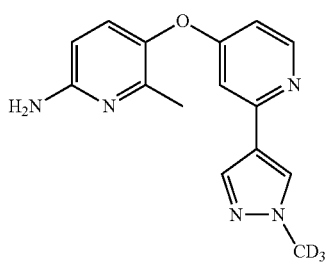 [SMILES: [2H]C([2H])([2H])n1cc(-c2cc(Oc3ccc(N)nc3C)ccn2)cn1]

Example A10

A suspension of Example A4 (0.744 g, 2.80 mmol), Example C3 (0.65 g, 3.08 mmol) and Cs$_2$CO$_3$ (2.74 g, 8.40 mmol) in DMF (7.45 mL) was sparged with Ar for 0.5 h under sonication, treated with Pd(PPh$_3$)$_4$ (0.323 g, 0.280 mmol), sparged again with Ar and heated at 90° C. overnight. The mixture was cooled to RT, diluted with EtOAc, filtered through diatomaceous earth and the filtrate concentrated to dryness and purified via silica gel chromatography (MeOH/DCM) to afford 2-methyl-6-nitro-3-((2-(1-(trideuteromethyl)-1H-pyrazol-4-yl)pyridin-4-yl)oxy)pyridine (880 mg, 100%) as a brown solid. $^1$H NMR (400 MHz, DMSO-d$_6$): δ 8.47 (d, J=5.6 Hz, 1H), 8.28 (d, J=0.7 Hz, 1H), 8.24 (d, J=8.7 Hz, 1H), 8.00 (d, J=0.7 Hz, 1H), 7.84 (d, J=8.7 Hz, 1H), 7.37 (d, J=2.4 Hz, 1H), 6.90 (dd, J=5.6, 2.4 Hz, 1H), 2.50 (s, 3H); MS (ESI) m/z: 315.1 (M+H$^+$).

A mixture of 2-methyl-6-nitro-3-((2-(1-(trideuteromethyl)-1H-pyrazol-4-yl)pyridin-4-yl)oxy)pyridine and NH$_4$Cl (4.27 g, 80 mmol) in MeOH (21 mL) and THF (21 mL) was treated portion-wise with zinc powder (2.134 g, 32.6 mmol) and stirred at RT for 0.5 h. The mixture was treated with EtOAc, the solids removed via filtration through diatomaceous earth, rinsed well with EtOAc and the filtrate concentrated to dryness. The residue was dissolved in hot EtOAc, allowed to cool to RT and the resulting solid collected via filtration to afford 6-methyl-5-((2-(1-(trideuteromethyl)-1H-pyrazol-4-yl)pyridin-4-yl)oxy)pyridin-2-amine (1.25 g, 86%) as a pink solid. $^1$H NMR (400 MHz, DMSO-d$_6$): δ 8.77 (d, J=5.7 Hz, 1H), 8.54 (d, J=0.7 Hz, 1H), 8.36 (d, J=0.7 Hz, 1H), 7.62 (d, J=8.6 Hz, 1H), 7.51 (m, 1H), 6.98 (dd, J=5.7, 2.4 Hz, 1H), 6.92 (dd, J=8.6, 0.7 Hz, 1H), 3.26 (s, 1H), 3.22 (s, 1H), 2.57 (s, 3H); MS (ESI) m/z: 285.1 (M+H$^+$).

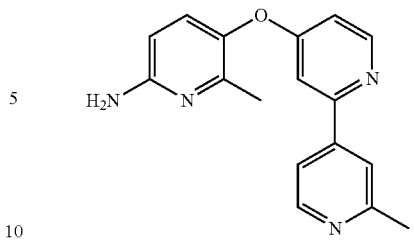

Example A11

A mixture of Example A8 (905 mg, 3.84 mmol), 2-methyl-4-(4,4,5,5-tetramethyl-1,3,2-dioxaborolan-2-yl)pyridine (1.010 g, 4.61 mmol), potassium carbonate (1.592 g, 11.52 mmol) and Pd(PPh$_3$)$_4$ (222 mg, 0.192 mmol) in dioxane (16 mL) and water (4 mL) was degassed with Ar, sealed and warmed to 85° C. overnight. The mixture was cooled to RT, diluted with EtOAc (40 mL) and water (50 mL), and filtered through diatomaceous earth. The organic phase was separated and washed with brine (50 mL). The organic phase was diluted with methanol (5 mL), treated with thiol-modified silica gel (4 g, 1.4 mmol thiol/g, 5.6 mmol)), and gently stirred for 3 h. The mixture was filtered, washing the slica gel plug with 3% MeOH/EtOAc (2×10 mL). The filtrates were evaporated at reduced pressure and the residue was purified by silica gel chromatography (0-10% MeOH/EtOAc) to give 6-methyl-5-((2'-methyl-[2,4'-bipyridin]-4-yl)oxy)pyridin-2-amine as a tan solid (806 mg, 71%). $^1$H NMR (400 MHz, DMSO-d$_6$): δ 9.07 (d, J=2.3 Hz, 1H), 8.48 (d, J=5.7 Hz, 1H), 8.25 (dd, J=8.1, 2.4 Hz, 1H), 7.50 (d, J=2.4 Hz, 1H), 7.33 (d, J=8.2 Hz, 1H), 7.21 (d, J=8.7 Hz, 1H), 6.67 (dd, J=5.7, 2.4 Hz, 1H), 6.35 (d, J=8.7 Hz, 1H), 5.96 (s, 2H), 2.50 (s, 3H), 2.08 (s, 3H). MS (ESI) m/z: 293.2 (M+H$^+$).

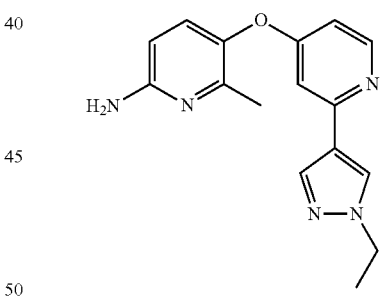

Example A12

A degassed solution of Example A8 (0.28 g, 1.188 mmol) in dioxane (6 mL) was treated with 1-ethylpyrazole-4-boronic acid (0.333 g, 2.376 mmol), a solution of K$_2$CO$_3$ (0.328 g, 2.376 mmol) in water (1.5 mL) and Pd(PPh$_3$)$_4$ (0.137 g, 0.119 mmol) and heated at 90° C. overnight. Additional 1-ethylpyrazole-4-boronic acid (0.333 g, 2.376 mmol), K$_2$CO$_3$ (0.328 g, 2.376 mmol) and Pd(PPh$_3$)$_4$ (0.137 g, 0.119 mmol) was added and the mixture heated at 100° C. for 4 h. The mixture was cooled to RT, treated with satd. NaHCO$_3$, extracted with EtOAc (3×) and the combined organics were washed with brine, dried over Na$_2$SO$_4$, concentrated to dryness and purified via silica gel chromatography (MeOH/DCM) to afford 5-((2-(1-ethyl-1H-pyrazol-4-yl)pyridin-4- yl)oxy)-6-methylpyridin-2-amine (272 mg, 77%). $^1$H NMR (400 MHz, DMSO-d$_6$): δ 8.30 (d, J=5.7 Hz, 1H), 8.27 (s, 1H), 7.94 (d, J=0.7 Hz, 1H), 7.17 (d, J=8.7 Hz, 1H), 7.11 (d, J=2.4 Hz, 1H), 6.49 (dd, J=5.7, 2.4 Hz, 1H), 6.34 (d, J=8.7 Hz, 1H), 5.93 (s, 2H), 4.13 (q, J=7.3 Hz, 2H), 2.06 (s, 3H), 1.37 (t, J=7.3 Hz, 3H); MS (ESI) m/z: 295.9 (M+H$^+$).

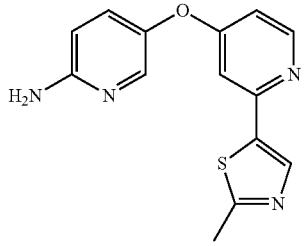

Example A13

A suspension of Pd(PPh$_3$)$_4$ (0.092 g, 0.079 mmol), K$_2$CO$_3$ (0.659 g, 4.77 mmol), 2-methyl-5-(4,4,5,5-tetramethyl-1,3,2-dioxaborolan-2-yl)thiazole (0.429 g, 1.908 mmol) and Example A1 (0.4 g, 1.590 mmol) in dioxane (6 mL) and water (1.5 mL) was sparged with Ar and heated at 90° C. overnight. The mixture was cooled to RT, treated with brine, extracted with EtOAc (3×) and the combined organics were dried over Na$_2$SO$_4$, concentrated to dryness and purified via silica gel chromatography (EtOAc/Hex) to afford 2-methyl-5-(4-((6-nitropyridin-3-yl)oxy)pyridin-2-yl)thiazole (191 mg, 38%). $^1$H NMR (400 MHz, DMSO-d$_6$): δ 8.61 (d, J=2.8 Hz, 1H), 8.52 (d, J=5.7 Hz, 1H), 8.42 (d, J=8.9 Hz, 1H), 8.35 (s, 1H), 8.02 (dd, J=8.9, 2.8 Hz, 1H), 7.79 (d, J=2.4 Hz, 1H), 7.10 (dd, J=5.7, 2.4 Hz, 1H), 2.65 (s, 3H); MS (ESI) m/z: 315.1 (M+H$^+$).

A 0° C. solution of 2-methyl-5-(4-((6-nitropyridin-3-yl)oxy)pyridin-2-yl)thiazole (0.191 g, 0.608 mmol) in THF (3 mL) and MeOH (3 mL) was treated with NH$_4$Cl (1.3 g, 24.31 mmol) followed by the slow addition of zinc dust (0.397 g, 6.08 mmol), the mixture allowed to warm to RT and stirred for 2 h. The mixture was treated with THF, the solids removed via filtration through diatomaceous earth, washed well with THF, the filtrate treated with EtOAc, washed with 1:1 brine/satd. NaHCO$_3$, dried over Na$_2$SO$_4$ and concentrated to dryness to afford 5-((2-(2-methylthiazol-5-yl)pyridin-4-yl)oxy)pyridin-2-amine (164 mg, 95%). $^1$H NMR (400 MHz, DMSO-d$_6$): δ 8.34 (d, J=5.8 Hz, 1H), 8.28 (s, 1H), 7.82 (d, J=2.9 Hz, 1H), 7.50 (d, J=2.4 Hz, 1H), 7.29 (dd, J=8.9, 3.0 Hz, 1H), 6.67 (dd, J=5.8, 2.4 Hz, 1H), 6.51 (d, J=8.9 Hz, 1H), 6.03 (s, 2H), 2.64 (s, 3H); MS (ESI) m/z: 285.1 (M+H$^+$).

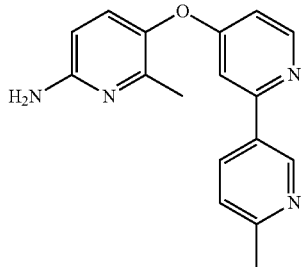 [SMILES: Cc1ccc(-c2cc(Oc3ccc(N)nc3C)ccn2)cn1]

Example A14

A degassed solution of Example A8 (0.237 g, 1.004 mmol) in dioxane (4 mL) was treated with a solution of K$_2$CO$_3$ (0.278 g, 2.008 mmol) in water (1 mL), Example C2 (0.286 g, 1.305 mmol), and Pd(PPh$_3$)$_4$ (0.116 g, 0.100 mmol) and heated at 80° C. overnight. The mixture was cooled to RT, treated with EtOAc, the solids removed via filtration through diatomaceous earth and the filtrate concentrated to dryness and purified via silica gel chromatography (MeOH/DCM) to afford 6-methyl-5-((6'-methyl-[2,3'-bipyridin]-4-yl)oxy)pyridin-2-amine (300 mg, 102%). $^1$H NMR (400 MHz, DMSO-d$_6$): δ 9.07 (d, J=2.3 Hz, 1H), 8.48 (d, J=5.7 Hz, 1H), 8.24 (dd, J=8.1, 2.4 Hz, 1H), 7.50 (d, J=2.4 Hz, 1H), 7.33 (d, J=8.1 Hz, 1H), 7.20 (d, J=8.7 Hz, 1H), 6.66 (dd, J=5.7, 2.4 Hz, 1H), 6.35 (d, J=8.7 Hz, 1H), 5.96 (s, 2H), 2.50 (s, 3H), 2.08 (s, 3H); MS (ESI) m/z: 412.2 (M+H$^+$).

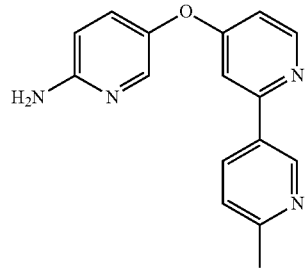 [SMILES: Cc1ccc(-c2cc(Oc3ccc(N)nc3)ccn2)cn1]

Example A15

A degassed solution of Example A9 (0.335 g, 1.510 mmol) in dioxane (6 mL) was treated with a solution of K$_2$CO$_3$ (0.417 g, 3.02 mmol) in water (1.5 mL), Example C2 (0.430 g, 1.963 mmol), and Pd(PPh$_3$)$_4$ (0.174 g, 0.151 mmol) and heated at 80° C. overnight. The mixture was cooled to RT, treated with EtOAc, the solids removed via filtration through diatomaceous earth and the filtrate concentrated to dryness and purified via silica gel chromatography (MeOH/DCM) to afford 5-((6'-methyl-[2,3'-bipyridin]-4-yl)oxy)pyridin-2-amine (420 mg, 100%). $^1$H NMR (400 MHz, DMSO-d$_6$): δ 9.07 (d, J=2.3 Hz, 1H), 8.49 (d, J=5.7 Hz, 1H), 8.24 (dd, J=8.1, 2.4 Hz, 1H), 7.83 (d, J=2.9 Hz, 1H), 7.53 (d, J=2.4 Hz, 1H), 7.34-7.29 (m, 2H), 6.75 (dd, J=5.7, 2.4 Hz, 1H), 6.52 (d, J=8.9 Hz, 1H), 6.03 (s, 2H), 2.50 (s, 3H); MS (ESI) m/z: 279.1 (M+H$^+$).

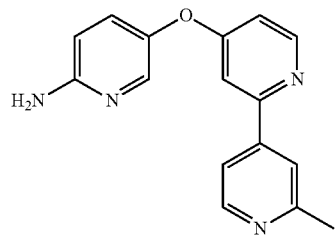 [SMILES: Cc1cc(-c2cc(Oc3ccc(N)nc3)ccn2)ccn1]

Example A16

A solution of Example A9 (0.440 g, 1.985 mmol) in dioxane (8 mL) was sparged with Ar, treated with a solution of K$_2$CO$_3$ (0.549 g, 3.97 mmol) in water (2 mL) and 2-methyl- 4-(4,4,5,5-tetramethyl-1,3,2-dioxaborolan-2-yl)pyridine (0.565 g, 2.58 mmol), sparged again with Ar, treated with Pd(PPh$_3$)$_4$ (0.229 g, 0.199 mmol) and heated at 80° C. overnight. The mixture was cooled to RT, diluted with EtOAc, the solids removed via filtration through diatomaceous earth and the filtrate concentrated to dryness and purified via silica gel chromatography (MeOH/DCM) to afford 5-((2'-methyl-[2,4'-bipyridin]-4-yl)oxy)pyridin-2-amine (490 mg, 89%) as a light brown solid. MS (ESI) m/z: 279.2 (M+H$^+$).

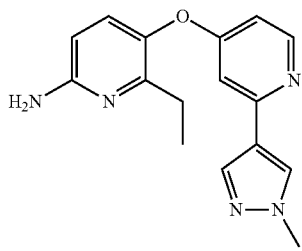 [SMILES: CCc1nc(N)ccc1Oc1ccnc(-c2cnn(C)c2)c1]

Example A17

A 0° C. solution of 2-amino-6-ethylpyridine (3.00 g, 24.56 mmol) in CHCl$_3$ (25 mL) was treated portion-wise with NBS (4.37 g, 24.56 mmol) over 30 minutes, stirred for 45 minutes, then concentrated to dryness. The residue was treated with EtOAc, the solids removed via filtration and the filtrate concentrated to dryness and purified via silica gel chromatography (EtOAc/Hex) to afford 5-bromo-6-ethylpyridin-2-amine (3.83 g, 78%) as a white solid. $^1$H NMR (400 MHz, DMSO-d$_6$): δ 7.42 (d, J=8.6 Hz, 1H), 6.20 (d, J=8.7 Hz, 1H), 6.03 (s, 2H), 2.60 (q, J=7.5 Hz, 2H), 1.10 (t, J=7.5 Hz, 3H); MS (ESI) m/z: 203.0 (M+H$^+$).

A 0° C. solution of H$_2$SO$_4$ (11 mL, 10.83 mmol) was treated slowly with 30% hydrogen peroxide (5.5 mL, 9.42 mmol) in an open flask, stirred for 5 minutes, treated dropwise with a solution of 5-bromo-6-ethylpyridin-2-amine (3.83 g, 19.05 mmol) in H2SO4 (11 mL) and stirred overnight as the cooling bath expired. The solution was poured into ice water, treated with DCM, cooled in an ice bath and treated slowly with 50% NaOH until pH~9. The layers were separated, the aqueous layer extracted with DCM (1×) and the combined organics were washed with brine, dried over Na$_2$SO$_4$, concentrated to dryness and purified via silica gel chromatography (EtOAc/Hex) to afford 3-bromo-2-ethyl-6-nitropyridine (2.31 g, 52%) as a yellow oil. $^1$H NMR (400 MHz, DMSO-d$_6$): δ 8.43 (d, J=8.5 Hz, 1H), 8.04-8.03 (m, 1H), 2.96 (q, J=7.5 Hz, 2H), 1.24 (t, J=7.5 Hz, 3H); MS (ESI) m/z: 233.0 (M+H$^+$).

A mixture of 3-bromo-2-ethyl-6-nitropyridine (2.31 g, 10.0 mmol), 2-chloropyridin-4-ol (2.59 g, 20.0 mmol) and K$_2$CO$_3$ (4.15 g, 30.0 mmol) in DMA (20 mL) was sparged with Ar and heated at 105° C. overnight. The mixture was cooled to RT, treated with EtOAc, washed successively with 10% K$_2$CO$_3$ (1×), 5% LiCl (1×) and brine (1×), dried over Na$_2$SO$_4$, concentrated to dryness and purified via silica gel chromatography (EtOAc/Hex) to afford 3-((2-chloropyridin-4-yl)oxy)-2-ethyl-6-nitropyridine (892 mg, 25%). MS (ESI) m/z: 280.1 (M+H$^+$).

A mixture of 1-methyl-4-(4,4,5,5-tetramethyl-1,3,2-dioxaborolan-2-yl)-1H-pyrazole (863 mg, 4.15 mmol), 3-((2-chloropyridin-4-yl)oxy)-2-ethyl-6-nitropyridine (892 mg, 3.19 mmol), K$_2$CO$_3$ (1.322 mg, 9.57 mmol) and Pd(PPh$_3$)$_4$ (184 mg, 0.159 mmol) in dioxane (6 mL) and water (1.5 mL) was sparged with Ar, heated at 80° C. for 24 h, then cooled to RT and stirred for 24 h. The mixture was treated with EtOAc, washed with satd. NaHCO$_3$ (1×), then brine (1×), dried over Na$_2$SO$_4$ and concentrated to dryness to afford 2-ethyl-3-((2-(1-methyl-1H-pyrazol-4-yl)pyridin-4-yl)oxy)-6-nitropyridine (100% yield assumed) as a thick oil. Material carried on to the next step without purification. MS (ESI) m/z: 326.1 (M+H$^+$).

A mixture of crude 2-ethyl-3-((2-(1-methyl-1H-pyrazol-4-yl)pyridin-4-yl)oxy)-6-nitropyridine (1.038 g, 3.19 mmol) in MeOH (12 mL) and THF (12 mL) was treated with NH$_4$Cl (6.83 g, 128 mmol), cooled to 0° C., treated portion-wise with zinc dust (2.08 g, 31.9 mmol) and stirred overnight as the cooling bath expired. The mixture was treated with EtOAc, the solids removed via filtration through diatomaceous earth, washed well with warm EtOAc and the filtrate concentrated to dryness. The residue was treated with EtOAc, heated to near-reflux, filtered to remove solids and the filtrate concentrated to dryness. The collected solids were treated again with EtOAc, heated to reflux and filtered hot to afford a white solid. The concentrated filtrate was purified via silica gel chromatography (MeOH/EtOAc) and combined with the solid isolated above to afford 6-ethyl-5-((2-(1-methyl-1H-pyrazol-4-yl)pyridin-4-yl)oxy)pyridin-2-amine (483 mg, 51%) as an off-white solid. $^1$H NMR (400 MHz, DMSO-d$_6$): δ 8.30 (d, J=5.7 Hz, 1H), 8.22 (s, 1H), 7.93 (s, 1H), 7.18-7.16 (m, 1H), 7.12 (d, J=2.4 Hz, 1H), 6.50-6.49 (m, 1H), 6.36-6.34 (m, 1H), 5.95-5.93 (m, 2H), 3.84 (s, 3H), 2.40-2.38 (m, 2H), 1.04 (t, J=7.5 Hz, 3H); MS (ESI) m/z: 296.2 (M+H$^+$).

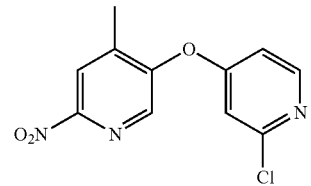 [SMILES: Cc1cc([N+](=O)[O-])ncc1Oc1ccnc(Cl)c1]

Example A18

Sulphuric acid (20 mL) was cooled to 0-5° C., treated with H$_2$O$_2$ (13.4 mL, 131 mmol), stirred for 10 minutes, treated with a solution of 2-amino-5-fluoro-4-methylpyridine (2.75 g, 21.8 mmol) in sulphuric acid (10 mL) at 0° C., stirred for 15 minutes, then warmed to RT and stirred for 1 h. The mixture was poured onto ice, treated with 10% sodium thiosulfate (50 mL) then solid Na$_2$CO$_3$ until solids precipitated and extracted with EtOAc (2×100 mL). The combined organics were washed with brine, dried over Na$_2$SO$_4$ and concentrated to dryness to afford 5-fluoro-4-methyl-2-nitropyridine (2.75 g, 81%) as an orange solid. MS (ESI) m/z: 157.1 (M+H$^+$).

A mixture of 5-fluoro-4-methyl-2-nitropyridine (2.75 g, 17.6 mmol), 4-hydroxy-2-chloropyridine (3.42 g, 26.4 mmol) and K$_2$CO$_3$ (2.44 g, 17.6 mmol) in DMF (40 mL) was heated at 80° C. for 16 h. The mixture was cooled to RT, diluted with water (400 mL) and extracted with EtOAc (3×100 mL). The combined organics were washed with water (100 mL) and 10% aq. LiCl (80 mL), dried over Na$_2$SO$_4$, concentrated to dryness and purified via silica gel chromatography (EtOAc/Hex) to afford 5-((2-chloropyridin-4-yl)oxy)-4-methyl-2-nitropyridine (3.0 g, 64%) as an off-white solid. MS (ESI) m/z: 266.0 (M+H$^+$).

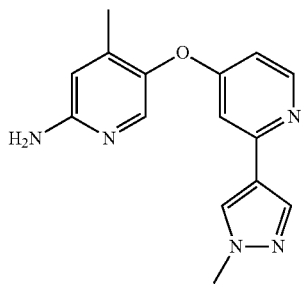 [SMILES: Cc1cc(N)ncc1Oc1ccnc(-c2cnn(C)c2)c1]

Example A19

A solution of Example A18 (0.85 g, 3.20 mmol) and 1-methyl-4-(4,4,5,5-tetramethyl-1,3,2-dioxaborolan-2-yl)-1H-pyrazole (0.865 g, 4.16 mmol) in dioxane (20 mL) was sparged with Ar, treated with a solution of K$_2$CO$_3$ (0.663 g, 4.80 mmol) in water (5 mL), Pd(PPh$_3$)$_4$ (0.185 g, 0.160 mmol) and heated at 80° C. for 4 h. The mixture was cooled to RT, treated with water, extracted with EtOAc (2×) and the combined organics were washed with brine, dried over Na$_2$SO$_4$, concentrated to dryness and purified via silica gel chromatography (MeOH/DCM) to afford 4-methyl-5-((2-(1-methyl-1H-pyrazol-4-yl)pyridin-4-yl)oxy)-2-nitropyridine (830 mg, 83%) as a light brown amorphous solid. MS (ESI) m/z: 312.1 (M+H$^+$).

A solution of 4-methyl-5-((2-(1-methyl-1H-pyrazol-4-yl)pyridin-4-yl)oxy)-2-nitropyridine (0.83 g, 2.67 mmol) in EtOAc (20 mL) was treated with palladium on carbon (50% wet, 0.284 g, 0.267 mmol) and hydrogenated (1 atm) overnight. The solids were removed via filtration through diatomaceous earth, rinsed well with EtOAc and the filtrate was concentrated to dryness to afford crude 4-methyl-5-((2-(1-methyl-1H-pyrazol-4-yl)pyridin-4-yl)oxy)pyridin-2-amine (750 mg, 100%) as a white amorphous solid which was carried on to the next step without further purification. $^1$H NMR (400 MHz, DMSO-d$_6$): δ 8.30 (d, J=5.7 Hz, 1H), 8.23 (s, 1H), 7.93 (d, J=0.7 Hz, 1H), 7.69 (s, 1H), 7.12 (d, J=2.4 Hz, 1H), 6.51 (dd, J=5.7, 2.4 Hz, 1H), 6.39 (s, 1H), 5.91 (s, 2H), 3.84 (s, 3H), 1.95 (s, 3H); MS (ESI) m/z: 282.1 (M+H$^+$).

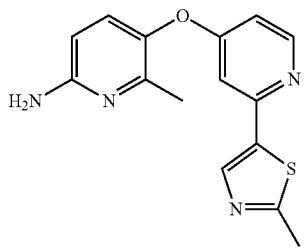 [SMILES: Cc1ncc(-c2cc(Oc3ccc(N)nc3C)ccn2)s1]

Example A20

A suspension of Pd(PPh$_3$)$_4$ (0.033 g, 0.028 mmol), K$_2$CO$_3$ (0.468 g, 3.39 mmol), 2-methyl-5-(4,4,5,5-tetramethyl-1,3,2-dioxaborolan-2-yl)thiazole (0.508 g, 2.259 mmol), and Example A4 (0.15 g, 0.565 mmol) in dioxane (6 mL) and water (1.5 mL) was sparged with Ar and heated at 90° C. overnight. The mixture was cooled to RT, treated with brine, extracted with EtOAc (3×) and the combined organics were dried over Na$_2$SO$_4$, concentrated to dryness and purified via silica gel chromatography (EtOAc/Hex) to afford 2-methyl-5-(4-((2-methyl-6-nitropyridin-3-yl)oxy)pyridin-2-yl)thiazole (74 mg, 51%). $^1$H NMR (400 MHz, DMSO-d$_6$): δ 8.51 (d, J=5.7 Hz, 1H), 8.35 (s, 1H), 8.25 (d, J=8.7 Hz, 1H), 7.89 (d, J=8.7 Hz, 1H), 7.73 (d, J=2.4 Hz, 1H), 7.03 (dd, J=5.7, 2.4 Hz, 1H), 2.66 (s, 3H), 2.51 (s, 3H); MS (ESI) m/z: 329.1 (M+H$^+$).

A solution of 2-methyl-5-(4-((2-methyl-6-nitropyridin-3-yl)oxy)pyridin-2-yl)thiazole (0.094 g, 0.286 mmol) in MeOH (30 mL) was flushed with Ar, treated with 10% Pd/C (50% wet, 0.305 g, 0.286 mmol) and hydrogenated (1 atm) overnight. The solids were removed via filtration through diatomaceous earth, washed well with MeOH and the filtrate was concentrated to dryness to afford 6-methyl-5-((2-(2-methylthiazol-5-yl)pyridin-4-yl)oxy)pyridin-2-amine (60 mg, 70%). $^1$H NMR (400 MHz, DMSO-d$_6$): δ 8.34 (d, J=5.8 Hz, 1H), 8.28 (s, 1H), 7.49 (d, J=2.4 Hz, 1H), 7.19 (d, J=8.7 Hz, 1H), 6.58 (dd, J=5.8, 2.4 Hz, 1H), 6.34 (d, J=8.7 Hz, 1H), 5.96 (s, 2H), 2.65 (s, 3H), 2.07 (s, 3H); MS (ESI) m/z: 299.1 (M+H$^+$).

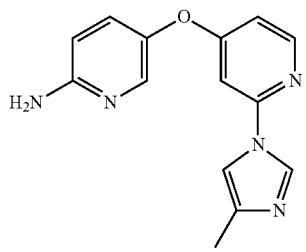 [SMILES: Cc1cn(-c2cc(Oc3ccc(N)nc3)ccn2)cn1]

Example A21

A mixture of toluene (60 mL) and dioxane (12 mL) was sparged with Ar, treated with Pd$_2$(dba)$_3$ (0.255 g, 0.278 mmol) and Me$_4$tBuXPhos [di-tert-butyl(2',4',6'-triisopropyl-3,4,5,6-tetramethyl-[1,1'-biphenyl]-2-yl)phosphine](0.267 g, 0.556 mmol) and heated at 120° C. for 15 min, partially cooled, treated with Example A1 (3.5 g, 13.91 mmol), K$_3$PO$_4$ (5.91 g, 27.8 mmol) and 4-methylimidazole (3.43 g, 41.7 mmol) and heated at 120° C. overnight. The mixture was cooled to RT, treated with brine and extracted with EtOAc (2×). The combined organics were washed with brine (2×), dried over MgSO$_4$, concentrated to dryness and purified via silica gel chromatography (EtOAc/Hex) to afford 2-(4-methyl-1H-imidazol-1-yl)-4-((6-nitropyridin-3-yl)oxy)pyridine (1.3 g, 31%). $^1$H NMR (400 MHz, DMSO-d$_6$): δ 8.64-8.63 (m, 1H), 8.44-8.43 (m, 2H), 8.41 (d, J=1.4 Hz, 1H), 8.06 (dd, J=8.9, 2.8 Hz, 1H), 7.65 (t, J=1.3 Hz, 1H), 7.56 (d, J=2.2 Hz, 1H), 7.12 (dd, J=5.7, 2.2 Hz, 1H), 2.13 (d, J=1.0 Hz, 3H); MS (ESI) m/z: 298.1 (M+H$^+$).

Method A: A solution of 2-(4-methyl-1H-imidazol-1-yl)-4-((6-nitropyridin-3-yl)oxy)pyridine (1.3 g, 4.37 mmol) in MeOH (20 mL)/THF (20 mL) was treated sequentially with NH$_4$Cl (7.02 g, 131 mmol) and zinc dust (2.86 g, 43.7 mmol) and stirred at RT for 2 h. The mixture was diluted with THF, the solids removed via filtration through diatomaceous earth, washed with THF and the filtrate concentrated to dryness. The material was treated with THF, the solids removed via filtration and the filtrate concentrated to dryness, treated with DCM and sonicated. The resulting solid was collected via filtration and dried to afford 5-((2-(4-methyl-1H-imidazol-1-yl)pyridin-4-yl)oxy)pyridin-2-amine (800 mg, 68%). $^1$H NMR (400 MHz, DMSO-d$_6$): δ 8.39 (d, J=1.4 Hz, 1H), 8.28 (d, J=5.8 Hz, 1H), 7.83 (d, J=2.9 Hz, 1H), 7.63 (s, 1H), 7.31-7.30 (m, 2H), 6.70 (dd, J=5.8, 2.2 Hz, 1H), 6.51 (d, J=8.9 Hz, 1H), 6.05 (s, 2H), 2.14 (d, J=1.0 Hz, 3H); MS (ESI) m/z: 268.2 (M+H⁺).

Method B: A solution of 2-(4-methyl-1H-imidazol-1-yl)-4-((6-nitropyridin-3-yl)oxy)pyridine (0.73 g, 2.46 mmol) in MeOH (10 mL)/THF (10 mL) was treated with 10% Pd/C (50% wet, 0.261 g, 0.122 mmol) and the mixture was hydrogenated (50 psi) for 16 h at RT. The mixture was filtered through diatomaceous earth and washed with 10% methanol-DCM (3×10 mL). The combined filtrate was concentrated to afford 5-((2-(4-methyl-1H-imidazol-1-yl)pyridin-4-yl)oxy)pyridin-2-amine (0.6 g, 91%) as an off-white solid. MS (ESI) m/z: 268.2 (M+H⁺).

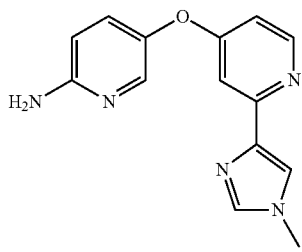 [SMILES: Cn1cnc(-c2cc(Oc3ccc(N)nc3)ccn2)c1]

Example A22

A mixture of Example A1 (1.5 g, 5.96 mmol), N-methyl-4-(tributylstannyl)imidazole (3.32 g, 8.94 mmol) and Pd(PPh₃)₄ (0.344 g, 0.298 mmol) in toluene (30 mL) sparged with Ar and heated at 110° C. overnight. The mixture was cooled to RT, treated with 10% KF and EtOAc, stirred at RT for 2 h, the solids removed via filtration through diatomaceous earth and washed with 5% MeOH/DCM. The layers of the filtrate were separated and the organic layer was washed with brine, dried over Na₂SO₄, concentrated to dryness and purified via silica gel chromatography (MeOH/DCM). The material was washed with a small amount of Et₂O and dried to afford 2-(1-methyl-1H-imidazol-4-yl)-4-((6-nitropyridin-3-yl)oxy)pyridine (1.61 g, 91%). ¹H NMR (400 MHz, Acetone-d₆): δ 8.54 (d, J=2.8 Hz, 1H), 8.50 (d, J=5.6 Hz, 1H), 8.44-8.43 (m, 1H), 7.98 (dd, J=8.9, 2.8 Hz, 1H), 7.69 (d, J=1.4 Hz, 1H), 7.62 (d, J=2.6 Hz, 1H), 7.55 (s, 1H), 6.97 (dd, J=5.6, 2.6 Hz, 1H), 3.81 (s, 3H); MS (ESI) m/z: 298.1 (M+H⁺).

A solution of 2-(1-methyl-1H-imidazol-4-yl)-4-((6-nitropyridin-3-yl)oxy)pyridine (1.61 g, 5.42 mmol) in MeOH (30 mL) was treated with 10% Pd/C (50% w/w water, 0.576 g, 0.542 mmol) and hydrogenated (50 psi) overnight. The solids were removed via filtration through diatomaceous earth, washed with warm MeOH and the filtrate was concentrated to dryness to afford 5-((2-(1-methyl-1H-imidazol-4-yl)pyridin-4-yl)oxy)pyridin-2-amine (1.311 g, 91%). ¹H NMR (400 MHz, DMSO-d₆): δ 8.31 (d, J=5.7 Hz, 1H), 7.81 (d, J=2.9 Hz, 1H), 7.65 (d, J=1.3 Hz, 1H), 7.58 (s, 1H), 7.29 (dd, J=8.9, 3.0 Hz, 1H), 7.19 (d, J=2.6 Hz, 1H), 6.73 (dd, J=5.7, 2.6 Hz, 1H), 6.52 (d, J=8.9 Hz, 1H), 6.03 (s, 2H), 3.67 (s, 3H); MS (ESI) m/z: 268.1 (M+H⁺).

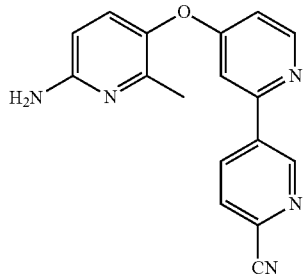 [SMILES: Cc1nc(N)ccc1Oc1ccnc(-c2ccc(C#N)nc2)c1]

Example A23

A solution of Example A8 (0.47 g, 1.994 mmol) in dioxane (12 mL) was sparged with Ar, treated with 5-(4,4,5,5-tetramethyl-1,3,2-dioxaborolan-2-yl)picolinonitrile (0.551 g, 2.393 mmol), a solution of K₂CO₃ (0.413 g, 2.99 mmol) in water (3 mL) and Pd(PPh₃)₄ (0.115 g, 0.100 mmol) and heated at 90° C. for 16 h. The mixture was cooled to RT, treated with water and extracted with EtOAc (2×). The combined organics were washed with brine, dried over Na₂SO₄ and concentrated to dryness. The material was treated with 60% EtOAc/Hex, sonicated and the resulting solid collected via filtration to afford 4-((6-amino-2-methylpyridin-3-yl)oxy)-[2,3'-bipyridine]-6'-carbonitrile (500 mg, 83%) as an orange solid. ¹H NMR (400 MHz, DMSO-d₆): δ 9.39 (d, J=2.2 Hz, 1H), 8.63 (dd, J=8.2, 2.2 Hz, 1H), 8.56 (d, J=5.7 Hz, 1H), 8.13 (d, J=8.2 Hz, 1H), 7.74 (d, J=2.4 Hz, 1H), 7.21 (d, J=8.7 Hz, 1H), 6.77 (dd, J=5.7, 2.4 Hz, 1H), 6.36 (d, J=8.7 Hz, 1H), 5.97-5.95 (m, 2H), 2.08 (s, 3H); MS (ESI) m/z: 304.1 (M+H⁺).

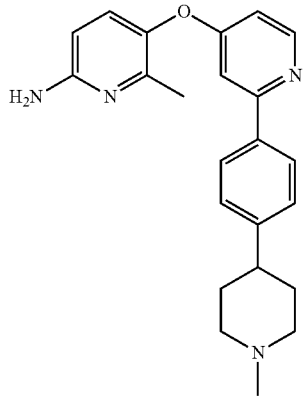 [SMILES: Cc1nc(N)ccc1Oc1ccnc(-c2ccc(C3CCN(C)CC3)cc2)c1]

Example A24

A mixture of Pd(PPh₃)₄ (0.325 g, 0.281 mmol), K₂CO₃ (1.165 g, 8.43 mmol), Example A4 (0.746 g, 2.81 mmol) and Example C4 (1.185 g, 3.93 mmol) in dioxane (11 mL) and water (2.8 mL) was sparged with Ar and heated at 90° C. overnight. The mixture was cooled to RT, treated with brine and EtOAc, and the solids removed via filtration through diatomaceous earth. The layers of the filtrate were separated, the aqueous layer extracted with EtOAc (3×) and the combined organics were dried over Na₂SO₄, concentrated to dryness and purified via silica gel chromatography (MeOH/DCM) to afford 2-methyl-3-((2-(4-(1-methylpiperidin-4-yl)phenyl)pyridin-4-yl)oxy)-6-nitropyridine (553 mg, 49%). MS (ESI) m/z: 405.2 (M+H⁺).

A solution of 2-methyl-3-((2-(4-(1-methylpiperidin-4-yl)phenyl)pyridin-4-yl)oxy)-6-nitropyridine (0.553 g, 1.367 mmol) in MeOH (20 mL) was treated with 10% Pd/C (50% wet, 0.146 g, 0.137 mmol) and hydrogenated (1 atm) overnight. The solids were removed via filtration, washed with MeOH and the filtrate was concentrated to dryness to afford 6-methyl-5-((2-(4-(1-methylpiperidin-4-yl)phenyl)pyridin-4-yl)oxy)pyridin-2-amine (446 mg, 87%). MS (ESI) m/z: 375.2 (M+H$^+$).

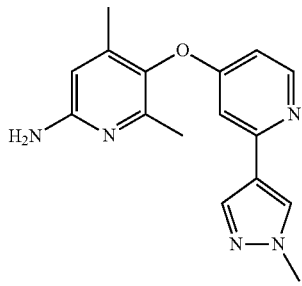 [SMILES: Cc1cc(N)nc(C)c1Oc1ccnc(-c2cnn(C)c2)c1]

Example A25

Hydrogen peroxide (30%, 5 mL) was slowly added to 0° C. $H_2SO_4$ (9 mL) in an open flask, stirred for 5 min., treated drop-wise with a solution of 5-bromo-4,6-dimethylpyridin-2-amine (3.00 g, 14.92 mmol) in $H_2SO_4$ (9 mL) and stirred at RT overnight as the cooling bath expired. The mixture was treated with ice (~150 mL), stirred until melted, the resulting solid collected via filtration, dissolved in DCM and washed with brine. The organic layer was dried over $Na_2SO_4$ and concentrated to dryness to afford 3-bromo-2,4-dimethyl-6-nitropyridine (2.26 g, 66%) as a pale yellow solid. $^1$H NMR (400 MHz, DMSO-$d_6$): δ 8.20 (s, 1H), 2.67 (s, 3H), 2.52 (s, 3H); MS (ESI) m/z: 231.0 (M+H$^+$).

A mixture of 3-bromo-2,4-dimethyl-6-nitropyridine (1.00 g, 4.33 mmol), 2-chloropyridin-4-ol (1.12 g, 8.66 mmol) and $K_2CO_3$ (1.79 g, 12.98 mmol) in DMA (5 mL) was sparged with Ar, heated at 105° C. overnight, then cooled to RT. The mixture was diluted with EtOAc, washed successively with 10% $K_2CO_3$, 5% LiCl, then brine, dried over $Na_2SO_4$, concentrated to dryness and purified via silica gel chromatography (EtOAc/Hex) to afford 3-((2-chloropyridin-4-yl)oxy)-2,4-dimethyl-6-nitropyridine (245 mg, 20%) as a white solid. $^1$H NMR (400 MHz, DMSO-$d_6$): δ 8.31 (d, J=5.2 Hz, 2H), 7.15 (d, J=2.3 Hz, 1H), 7.01 (dd, J=5.8, 2.3 Hz, 1H), 2.33 (s, 3H), 2.23 (s, 3H); MS (ESI) m/z: 280.0 (M+H$^+$).

A mixture of 1-methyl-4-(4,4,5,5-tetramethyl-1,3,2-dioxaborolan-2-yl)-1H-pyrazole (237 mg, 1.139 mmol), 3-((2-chloropyridin-4-yl)oxy)-2,4-dimethyl-6-nitropyridine (245 mg, 0.876 mmol), $K_2CO_3$ (363 mg, 2.63 mmol) and Pd(PPh$_3$)$_4$ (51 mg, 0.044 mmol) in dioxane (4 mL) and water (1 mL) was sparged with Ar, heated at 80° C. for 24 h, then cooled to RT. The mixture was diluted with EtOAc. Washed with satd. NaHCO$_3$, then brine, dried over $Na_2SO_4$ and concentrated to dryness to afford 2,4-dimethyl-3-((2-(1-methyl-1H-pyrazol-4-yl)pyridin-4-yl)oxy)-6-nitropyridine (100% yield assumed) which was used without further purification. MS (ESI) m/z: 326.1 (M+H$^+$).

A 0° C. mixture of 2,4-dimethyl-3-((2-(1-methyl-1H-pyrazol-4-yl)pyridin-4-yl)oxy)-6-nitropyridine (285 mg, 0.876 mmol) and NH$_4$Cl (1.87 g, 35 mmol) in MeOH (5 mL) and THF (5 mL) was treated portion-wise with zinc dust (573 mg, 8.76 mmol), allowed to warm to RT and stirred overnight. The mixture was diluted with EtOAc, warmed slightly, the solids removed via filtration through diatomaceous earth and washed with EtOAc. The filtrate was concentrated to dryness and purified via silica gel chromatography (MeOH/EtOAc) to afford 4,6-dimethyl-5-((2-(1-methyl-1H-pyrazol-4-yl)pyridin-4-yl)oxy)pyridin-2-amine (156 mg, 60%) as a white amorphous solid. $^1$H NMR (400 MHz, DMSO-$d_6$): δ 8.30 (d, J=5.7 Hz, 1H), 8.23 (s, 1H), 7.93 (s, 1H), 7.10 (d, J=2.4 Hz, 1H), 6.44 (dd, J=5.7, 2.4 Hz, 1H), 6.22 (s, 1H), 5.81 (s, 2H), 3.84 (s, 3H), 2.02 (s, 3H), 1.92 (s, 3H); MS (ESI) m/z: 296.1 (M+H$^+$).

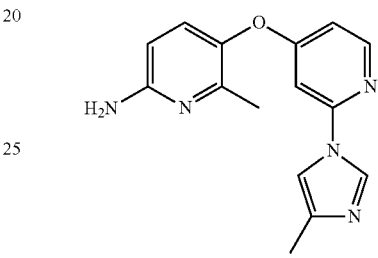

Example A26

A solution of Pd$_2$(dba)$_3$ (0.172 g, 0.188 mmol) and Me$_4$t-BuXPhos (0.181 g, 0.376 mmol) in toluene (2 mL) and dioxane (4 mL) was heated at 120° C. for 3 min, cooled to RT, added to a degassed suspension of Example A4 (2.500 g, 9.41 mmol), 4-methyl imidazole (1.00 g, 12.18 mmol) and $K_3PO_4$ (4.00 g, 18.82 mmol) in toluene (4 mL) and dioxane (8 mL) and heated at 110° C. overnight. The mixture was cooled to RT, the solids were removed via filtration and washed with THF, and the filtrate was concentrated to dryness and purified via silica gel chromatography (EtOAc/DCM) to afford 2-methyl-3-((2-(4-methyl-1H-imidazol-1-yl)pyridin-4-yl)oxy)-6-nitropyridine (1.52 g, 52%). $^1$H NMR (400 MHz, DMSO-$d_6$): δ 8.41 (m, 2H), 8.25 (d, J=8.7 Hz, 1H), 7.93 (d, J=8.7 Hz, 1H), 7.64 (t, J=1.3 Hz, 1H), 7.47 (d, J=2.2 Hz, 1H), 7.04 (dd, J=5.7, 2.2 Hz, 1H), 2.49 (s, 3H), 2.13 (s, 3H); MS (ESI) m/z: 312.1 (M+H$^+$).

A suspension of 2-methyl-3-((2-(4-methyl-1H-imidazol-1-yl)pyridin-4-yl)oxy)-6-nitropyridine (1.50 g, 4.82 mmol) and NH$_4$Cl (6.00 g, 112 mmol) in MeOH (30 mL) was treated with zinc dust (3.00 g, 45.9 mmol) and heated at 40° C. for 3 h. The mixture was diluted with DCM, the solids removed via filtration, washed with MeOH/DCM and the filtrate concentrated to dryness. The residue was treated with DCM, the solids again removed via filtration and the filtrate concentrated to dryness to afford 6-methyl-5-((2-(4-methyl-1H-imidazol-1-yl)pyridin-4-yl)oxy)pyridin-2-amine (1.02 g, 75%). $^1$H NMR (400 MHz, DMSO-$d_6$): δ 8.37 (d, J=1.4 Hz, 1H), 8.26 (d, J=5.8 Hz, 1H), 7.61 (t, J=1.3 Hz, 1H), 7.28 (d, J=2.2 Hz, 1H), 7.20 (d, J=8.7 Hz, 1H), 6.60 (dd, J=5.8, 2.2 Hz, 1H), 6.34 (d, J=8.7 Hz, 1H), 5.97 (s, 2H), 2.13 (s, 3H), 2.07 (s, 3H); MS (ESI) m/z: 282.1 (M+H$^+$).

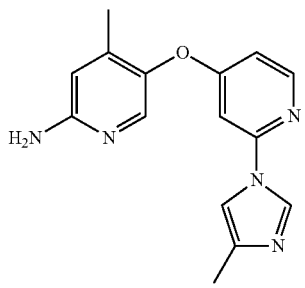 [SMILES: Cc1cn(-c2cc(Oc3cnc(N)cc3C)ccn2)cn1]

Example A27

Me₄t-BuXPhos (0.594 g, 1.235 mmol) and Pd₂(dba)₃ (0.565 g, 0.617 mmol) were combined in a degassed mixture of dioxane (18 mL) and toluene (36 mL) and the mixture was heated to 105° C. under argon for a few min. To this solution was added 4-methylimidazole (3.80 g, 46.3 mmol), Example A18 (4.1 g, 15.43 mmol) and K₃PO₄ (2.62 g, 12.35 mmol) and stirring was continued at 105° C. for 20 h. The mixture was cooled to RT and diluted with EtOAc (40 mL). The solids were removed by filtration through diatomaceous earth and washed with EtOAc. (3×15 mL) The filtrate was washed with water (2×50 mL) and the combined aqueous was extracted with EtOAc (2×40 mL). The combined organics were washed with brine, dried over Na₂SO₄, concentrated to dryness and purified via silica gel chromatography (EtOAc/DCM) to afford 4-methyl-5-((2-(4-methyl-1H-imidazol-1-yl)pyridin-4-yl)oxy)-2-nitropyridine (2.5 g, 52%). ¹H NMR (400 MHz, DMSO-d₆): δ 8.50 (s, 2H), 8.40-8.39 (m, 2H), 7.65 (t, J=1.3 Hz, 1H), 7.41 (d, J=2.2 Hz, 1H), 7.00 (dd, J=5.7, 2.2 Hz, 1H), 2.35 (s, 3H), 2.13 (s, 3H); MS (ESI) m/z: 312.1 (M+H⁺).

A solution of 4-methyl-5-((2-(4-methyl-1H-imidazol-1-yl)pyridin-4-yl)oxy)-2-nitropyridine (2.5 g, 8.03 mmol) in MeOH (40 mL) and THF (20 mL) was treated with 10% Pd/C (50% w/w water, 0.855 g, 0.8 mmol) and hydrogenated (50 psi) for 24 h. The solids were removed via filtration through diatomaceous earth, washed with MeOH and the filtrate concentrated to dryness. The residue was stirred with 60% EtOAc/Hex for 15 min. The suspension was collected by filtration, washed with 60% EtOAc/Hex, and dried in vacuo to afford 4-methyl-5-((2-(4-methyl-1H-imidazol-1-yl)pyridin-4-yl)oxy)pyridin-2-amine (1.75 g, 77%). ¹H NMR (400 MHz, DMSO-d₆): δ 8.38 (d, J=1.3 Hz, 1H), 8.27 (d, J=5.8 Hz, 1H), 7.72 (s, 1H), 7.62 (s, 1H), 7.30 (d, J=2.2 Hz, 1H), 6.62 (dd, J=5.8, 2.2 Hz, 1H), 6.39 (s, 1H), 5.94 (s, 2H), 2.13 (s, 3H), 1.96 (s, 3H); MS (ESI) m/z: 282.2 (M+H⁺).

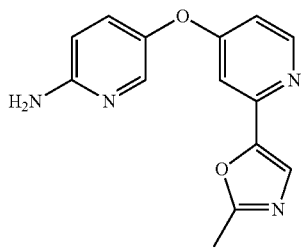

Example A28

A mixture of Example A1 (600 mg, 2.38 mmol), 2-methyl-5-(4,4,5,5-tetramethyl-1,3,2-dioxaborolan-2-yl)oxazole (648 mg, 3.10 mmol), K₂CO₃ (989 mg, 7.15 mmol) and Pd(PPh₃)₄ (138 mg, 0.119 mmol) in dioxane (8 mL) and water (2 mL) was sparged with Ar and heated at 80° C. overnight. Additional 2-methyl-5-(4,4,5,5-tetramethyl-1,3,2-dioxaborolan-2-yl)oxazole (100 mg) and Pd(PPh₃)₄ (50 mg) were added, the mixture heated at 80° C. for 5 h, then cooled to RT and treated with water and EtOAc. The solids were removed via filtration through diatomaceous earth, the layers of the filtrate separated and the organic layer was washed with brine, dried over Na₂SO₄, concentrated to dryness and purified via silica gel chromatography (MeOH/EtOAc) to afford 2-methyl-5-(4-((6-nitropyridin-3-yl)oxy)pyridin-2-yl)oxazole (323 mg, 45%). MS (ESI) m/z: 299.1 (M+H⁺).

A 0° C. mixture of 2-methyl-5-(4-((6-nitropyridin-3-yl)oxy)pyridin-2-yl)oxazole (323 mg, 1.083 mmol) and NH₄Cl (2.317 g, 43.3 mmol) in MeOH (8 mL) and THF (8 mL) was treated portion-wise with zinc dust (708 mg, 10.83 mmol), allowed to warm to RT and stirred overnight. The mixture was diluted with EtOAc, warmed slightly, the solids removed via filtration through diatomaceous earth and washed with EtOAc. The filtrate was concentrated to dryness, treated with EtOAc, heated to reflux, the solids removed via hot filtration and the filtrate concentrated to dryness to afford 5-((2-(2-methyloxazol-5-yl)pyridin-4-yl)oxy)pyridin-2-amine (324 mg, 112%). ¹H NMR (400 MHz, DMSO-d₆): δ 8.43 (d, J=5.7 Hz, 1H), 7.83 (d, J=2.9 Hz, 1H), 7.60 (s, 1H), 7.31 (dd, J=8.9, 3.0 Hz, 1H), 7.06 (d, J=2.5 Hz, 1H), 6.83 (dd, J=5.7, 2.5 Hz, 1H), 6.53 (d, J=8.9 Hz, 1H), 6.07 (s, 2H), 2.46 (s, 3H); MS (ESI) m/z: 269.1 (M+H⁺).

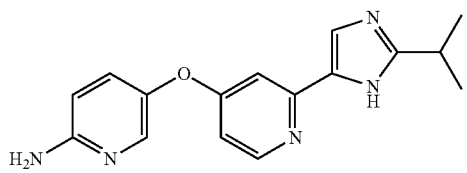 [SMILES: CC(C)c1ncc(-c2cc(Oc3ccc(N)nc3)ccn2)[nH]1]

Example A29

A mixture of 2-isopropylimidazole (3.0 g, 27.2 mmol) and DIEA (5.28 g, 40.9 mmol) in DCM (75 mL) was treated drop-wise with methoxyethoxymethyl chloride [MEM-Cl] (4.24 g, 34.0 mmol) and stirred at RT for 16 h. The mixture was washed with water, then brine, dried over Na₂SO₄ and concentrated to dryness to afford 2-isopropyl-1-((2-methoxyethoxy)methyl)-1H-imidazole (3.91 g, 72%). ¹H NMR (400 MHz, DMSO-d₆): δ 7.11 (d, J=1.3 Hz, 1H), 6.74 (d, J=1.3 Hz, 1H), 5.30 (s, 2H), 3.47-3.46 (m, 2H), 3.38-3.37 (m, 2H), 3.19 (s, 3H), 3.08-3.07 (m, 1H), 1.18 (d, J=6.8 Hz, 6H).

A −78° C. solution of 2-isopropyl-1-((2-methoxyethoxy)methyl)-1H-imidazole (1.50 g, 7.57 mmol) in THF (30 mL) was treated drop-wise with n-BuLi (2.5N, 4.24 mL, 10.59 mmol), stirred for 10 min, then warmed to 0° C. for 45 min. The solution was re-cooled to −78° C., treated drop-wise with trimethyltin chloride (1.0 N, 7.19 mL, 7.19 mmol), over 5 min, warmed to RT and stirred overnight. The mixture was diluted with EtOAc, washed with brine, dried over Na₂SO₄ and concentrated to dryness to afford 2-isopropyl-1-((2-methoxyethoxy)methyl)-5-(trimethylstannyl)-1H-imidazole (2.45 g, 90%). MS (ESI) m/z: 363.1 (M+H⁺).

A mixture of 2-isopropyl-1-((2-methoxyethoxy)methyl)-5-(trimethylstannyl)-1H-imidazole (2.45 g, 6.79 mmol) in touene (15 mL) was sparged with Ar, treated with Example A1 (759 mg, 3.02 mmol) and Pd(PPh₃)₄ (174 mg, 0.151 mmol) and heated at 100° C. for 20 h. The mixture was cooled to RT, diluted with EtOAc and satd. NaHCO₃ and the solids removed via filtration through diatomaceous earth and washed with EtOAc and water. The layers of the filtrate were separated, and the organic layer washed with brine, dried over Na₂SO₄, concentrated to dryness and purified via reverse-phase chromatography (MeCN/H₂O with 0.1% TFA). The organics were removed under reduced pressure, the aqueous residue was neutralized with satd. NaHCO₃ and extracted with EtOAc (2×). The combined organics were washed with brine, dried over Na₂SO₄ and concentrated to dryness to afford 2-(2-isopropyl-1-((2-methoxyethoxy)methyl)-1H-imidazol-5-yl)-4-((6-nitropyridin-3-yl)oxy)pyridine (660 mg, 52%). MS (ESI) m/z: 414.2 (M+H⁺).

A solution of 2-(2-isopropyl-1-((2-methoxyethoxy)methyl)-1H-imidazol-5-yl)-4-((6-nitropyridin-3-yl)oxy)pyridine (783 mg, 1.894 mmol) in dioxane (15 mL) was treated with 6N HCl (9.0 mL), heated at 50° C. for 16 h, then cooled to RT and evaporated to remove most of the organics. The aqueous residue was treated with EtOAc, made basic with 1N NaOH, the layers separated and the aqueous layer extracted with additional EtOAc. The combined organics were washed with brine, dried over Na₂SO₄ and concentrated to dryness to afford 2-(2-isopropyl-1H-imidazol-5-yl)-4-((6-nitropyridin-3-yl)oxy)pyridine (612 mg, 99%). ¹H NMR (400 MHz, DMSO-d₆): δ 12.01 (s, 1H), 8.58 (d, J=2.8 Hz, 1H), 8.47 (d, J=5.6 Hz, 1H), 8.41 (d, J=8.9 Hz, 1H), 7.95 (dd, J=8.9, 2.8 Hz, 1H), 7.61 (d, J=2.1 Hz, 1H), 7.45 (d, J=2.5 Hz, 1H), 6.97 (dd, J=5.4, 2.7 Hz, 1H), 2.95-2.94 (m, 1H), 1.23 (t, J=6.9 Hz, 6H); MS (ESI) m/z: 326.1 (M+H⁺).

A mixture of 2-(2-isopropyl-1H-imidazol-5-yl)-4-((6-nitropyridin-3-yl)oxy)pyridine (612 mg, 1.881 mmol) and 10% Pd/C (50% wet, 200 mg, 0.188 mmol) in MeOH (10 mL) was hydrogenated (1 atm) for 24 h. The solids were removed via filtration through diatomaceous earth, washed with MeOH and the filtrate concentrated to dryness to afford 5-((2-(2-isopropyl-1H-imidazol-5-yl)pyridin-4-yl)oxy)pyridin-2-amine (529 mg, 95%). ¹H NMR (400 MHz, DMSO-d₆): δ 11.96 (s, 1H), 8.30 (d, J=5.6 Hz, 1H), 7.81 (d, J=2.9 Hz, 1H), 7.51 (s, 1H), 7.29 (dd, J=8.9, 3.0 Hz, 1H), 7.20 (d, J=2.5 Hz, 1H), 6.67 (dd, J=5.7, 2.5 Hz, 1H), 6.52 (d, J=8.9 Hz, 1H), 6.03 (s, 2H), 2.97 (m, 1H), 1.21 (d, J=7.0 Hz, 6H); MS (ESI) m/z: 296.1 (M+H⁺).

between EtOAc (200 mL) and water (200 mL) and stirred for a few minutes. The resultant emulsion was filtered through diatomaceous earth, washing with water (2×20 mL) and EtOAc (3×20 mL). The filtrate layers were separated and the aqueous layer was extracted with EtOAc (50 mL). The combined organics were washed with brine, dried (Na₂SO₄) and concentrated. The residue was purified by silica gel chromatography (EtOAc/Hex) to afford 3-((2-ethynylpyridin-4-yl)oxy)-2-methyl-6-nitropyridine (0.51 g, 10.6%) as a light brown solid. MS (ESI) m/z: 256.1 (M+H⁺).

A solution of 3-((2-ethynylpyridin-4-yl)oxy)-2-methyl-6-nitropyridine (0.2 g, 0.78 mmol) and azidomethyl pivalate (0.209 g, 1.33 mmol; See: Syn Lett. 2005, (18), 2847-2850) were combined in tert-butanol (3 mL) and treated with copper (I) iodide (0.030 g, 0.157 mmol) followed by a solution of 2,6-lutidine (0.091 mL, 0.78 mmol) in MeCN (3 mL) and the resultant mixture was stirred at RT for 3 h. The mixture was partitioned between water (30 mL) and EtOAc (30 mL). The aqueous layer was extracted with EtOAc and the combined organics were washed with brine, dried (Na₂SO₄) and concentrated. The crude product was purified by silica gel chromatography (EtOAc/Hex) to afford (4-(4-((2-methyl-6-nitropyridin-3-yl)oxy)pyridin-2-yl)-1H-1,2,3-triazol-1-yl)methyl pivalate (0.27 g, 84%) as an orange foam. ¹H NMR (400 MHz, DMSO-d₆): δ 8.74 (s, 1H), 8.60 (d, J=5.7 Hz, 1H), 8.26 (d, J=8.7 Hz, 1H), 7.94 (d, J=8.7 Hz, 1H), 7.64 (d, J=2.4 Hz, 1H), 7.12 (dd, J=5.6, 2.5 Hz, 1H), 6.37 (s, 2H), 2.50 (s, 3H), 1.11 (s, 9H); MS (ESI) m/z: 413.2 (M+H⁺).

A solution of (4-(4-((2-methyl-6-nitropyridin-3-yl)oxy)pyridin-2-yl)-1H-1,2,3-triazol-1-yl)methyl pivalate (0.27 g, 0.655 mmol) in EtOAc (5 mL) was treated with 10% Pd/C (50% wet, 0.070 g, 0.066 mmol) and the mixture was stirred under hydrogen (1 atm) at RT for 24 h. The mixture was filtered through diatomaceous earth and the filter cake was washed with EtOAc. The combined filtrates were evaporated to dryness to give (4-(4-((6-amino-2-methylpyridin-3-yl)oxy)pyridin-2-yl)-1H-1,2,3-triazol-1-yl)methyl pivalate (0.24 g, 96%) as colorless foam. ¹H NMR (400 MHz, DMSO-d₆): δ 8.67 (s, 1H), 8.45 (d, J=5.7 Hz, 1H), 7.35 (d, J=2.5 Hz, 1H), 7.23 (d, J=8.7 Hz, 1H), 6.86 (dd, J=5.7, 2.6 Hz, 1H), 6.38-6.35 (m, 3H); 5.99 (s, 2H), 2.06 (s, 3H), 1.11 (s, 9H); MS (ESI) m/z: 383.2 (M+H⁺).

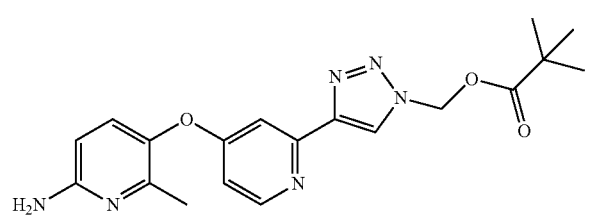 [SMILES: Cc1nc(N)ccc1Oc1ccnc(-c2cn(COC(=O)C(C)(C)C)nn2)c1]

Example A30

To a degassed solution of Example A4 (5.0 g, 18.8 mmol) in DMF (30 mL) was added TEA (7.87 mL, 56.5 mmol), Pd(PPh₃)₂Cl₂ (0.661 g, 0.941 mmol), copper(I) iodide (0.179 g, 0.941 mmol), and trimethylsilylacetylene (7.9 mL, 56 mmol) and the mixture was stirred at 50° C. for 16 h. The mixture was diluted with EtOAc (60 mL) and filtered through diatomaceous earth, washing the pad with EtOAc (5×10 mL). The combined filtrates were concentrated to a volume of ~20 mL, treated with a solution of TBAF (1M in THF, 38 mL, 38 mmol), and stirred at RT for 3 h. The mixture was partitioned

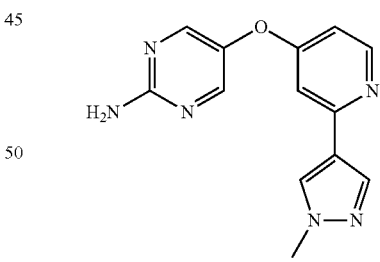

Example A31

A solution of 2-amino-5-hydroxypyrimidine (1.00 g, 9.00 mmol) in DMA (25 mL) was treated with potassium tert-butoxide (1.24 g, 11.05 mmol). The thick mixture was stirred at RT for 1 h. To this was added a solution of 2,4-dichloropyridine (1.21 g, 8.18 mmol) in DMA (10 mL) and the reaction was stirred at RT overnight under Ar. The mixture was partitioned into EtOAc (100 mL) and water (100 mL). The organic phase was separated and the aqueous was extracted with EtOAc (100 mL). The combined EtOAc layers were washed with 5% LiCl (100 mL) and brine (100 mL) and then dried over sodium sulfate. The solvents were evaporated at reduced pressure to give 5-((2-chloropyridin-4-yl)oxy)pyrimidin-2-amine as a pale yellow solid (592 mg, 32%). MS (ESI) m/z: 223.0 (M+H$^+$).

5-((2-chloropyridin-4-yl)oxy)pyrimidin-2-amine (676 mg, 3.04 mmol), 1-methyl-4-(4,4,5,5-tetramethyl-1,3,2-dioxaborolan-2-yl)-1H-pyrazole (758 mg, 3.64 mmol), potassium carbonate (1.259 g, 9.11 mmol) and Pd(PPh$_3$)$_4$ (175 mg, 0.152 mmol) were combined in dioxane (12 mL) and water (3 mL). The mixture was degassed with argon, and warmed to 85° C. overnight. The mixture was diluted with EtOAc (75 mL) and water (40 mL) and was filtered to collect an off-white solid. The organic phase was separated, washed with brine (40 mL) and evaporated at reduced pressure to give additional off-white solid. The two crops of solids were combined and triturated with EtOAc (15 mL) with sonication. The solid was collected by filtration, washed with EtOAc (2×5 mL) and dried under vacuum to provide 5-((2-(1-methyl-1H-pyrazol-4-yl)pyridin-4-yl)oxy)pyrimidin-2-amine (455 mg, 55%). $^1$H NMR (DMSO-d$_6$): δ 8.34 (d, J=5.7 Hz, 1H), 8.26 (s, 1H), 8.22 (s, 2H), 7.96 (s, 1H), 7.19 (d, J=2.4 Hz, 1H), 6.77 (s, 2H), 6.67 (dd, J=5.7, 2.5 Hz, 1H), 3.84 (s, 3H); MS (ESI) m/z: 269.1 (M+H$^+$).

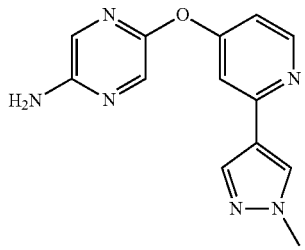 [SMILES: Cn1cc(-c2cc(Oc3cnc(N)cn3)ccn2)cn1]

Example A32

A mixture of 2,5-dibromopyrazine (2.42 g, 10.2 mmol), 2-chloro-4-hydroxy pyridine (1.2 g, 9.3 mmol) and Cs$_2$CO$_3$ (3.02 g, 9.26 mmol) in DMF (15 mL) was heated at 70° C. for 16 h with stirring. The mixture was poured into water (150 mL) and stirred for 15 min. The resultant precipitate was collected by filtration, washed with water (4×4 mL) and dried in vacuo to provide 2-bromo-5-((2-chloropyridin-4-yl)oxy) pyrazine (2.24 g, 84%) as an off-white solid. MS (ESI) m/z: 285.9/287.9 (M+H$^+$).

A solution of 2-bromo-5-((2-chloropyridin-4-yl)oxy)pyrazine (1.2 g, 4.19 mmol) in dioxane (20 mL) was degassed, treated with acetamide (0.495 g, 8.38 mmol), Cs$_2$CO$_3$ (2.05 g, 6.28 mmol), X-Phos (0.200 g, 0.419 mmol) and Pd$_2$(dba)$_3$ (0.192 g, 0.209 mmol) and heated at 80° C. for 3 h. The mixture was cooled to RT and diluted with EtOAc. The solids were removed via filtration through diatomaceous earth, rinsed well with EtOAc, and the filtrate washed with H$_2$O, then brine, dried over Na$_2$SO$_4$, concentrated to dryness and purified via silica gel chromatography (EtOAc/Hex) to afford N-(5-((2-chloropyridin-4-yl)oxy)pyrazin-2-yl)acetamide (0.35 g, 31%). MS (ESI) m/z: 265.0 (M+H$^+$).

To a degassed solution of N-(5-((2-chloropyridin-4-yl) oxy)pyrazin-2-yl)acetamide (0.25 g, 0.945 mmol) in dioxane (6 mL) was added a solution of K$_2$CO$_3$ (0.261 g, 1.889 mmol) in water (1.5 mL), 1-methyl-4-(4,4,5,5-tetramethyl-1,3,2-dioxaborolan-2-yl)-1H-pyrazole (0.255 g, 1.228 mmol), and Pd(PPh$_3$)$_4$ (0.109 g, 0.094 mmol). The mixture was stirred at 80° C. for 3 h. The mixture was diluted with water (30 mL) and extracted with EtOAc (2×80 mL). The combined organics were washed with brine, dried (Na$_2$SO$_4$) and concentrated in vacuo. The crude product was purified by silica gel chromatography (MeOH/DCM) to afford N-(5-((2-(1-methyl-1H-pyrazol-4-yl)pyridin-4-yl)oxy)pyrazin-2-yl)acetamide (240 mg, 82%) product as white solid. $^1$H NMR (400 MHz, DMSO-d$_6$): δ 10.86 (s, 1H), 8.97 (d, J=1.4 Hz, 1H), 8.43 (dd, J=5.6, 0.5 Hz, 1H), 8.40 (d, J=1.4 Hz, 1H), 8.27 (s, 1H), 7.98 (d, J=0.7 Hz, 1H), 7.40 (m, 1H), 6.92 (dd, J=5.6, 2.4 Hz, 1H), 3.85 (s, 3H), 2.12 (s, 3H); MS (ESI) m/z: 311.1 (M+H$^+$).

A solution of N-(5-((2-(1-methyl-1H-pyrazol-4-yl)pyridin-4-yl)oxy)pyrazin-2-yl)acetamide (0.38 g, 1.22 mmol) in THF (10 mL) was treated with aqueous HCl (2 M, 6.12 mL, 12.24 mmol) and the solution was stirred at 60° C. for 4 h. The solvent was evaporated and the crude residue was diluted with water (40 mL), basified with solid NaHCO$_3$, and extracted with EtOAc (2×30 mL). The combined organics were washed with brine, dried (Na$_2$SO$_4$) and concentrated to afford 5-((2-(1-methyl-1H-pyrazol-4-yl)pyridin-4-yl)oxy)pyrazin-2-amine (0.32 g, 97%) as a white foam. $^1$H NMR (400 MHz, DMSO-d$_6$): δ 8.34 (d, J=5.7 Hz, 1H), 8.25 (s, 1H), 7.95 (d, J=0.7 Hz, 1H), 7.91 (d, J=1.4 Hz, 1H), 7.61 (d, J=1.4 Hz, 1H), 7.21 (d, J=2.4 Hz, 1H), 6.69 (dd, J=5.7, 2.4 Hz, 1H), 6.44 (s, 2H), 3.84 (s, 3H); MS (ESI) m/z: 269.1 (M+H$^+$).

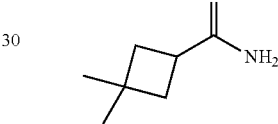

Example B1

A solution of 3,3-dimethylcyclobutane carboxylic acid (0.5 g, 3.90 mmol) and oxalyl chloride (0.512 mL, 5.85 mmol) in DCM (10 mL) was treated with DMF (1 drop) and stirred at RT for 2 h. The mixture was concentrated to dryness, treated with DCM (5 mL) and concentrated to dryness a second time. The crude acid chloride was dissolved in THF (5 mL), added drop-wise to a solution of NH$_4$OH (~15M, 3.80 mL, ~57 mmol) in THF (5 mL), stirred for 30 min, diluted with brine and extracted with EtOAc (3×). The combined organics were dried over MgSO$_4$ and evaporated to afford 3,3-dimethylcyclobutanecarboxamide (448 mg, 90%). $^1$H NMR (400 MHz, DMSO-d$_6$): δ 7.07 (s, 1H), 6.64 (s, 1H), 2.86 (m, 1H), 1.86 (m, 2H), 1.75 (m, 2H), 1.10 (s, 3H), 1.00 (s, 3H).

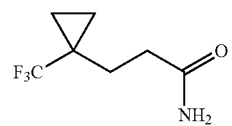

Example B2

A solution of 1-(trifluoromethyl)cyclopropane-1-carboxylic acid (3 g, 19.47 mmol) in THF (32.4 mL) was treated with borane-THF complex (1.0 M, 31.2 mL, 31.2 mmol) and heated at 40° C. overnight. The mixture was cooled in an ice bath, carefully quenched with satd. NH$_4$Cl, filtered through diatomaceous earth and rinsed well with EtOAc. The filtrate was extracted with EtOAc (2×) and the combined organics were washed with satd. NaHCO₃, then brine, dried over Na₂SO₄ and concentrated to afford (1-(trifluoromethyl)cyclopropyl)methanol (2.46 g, 90%). ¹H NMR (400 MHz, DMSO-d₆): δ 4.93 (t, J=6.0 Hz, 1H), 3.52 (d, J=6.0 Hz, 2H), 0.86-0.75 (m, 4H).

A 0° C. solution of (1-(trifluoromethyl)cyclopropyl)methanol (2.46 g, 17.56 mmol), TEA (2.94 mL, 21.1 mmol) and DMAP (0.215 g, 1.76 mmol) in DCM (35 mL) was treated with p-toluenesulfonyl chloride (3.38 g, 17.7 mmol), allowed to warm to RT and stirred overnight. The mixture was treated with additional DCM, washed with 2N HCl (3×), followed by satd. NaHCO₃, dried over Na₂SO₄, concentrated to dryness and purified via silica gel chromatography (EtOAc/Hex) to afford (1-(trifluoromethyl)cyclopropyl)methyl 4-methylbenzenesulfonate (3.42 g, 66%). ¹H NMR (400 MHz, DMSO-d₆): δ 7.77 (m, 2H), 7.48 (m, 2H), 4.16 (s, 2H), 2.41 (s, 3H), 1.04 (m, 2H), 0.92 (m, 2H); MS (ESI) m/z: 295.1 (M+H⁺).

A 0° C. solution of diisopropyl malonate (4.10 mL, 21.58 mmol) in DMF (30 mL) was treated with NaH (60% in mineral oil, 1.036 g, 25.9 mmol), warmed to RT, treated with NaI (0.647 g, 4.32 mmol) followed by the drop-wise addition of a solution of (1-(trifluoromethyl)cyclopropyl)methyl 4-methylbenzenesulfonate (2.54 g, 8.63 mmol) in DMF (30 mL) and heated at 80° C. overnight. The mixture was cooled to RT, quenched with satd. NH₄Cl, extracted with hexane (3×) and the combined organics were dried over Na₂SO₄, concentrated to dryness and purified via silica gel chromatography (MTBE/Hex) to afford diisopropyl 2-((1-(trifluoromethyl)cyclopropyl)methyl)malonate (1.53 g, 57.1%). ¹H NMR (400 MHz, DMSO-d₆): δ 4.91 (m, 2H), 3.47 (t, J=7.2 Hz, 1H), 2.10 (d, J=7.2 Hz, 2H), 1.17 (dd, J=7.3, 6.3 Hz, 12H), 0.89 (m, 2H), 0.76 (m, 2H).

A solution of diisopropyl 2-((1-(trifluoromethyl)cyclopropyl)methyl)malonate (1.53 g, 4.93 mmol) in MeOH (10 mL), dioxane (10 mL) and H₂O (10 mL) was treated with NaOH (1.183 g, 29.6 mmol) and heated at 40° C. overnight. The mixture was cooled to RT, the organics removed under reduced pressure, the aqueous residue acidified with 3M HCl, extracted with DCM and the combined organics were dried over Na₂SO₄ and concentrated to dryness to afford 2-((1-(trifluoromethyl)cyclopropyl)methyl)malonic acid (1.13 g, 101%). ¹H NMR (400 MHz, DMSO-d₆): δ 12.91 (s, 2H), 3.36-3.34 (t, J=7.09 Hz, 1H), 2.08 (d, J=7.0 Hz, 2H), 0.88 (m, 2H), 0.77 (m, 2H).

A solution of 2-((1-(trifluoromethyl)cyclopropyl)methyl)malonic acid (1.13 g, 5.00 mmol) in pyridine (25 mL) was heated at 100° C. overnight, cooled to RT and concentrated to dryness. The residue was dissolved in 3N HCl, extracted with DCM (3×) and the combined organics were dried over Na₂SO₄ and concentrated to dryness to afford 3-(1-(trifluoromethyl)cyclopropyl)propanoic acid (664 mg, 73%). ¹H NMR (400 MHz, DMSO-d₆): δ 12.18 (s, 1H), 2.32 (t, J=8.0 Hz, 2H), 1.79 (t, J=8.0 Hz, 2H), 0.86 (m, 2H), 0.75 (m, 2H).

A solution of 3-(1-(trifluoromethyl)cyclopropyl)propanoic acid (0.2 g, 1.098 mmol) and oxalyl chloride (0.144 mL, 1.647 mmol) in DCM (5 mL) and DMF (1 drop) was stirred at RT for 2 h, then concentrated to dryness. The residue was co-evaporated with DCM (1×), then dissolved in THF (5 mL), added drop-wise to a solution of NH₄OH (~15 M, 1.07 mL, ~16 mmol) in THF (5 mL) and stirred at RT for 0.5 h. The mixture was treated with brine, extracted with EtOAc (3×) and the combined organics were dried over Na₂SO₄ and concentrated to dryness to afford 3-(1-(trifluoromethyl)cyclopropyl)propanamide (179 mg, 90%). ¹H NMR (400 MHz, DMSO-d₆): δ 7.30 (s, 1H), 6.77 (s, 1H), 2.16 (m, 2H), 1.75 (m, 2H), 0.85 (m, 2H), 0.71 (m, 2H).

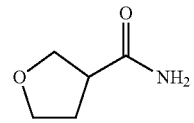

Example B3

A solution of tetrahydrofuran-3-carboxylic acid (1.50 g, 12.92 mmol) in DCM (20 mL) was treated with oxalyl chloride (2.00 g, 15.76 mmol) followed by 1 drop of DMF, stirred at RT for 2 h, concentrated to dryness, treated with ammonia (0.5 M in THF, 40 mL, 20 mmol) and stirred at RT for 1 h. The mixture was concentrated to dryness, treated with DCM, the solids removed via filtration and the filtrate concentrated to dryness to afford tetrahydrofuran-3-carboxamide (980 mg, 66%) as an off-white solid. ¹H NMR (400 MHz, DMSO-d₆): δ 7.35 (s, 1H), 6.84 (s, 1H), 3.79 (t, J=8.2 Hz, 1H), 3.61 (m, 3H), 2.84 (m, 1H), 1.91 (m, 2H); MS (ESI) m/z: 138.1 (M+Na⁺).

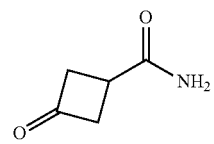

Example B4

A solution of 3-oxocyclobutanecarboxylic acid (0.500 g, 4.38 mmol) in EtOAc (10 mL) was treated with CDI (0.924 g, 5.70 mmol), stirred at RT for 30 min, then treated with NH₄OH (14 M, 1.565 mL, 21.91 mmol) and stirred at RT for 1 h. The mixture was concentrated to dryness, treated with H₂O, then satd. NaHCO₃, and washed with EtOAc (2×). The aqueous layer was treated with solid NaCl until saturated and extracted with 1:1 EtOAc/THF (6×). The combined organics were dried over MgSO₄, concentrated to dryness and purified via silica gel chromatography (MeOH/DCM) to afford 3-oxocyclobutanecarboxamide (327 mg, 66%) as a white solid. ¹H NMR (400 MHz, DMSO-d₆): δ 7.56 (s, 1H), 7.01 (s, 1H), 3.20-3.00 (m, 5H).

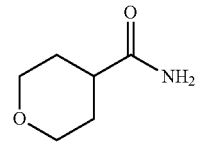

Example B5

A 0° C. solution of tetrahydro-2H-pyran-4-carboxylic acid (0.5 g, 3.84 mmol) in MeCN (15 mL) was treated with EDC (0.884 g, 4.61 mmol) and HOBT (0.706 g, 4.61 mmol) under an argon atmosphere and stirred at 0° C. for 1 h. Ammonium hydroxide (~15M, 0.512 mL, 7.68 mmol) was added slowly and the mixture was warmed to RT and stirred overnight. The mixture was treated with water, saturated with solid NaCl and the aqueous layer was extracted with THF (2x). The combined organics were washed with brine, dried over Na$_2$SO$_4$ and concentrated to afford tetrahydro-2H-pyran-4-carboxamide (0.23 g, 46%) as a white solid. $^1$H NMR (400 MHz, DMSO-d$_6$): δ 7.20 (s, 1H), 6.73 (s, 1H), 3.82-3.81 (m, 2H), 3.30-3.21 (m, 2H), 2.30-2.27 (m, 1H), 1.60-1.46 (m, 4H).

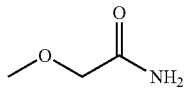

Example B6

A solution of methoxyacetyl chloride (0.421 mL, 4.61 mmol) in THF (5 mL) was added drop-wise to a mixture of NH$_4$OH (~15 M, 12.3 mL, ~184 mmol) in THF (12.29 mL) and stirred at RT for 0.5 h. The mixture was satd. with solid NaCl, extracted with DCM (5x) and the combined organics were washed with satd. NaHCO$_3$, dried over Na$_2$SO$_4$ and concentrated to dryness to afford 2-methoxyacetamide (226 mg, 55%) as a white solid. $^1$H NMR (400 MHz, DMSO-d$_6$): δ 7.20 (s, 2H), 3.70 (s, 2H), 3.27 (s, 3H).

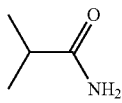

Example B7

A solution of isobutyryl chloride (0.983 mL, 9.39 mmol) in THF (5 mL) was added drop-wise to a mixture of THF (25 mL) and NH$_4$OH (~15 M, 25 mL, ~375 mmol), stirred at RT for 30 min, treated with solid NaCl until saturated and extracted with DCM (5x). The combined organics were washed with satd. NaHCO$_3$, dried over Na$_2$SO$_4$ and concentrated to dryness to afford isobutyramide (811 mg, 99%) as a white solid. $^1$H NMR (400 MHz, DMSO-d$_6$): δ 7.15 (s, 1H), 6.62 (s, 1H), 2.34-2.24 (m, 1H), 0.96 (d, J=6.9 Hz, 6H); MS (ESI) m/z: 88.2 (M+H$^+$).

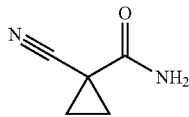

Example B8

Carbonyldiimidazole (0.730 g, 4.50 mmol) was slowly added to a solution of 1-cyano-1-cyclopropanecarboxylic acid (0.5 g, 4.50 mmol) in EtOAc (45 mL) under argon, heated to 50° C. for 1 h, then cooled to RT and added drop-wise to NH$_4$OH (~15 M, 2.4 mL, ~36 mmol). The mixture was stirred at RT for 0.5 h, treated with satd. NaHCO$_3$ and extracted with EtOAc (5x). The combined organics were dried over Na$_2$SO$_4$ and concentrated to dryness to afford 1-cyanocyclopropanecarboxamide (412 mg, 83%) as an off-white solid. MS (ESI) m/z: 111.1 (M+H$^+$).

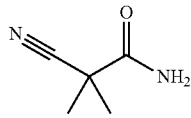

Example B9

A solution of KOH (2.63 g, 46.8 mmol) in MeOH (26.2 mL) was treated with methyl 2-cyano-2,2-dimethylpropanoate (0.5 g, 3.93 mmol) and stirred at RT for 1 h. The mixture was concentrated to dryness, dissolved in H$_2$O, acidified to pH=2 with 3M HCl, extracted with EtOAc (3x) and the combined organics were dried over Na$_2$SO$_4$ and concentrated to dryness to afford 2-cyano-2-methylpropanoic acid (320 mg, 72%) as a white amorphous solid.

CDI (0.717 g, 4.42 mmol) was added slowly to a solution of 2-cyano-2-methylpropanoic acid (0.5 g, 4.42 mmol) in EtOAc (44 mL) under argon, heated to 50° C. for 1 h, then cooled to RT and added drop-wise to NH$_4$OH (2.357 mL, 35.4 mmol). The mixture was stirred at RT for 0.5 h, treated with satd. NaHCO$_3$ and extracted with EtOAc (5x). The combined organics were dried over Na$_2$SO$_4$ and concentrated to dryness to afford 2-cyano-2-methylpropanamide (347 mg, 70%) as an off-white solid.

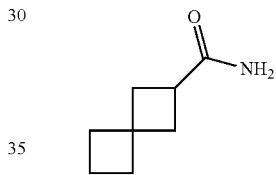

Example B10

A 0° C. solution of diethyl 1,1-cyclobutanedicarboxylate (3 g, 14.98 mmol) in Et$_2$O (74.9 mL) was treated slowly with LiAlH$_4$ (2M in THF, 15 mL, 30.0 mmol), heated at 35° C. for 3 h, cooled to 0° C. and carefully quenched with H$_2$O (1.14 mL), 20% KOH (1.14 mL), and H$_2$O (3.42 mL). The mixture was stirred for 30 min, dried over MgSO$_4$ and the insolubles removed via filtration and washed well with EtOAc. The filtrate was concentrated to dryness to afford cyclobutane-1,1-diyldimethanol (1.77 g, 102%).

A 0° C. solution of cyclobutane-1,1-diyldimethanol (1.77 g, 15.24 mmol) in pyridine (30 mL) was treated portion-wise with p-toluenesulfonyl chloride (8.72 g, 45.7 mmol) over 10 min, allowed to slowly warm to RT and stirred overnight. Solids were removed via filtration, washed with DCM and the filtrate was treated with H$_2$O and extracted with DCM (2x). The combined organics were washed with 2M HCl (2x), then satd. NaHCO$_3$ (1x), dried over Na$_2$SO$_4$ and concentrated to dryness to afford cyclobutane-1,1-diylbis(methylene)bis(4-methylbenzenesulfonate) (5.92 g, 92%). $^1$H NMR (400 MHz, DMSO-d): δ 7.72 (m, 4H), 7.46 (d, J=8.1 Hz, 4H), 3.93 (s, 4H), 2.41 (s, 6H), 1.76-1.64 (m, 6H); MS (ESI) m/z: 447.1 (M+Na$^+$).

A suspension of NaH (60% in mineral oil, 1.394 g, 34.9 mmol) in DMF (35 mL) was treated drop-wise with diisopropyl malonate (5.30 mL, 27.9 mmol) followed by cyclobutane-1,1-diylbis(methylene)bis(4-methylbenzenesulfonate) (5.92 g, 13.94 mmol) and KI (0.231 g, 1.394 mmol) and heated at 140° C. overnight. The mixture was cooled to RT, poured on satd. NH₄Cl, extracted with hexane (2×) and the combined organics were washed with H₂O, dried over MgSO₄ and concentrated to dryness to afford crude diisopropyl spiro[3.3] heptane-2,2-dicarboxylate (5.17 g, 138%) which was carried on without purification.

A solution of diisopropyl spiro[3.3]heptane-2,2-dicarboxylate (2.85 g, 10.62 mmol) in MeOH (20 mL) was treated with 2N NaOH (31.9 mL, 63.7 mmol) and heated at 50° C. overnight. The organics were removed under reduced pressure, the aqueous residue acidified with 3M HCl, cooled to 5° C. and the solid collected via filtration. The filtrate was extracted with DCM (2×), then EtOAc (2×) and the combined organics were dried over Na₂SO₄, concentrated to dryness and combined with the first solid to afford spiro[3.3]heptane-2,2-dicarboxylic acid (1.737 g, 89%). ¹H NMR (400 MHz, DMSO-d₆): δ 12.58 (s, 2H), 2.39 (s, 4H), 1.91 (t, J=7.5 Hz, 4H), 1.71 (m, 2H).

A solution of spiro[3.3]heptane-2,2-dicarboxylic acid (1.737 g, 9.43 mmol) in pyridine (20 mL) was heated at 115° C. overnight, cooled to RT and concentrated to dryness. The residue was treated with 6M HCL, extracted with DCM (3×) and the combined organics were dried over Na₂SO₄ and concentrated to dryness to afford spiro[3.3]heptane-2-carboxylic acid (1.21 g, 92%). ¹H NMR (400 MHz, DMSO-d₆): δ 11.98 (s, 1H), 2.85 (m, 1H), 2.15-2.03 (m, 4H), 1.96 (t, J=7.3 Hz, 2H), 1.84 (t, J=7.3 Hz, 2H), 1.76-1.70 (m, 2H).

A solution of spiro[3.3]heptane-2-carboxylic acid (0.5 g, 3.57 mmol) in DCM (5 mL) was treated with oxalyl chloride (0.406 mL, 4.64 mmol) and 1 drop of DMF and stirred at RT for 2 h. The mixture was added drop-wise to a mixture of NH₄OH (5 mL, 128 mmol) and THF (5 mL) and stirred at RT overnight. The mixture was treated with H₂O, the solids removed via filtration, the filtrate saturated with solid NaCl, extracted with 3:1 DCM/THF (3×) and the combined organics were washed with satd. NaHCO₃, then brine, dried over Na₂SO₄ and concentrated to dryness to afford spiro[3.3]heptane-2-carboxamide (440 mg, 89%). ¹H NMR (400 MHz, DMSO-d₆): δ 7.07 (s, 1H), 6.62 (s, 1H), 2.76 (m, 1H), 2.01 (m, 4H), 1.96 (t, J=7.2 Hz, 2H), 1.80 (m, 2H), 1.76-1.69 (m, 2H).

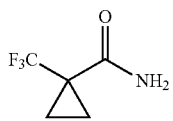

Example B11

A solution of 1-(trifluoromethyl)cyclopropane-1-carboxylic acid (0.5 g, 3.24 mmol) in DCM (5 mL) was treated with oxalyl chloride (0.355 mL, 4.06 mmol) and 1 drop of DMF, stirred for 1 h at RT, added drop-wise to a solution of NH₄OH (~15M, 5 mL, ~75 mmol) in THF (5 mL) and stirred at RT overnight. The solids were removed via filtration through diatomaceous earth and rinsed well with 4:1 DCM/THF. The filtrate was saturated with solid NaCl, extracted with 4:1 DCM/THF (3×) and the combined organics were dried over Na₂SO₄ and concentrated to dryness to afford 1-(trifluoromethyl)cyclopropanecarboxamide (440 mg, 89%). ¹H NMR (400 MHz, DMSO-d₆): δ 7.31 (s, 1H), 7.15 (s, 1H), 1.29-1.24 (m, 2H), 1.19-1.15 (m, 2H).

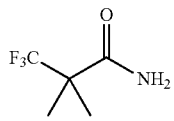

Example B12

A solution of 3,3,3-trifluoro-2,2-dimethylpropionic acid (0.5 g, 3.20 mmol) in DCM (5 mL) was treated with oxalyl chloride (0.350 mL, 4.00 mmol) and 1 drop of DMF, stirred at RT for 1 h, added drop-wise to a solution of NH₄OH (~15M, 5 mL, ~75 mmol) in THF (5 mL) and stirred at RT overnight. Solids were removed via filtration through diatomaceous earth, rinsed well with 4:1 DCM/THF, the filtrate saturated with solid NaCl, extracted with 4:1 DCM/THF (3×) and the combined organics were dried over Na₂SO₄ and concentrated to dryness to afford 3,3,3-trifluoro-2,2-dimethylpropanamide (370 mg, 74%). ¹H NMR (400 MHz, DMSO-d₆): δ 7.42 (s, 1H), 7.35 (s, 1H), 1.29 (s, 6H).

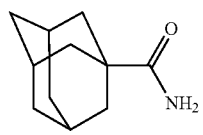 [SMILES: NC(=O)C12CC3CC(CC(C3)C1)C2]

Example B13

A solution of adamantane-1-carboxylic acid (2.00 g, 11.10 mmol) in EtOAc (20 mL) was treated with CDI (2.00 g, 12.33 mmol), stirred at RT for 20 minutes, treated with NH₄OH (~14M, 5 mL, ~70 mmol) and stirred at RT for 20 minutes. The mixture was concentrated to dryness, treated with satd. NaHCO₃ and the solids collected via filtration and dried to afford adamantane-1-carboxamide (1.74 g, 87%) as a white solid. ¹H NMR (400 MHz, DMSO-d₆): δ 6.91 (s, 1H), 6.65 (s, 1H), 1.92 (m, 3H), 1.74-1.71 (m, 6H), 1.68-1.57 (m, 6H); MS (ESI) m/z: 180.1 (M+H⁺).

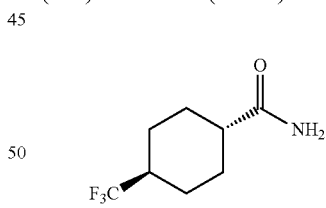

Example B14

A solution of trans-4-trifluoromethylcyclohexanecarboxylic acid (0.5 g, 2.55 mmol) in thionyl chloride (3.70 mL, 51.0 mmol) was heated to 60° C. for 1 h, cooled to RT and concentrated to dryness. The material was co-evaporated with toluene (2×), dissolved in EtOAc (5 mL), treated with satd. NaHCO₃ (5 mL) followed by NH₄OH (~13M, 0.588 mL, ~7.65 mmol) and stirred at RT for 0.5 h. The layers were separated, the aqueous layer extracted with EtOAc (2×) and the combined organics were dried over Na₂SO₄ and concentrated to dryness to afford trans-4-(trifluoromethyl)cyclohexanecarboxamide (380 mg, 76%) as a white solid.

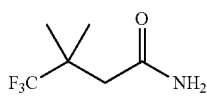

Example B15

A solution of 4,4,4-trifluoro-3,3-dimethylbutanoic acid [See: US2010/0240663] (0.6 g, 3.53 mmol) in thionyl chloride (6 mL, 82 mmol) was heated at 60° C. for 2 h, cooled to RT and concentrated to dryness. The residue was dissolved in DCM (2 mL), added drop-wise to a mixture of THF (8 mL) and NH$_4$OH (~15M, 8 mL, ~120 mmol) and stirred at RT overnight. Solid NaCl was added until saturated, the mixture extracted with 4:1 DCM/THF (3×) and the combined organics were washed with satd. NaHCO$_3$, then brine, dried over Na$_2$SO$_4$ and concentrated to dryness to afford 4,4,4-trifluoro-3,3-dimethylbutanamide (240 mg, 40%). $^1$H NMR (400 MHz, DMSO-d$_6$): δ 7.46 (s, 1H), 6.93 (s, 1H), 2.20 (s, 2H), 1.18 (s, 6H).

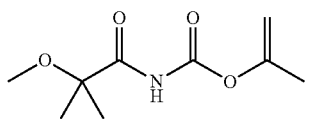

Example B16

A 0° C. solution of methyl 2-hydroxyisobutyrate (2 g, 16.93 mmol) in DMF (20 mL) was treated with NaH (60% in mineral oil, 0.813 g, 20.33 mmol), stirred for 0.5 h at 0° C., treated with iodomethane (1.269 mL, 20.29 mmol), allowed to warm to RT and stirred overnight. The mixture was diluted with EtOAc, quenched with cold satd. NH$_4$Cl, extracted with EtOAc (3×) and the combined organics were washed with satd. NaHCO$_3$, 10% LiCl, then brine, dried over Na$_2$SO$_4$ and concentrated to dryness to afford methyl 2-methoxy-2-methylpropanoate (2.08 g, 93%). $^1$H NMR (400 MHz, DMSO-d$_6$): δ 3.64 (s, 3H), 3.11 (s, 3H), 1.30 (s, 6H).

A solution of methyl 2-methoxy-2-methylpropanoate (2.08 g, 15.74 mmol) in MeOH (20 mL) was treated with a solution of KOH (1.766 g, 31.5 mmol) in water (10 mL) and stirred at RT for 4 h. The organics were removed under reduced pressure, the aqueous residue washed with 1:1 hex/Et$_2$O, acidified with 3N HCl, extracted with DCM (3×) and the combined organics were dried over Na$_2$SO$_4$ and concentrated to dryness to afford 2-methoxy-2-methylpropanoic acid (1.24 g, 67%). $^1$H NMR (400 MHz, DMSO-d$_6$): δ 12.48 (s, 1H), 3.12 (s, 3H), 1.27 (s, 6H).

A solution of 2-methoxy-2-methylpropanoic acid (1.24 g, 10.50 mmol) and HOBt (2.090 g, 13.65 mmol) in MeCN (26.2 mL) was treated portion-wise with EDC (2.62 g, 13.65 mmol) and stirred at RT for 2 h. NH$_4$OH (~15 M, 2.04 mL, ~30.6 mmol) was added and the mixture was stirred at RT overnight. The mixture was treated with 50% satd. brine, saturated with solid NaHCO$_3$, extracted with EtOAc (3×) and the combined organics were dried over Na$_2$SO$_4$ and concentrated to dryness to afford 2-methoxy-2-methylpropanamide (860 mg, 70%). $^1$H NMR (400 MHz, DMSO-d6): δ 7.14 (s, 1H), 7.02 (s, 1H), 3.12 (s, 3H), 1.21 (s, 6H).

A −78° C. solution of 2-methoxy-2-methylpropanamide (0.25 g, 2.134 mmol) in THF (6 mL) was treated drop-wise with lithium bis(trimethylsilyl)amide (1M in THF, 2.77 mL, 2.77 mmol) stirred for 0.5 h. A solution of isopropenyl chloroformate (0.257 mL, 2.347 mmol) in THF (1 mL) was added drop-wise and the mixture was stirred at −78° C. for 1 h. The mixture was warmed to RT, stirred for 1 h, quenched with satd. NaHCO$_3$, extracted with EtOAc (3×) and the combined organics were dried over Na$_2$SO$_4$ and concentrated to dryness to afford prop-1-en-2-yl (2-methoxy-2-methylpropanoyl)carbamate (440 mg, 102%). MS (ESI) m/z: 202.1 (M+H$^+$).

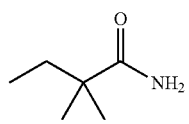

Example B17

A solution of 2,2-dimethylbutyric acid (1.0 g, 8.61 mmol) in DCM (30 mL) was treated with oxalyl chloride (1.130 mL, 12.91 mmol), followed by a catalytic amount of DMF (1 drop) and stirred at RT for 2 h. A solution of NH$_4$OH (~15M, 4 mL, 60 mmol) in THF (10 mL) was added drop-wise and the mixture stirred at RT overnight. The mixture was concentrated to dryness and the residue was dissolved in EtOAc, washed with brine, dried over MgSO$_4$ and concentrated to dryness to afford 2,2-dimethylbutanamide (500 mg, 50%). $^1$H NMR (400 MHz, DMSO-d$_6$): δ 6.95 (s, 1H), 6.69 (s, 1H), 1.42 (q, J=7.5 Hz, 2H), 1.00 (s, 6H), 0.73 (t, J=7.5 Hz, 3H); MS (ESI) m/z: 116.2 (M+H$^+$).

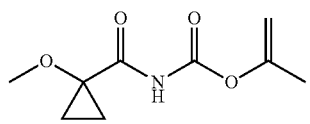

Example B18

A 0° C. solution of methyl 1-hydroxycyclopropane-1-carboxylate (1 g, 8.61 mmol) in DMF (10 mL) was treated with NaH (60% in mineral oil, 0.689 g, 17.22 mmol), stirred at 0° C. for 0.5 h, treated with iodomethane (0.646 mL, 10.33 mmol), allowed to slowly warm to RT and stirred for 2 h. The mixture was quenched with satd. NH$_4$Cl, diluted with water and extracted with Et$_2$O (3×). The combined organics were washed with water, then brine, dried and concentrated to afford methyl 1-methoxycyclopropane-1-carboxylate (1.10 g, 98%). $^1$H NMR (400 MHz, DMSO-d$_6$): δ 3.62 (s, 3H), 3.27 (s, 3H), 1.12-1.11 (m, 4H).

A solution of methyl 1-methoxycyclopropane-1-carboxylate (1.10 g, 8.45 mmol) in MeOH (10 mL) was treated drop-wise with a solution of KOH (0.948 g, 16.90 mmol) in water (5 mL) and stirred at RT overnight. The mixture was concentrated to a small volume, washed with 1:1 Hex/Et$_2$O and the aqueous layer poured onto ice and acidified with 3M HCl. The mixture was extracted with DCM (3×) and the combined organics were dried over Na$_2$SO$_4$ and concentrated to dryness to afford 1-methoxycyclopropane-1-carboxylic acid (392 mg, 40%). $^1$H NMR (400 MHz, DMSO-d$_6$): δ 12.53 (s, 1H), 3.26 (s, 3H), 1.06-1.05 (m, 4H).

A solution of 1-methoxycyclopropane-1-carboxylic acid (0.392 g, 3.38 mmol) and HOBt (0.672 g, 4.39 mmol) in MeCN (8.44 mL) was treated portion-wise with EDC (0.841 g, 4.39 mmol), stirred at RT for 2 h, treated with NH₄OH (~15M, 0.657 mL, ~9.9 mmol) and stirred at RT overnight. The mixture was treated with brine, extracted with 4:1 EtOAc/THF (4×) and the combined organics were washed with satd. NaHCO₃, then brine, dried over Na₂SO₄ and concentrated to dryness to afford 1-methoxycyclopropane-1-carboxamide (230 mg, 59%). ¹H NMR (400 MHz, DMSO-d₆): δ 7.47 (s, 1H), 7.26 (s, 1H), 3.21 (s, 3H), 0.95-0.94 (m, 4H).

A −78° C. solution of 1-methoxycyclopropane-1-carboxamide (0.23 g, 1.998 mmol) in THF (6 mL) was treated drop-wise with lithium bis(trimethylsilyl)amide (1M THF, 2.80 mL, 2.80 mmol), stirred for 0.5 h, treated drop-wise with a solution of isopropenyl chloroformate (0.262 mL, 2.397 mmol) in dry THF (1 mL), stirred for 1 h at −78° C., allowed to slowly warm to RT and stirred for 1 h. The mixture was quenched with satd. NaHCO₃), extracted with EtOAc (3×) and the combined organics were dried over Na₂SO₄ and concentrated to dryness to afford prop-1-en-2-yl (1-methoxycyclopropane-1-carbonyl)carbamate (0.423 g, 106%). MS (ESI) m/z: 222.1 (M+Na⁺).

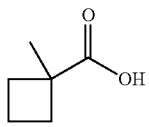

Example B19

A 0° C. solution of diisopropylamine (17 mL, 121 mmol) in THF (50 mL) was treated with n-butyl lithium (2.5M in hexane, 48 mL, 120 mmol), stirred for 10 minutes, treated with cyclobutane carboxylic acid (5.00 g, 49.9 mmol) and stirred for 0.5 h. Methyl iodide (9.00 g, 63.4 mmol) was added and the mixture was stirred at RT for 3 h, then concentrated to dryness. The mixture was treated with satd. NH₄Cl, extracted with DCM (2×) and the combined organics were washed with brine, dried over Na₂SO₄ and concentrated to dryness to afford 1-methylcyclobutanecarboxylic acid (3.54 g, 62%) as a brown oil.

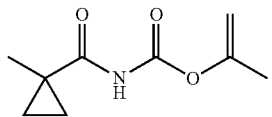

Example B20

A solution of 1-methylcyclopropane-1-carboxylic acid (1.24 g, 12.39 mmol) and HOBt (2.47 g, 16.1 mmol) in MeCN (31 mL) was treated portion-wise with EDC (3.09 g, 16.1 mmol), stirred at RT for 2 h, treated with NH₄OH (~15M, 2.4 mL, ~36 mmol) and stirred at RT overnight. The mixture was treated with 50% satd. brine, then solid NaHCO₃ until saturated, and extracted with EtOAc (3×). The combined organics were dried over Na₂SO₄ and concentrated to dryness to afford 1-methylcyclopropanecarboxamide (1.35 g, 110%) which was used without further purification. ¹H NMR (400 MHz, DMSO-d₆): δ 7.01 (br s, 1H), 6.81 (br s, 1H), 1.20 (s, 3H), 0.92-0.88 (m, 2H), 0.47-0.43 (m, 2H).

A −78° C. solution of 1-methylcyclopropanecarboxamide (1.35 g, 13.62 mmol) in THF (30 mL) was treated drop-wise with lithium bis(trimethylsilyl)amide (1 M THF, 17.7 mL, 17.7 mmol), stirred for 0.5 h, treated drop-wise with a solution of isopropenyl chloroformate (1.94 mL, 17.7 mmol) in THF (5 mL), stirred at −78° C. for 1 h, then allowed to warm to RT and stirred for 1 h. The mixture was quenched with satd. NaHCO₃, extracted with EtOAc (3×) and the combined organics were dried over Na₂SO₄ and concentrated to dryness to afford crude prop-1-en-2-yl (1-methylcyclopropanecarbonyl)carbamate (2.9 g, 116%) which was used without further purification.

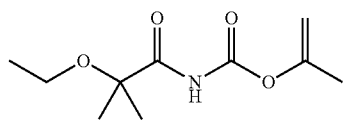

Example B21

A 0° C. suspension of NaH (60% wt. in mineral oil, 1.4 g, 35.0 mmol) in DMF (11 mL) under Ar was treated drop-wise with a solution of methyl 2-hydroxyisobutyrate (2.0 g, 16.93 mmol) in THF (5 mL), stirred at 0° C. for 0.5 h, allowed to warm to RT, and stirred for 0.5 h. The mixture was re-cooled to 0° C., treated drop-wise with iodoethane (6.0 g, 35.3 mmol) and stirred overnight as the cooling bath expired. The mixture was diluted with water, extracted with Et₂O (5×) and the combined organics were dried over MgSO₄ and concentrated to dryness to afford methyl 2-ethoxy-2-methylpropanoate (1.6 g, 65%) as a pale yellow oil. ¹H NMR (400 MHz, DMSO-d₆): δ 3.63 (s, 3H), 3.31 (q, J=7.0 Hz, 2H), 1.30 (s, 6H), 1.06 (t, J=7.0 Hz, 3H).

A solution of methyl 2-ethoxy-2-methylpropanoate (1.6 g, 10.95 mmol) in MeOH (14 mL) was treated drop-wise with a solution of KOH (1.228 g, 21.89 mmol) in water (7 mL) and stirred at RT overnight. The mixture was treated with water, washed with Et₂O (2×) and the aqueous layer was acidified to pH 2 with 2M HCl. The mixture was extracted with EtOAc (4×) and the combined organics were dried over MgSO₄ and concentrated to dryness to afford 2-ethoxy-2-methylpropanoic acid (1.1 g, 76%) as a colorless oil. ¹H NMR (400 MHz, DMSO-d₆): δ 12.42 (s, 1H), 3.34 (q, J=7.0 Hz, 2H), 1.28 (s, 6H), 1.06 (t, J=7.0 Hz, 3H).

A solution of 2-ethoxy-2-methylpropanoic acid (1.1 g, 8.32 mmol) in MeCN (15 mL) was treated with EDC (1.596 g, 8.32 mmol) and HOBT (1.275 g, 8.32 mmol), stirred at RT for 2 h, treated with NH₄OH (~15M, 1.7 mL, ~25.5 mmol) and stirred at RT overnight. The mixture was treated with satd. NaHCO₃ and water, extracted with EtOAc (5×) and the combined organics were dried over MgSO₄ and concentrated to dryness to afford 2-ethoxy-2-methylpropanamide (1.1 g, 101%) as a solid. ¹H NMR (400 MHz, DMSO-d₆): δ 7.03 (s, 2H), 3.31 (q, J=7.0 Hz, 2H), 1.21 (s, 6H), 1.10 (t, J=7.0 Hz, 3H).

A −78° C. solution of 2-ethoxy-2-methylpropanamide (1.1 g, 8.39 mmol) in THF (37 mL), under Ar, was treated with LiHMDS (1 M in THF, 11 mL, 11 mmol) stirred for 0.5 h, treated with a solution of isopropenyl chloroformate (1.46 g, 12.10 mmol) in THF (2 mL), stirred for 15 minutes at −78° C. then slowly warmed to RT as the cooling bath expired. The mixture was treated with satd. NH₄Cl, extracted with DCM (4×) and the combined organics were dried over MgSO₄ and concentrated to dryness to afford prop-1-en-2-yl (2-ethoxy-2-methylpropanoyl)carbamate (2.0 g, 84%) as an orange oil.

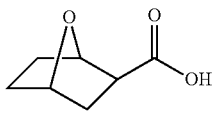

Example B22

Acrylonitrile (2.50 g, 47.1 mmol) was treated portion-wise with zinc chloride (1.926 g, 14.13 mmol), stirred at RT for 10 minutes, treated with furan (10.38 mL, 143 mmol) and stirred at RT for 14 h. The mixture was treated with water, extracted with EtOAc (3×) and the combined organics were washed with brine, dried over $Na_2SO_4$ and concentrated to afford an exo/endo mixture of 7-oxabicyclo[2.2.1]hept-5-ene-2-carbonitrile (4.75 g, 83%) as a pale oil.

The exo/endo-mixture of 7-oxabicyclo[2.2.1]hept-5-ene-2-carbonitrile (4.70 g, 38.8 mmol) in EtOAc (30 mL) was dissolved in EtOAc (30 mL), treated with 10% Pd/C (0.300 g, 0.282 mmol) and hydrogenated (20 psi) for 2 h. The solids were removed via filtration, washed with EtOAc and the filtrate concentrated in vacuo to afford an exo/endo-mixture of 7-oxabicyclo[2.2.1]heptane-2-carbonitrile (4.80 g, 100%) as a colorless oil.

A solution of the exo/endo-mixture of 7-oxabicyclo[2.2.1]heptane-2-carbonitrile (4.80 g, 39.0 mmol) in EtOH (30 mL) was treated with KOH (10 M, 10 mL, 100 mmol), heated at 100° C. for 90 minutes, then cooled to RT and stirred overnight. The mixture was concentrated to dryness, treated with water, acidified to pH 1 with conc. HCl, saturated with solid NaCl and extracted with MTBE (3×). The combined organics were dried over $Na_2SO_4$ and concentrated to dryness to afford exo-7-oxabicyclo[2.2.1]heptane-2-carboxylic acid (2.40 g, 43%) as a light brown solid. $^1$H NMR (400 MHz, DMSO-d$_6$): δ 12.13 (s, 1H), 4.64 (d, J=4.6 Hz, 1H), 4.51 (t, J=4.8 Hz, 1H), 2.57 (dd, J=9.1, 4.8 Hz, 1H), 1.88-1.83 (m, 1H), 1.63-1.38 (m, 5H).

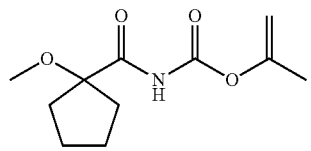 [SMILES: C=C(C)OC(=O)NC(=O)C1(OC)CCCC1]

Example B23

A solution of cyclopentanone (2.0 g, 23.78 mmol) in DCM (30 mL) was treated with zinc chloride (0.5M in THF, 4.76 mL, 2.378 mmol) followed by trimethylsilyl cyanide (3.83 mL, 28.5 mmol) and stirred at RT overnight. The mixture was treated with satd. NaHCO$_3$, extracted with DCM (1×) and the organic layer was washed with brine, dried over Na$_2$SO$_4$ and concentrated to dryness. The residue was treated with THF (5 mL) and HCl (2M, 4 mL), stirred at RT for 3 h, then the organics removed under reduced pressure. Additional HCl (12 M, 5 mL) was added, the mixture heated at 100° C. for 3 h, then cooled to RT, treated with water and extracted with EtOAc (2×). The combined organics were washed with brine, dried over Na$_2$SO$_4$ and concentrated to dryness to afford 1-hydroxycyclopentanecarboxylic acid (2.3 g, 74%). $^1$H NMR (400 MHz, DMSO-d$_6$): δ 12.28 (s, 1H), 4.92 (s, 1H), 1.93-1.83 (m, 2H), 1.74-1.57 (m, 6H).

A solution of 1-hydroxycyclopentanecarboxylic acid (1.4 g, 10.76 mmol) in MeOH (10 mL) was treated with conc. H$_2$SO$_4$ (1 drop), heated at 65° C. for 2 h, cooled to RT and concentrated to dryness. The residue was treated with satd. NaHCO$_3$, extracted with DCM (3×) and the combined organics were washed with brine, dried over Na$_2$SO$_4$ and concentrated to dryness to afford methyl 1-hydroxycyclopentanecarboxylate (1.45 g, 92%). $^1$H NMR (400 MHz, CDCl$_3$): δ 3.79 (s, 3H), 2.92 (br s, 1H), 2.11-2.00 (m, 2H), 1.91-1.83 (m, 2H), 1.82-1.72 (m, 4H).

A 0° C. suspension of NaH (60% in mineral oil, 0.644 g, 16.09 mmol) (pre-washed with hexanes, 2×) in THF (10 mL) was treated slowly with a solution of methyl 1-hydroxycyclopentanecarboxylate (1.45 g, 10.06 mmol) in THF (10 mL), stirred at 0° C. for 15 min, treated with iodomethane (1.258 mL, 20.12 mmol), warmed to RT and stirred overnight. The mixture was poured into satd. NH$_4$Cl, extracted with EtOAc (3×) and the combined organics were washed with brine, dried over Na$_2$SO$_4$ and concentrated to dryness to afford methyl 1-methoxycyclopentanecarboxylate (1.0 g, 63%). $^1$H NMR (400 MHz, CDCl$_3$): δ 3.76 (s, 3H), 3.24 (s, 3H), 1.98-1.96 (m, 4H), 1.76-1.74 (m, 4H).

A solution of methyl 1-methoxycyclopentanecarboxylate (1.00 g, 6.32 mmol) in THF (10 mL) was treated with a solution of LiOH (0.531 g, 12.64 mmol) in water (5 mL), stirred at RT overnight and concentrated to dryness. The residue was diluted with water, acidified with HCl (2M, 6 mL), extracted with EtOAc (3×) and the combined organics were washed with brine, dried over Na$_2$SO$_4$ and concentrated to dryness to afford 1-methoxycyclopentanecarboxylic acid (900 mg, 99%). $^1$H NMR (400 MHz, CDCl$_3$): δ 3.31 (s, 3H), 2.05-2.03 (m, 4H), 1.78-1.77 (m, 4H) [CO$_2$H not observed].

A solution of 1-methoxycyclopentanecarboxylic acid (0.9 g, 6.24 mmol) in EtOAc (30 mL) was treated with CDI (1.316 g, 8.12 mmol), stirred at RT for 0.5 h, treated with NH$_4$OH (~15M, 0.729 mL, ~10.9 mmol) and stirred at RT overnight. The mixture was treated with water, extracted with EtOAc (3×) and the combined organics were washed with brine, dried over Na$_2$SO$_4$ and concentrated to dryness to afford 1-methoxycyclopentanecarboxamide (900 mg, 101%). $^1$H NMR (400 MHz, CDCl$_3$): δ 6.45 (br s, 1H), 5.42 (br s, 1H), 3.24 (s, 3H), 2.07-2.04 (m, 2H), 1.90-1.87 (m, 2H), 1.75-1.73 (m, 4H).

A −78° C. solution of 1-methoxycyclopentanecarboxamide (0.9 g, 6.29 mmol) in THF (40 mL), under Ar, was treated with LiHMDS (1M in THF, 8.17 mL, 8.17 mmol), stirred for 0.5 h, treated with a solution of isopropenyl chloroformate (0.824 mL, 7.54 mmol) in THF (5 mL), stirred at −78° C. for 15 min, warmed to RT and stirred for 1 h. The mixture was treated with satd. NH$_4$Cl, the layers separated and the aqueous layer extracted with EtOAc (1×). The combined organics were washed with brine, dried over Na$_2$SO$_4$ and concentrated to dryness to afford crude prop-1-en-2-yl (1-methoxycyclopentanecarbonyl)carbamate (1.5 g, 105%) which was used without further purification. MS (ESI) m/z: 228.1 (M+H$^+$).

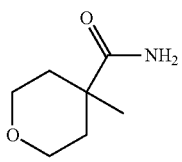

Example B24

A solution of methyl 4-methyltetrahydro-2H-pyran-4-carboxylate (5.00 g, 31.6 mmol) in 1:1:1 dioxane/water/MeOH (60 mL) was treated with lithium hydroxide hydrate (5.31 g, 126 mmol) and stirred at RT overnight. The mixture was partially concentrated, diluted with water and EtOAc and acidified to pH=1 with 6M HCl. The layers were separated, the aqueous layer extracted with additional EtOAc (50 mL) and the combined organics were washed with brine, dried over Na$_2$SO$_4$ and concentrated to dryness to afford 4-methyltetrahydro-2H-pyran-4-carboxylic acid (4.61 g, 100%). $^1$H NMR (400 MHz, DMSO-d$_6$): δ 12.29 (s, 1H), 3.65 (dt, J=11.8, 4.3 Hz, 2H), 3.33-3.32 (m, 2H), 1.87-1.86 (m, 2H), 1.35 (ddd, J=13.5, 9.9, 4.1 Hz, 2H), 1.13 (s, 3H).

A mixture of 4-methyltetrahydro-2H-pyran-4-carboxylic acid (2.60 g, 18.0 mmol), HOBt (2.76 g, 18.0 mmol) and EDC (4.49 g, 23.4 mmol) in MeCN (75 mL) was stirred at RT for 3 h, treated with NH$_4$OH (~15M, 7 mL, ~105 mmol) and stirred at RT overnight. The mixture was concentrated to dryness, and the residue was partitioned between satd. brine (40 mL) and DCM (100 mL). The aqueous was extracted with THF (50 mL) and DCM (5×30 mL). The combined organics were washed with 10% aq K$_2$CO$_3$ (50 mL), dried over Na$_2$SO$_4$ and concentrated in vacuo to afford 4-methyltetrahydro-2H-pyran-4-carboxamide (1.83 g, 70%). $^1$H NMR (400 MHz, DMSO-d$_6$): δ 7.14 (s, 1H), 6.86 (s, 1H), 3.60 (dt, J=11.7, 4.5 Hz, 2H), 3.36 (m, 2H), 1.91-1.89 (m, 2H), 1.30 (m, 2H), 1.08 (s, 3H).

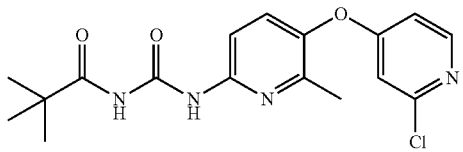 [SMILES: Cc1nc(NC(=O)NC(=O)C(C)(C)C)ccc1Oc1ccnc(Cl)c1]

Example C1

A solution of 2,2,2-trimethylacetamide (0.330 g, 3.26 mmol) in DCE (9.05 mL) was treated drop-wise with oxalyl chloride (0.285 mL, 3.26 mmol), heated at 80° C. for 2 h, cooled to RT, added drop-wise to a solution of Example A8 (0.640 g, 2.72 mmol) and pyridine (1.289 g, 16.29 mmol) in THF (9.05 mL) and stirred at RT overnight. The mixture was treated with satd. Na$_2$CO$_3$, extracted with EtOAc (4×) and the combined organics were dried over Na$_2$SO$_4$ and concentrated to dryness. The material was treated with MeCN, the solid collected via filtration and dried to afford N-((5-((2-chloropyridin-4-yl)oxy)-6-methylpyridin-2-yl)carbamoyl)pivalamide (813 mg, 83%) as an off-white solid. $^1$H NMR (400 MHz, DMSO-d$_6$): δ 11.15 (s, 1H), 10.40 (s, 1H), 8.27 (d, J=5.8 Hz, 1H), 7.90 (d, J=8.9 Hz, 1H), 7.65 (d, J=8.8 Hz, 1H), 7.02 (d, J=2.3 Hz, 1H), 6.92 (dd, J=5.8, 2.3 Hz, 1H), 2.22 (s, 3H), 1.19 (s, 9H); MS (ESI) m/z: 363.1 (M+H$^+$).

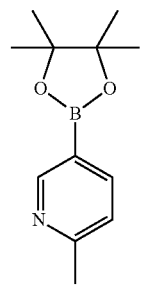

Example C2

A suspension of 5-bromo-2-methylpyridine (0.4 g, 2.325 mmol), bis(pinacolato)diboron (0.768 g, 3.02 mmol), KOAc (0.685 g, 6.98 mmol), and PdCl$_2$(dppf)-DCM adduct (0.114 g, 0.140 mmol) in dioxane (7.05 mL) was heated at 85° C. for 16 h. The mixture was cooled to RT, treated with EtOAc, the solids removed via filtration through diatomaceous earth and rinsed well with EtOAc. The filtrate was concentrated to dryness to afford 2-methyl-5-(4,4,5,5-tetramethyl-1,3,2-dioxaborolan-2-yl)pyridine (509 mg, 100%) as a brown oil.

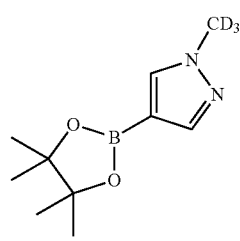 [SMILES: [2H]C([2H])([2H])n1cc(B2OC(C)(C)C(C)(C)O2)cn1]

Example C3

A 0° C. suspension of sodium hydride (60% in mineral oil, 0.928 g, 23.2 mmol) in DMF (12 mL) was treated with 4-(4,4,5,5-tetramethyl-1,3,2-dioxaborolan-2-yl)-1H-pyrazole (3.00 g, 15.46 mmol) under argon and stirred for 0.5 h. Trideuteroiodomethane (2.98 g, 20.56 mmol) was added, the mixture warmed to RT and stirred overnight. The mixture was cooled to 0° C., treated with satd. NH$_4$Cl, extracted with EtOAc (2×) and the combined organics were dried over Na$_2$SO$_4$ and concentrated to dryness to afford 4-(4,4,5,5-tetramethyl-1,3,2-dioxaborolan-2-yl)-1-(trideuteromethyl)-1H-pyrazole (1.05 g, 32%) as an oil. MS (ESI) m/z: 212.2 (M+H$^+$).

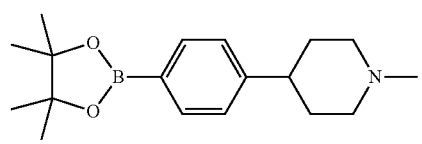

Example C4

A suspension of 4-(4-bromo-phenyl)-1-methyl-piperidine (0.3 g, 1.18 mmol), bis(pinacolato)diboron (0.390 g, 1.534 mmol), potassium acetate [KOAc] (0.232 g, 2.361 mmol), and PdCl$_2$(dppf)-DCM adduct (0.096 g, 0.118 mmol) in dioxane (6 mL) was sparged with Ar and heated at 85° C. overnight. The mixture was cooled to RT, treated with EtOAc and the solids removed via filtration through diatomaceous earth. The filtrate was concentrated to dryness to afford 1-methyl-4-(4-(4,4,5,5-tetramethyl-1,3,2-dioxaborolan-2-yl)phenyl) piperidine (100% yield assumed). MS (ESI) m/z: 302.3 (M+H⁺).

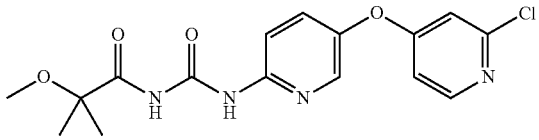 [SMILES: COC(C)(C)C(=O)NC(=O)Nc1ccc(Oc2ccnc(Cl)c2)cn1]

Example C5

A solution of Example B16 (0.545 g, 2.71 mmol), Example A9 (0.30 g, 1.354 mmol) and N-methylpyrrolidine (0.141 mL, 1.354 mmol) in dioxane (10 mL was heated at 80° C. overnight and then cooled to RT. The mixture was treated with satd. NaHCO₃, extracted with EtOAc (3×) and the combined organics were washed with brine, dried over Na₂SO₄ and concentrated to dryness. The crude was purified by silica gel chromatography (EtOAc/Hex) to afford N-((5-((2-chloropyridin-4-yl)oxy)pyridin-2-yl)carbamoyl)-2-methoxy-2-methylpropanamide (0.25 g, 50%). MS (ESI) m/z: 365.1 (M+H⁺).

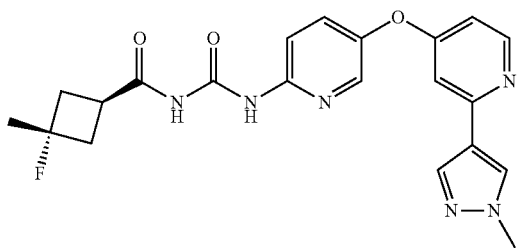

Example 1

Carbonyldiimidazole (42.6 g, 263 mmol) was slowly added to a solution of 3-oxo-cyclopropane carboxylic acid (25.0 g, 219 mmol) in DCM (500 mL), stirred at RT for 2 h, treated with benzyl alcohol (24.17 g, 223 mmol) and stirred at RT for 16 h. The mixture was diluted with water, extracted with DCM (2×) and the combined organics were washed with brine, dried over Na₂SO₄, concentrated to dryness and purified by silica gel chromatography (EtOAc/Hex) to afford benzyl 3-oxocyclobutanecarboxylate (29.5 g, 66%) as a colorless syrup. ¹H NMR (400 MHz, DMSO-d₆): δ 7.38-7.35 (m, 5H); 5.14 (s, 2H); 3.62 (m, 5H); MS (ESI) m/z: 227.1 (M+Na⁺).

A −78° C. solution of benzyl 3-oxocyclobutanecarboxylate (11.05 g, 54.1 mmol) in THF (155 mL) was treated drop-wise with methyl magnesium bromide (3M in Et₂O, 27.1 mL, 81 mmol) and the mixture stirred at −78° C. for 30 min. Saturated NH₄Cl was added, the mixture extracted with EtOAc (2×) and the combined organic extracts were dried, evaporated and purified via silica gel chromatography (acetone/Hex) to afford benzyl 3-hydroxy-3-methylcyclobutanecarboxylate (5.589 g, 47%) as a colorless oil. ¹H NMR (400 MHz, DMSO-d₆): δ 7.36-7.29 (m, 5H); 5.08 (m, 3H); 2.75-2.66 (m, 1H); 2.13-2.12 (m, 4H); 1.21 (s, 3H); MS (ESI) m/z: 243.1 (M+Na⁺).

A −78° C. solution of benzyl 3-hydroxy-3-methylcyclobutanecarboxylate (5.589 g, 25.4 mmol) in DCM (125 mL), under Ar, was treated with DAST (5.03 mL, 38.1 mmol), the mixture stirred at −78° C. for 0.5 h, then allowed to warm to RT overnight. The mixture was quenched with satd. NaHCO₃, extracted with EtOAc (2×) and the combined organics were dried over MgSO₄, concentrated to dryness and purified via silica gel chromatography (Et₂O/Hex) to afford benzyl 3-methyl-trans(3-fluorocyclobutanecarboxylate) (3.82 g, 68%) as a colorless oil. ¹H NMR (400 MHz, DMSO-d₆): δ 7.35 (m, 5H); 5.10 (s, 2H); 3.23 (m, 1H); 2.54 (m, 2H); 2.32 (m, 2H); 1.38 (d, J=22.3 Hz, 3H); MS (ESI) m/z: 245.1 (M+Na⁺).

A solution of benzyl 3-methyl-trans(3-fluorocyclobutanecarboxylate) (3.823 g, 17.20 mmol) in MeOH (100 mL) was treated with 10% palladium on carbon (dry) (1.831 g, 1.720 mmol) and hydrogenated at atmospheric pressure (balloon) overnight. The mixture was filtered through diatomaceous earth and the filtrate concentrated to dryness to afford 3-methyl-trans(3-fluorocyclobutanecarboxylic acid) (1.83 g, 81%) as a colorless oil. ¹H NMR (400 MHz, DMSO-d₆): δ 12.29 (s, 1H); 3.10-3.01 (m, 1H); 2.48-2.47 (m, 2H); 2.32-2.21 (m, 2H); 1.39 (d, J=22.3 Hz, 3H).

A solution of 3-methyl-trans(3-fluorocyclobutanecarboxylic acid) (0.124 g, 0.935 mmol) in DCM (5 mL) was treated with oxalyl chloride (0.246 mL, 2.81 mmol) and catalytic DMF (1 drop) and stirred at RT for 2 h. The mixture was concentrated to dryness, dissolved in toluene (5 mL), treated with powdered silver cyanate (0.561 g, 3.74 mmol) and heated at 90° C. for 2 h. The mixture was cooled to RT, treated with a solution of Example A2 (0.1 g, 0.374 mmol) in pyridine (5 mL) and stirred at RT overnight. The mixture was treated with EtOAc and 1N NaOH, filtered through diatomaceous earth and the layers of the filtrate separated. The aqueous layer was extracted with EtOAc (2×); the aqueous layer neutralized with 2N HCl and extracted with EtOAc (2×). The filter cake was washed with 2N HCl, the filtrate neutralized with NaHCO₃ and extracted with EtOAc (2×). All of the organic extracts were combined, dried over MgSO₄, concentrated to dryness and purified via preparative TLC (MeOH/DCM). The material was washed off the silica with MeOH/DCM, concentrated to dryness, dissolved in MeCN/H₂O, frozen and lyophilized to afford trans-3-fluoro-3-methyl-N-((5-((2-(1-methyl-1H-pyrazol-4-yl)pyridin-4-yl)oxy)pyridin-2-yl)carbamoyl)cyclobutanecarboxamide (15 mg, 9.5%) as a white solid. ¹H NMR (400 MHz, DMSO-d₆): δ 10.95 (s, 1H), 10.81 (s, 1H), 8.32 (d, J=5.7 Hz, 1H), 8.22-8.20 (m, 2H), 8.03 (d, J=9.0 Hz, 1H), 7.91 (d, J=0.7 Hz, 1H), 7.68 (dd, J=9.0, 3.0 Hz, 1H), 7.18 (d, J=2.4 Hz, 1H), 6.65 (dd, J=5.7, 2.4 Hz, 1H), 3.82 (m, 1H), 3.79 (s, 3H), 2.39-2.25 (m, 4H), 1.35 (m, 3H); MS (ESI) m/z: 425.2 (M+H⁺).

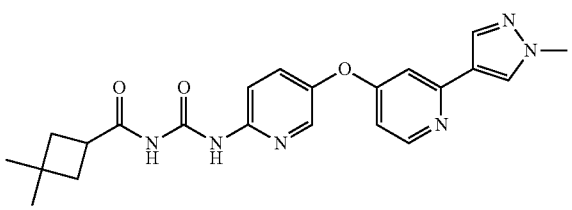

Example 2

A suspension of Example B1 (0.074 g, 0.584 mmol) in DCE (6 mL) was treated with oxalyl chloride (0.051 mL, 0.584 mmol), stirred at RT for 30 min, then warmed to 83° C. for 3 h. The mixture was cooled to RT and added drop-wise to a solution of Example A2 (0.13 g, 0.486 mmol) in THF (6.0 mL) and pyridine (0.197 mL, 2.43 mmol). The mixture was stirred at RT for 1 h, treated with satd. NaHCO$_3$, extracted with EtOAc (3×) and the combined organics were dried over MgSO$_4$ and concentrated to dryness. The residue was triturated with MeCN, sonicated for 5 min and the solid was collected via filtration and dried to afford 3,3-dimethyl-N-((5-((2-(1-methyl-1H-pyrazol-4-yl)pyridin-4-yl)oxy)pyridin-2-yl)carbamoyl)cyclobutanecarboxamide (125 mg, 61%) as a white solid. $^1$H NMR (400 MHz, DMSO-d$_6$): δ 11.11 (s, 1H), 10.70 (s, 1H), 8.37 (d, J=5.7 Hz, 1H), 8.27-8.25 (m, 2H), 8.07 (d, J=9.0 Hz, 1H), 7.96 (d, J=0.7 Hz, 1H), 7.72 (dd, J=9.0, 2.9 Hz, 1H), 7.23 (d, J=2.4 Hz, 1H), 6.70 (dd, J=5.7, 2.4 Hz, 1H), 3.84 (s, 3H), 3.24 (m, 1H), 2.03-1.87 (m, 4H), 1.13 (s, 3H), 1.05 (s, 3H); MS (ESI) m/z: 421.2 (M+H$^+$).

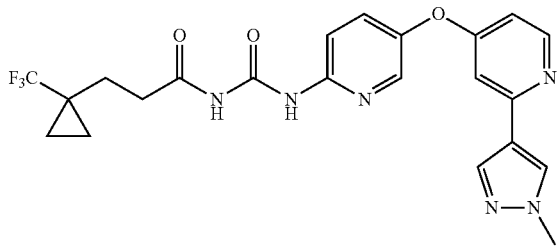 [SMILES: Cn1cc(-c2cc(Oc3ccc(NC(=O)NC(=O)CCC4(C(F)(F)F)CC4)nc3)ccn2)cn1]

Example 3

A suspension of Example B2 (0.081 g, 0.449 mmol) in DCE (6 mL) was treated with oxalyl chloride (0.039 mL, 0.449 mmol), stirred at RT for 0.5 h, then heated to 83° C. for 3 h. The mixture was cooled to RT, added drop-wise to a solution of Example A2 (0.10 g, 0.374 mmol) and pyridine (0.151 mL, 1.871 mmol) in THF (6 mL) and stirred at RT for 1 h. The mixture was treated with satd. NaHCO$_3$, extracted with EtOAc (3×) and the combined organics were dried over Na$_2$SO$_4$ and concentrated to dryness. The material was treated with MeCN, sonicated for 5 min and the resulting solid collected via filtration and dried to afford N-((5-((2-(1-methyl-1H-pyrazol-4-yl)pyridin-4-yl)oxy)pyridin-2-yl)carbamoyl)-3-(1-(trifluoromethyl)cyclopropyl)propanamide (98 mg, 55%) as a white solid. $^1$H NMR (400 MHz, DMSO-d$_6$): δ 10.98 (s, 1H), 10.89 (s, 1H), 8.37 (d, J=5.7 Hz, 1H), 8.27-8.25 (m, 2H), 8.08 (d, J=9.0 Hz, 1H), 7.96 (s, 1H), 7.73 (dd, J=9.0, 2.9 Hz, 1H), 7.23 (d, J=2.4 Hz, 1H), 6.70 (dd, J=5.7, 2.4 Hz, 1H), 3.84 (s, 3H), 2.57 (t, J=8.0 Hz, 2H), 1.87 (t, J=8.0 Hz, 2H), 0.91 (m, 2H), 0.78 (m, 2H); MS (ESI) m/z: 475.1 (M+H$^+$).

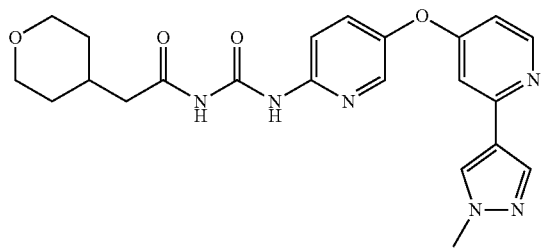 [SMILES: Cn1cc(-c2cc(Oc3ccc(NC(=O)NC(=O)CC4CCOCC4)nc3)ccn2)cn1]

Example 4

A 0° C. solution of tetrahydropyran-4-ylacetyl chloride (0.500 g, 3.07 mmol) in THF (25 mL) was treated drop-wise with NH$_4$OH (~15M, 2.05 mL, ~30.7 mmol), allowed to warm to RT and stirred overnight. The mixture was concentrated to dryness, co-evaporated with IPA (2×), then suspended in IPA and the solids removed via filtration. The filtrate was concentrated to dryness to afford 2-(tetrahydro-2H-pyran-4-yl)acetamide (510 mg, 116%) as a white solid. $^1$H NMR (400 MHz, DMSO-d$_6$): δ 7.25 (s, 1H), 6.73 (s, 1H), 3.78 (dd, J=11.4, 4.1 Hz, 2H), 3.29-3.19 (m, 2H), 2.15-1.92 (m, 2H), 1.91-1.78 (m, 1H), 1.58-1.48 (m, 2H), 1.23-1.06 (m, 2H); MS (ESI) m/z: 144.1 (M+H$^+$).

A suspension of 2-(tetrahydro-2H-pyran-4-yl)acetamide (0.44 g, 3.07 mmol) in DCE (15 mL) was treated drop-wise with oxalyl chloride (0.336 mL, 3.84 mmol) then heated at 80° C. overnight. The mixture was cooled to RT and concentrated to dryness to afford crude 2-(tetrahydro-2H-pyran-4-yl)acetyl isocyanate (470 mg, 90%). A solution of the crude 2-(tetrahydro-2H-pyran-4-yl)acetyl isocyanate (0.100 g, 0.591 mmol) and Example A2 (0.105 g, 0.394 mmol) in THF (6 mL) was stirred at RT overnight. The solids were removed via filtration and the filtrate concentrated to dryness and purified via silica gel chromatography (MeOH/EtOAc). The isolated material was re-purified via reverse-phase chromatography (MeCN/H$_2$O with 0.1% TFA) and the organics removed under reduced pressure. The aqueous residue was frozen and lyophilized. The solid was treated with satd. NaHCO$_3$, extracted with DCM (3×) and the combined organics were washed with H$_2$O, concentrated to dryness, dissolved in 4:1 MeCN/H$_2$O, frozen and lyophilized to afford N-((5-((2-(1-methyl-1H-pyrazol-4-yl)pyridin-4-yl)oxy)pyridin-2-yl)carbamoyl)-2-(tetrahydro-2H-pyran-4-yl)acetamide (22 mg, 13%) as a white solid. $^1$H NMR (400 MHz, DMSO-d$_6$): δ 11.44 (s, 1H), 10.89 (s, 1H), 8.36 (d, J=5.7 Hz, 1H), 8.25 (s, 1H), 8.19 (d, J=2.9 Hz, 1H), 8.13 (d, J=9.1 Hz, 1H), 7.95 (s, 1H), 7.64 (m, 1H), 7.20 (d, J=2.4 Hz, 1H), 6.68 (dd, J=5.7, 2.5 Hz, 1H), 3.84 (s, 3H), 3.80 (m, 2H), 3.26 (d, J=11.7 Hz, 2H), 2.22 (d, J=7.0 Hz, 2H), 1.94 (m, 1H), 1.56 (d, J=13.1 Hz, 2H), 1.18 (m, 2H); MS (ESI) m/z: 437.2 (M+H$^+$).

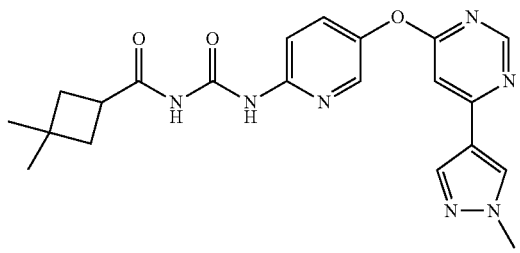

Example 5

A −10° C. suspension of NaH (60% in mineral oil, 0.726 g, 18.16 mmol) in anhydrous DMA (15 mL) was treated with 6-aminopyridin-3-ol (1.0 g, 9.08 mmol), stirred cold for 30 min, treated drop-wise with a solution of 4,6-dichloropyrimidine (2.029 g, 13.62 mmol) in DMA (10 mL), warmed to RT and stirred for 2 h. The mixture was treated with H$_2$O, extracted with DCM (3×) and the combined organics were washed with 5% LiCl, then brine, dried over Na$_2$SO$_4$, concentrated to dryness and purified via silica gel chromatography (EtOAc) to afford 5-((6-chloropyrimidin-4-yl)oxy)pyridin-2-amine (1.0 g, 49%). ¹H NMR (400 MHz, DMSO-d₆): δ 8.62 (d, J=0.9 Hz, 1H), 7.79 (d, J=2.9 Hz, 1H), 7.33-7.26 (m, 2H), 6.48 (d, J=8.9 Hz, 1H), 6.00 (s, 2H); MS (ESI) m/z: 223.0 (M+H⁺).

A mixture of 5-((6-chloropyrimidin-4-yl)oxy)pyridin-2-amine (0.50 g, 2.246 mmol), 1-methyl-4-(4,4,5,5-tetramethyl-1,3,2-dioxaborolan-2-yl)-1H-pyrazole (0.467 g, 2.246 mmol), and Cs₂CO₃ (1.463 g, 4.49 mmol) in dioxane/H₂O (5:1, 6 mL) was sparged with argon, treated with Pd(PPh₃)₄ (0.260 g, 0.225 mmol), sparged again with argon and heated at 90° C. overnight. The mixture was cooled to RT, the solids removed via filtration, rinsed with dioxane and the filtrate concentrated to dryness. The material was treated with EtOAc, the solid collected via filtration, rinsed with EtOAc and H₂O and dried to obtain product. The layers of the filtrate were separated, the organic layer washed with brine, dried over Na₂SO₄, concentrated to dryness, triturated with EtOAc and the solid collected via filtration and combined with the above-isolated product to afford 5-((6-(1-methyl-1H-pyrazol-4-yl)pyrimidin-4-yl)oxy)pyridin-2-amine (410 mg, 68%). ¹H NMR (400 MHz, DMSO-d₆): δ 8.60 (d, J=1.1 Hz, 1H), 8.44 (s, 1H), 8.12 (s, 1H), 7.78 (d, J=2.9 Hz, 1H), 7.30-7.25 (m, 2H), 6.48 (d, J=8.9 Hz, 1H), 5.94 (s, 2H), 3.88 (s, 3H); MS (ESI) m/z: 269.1 (M+H⁺).

A solution of Example B1 (0.120 g, 0.944 mmol) in dioxane (10 mL) was treated with oxalyl chloride (0.120 g, 0.945 mmol), heated at 100° C. for 3 h, concentrated to dryness, dissolved in DCM (10 mL), added to a solution of 5-((6-(1-methyl-1H-pyrazol-4-yl)pyrimidin-4-yl)oxy)pyridin-2-amine (0.120 g, 0.447 mmol) in DCM (10 mL) and pyridine (0.070 g, 0.885 mmol) and stirred at RT overnight. The mixture was concentrated to dryness treated with MeCN and the solid collected via filtration and dried to afford 3,3-dimethyl-N-((5-((6-(1-methyl-1H-pyrazol-4-yl)pyrimidin-4-yl)oxy)pyridin-2-yl)carbamoyl)cyclobutanecarboxamide (95 mg, 49%) as an off-white solid. ¹H NMR (400 MHz, DMSO-d₆): δ 11.07 (s, 1H), 10.71 (s, 1H), 8.63 (s, 1H), 8.47 (s, 1H), 8.26 (d, J=2.8 Hz, 1H), 8.16 (s, 1H), 8.05 (d, J=9.0 Hz, 1H), 7.75 (dd, J=9.0, 2.8 Hz, 1H), 7.43 (s, 1H), 3.89 (s, 3H), 3.30 (m, 1H), 2.00 (m, 4H), 1.13 (s, 3H), 1.05 (s, 3H); MS (ESI) m/z: 422.2 (M+H⁺).

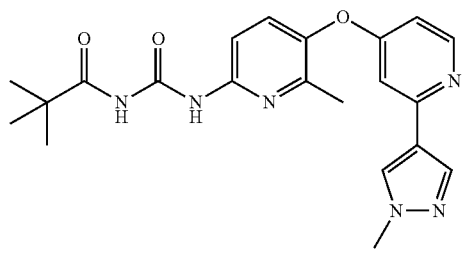

Example 6

A suspension of 2,2,2-trimethylacetamide (0.065 g, 0.640 mmol) in DCE (4 mL) was treated with oxalyl chloride (0.056 mL, 0.640 mmol), stirred at RT for 1 h, heated to 80° C. for 2.5 h, then cooled to RT and added drop-wise to a solution of Example A6 (0.15 g, 0.533 mmol) in THF (4 mL) and pyridine (0.215 mL, 2.67 mmol). The mixture was stirred at RT for 1 h, treated with satd. NaHCO₃, extracted with EtOAc (2×) and the combined organics were washed with brine, dried over Na₂SO₄ and concentrated to dryness. The material was treated with EtOAc, allowed to stand at RT and the resulting solid collected via filtration and dried to afford N-((6-methyl-5-((2-(1-methyl-1H-pyrazol-4-yl)pyridin-4-yl)oxy)pyridin-2-yl)carbamoyl)pivalamide (150 mg, 69%) as a white solid. ¹H NMR (400 MHz, DMSO-d₆): δ 11.16 (s, 1H), 10.41 (s, 1H), 8.35 (d, J=5.7 Hz, 1H), 8.25 (s, 1H), 7.96 (d, J=0.7 Hz, 1H), 7.91 (m, 1H), 7.63 (d, J=8.8 Hz, 1H), 7.16 (d, J=2.4 Hz, 1H), 6.61 (dd, J=5.7, 2.5 Hz, 1H), 3.84 (s, 3H), 2.26 (s, 3H), 1.21 (s, 9H); MS (ESI) m/z: 409.2 (M+H⁺).

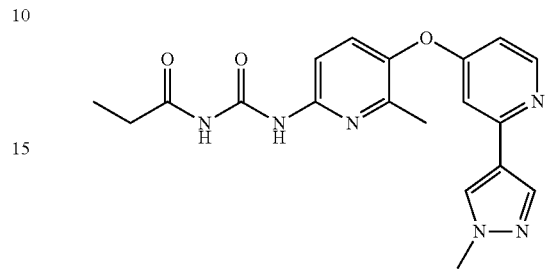

Example 7

A suspension of propionamide (0.047 g, 0.640 mmol) in DCE (4 mL) was treated with oxalyl chloride (0.056 mL, 0.640 mmol), stirred at RT for 1 h, warmed to 80° C. for 2.5 h, cooled to RT, added drop-wise to a solution of Example A6 (0.15 g, 0.533 mmol) in THF (4 mL) and pyridine (0.215 mL, 2.67 mmol) and stirred at RT for 1 h. The mixture was treated with NaHCO₃, extracted with EtOAc (2×) and the combined organics were washed with brine, dried over Na₂SO₄ and concentrated to dryness. The resulting material was treated with EtOAc, allowed to stand at RT and the solid collected via filtration and dried to afford N-((6-methyl-5-((2-(1-methyl-1H-pyrazol-4-yl)pyridin-4-yl)oxy)pyridin-2-yl)carbamoyl)propionamide (110 mg, 54%) as a white solid. ¹H NMR (400 MHz, DMSO-d₆): δ 11.00 (s, 1H), 10.80 (s, 1H), 8.35 (d, J=5.7 Hz, 1H), 8.25 (s, 1H), 7.96 (d, J=0.7 Hz, 1H), 7.91 (d, J=8.8 Hz, 1H), 7.62 (d, J=8.8 Hz, 1H), 7.17 (d, J=2.4 Hz, 1H), 6.61 (dd, J=5.7, 2.4 Hz, 1H), 3.84 (s, 3H), 2.41 (q, J=7.5 Hz, 2H), 2.26 (s, 3H), 1.05 (t, J=7.5 Hz, 3H); MS (ESI) m/z: 381.2 (M+H⁺).

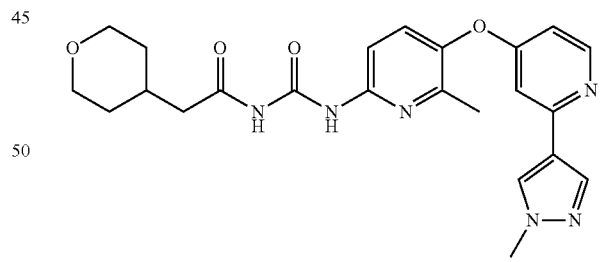

Example 8

A solution of crude 2-(tetrahydro-2H-pyran-4-yl)acetyl isocyanate (0.110 g, 0.650 mmol, see Example 4) in DCE (7 mL) was treated with Example A6 (0.183 g, 0.650 mmol) and stirred at RT overnight. Pyridine (0.11 mL, 1.3 mmol) was added, the mixture stirred at RT for 4 h, treated with THF, then washed with satd. NaHCO₃ and brine, dried over MgSO₄ and concentrated to dryness. The resulting material was treated with MeCN, and the solid collected via filtration and dried to afford N-((6-methyl-5-((2-(1-methyl-1H-pyrazol-4-yl)pyridin-4-yl)oxy)pyridin-2-yl)carbamoyl)-2-(tetrahydro-2H-pyran-4-yl)acetamide (56 mg, 19%) as a pale tan solid. MS (ESI) m/z: 451.2 (M+H⁺).

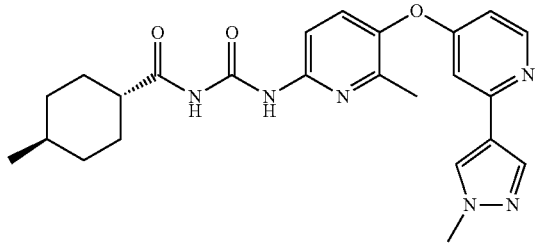 [SMILES: Cc1nc(NC(=O)NC(=O)[C@H]2CC[C@H](C)CC2)ccc1Oc1ccnc(-c2cnn(C)c2)c1]

Example 9

A solution of trans-4-methylcyclohexane carboxylic acid (1.00 g, 7.03 mmol) in EtOAc (15 mL) was treated with CDI (1.425 g, 8.79 mmol) and stirred at RT for 20 minutes. Ammonium hydroxide (~14M, 5.00 mL, ~70.0 mmol) was added, the mixture stirred for 20 minutes, then concentrated to dryness. The material was treated with satd. NaHCO₃ and the solids collected via filtration and dried to afford trans-4-methylcyclohexanecarboxamide (842 mg, 85%) as a white solid. ¹H NMR (400 MHz, DMSO-d₆): δ 7.13 (s, 1H), 6.61 (s, 1H), 1.94 (m, 1H), 1.70 (m, 4H), 1.25 (m, 3H), 0.84 (m, 5H); MS (ESI) m/z: 142.1 (M+H⁺).

A solution of trans-4-methylcyclohexanecarboxamide (0.275 g, 1.94 mmol) in dioxane (7.5 mL) was treated with oxalyl chloride (0.300 g, 2.36 mmol) and heated at 100° C. for 2 h. The mixture was cooled to RT and concentrated to dryness. The residue was dissolved in DCM (8 mL) and added to a suspension of Example A6 (0.250 g, 0.889 mmol) in DCM (8 mL) and pyridine (0.100 g, 1.264 mmol) and the mixture was stirred at RT overnight. The mixture was concentrated to dryness, treated with MeCN and the solid was collected via filtration and dried to afford trans-4-methyl-N-((6-methyl-5-((2-(1-methyl-1H-pyrazol-4-yl)pyridin-4-yl)oxy)pyridin-2-yl)carbamoyl)cyclohexanecarboxamide (262 mg, 65%) as a white solid. ¹H NMR (400 MHz, DMSO-d₆): δ 11.05 (s, 1H), 10.80 (s, 1H), 8.35 (d, J=5.7 Hz, 1H), 8.25 (s, 1H), 7.95 (d, J=0.7 Hz, 1H), 7.90 (d, J=8.8 Hz, 1H), 7.61 (d, J=8.8 Hz, 1H), 7.16 (d, J=2.4 Hz, 1H), 6.60 (dd, J=5.7, 2.4 Hz, 1H), 3.84 (s, 3H), 2.36 (m, 1H), 2.25 (s, 3H), 1.75 (m, 4H), 1.38 (m, 3H), 0.88 (m, 5H); MS (ESI) m/z: 449.2 (M+H⁺).

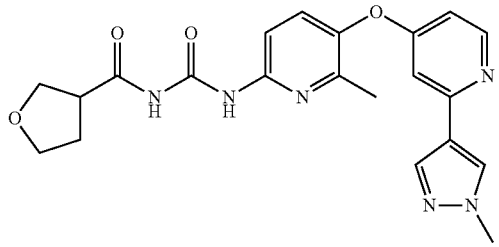 [SMILES: Cc1nc(NC(=O)NC(=O)C2CCOC2)ccc1Oc1ccnc(-c2cnn(C)c2)c1]

Example 10

Method A: A solution of Example B3 (0.200 g, 1.737 mmol) in dioxane (10 mL) was treated with oxalyl chloride (0.200 g, 1.576 mmol), heated at 100° C. for 3 h, then cooled to RT and concentrated to dryness. The residue was dissolved in DCM (8 mL) and added to a solution of Example A6 (0.202 g, 0.716 mmol) in a DCM (8 mL) and pyridine (0.170 g, 2.149 mmol) and stirred at RT overnight. The mixture was concentrated to dryness and purified via silica gel chromatography (MeOH/DCM) to afford N-((6-methyl-5-((2-(1-methyl-1H-pyrazol-4-yl)pyridin-4-yl)oxy)pyridin-2-yl)carbamoyl)tetrahydrofuran-3-carboxamide (50 mg, 16%) as a white solid. MS (ESI) m/z: 423.2 (M+H⁺).

Method B: A solution of tetrahydrofuran-3-carboxylic acid (4.00 g, 34.4 mmol) in DCM (40 mL) was treated with oxalyl chloride (5.00 g, 39.4 mmol) and a drop of DMF and the mixture was stirred at RT for 1 h. The reaction was concentrated to dryness. The residue was dissolved in DCM (40 mL), treated with silver cyanate (8.00 g, 53.4 mmol), and stirred at RT for 1 h. Example A6 (3.20 g, 11.4 mmol) and pyridine (0.090 g, 1.138 mmol) were added and the mixture was stirred at RT overnight. The mixture was filtered and the solids were washed with DCM and THF. The combined filtrates were concentrated to dryness and purified via silica gel chromatography (THF/EtOAc). The purified residue was stirred in water (60 mL) for 4 h and the solid was collected by filtration, washed, and dried in vacuo to provide N-((6-methyl-5-((2-(1-methyl-1H-pyrazol-4-yl)pyridin-4-yl)oxy)pyridin-2-yl)carbamoyl)tetrahydrofuran-3-carboxamide (2.3 g, 48%) as a white solid. ¹H NMR (400 MHz, DMSO-d₆): δ 10.98 (s, 1H), 10.95 (s, 1H), 8.35 (d, J=5.7 Hz, 1H), 8.25 (s, 1H), 7.96 (s, 1H), 7.90 (d, J=8.8 Hz, 1H), 7.62 (d, J=8.8 Hz, 1H), 7.17 (d, J=2.4 Hz, 1H), 6.60 (dd, J=5.7, 2.4 Hz, 1H), 3.88 (t, J=8.4 Hz, 1H), 3.84 (s, 3H), 3.79-3.73 (m, 2H), 3.68 (m, 1H), 3.24 (m, 1H), 2.26 (s, 3H), 2.07 (m, 2H); MS (ESI) m/z: 423.2 (M+H⁺).

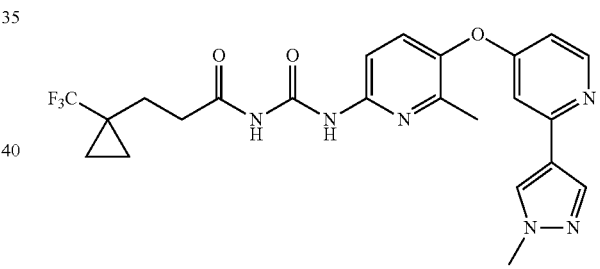

Example 11

A solution of Example B2 (0.087 g, 0.480 mmol) in DCE (3 mL) was treated with oxalyl chloride (0.048 mL, 0.544 mmol) and heated at 80° C. for 4 h. The mixture was cooled to RT, added to a solution of Example A6 (0.09 g, 0.320 mmol) and TEA (0.133 mL, 0.960 mmol) in DCM (2 mL) and stirred at RT overnight. The mixture was concentrated to dryness, purified via silica gel chromatography (MeOH/DCM), dissolved in MeCN/H₂O, frozen and lyophilized to afford N-((6-methyl-5-((2-(1-methyl-1H-pyrazol-4-yl)pyridin-4-yl)oxy)pyridin-2-yl)carbamoyl)-3-(1-(trifluoromethyl)cyclopropyl)propanamide (107 mg, 68%) as a white solid. ¹H NMR (400 MHz, DMSO-d₆): δ 10.92 (s, 1H), 10.87 (s, 1H), 8.35 (d, J=5.7 Hz, 1H), 8.26 (s, 1H), 7.96 (s, 1H), 7.90 (d, J=8.8 Hz, 1H), 7.62 (d, J=8.8 Hz, 1H), 7.18 (s, 1H), 6.62 (s, 1H), 3.84 (s, 3H), 2.57 (t, J=8.0 Hz, 2H), 2.25 (s, 3H), 1.87 (t, J=8.0 Hz, 2H), 0.91 (t, J=5.9 Hz, 2H), 0.78 (m, 2H); MS (ESI) m/z: 489.2 (M+H⁺).

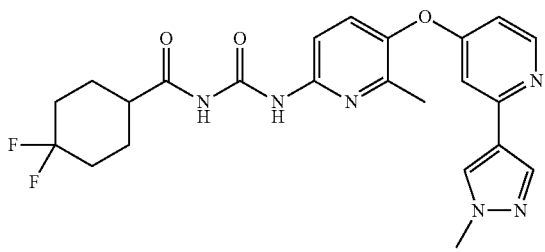 [SMILES: Cc1nc(NC(=O)NC(=O)C2CCC(F)(F)CC2)ccc1Oc1ccnc(-c2cnn(C)c2)c1]

Example 12

A solution of triethylamine trihydrofluoride (0.479 mL, 2.94 mmol) in DCE (6 mL) at RT was treated with XtalFluor-M (1.071 g, 4.41 mmol) followed by ethyl 4-oxo-cyclohexanecarboxylate (0.500 g, 2.94 mmol) and the mixture heated to reflux for 2.5 h. The mixture was cooled to RT, treated with satd. NaHCO$_3$ and stirred overnight. The mixture was diluted with DCM, the layers separated, the aqueous layer extracted with additional DCM (1×) and the combined organics were dried over MgSO$_4$ and filtered through a small pad of silica gel, rinsing well with DCM. The filtrate was concentrated to dryness and purified via silica gel chromatography (DCM/Hex) to afford ethyl 4,4-difluorocyclohexanecarboxylate (390 mg, 69%) as a colorless oil. $^1$H NMR (400 MHz, DMSO-d$_6$): δ 4.05 (q, J=7.1 Hz, 2H), 2.49 (m, 1H), 2.02-1.77 (m, 6H), 1.65-1.50 (m, 2H), 1.16 (t, J=7.1 Hz, 3H).

A solution of ethyl 4,4-difluorocyclohexanecarboxylate (0.385 g, 2.003 mmol) in THF (12 mL) was treated with H$_2$O (6 mL) followed by lithium hydroxide monohydrate (0.420 g, 10.02 mmol) and the mixture stirred vigorously at RT overnight. The mixture was treated with EtOAc, acidified with 1M HCl until pH 4, the layers separated and the aqueous layer extracted with additional EtOAc (1×). The combined organics were washed with brine, dried over MgSO$_4$ and concentrated to dryness to afford 4,4-difluorocyclohexanecarboxylic acid (318 mg, 97%) as a white solid. $^1$H NMR (400 MHz, DMSO-d$_6$): δ 12.28 (s, 1H), 2.40 (m, 1H), 2.02-1.75 (m, 6H), 1.59 (m, 2H).

A solution of 4,4-difluorocyclohexanecarboxylic acid (0.217 g, 1.322 mmol) in DCM (4 mL) was treated with oxalyl chloride (0.174 mL, 1.983 mmol) followed by catalytic DMF (1 drop) and the mixture stirred at RT for 1.5 h. The mixture was concentrated to dryness, co-evaporated with DCM (1×) and the resulting residue dissolved in THF (2 mL), added to a stirring solution of NH$_4$OH (~14M, 2 mL, 28.0 mmol) in THF (2 mL) and stirred for 30 minutes. The mixture was diluted with brine, extracted with EtOAc (3×) and the combined organics were dried over MgSO$_4$ and concentrated to dryness to afford 4,4-difluorocyclohexanecarboxamide (167 mg, 77%) as a white solid. $^1$H NMR (400 MHz, DMSO-d$_6$): δ 7.28 (s, 1H), 6.79 (s, 1H), 2.20 (m, 1H), 2.00 (m, 2H), 1.86-1.67 (m, 4H), 1.57 (m, 2H).

A thin suspension of 4,4-difluorocyclohexanecarboxamide (0.083 g, 0.510 mmol) in DCE (5 mL) was treated with oxalyl chloride (0.045 mL, 0.510 mmol), stirred at RT for 30 minutes, then heated to reflux for 3 h. The mixture was cooled to RT, added drop-wise to a solution of Example A6 (0.120 g, 0.425 mmol) and pyridine (0.172 mL, 2.126 mmol) in THF (5 mL) and stirred at RT overnight. The mixture was treated with satd. NaHCO$_3$, extracted with EtOAc (2×) and the combined organics were dried over MgSO$_4$ and concentrated to dryness. The resulting material was triturated with DCM, the solid collected via filtration and dried to afford 4,4-difluoro-N-((6-methyl-5-((2-(1-methyl-1H-pyrazol-4-yl)pyridin-4-yl)oxy)pyridin-2-yl)carbamoyl)cyclohexanecarboxamide (88 mg, 44%) as a white solid. $^1$H NMR (400 MHz, DMSO-d$_6$): δ 10.94 (s, 1H), 10.91 (s, 1H), 8.35 (d, J=5.7 Hz, 1H), 8.24 (s, 1H), 7.95 (s, 1H), 7.90 (d, J=8.8 Hz, 1H), 7.62 (d, J=8.8 Hz, 1H), 7.16 (d, J=2.4 Hz, 1H), 6.60 (dd, J=5.7, 2.4 Hz, 1H), 3.84 (s, 3H), 2.58 (m, 1H), 2.25 (s, 3H), 2.08 (m, 2H), 1.98-1.57 (m, 6H); MS (ESI) m/z: 471.1 (M+H$^+$).

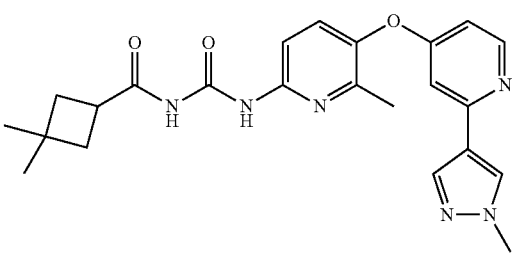

Example 13

A suspension of Example B (0.054 g, 0.427 mmol) in DCE (4 mL) was treated with oxalyl chloride (0.037 mL, 0.427 mmol), heated at 83° C. for 2 h, cooled to RT and added drop-wise to a solution of Example A6 (0.1 g, 0.355 mmol) in THF (4 mL) and pyridine (0.144 mL, 1.777 mmol). The mixture was stirred at RT for 2 h, treated with satd. NaHCO$_3$, extracted with EtOAc (3×) and the combined organics were dried over MgSO$_4$, concentrated to dryness, triturated with MeCN, and the solid collected via filtration and dried to afford 3,3-dimethyl-N-((6-methyl-5-((2-(1-methyl-1H-pyrazol-4-yl)pyridin-4-yl)oxy)pyridin-2-yl)carbamoyl)cyclobutanecarboxamide (134 mg, 87%) as a white solid. $^1$H NMR (400 MHz, DMSO-d$_6$): δ 11.06 (s, 1H), 10.69 (s, 1H), 8.35 (d, J=5.7 Hz, 1H), 8.25 (s, 1H), 7.95 (s, 1H), 7.90 (d, J=8.8 Hz, 1H), 7.61 (d, J=8.8 Hz, 1H), 7.16 (d, J=2.4 Hz, 1H), 6.60 (dd, J=5.7, 2.4 Hz, 1H), 3.84 (s, 3H), 3.24 (m, 1H), 2.26 (s, 3H), 2.02-1.87 (m, 4H), 1.13 (s, 3H), 1.05 (s, 3H); MS (ESI) m/z: 435.2 (M+H$^+$).

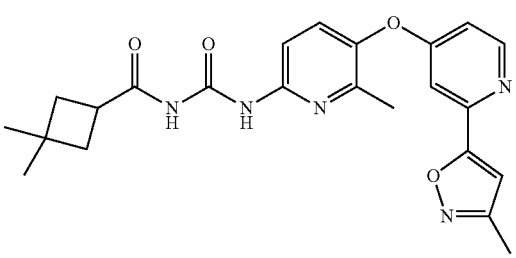

Example 14

A solution of Example B1 (0.028 g, 0.221 mmol) in DCE (4 mL) was treated with oxalyl chloride (0.019 mL, 0.221 mmol), heated at 83° C. for 2 h, cooled to RT, added drop-wise to a solution of Example A7 (0.052 g, 0.184 mmol) and pyridine (0.074 mL, 0.921 mmol) in THF (4.0 mL) and stirred at RT for 2 h. The mixture was treated with satd. NaHCO$_3$, extracted with EtOAc (3×) and the combined organics were dried over MgSO$_4$ and concentrated to dryness. The resulting material was treated with MeCN and the solid collected via filtration and dried to afford 3,3-dimethyl-N-((6-methyl-5-((2-(3-methylisoxazol-5-yl)pyridin-4-yl)oxy)pyridin-2-yl)carbamoyl)cyclobutanecarboxamide (51 mg, 64%) as a white solid. ¹H NMR (400 MHz, DMSO-d₆): δ 11.08 (s, 1H), 10.70 (s, 1H), 8.56 (d, J=5.7 Hz, 1H), 7.92 (d, J 8.8 Hz, 1H), 7.68 (d, J=8.8 Hz, 1H), 7.35 (d, J=2.5 Hz, 1H), 6.98-6.95 (m, 2H), 3.25 (m, 1H), 2.28 (s, 3H), 2.26 (s, 3H), 2.02-1.88 (m, 4H), 1.13 (s, 3H), 1.05 (s, 3H); MS (ESI) m/z: 436.2 (M+H⁺).

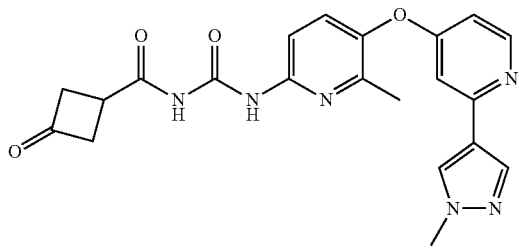 [SMILES: Cc1nc(NC(=O)NC(=O)C2CC(=O)C2)ccc1Oc1ccnc(-c2cnn(C)c2)c1]

Example 15

A thin suspension of Example B4 (0.055 g, 0.407 mmol) in DCE (4 mL) was treated with oxalyl chloride (0.036 mL, 0.407 mmol), stirred at RT for 30 minutes, then heated to reflux for 3 h. The mixture was cooled to RT, added drop-wise to a solution of Example A6 (0.095 g, 0.339 mmol) and pyridine (0.137 mL, 1.696 mmol) in THF (4 mL) and stirred at RT for 1 h. The mixture was treated with satd. NaHCO₃, extracted with EtOAc (2×), and the combined organics dried over MgSO₄ and concentrated to dryness. The material was triturated with Et₂O, the solid collected via filtration and dried to afford N-((6-methyl-5-((2-(1-methyl-1H-pyrazol-4-yl)pyridin-4-yl)oxy)pyridin-2-yl)carbamoyl)-3-oxocyclobutanecarboxamide (116 mg, 81%) as a tan solid. ¹H NMR (400 MHz, DMSO-d₆): δ 11.11 (s, 1H), 10.94 (s, 1H), 8.35 (d, J=5.7 Hz, 1H), 8.25 (s, 1H), 7.95 (s, 1H), 7.91 (d, J=8.8 Hz, 1H), 7.63 (d, J=8.8 Hz, 1H), 7.17 (d, J=2.4 Hz, 1H), 6.60 (dd, J=5.7, 2.4 Hz, 1H), 3.84 (s, 3H), 3.42 (m, 1H), 3.30 (m, 2H), 3.29 (m, 2H), 2.26 (s, 3H); MS (ESI) m/z: 421.1 (M+H⁺).

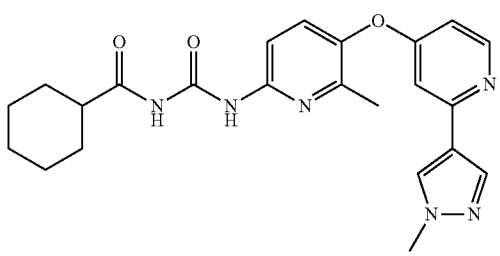 [SMILES: Cc1nc(NC(=O)NC(=O)C2CCCCC2)ccc1Oc1ccnc(-c2cnn(C)c2)c1]

Example 16

A solution of cyclohexanecarboxylic acid (1.00 g, 7.80 mmol) in EtOAc (10 mL) was treated with CDI (1.581 g, 9.75 mmol), stirred at RT for 20 minutes, treated with ammonium hydroxide (5.00 mL, 70.0 mmol) and stirred for 20 minutes. The mixture was treated with satd. NaHCO₃, extracted with EtOAc (2×) and the combined organics were dried over Na₂SO₄ and concentrated to dryness to afford cyclohexanecarboxamide (1.109 g, 112%) as a white solid. ¹H NMR (400 MHz, CDCl₃): δ 5.61 (s, 2H), 2.13 (m, 1H), 1.89 (m, 2H), 1.78 (m, 2H), 1.66 (m, 1H), 1.42 (m, 2H), 1.24 (m, 3H).

A solution of cyclohexanecarboxamide (0.260 g, 2.044 mmol) in dioxane (5 mL) was treated with oxalyl chloride (0.15 mL, 1.747 mmol), heated at 100° C. for 1.5 h, cooled to RT and concentrated to dryness. The residue was dissolved in DCM (5 mL), treated drop-wise with a solution of Example A6 (0.100 g, 0.355 mmol) in DCM (1 mL) and pyridine (0.2 mL, 2.483 mmol) and stirred at RT for 1 h. The mixture was treated with H₂O, the layers separated and the aqueous layer extracted with DCM (2×). The combined organics were dried over Na₂SO₄ and concentrated to dryness. The resulting material was suspended in MeCN and briefly sonicated. The solid was collected via filtration, and further purified via silica gel chromatography (MeOH/DCM). The material was suspended in MeCN/H₂O, frozen, lyophilized and dried under vacuum at 80° C. to afford N-((6-methyl-5-((2-(1-methyl-1H-pyrazol-4-yl)pyridin-4-yl)oxy)pyridin-2-yl)carbamoyl)cyclohexanecarboxamide (93 mg, 60%) as a white solid. ¹H NMR (400 MHz, DMSO-d₆): δ 11.05 (s, 1H), 10.78 (s, 1H), 8.35 (d, J=5.7 Hz, 1H), 8.25 (s, 1H), 7.95, (s, 1H), 7.90 (d, J=8.8 Hz, 1H), 7.61 (d, J=8.8 Hz, 1H), 7.16 (d, J=2.4 Hz, 1H), 6.60 (dd, J=5.7, 2.5 Hz, 1H), 3.84 (s, 3H), 2.44-2.38 (m, 1H), 2.25 (s, 3H), 1.84-1.66 (m, 4H), 1.65-1.57 (m, 1H), 1.42-1.10 (m, 5H); MS (ESI) m/z: 435.2 (M+H⁺).

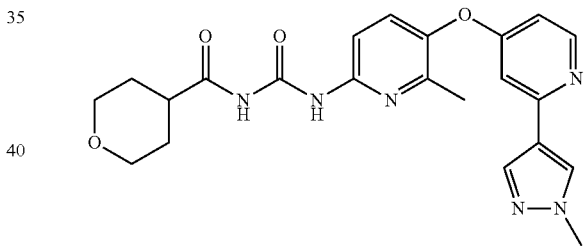

Example 17

A solution of Example B5 (0.103 g, 0.800 mmol) in DCE (3 mL) was treated with oxalyl chloride (0.070 mL, 0.800 mmol) and heated at 80° C. for 4 h. The mixture was cooled to RT, added to a solution of Example A6 (0.09 g, 0.320 mmol) and TEA (0.129 g, 1.280 mmol) in DCM (2 mL) and stirred at RT overnight. The mixture was concentrated to dryness and purified via silica gel chromatography (MeOH/DCM) to afford N-((6-methyl-5-((2-(1-methyl-1H-pyrazol-4-yl)pyridin-4-yl)oxy)pyridin-2-yl)carbamoyl)tetrahydro-2H-pyran-4-carboxamide (88 mg, 63%) as a white solid. ¹H NMR (400 MHz, DMSO-d₆): δ 11.00 (s, 1H), 10.87 (s, 1H), 8.35 (d, J=5.7 Hz, 1H), 8.25 (s, 1H), 7.95 (s, 1H), 7.90 (d, J=8.8 Hz, 1H), 7.62 (d, J=8.8 Hz, 1H), 7.16 (d, J=2.4 Hz, 1H), 6.60 (dd, J=5.7, 2.4 Hz, 1H), 3.89-3.87 (m, 2H), 3.84 (s, 3H), 3.32-3.28 (m, 2H), 2.70-2.67 (m, 1H), 2.25 (s, 3H), 1.72 (d, J=12.9 Hz, 2H), 1.61-1.58 (m, 2H); MS (ESI) m/z: 437.2 (M+H⁺).

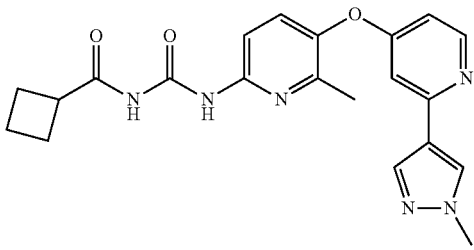 [SMILES: Cc1nc(NC(=O)NC(=O)C2CCC2)ccc1Oc1ccnc(-c2cnn(C)c2)c1]

Example 18

A solution of cyclobutanecarboxylic acid (0.75 g, 7.49 mmol) in DCM was treated with oxalyl chloride (0.820 mL, 9.36 mmol) followed by DMF (1 drop) and stirred at RT for 2 h. The mixture was added drop-wise to a solution of NH$_4$OH (~15M, 15 mL, ~225 mmol) in THF (15 mL) and stirred at RT overnight. The solid was removed via filtration. The filtrate was treated with solid NaCl until saturated, extracted with 4:1 DCM/THF (3×) and the combined organics were washed with brine, dried over Na$_2$SO$_4$ and concentrated to dryness to afford cyclobutanecarboxamide (507 mg, 68%). $^1$H NMR (400 MHz, DMSO-d$_6$): δ 7.07 (s, 1H), 6.63 (s, 1H), 2.93 (td, J=8.5, 1.0 Hz, 1H), 2.12-2.02 (m, 2H), 2.01-1.92 (m, 2H), 1.89-1.77 (m, 1H), 1.75-1.65 (m, 1H).

A solution of cyclobutanecarboxamide (0.042 g, 0.427 mmol) in DCE (4 mL) was treated with oxalyl chloride (0.037 mL, 0.427 mmol), heated at 83° C. for 2 h, cooled to RT, added to a solution of Example A6 (0.1 g, 0.355 mmol) in THF (4 mL) and pyridine (0.173 mL, 2.133 mmol) and stirred at RT overnight. The mixture was diluted with satd. NaHCO$_3$, extracted with EtOAc (3×) and the combined organics were dried over MgSO$_4$ and concentrated to dryness. The material was triturated with MeCN and the resulting solid collected via filtration and dried to afford N-((6-methyl-5-((2-(1-methyl-1H-pyrazol-4-yl)pyridin-4-yl)oxy)pyridin-2-yl)carbamoyl)cyclobutanecarboxamide (81 mg, 56%) as a white solid. $^1$H NMR (400 MHz, DMSO-d$_6$): δ 11.04 (s, 1H), 10.69 (s, 1H), 8.35 (d, J=5.7 Hz, 1H), 8.25 (s, 1H), 7.95 (d, J=0.7 Hz, 1H), 7.90 (d, J=8.8 Hz, 1H), 7.61 (d, J=8.8 Hz, 1H), 7.16 (d, J=2.4 Hz, 1H), 6.61 (dd, J=5.7, 2.4 Hz, 1H), 3.84 (s, 3H), 3.31 (m, 1H), 2.26 (s, 3H), 2.26-2.06 (m, 4H), 1.99-1.88 (m, 1H), 1.85-1.76 (m, 1H); MS (ESI) m/z: 407.2 (M+H$^+$).

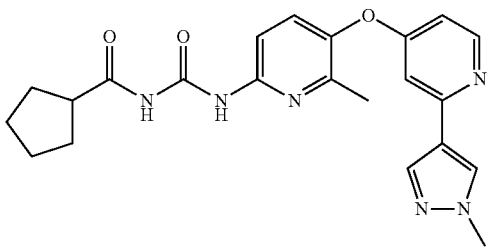 [SMILES: Cc1nc(NC(=O)NC(=O)C2CCCC2)ccc1Oc1ccnc(-c2cnn(C)c2)c1]

Example 19

A solution of cyclopentylcarbonyl chloride (0.6 g, 4.53 mmol) in THF (5 mL) and added drop-wise to a solution of NH$_4$OH (~15M, 15 mL, ~225 mmol) in THF (15 mL) and stirred at RT overnight. The mixture was saturated with solid NaCl, extracted with EtOAc (3×) and the combined organics were dried over Na$_2$SO$_4$ and concentrated to dryness to afford cyclopentanecarboxamide (584 mg, 114%). $^1$H NMR (400 MHz, DMSO-d$_6$): δ 7.18 (s, 1H), 6.63 (s, 1H), 2.53-2.44 (m, 1H), 1.74-1.65 (m, 2H), 1.62-1.52 (m, 4H), 1.50-1.42 (m, 2H).

A solution of cyclopentanecarboxamide (0.048 g, 0.427 mmol) in DCE (4 mL) was treated with oxalyl chloride (0.037 mL, 0.427 mmol), heated at 83° C. for 2 h, cooled to RT, added to a solution of Example A6 (0.1 g, 0.355 mmol) in THF (4 mL) and pyridine (0.173 mL, 2.133 mmol) and stirred at RT overnight. The mixture was diluted with satd. NaHCO$_3$, extracted with EtOAc (3×) and the combined organics were dried over MgSO$_4$ and concentrated to dryness. The resulting material was triturated with MeCN and the solid was collected via filtration to afford crop 1. The filtrate was concentrated to dryness, triturated again with MeCN, and the solid was collected via filtration and combined with crop 1 to afford N-((6-methyl-5-((2-(1-methyl-1H-pyrazol-4-yl)pyridin-4-yl)oxy)pyridin-2-yl)carbamoyl)cyclopentanecarboxamide (57 mg, 38%) as a light pink solid. $^1$H NMR (400 MHz, DMSO-d$_6$): δ 11.06 (s, 1H), 10.84 (s, 1H), 8.35 (d, J=5.7 Hz, 1H), 8.25 (s, 1H), 7.95 (s, 1H), 7.91 (d, J=8.8 Hz, 1H), 7.62 (d, J=8.8 Hz, 1H), 7.16 (d, J=2.4 Hz, 1H), 6.60 (dd, J=5.7, 2.4 Hz, 1H), 3.84 (s, 3H), 2.86 (m, 1H), 2.25 (s, 3H), 1.85 (m, 2H), 1.74-1.61 (m, 4H), 1.54 (m, 2H); MS (ESI) m/z: 421.2 (M+H$^+$).

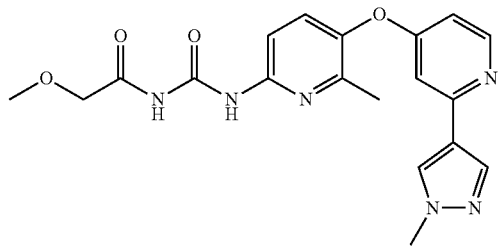 [SMILES: COCC(=O)NC(=O)Nc1ccc(Oc2ccnc(-c3cnn(C)c3)c2)c(C)n1]

Example 20

A suspension of Example B6 (0.057 g, 0.640 mmol) in DCE (4 mL) was treated with oxalyl chloride (0.056 mL, 0.640 mmol), stirred at RT for 1 h, then heated to 80° C. for 1.5 h. The mixture was cooled to RT, added drop-wise to a solution of Example A6 (0.15 g, 0.533 mmol) and pyridine (0.215 mL, 2.67 mmol) in THF (4 mL) and stirred at RT overnight. The mixture was treated with satd. Na$_2$CO$_3$, extracted with EtOAc (4×) and the combined organics were dried over Na$_2$SO$_4$ and concentrated to dryness. The material was treated with MeCN, sonicated and the resulting solid collected via filtration to afford 2-methoxy-N-((6-methyl-5-((2-(1-methyl-1H-pyrazol-4-yl)pyridin-4-yl)oxy)pyridin-2-yl)carbamoyl)acetamide (152 mg, 72%) as a white solid. $^1$H NMR (400 MHz, DMSO-d$_6$): δ 10.69 (s, 1H), 8.35 (d, J=5.7 Hz, 1H), 8.25 (s, 1H), 7.96 (d, J=0.7 Hz, 1H), 7.84 (m, 1H), 7.63 (d, J=8.8 Hz, 1H), 7.17 (d, J=2.4 Hz, 1H), 6.61 (dd, J=5.7, 2.4 Hz, 1H), 4.10 (s, 2H), 3.84 (s, 3H), 3.34 (s, 3H), 2.27 (s, 3H); MS (ESI) m/z: 397.1 (M+H$^+$).

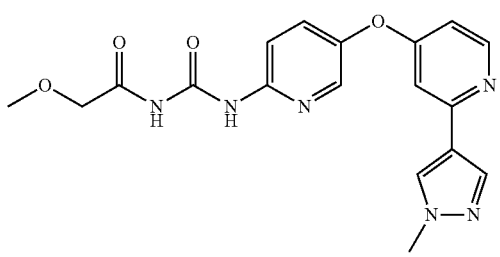 [SMILES: COCC(=O)NC(=O)Nc1ccc(Oc2ccnc(-c3cnn(C)c3)c2)cn1]

Example 21

A suspension of Example B6 (0.060 g, 0.673 mmol) in DCE (4 mL) was treated with oxalyl chloride (0.059 mL, 0.673 mmol), stirred at RT for 1 h, then heated to 80° C. for 1.5 h. The mixture was cooled to RT, added drop-wise to a solution of Example A2 (0.15 g, 0.561 mmol) and pyridine (0.226 mL, 2.81 mmol) in THF (4 mL) and stirred at RT overnight. The mixture was treated with satd. Na$_2$CO$_3$, extracted with EtOAc (4×) and the combined organics were dried over Na$_2$SO$_4$ and concentrated to dryness. The material was treated with MeCN, sonicated and the resulting solid collected via filtration to afford 2-methoxy-N-((5-((2-(1-methyl-1H-pyrazol-4-yl)pyridin-4-yl)oxy)pyridin-2-yl)carbamoyl)acetamide (186 mg, 87%) as an off-white solid. $^1$H NMR (400 MHz, DMSO-d$_6$): δ 10.78 (s, 1H), 10.71 (s, 1H), 8.37 (d, J=5.7 Hz, 1H), 8.27 (d, J=2.9 Hz, 1H), 8.26 (s, 1H), 8.03 (m, 1H), 7.96 (d, J=0.7 Hz, 1H), 7.74 (dd, J=9.0, 2.9 Hz, 1H), 7.23 (d, J=2.4 Hz, 1H), 6.71 (dd, J=5.7, 2.4 Hz, 1H), 4.11 (s, 2H), 3.84 (s, 3H), 3.34 (s, 3H); MS (ESI) m/z: 383.1 (M+H$^+$).

Example 22

A 0° C. solution of Example 16 (0.10 g, 0.238 mmol) in DCM (20 mL) was treated with DAST (0.157 mL, 1.189 mmol), warmed to RT, stirred for 3 h, then heated at 40° C. overnight. Additional DAST (0.1 mL) and DCM (10 mL) were added and the mixture heated at 40° C. overnight. The solid was collected via filtration, treated with DCE (5 mL), heated at 70° C. for 3 h and at 55° C. overnight. The solid was collected via filtration and further purified via reverse-phase chromatography (MeCN/H$_2$O with 0.1% TFA). The enriched fractions were combined and co-evaporated with MeOH and the remaining aqueous mixture was neutralized with satd. NaHCO$_3$, extracted with EtOAc (3×). The combined organics were washed with brine, dried over Na$_2$SO$_4$ and concentrated to dryness to afford crop 1. The filtrate from the initial reaction mixture filtration was concentrated to dryness and purified via silica gel chromatography (EtOAc/Hex) to provide crop 2. The two crops were combined, treated with 1:1 MeCN/H$_2$O, frozen and lyophilized to afford 3,3-difluoro-N-((6-methyl-5-((2-(1-methyl-1H-pyrazol-4-yl)pyridin-4-yl)oxy)pyridin-2-yl)carbamoyl)cyclobutanecarboxamide (19 mg, 18%) as a pale gray solid. $^1$H NMR (400 MHz, DMSO-d$_6$): δ 10.98 (s, 1H), 10.86 (s, 1H), 8.35 (d, J=5.7 Hz, 1H), 8.25 (s, 1H); 7.95 (s, 1H), 7.90 (d, J=8.8 Hz, 1H), 7.63 (d, J=8.8 Hz, 1H), 7.17 (d, J=2.4 Hz, 1H), 6.60 (dd, J=5.7, 2.4 Hz, 1H), 3.84 (s, 3H), 3.20 (m, 1H), 2.80 (m, 4H), 2.26 (s, 3H); MS (ESI) m/z: 443.1 (M+H$^+$).

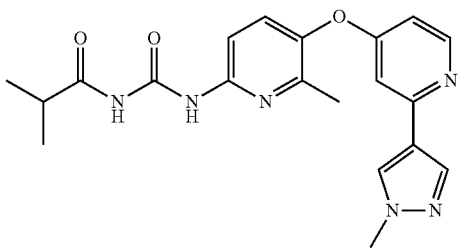 [SMILES: Cc1nc(NC(=O)NC(=O)C(C)C)ccc1Oc1ccnc(-c2cnn(C)c2)c1]

Example 23

A suspension of Example B7 (0.056 g, 0.640 mmol) in DCE (4 mL) was treated with oxalyl chloride (0.056 mL, 0.640 mmol), stirred at RT for 1 h, warmed to 80° C. for 1.5 h, cooled to RT and added drop-wise to a solution of Example A6 (0.15 g, 0.533 mmol) in THF (4 mL) and pyridine (0.215 mL, 2.67 mmol). The mixture was stirred at RT overnight, treated with satd. Na$_2$CO$_3$, extracted with EtOAc (4×) and the combined organics were dried over Na$_2$SO$_4$, concentrated to dryness and purified via silica gel chromatography (MeOH/DCM). The resulting material was dissolved in MeCN/H$_2$O, frozen and lyophilized to afford N-((6-methyl-5-((2-(1-methyl-1H-pyrazol-4-yl)pyridin-4-yl)oxy)pyridin-2-yl)carbamoyl)isobutyramide (59 mg, 28%) as a white solid. $^1$H NMR (400 MHz, DMSO-d$_6$): δ 11.05 (s, 1H), 10.84 (s, 1H), 8.35 (d, J=5.8 Hz, 1H), 8.25 (d, J=0.7 Hz, 1H), 7.95 (d, J=0.7 Hz, 1H), 7.90 (m, 1H), 7.62 (d, J=8.9 Hz, 1H), 7.16 (m, 1H), 6.60 (dd, J=5.7, 2.5 Hz, 1H), 3.84 (s, 3H), 2.43 (m, 1H), 2.25 (s, 3H), 1.09 (d, J=6.8 Hz, 6H); MS (ESI) m/z: 395.2 (M+H$^+$).

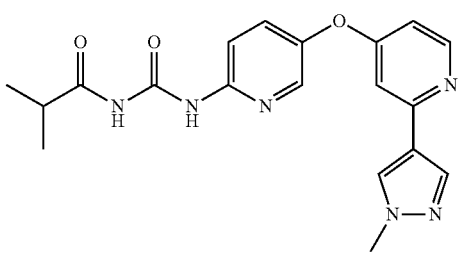 [SMILES: CC(C)C(=O)NC(=O)Nc1ccc(Oc2ccnc(-c3cnn(C)c3)c2)cn1]

Example 24

A suspension of Example B7 (0.059 g, 0.673 mmol) in DCE (4 mL) was treated with oxalyl chloride (0.059 mL, 0.673 mmol), stirred at RT for 1 h, warmed to 80° C. for 2.5 h, cooled to RT and added drop-wise to a solution of Example A2 (0.15 g, 0.561 mmol) in THF (4 mL) and pyridine (0.226 mL, 2.81 mmol). The mixture was stirred at RT overnight, treated with satd. Na$_2$CO$_3$, extracted with EtOAc (4×) and the combined organics were dried over Na$_2$SO$_4$, concentrated to dryness and purified via silica gel chromatography (MeOH/

DCM). The resulting material was dissolved in MeCN/H₂O, frozen and lyophilized to afford N-((5-((2-(1-methyl-1H-pyrazol-4-yl)pyridin-4-yl)oxy)pyridin-2-yl)carbamoyl)isobutyramide (89 mg, 42%) as a white solid. ¹H NMR (400 MHz, DMSO-d₆): δ 11.11 (s, 1H), 10.85 (s, 1H), 8.37 (d, J=5.7 Hz, 1H), 8.26-8.25 (m, 2H), 8.09 (d, J=9.0 Hz, 1H), 7.96 (d, J=0.7 Hz, 1H), 7.73 (dd, J=9.0, 3.0 Hz, 1H), 7.22 (d, J=2.4 Hz, 1H), 6.70 (dd, J=5.7, 2.4 Hz, 1H), 3.84 (s, 3H), 2.43 (m, 1H), 1.09 (d, J=6.8 Hz, 6H); MS (ESI) m/z: 381.1 (M+H⁺).

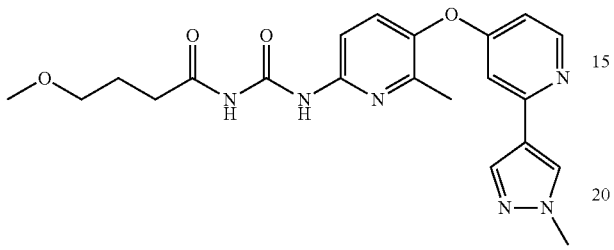

Example 25

A solution of methyl 4-methoxybutanoate (1.0 g, 7.57 mmol) in THF (20 mL) was treated with a solution of LiOH (0.362 g, 15.13 mmol) in H₂O (5 mL) and stirred at RT for 16 h. The mixture was concentrated to dryness, acidified with 2M HCl, diluted with H₂O, extracted with EtOAc (2×) and the combined organics were washed with brine, dried over Na₂SO₄ and concentrated to dryness to afford 4-methoxybutanoic acid (860 mg, 96%) as a viscous oil. ¹H NMR (400 MHz, DMSO-d₆): δ 12.02 (s, 1H), 3.28 (t, J=6.4 Hz, 2H), 3.19 (s, 3H), 2.21 (t, J=7.4 Hz, 2H), 1.69 (m, 2H).

A solution of 4-methoxybutanoic acid (0.86 g, 7.28 mmol) in MeCN (30 mL) was treated with EDC (1.814 g, 9.46 mmol) and HOBT (1.449 g, 9.46 mmol), stirred at RT for 1 h, then treated with NH₄OH (~15M, 0.850 mL, ~12.8 mmol) and stirred at RT for 16 h. The mixture was treated with satd. NaHCO₃, saturated with solid NaCl, extracted with THF (2×), and the combined organics were washed with H₂O, then brine, dried over Na₂SO₄ and concentrated to dryness to afford 4-methoxybutanamide (390 mg, 46%) as a white solid. ¹H NMR (400 MHz, DMSO-d₆): δ 7.22 (s, 1H), 6.69 (s, 1H), 3.26 (t, J=6.5 Hz, 2H), 3.19 (s, 3H), 2.05 (t, J=7.5 Hz, 2H), 1.68-1.66 (m, 2H).

A solution of 4-methoxybutanamide (0.083 g, 0.711 mmol) in DCE (4 mL) was treated with oxalyl chloride (0.062 mL, 0.711 mmol) and heated at 80° C. for 4 h. The mixture was cooled to RT, treated with a solution of Example A6 (0.1 g, 0.355 mmol) and TEA (0.197 mL, 1.422 mmol) in DCM (2 mL) and stirred at RT for 2 h. The mixture was concentrated to dryness, purified via silica gel chromatography (MeOH/DCM), dissolved in MeCN/H₂O, frozen and lyophilized to afford 4-methoxy-N-((6-methyl-5-((2-(1-methyl-1H-pyrazol-4-yl)pyridin-4-yl)oxy)pyridin-2-yl)carbamoyl)butanamide (105 mg, 70%) as a white solid. ¹H NMR (400 MHz, DMSO-d₆): δ 11.00 (s, 1H), 10.82 (s, 1H), 8.36 (d, J=5.8 Hz, 1H), 8.27 (s, 1H), 7.97 (s, 1H), 7.91 (d, J=8.8 Hz, 1H), 7.62 (d, J=8.8 Hz, 1H), 7.19 (s, 1H), 6.64 (m, 1H), 3.84 (s, 3H), 3.33 (t, J=6.3 Hz, 2H), 3.21 (s, 3H), 2.44 (t, J=7.3 Hz, 2H), 2.26 (s, 3H), 1.82-1.74 (m, 2H); MS (ESI) m/z: 425.2 (M+H⁺).

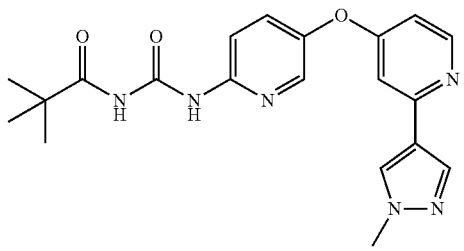 [SMILES: Cn1cc(-c2cc(Oc3ccc(NC(=O)NC(=O)C(C)(C)C)nc3)ccn2)cn1]

Example 26

A suspension of 2,2,2-trimethylacetamide (0.045 g, 0.449 mmol) in DCE (4 mL) was treated with oxalyl chloride (0.039 mL, 0.449 mmol), stirred at RT for 1 h, heated to 80° C. for 2.5 h, then cooled to RT and added drop-wise to a solution of Example A2 (0.10 g, 0.374 mmol) in THF (4 mL) and pyridine (0.215 mL, 2.67 mmol). The mixture was stirred at RT for 1 h, treated with satd. NaHCO₃, extracted with EtOAc (2×) and the combined organics were washed with brine, dried over Na₂SO₄ and concentrated to dryness. The material was treated with MeCN, sonicated, and the resulting solid collected via filtration and dried to afford N-((5-((2-(1-methyl-1H-pyrazol-4-yl)pyridin-4-yl)oxy)pyridin-2-yl)carbamoyl)pivalamide (106 mg, 72%) as an off-white solid. ¹H NMR (400 MHz, DMSO-d₆): δ 11.22 (s, 1H), 10.44 (s, 1H), 8.37 (d, J=5.7 Hz, 1H), 8.27-8.25 (m, 2H), 8.09 (d, J=9.0 Hz, 1H), 7.96 (s, 1H), 7.74 (dd, J=9.0, 2.9 Hz, 1H), 7.23 (d, J=2.4 Hz, 1H), 6.70 (dd, J=5.7, 2.4 Hz, 1H), 3.84 (s, 3H), 1.21 (s, 9H); MS (ESI) m/z: 395.2 (M+H⁺).

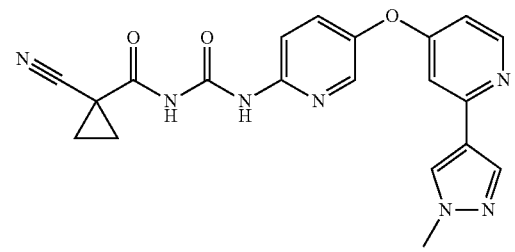 [SMILES: Cn1cc(-c2cc(Oc3ccc(NC(=O)NC(=O)C4(C#N)CC4)nc3)ccn2)cn1]

Example 27

A suspension of Example B8 (0.074 g, 0.673 mmol) in DCE (4 mL) was treated with oxalyl chloride (0.059 mL, 0.673 mmol), stirred at RT for 1 h, then heated to 80° C. for 1.5 h. The mixture was cooled to RT, added drop-wise to a solution of Example A2 (0.15 g, 0.561 mmol) and pyridine (0.226 mL, 2.81 mmol) in THF (4 mL) and stirred at RT overnight. The mixture was treated with satd. NaHCO₃, extracted with EtOAc (4×) and the combined organics were dried over Na₂SO₄, concentrated to dryness and purified via silica gel chromatography (MeOH/DCM) to afford 1-cyano-N-((5-((2-(1-methyl-1H-pyrazol-4-yl)pyridin-4-yl)oxy)pyridin-2-yl)carbamoyl)cyclopropanecarboxamide (176 mg, 78%) as an off-white solid. MS (ESI) m/z: 404.1 (M+H⁺).

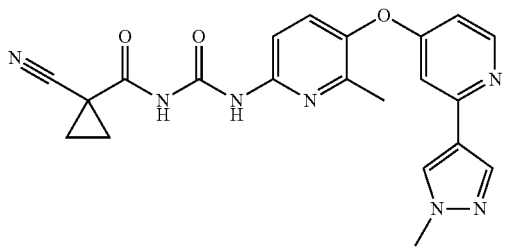 [SMILES: Cc1nc(NC(=O)NC(=O)C2(C#N)CC2)ccc1Oc1ccnc(-c2cnn(C)c2)c1]

Example 28

A suspension of Example B8 (0.070 g, 0.640 mmol) in DCE (4 mL) was treated with oxalyl chloride (0.056 mL, 0.640 mmol), stirred at RT for 1 h, then heated to 80° C. for 1.5 h. The mixture was cooled to RT, added drop-wise to a solution of Example A6 (0.15 g, 0.533 mmol) and pyridine (0.215 mL, 2.67 mmol) in THF (4 mL) and stirred at RT overnight. The mixture was treated with satd. NaHCO$_3$, extracted with EtOAc (4×) and the combined organics were dried over Na$_2$SO$_4$, concentrated to dryness and purified via silica gel chromatography (MeOH/DCM) to afford 1-cyano-N-((6-methyl-5-((2-(1-methyl-1H-pyrazol-4-yl)pyridin-4-yl)oxy)pyridin-2-yl)carbamoyl)cyclopropanecarboxamide (103 mg, 46%) as an off-white solid. MS (ESI) m/z: 418.1 (M+H$^+$).

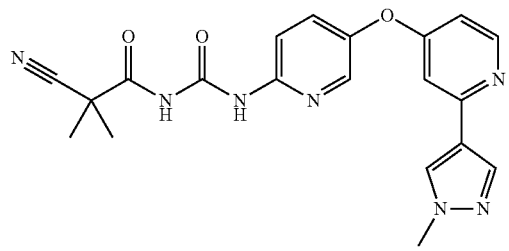

Example 30

A suspension of Example B9 (0.076 g, 0.673 mmol) in DCE (4 mL) was treated with oxalyl chloride (0.059 mL, 0.673 mmol), stirred at RT for 1 h, then heated to 80° C. for 1.5 h. The mixture was cooled to RT, added drop-wise to a solution of Example A2 (0.15 g, 0.561 mmol) and pyridine (0.226 mL, 2.81 mmol) in THF (4 mL) and stirred at RT overnight. The mixture was treated with satd. Na$_2$CO$_3$, extracted with EtOAc (4×) and the combined organics were dried over Na$_2$SO$_4$, concentrated to dryness and purified via silica gel chromatography (MeOH/DCM) to afford 2-cyano-2-methyl-N-((5-((2-(1-methyl-1H-pyrazol-4-yl)pyridin-4-yl)oxy)pyridin-2-yl)carbamoyl)propanamide (178 mg, 78%) as a white solid. $^1$H NMR (400 MHz, DMSO-d$_6$): δ 11.16 (s, 1H), 10.71 (s, 1H), 8.38 (d, J=5.7 Hz, 1H), 8.28 (d, J=2.9 Hz, 1H), 8.26 (s, 1H), 8.04 (m, 1H), 7.96 (s, 1H), 7.76 (dd, J=9.0, 2.9 Hz, 1H), 7.24 (d, J=2.4 Hz, 1H), 6.71 (dd, J=5.7, 2.4 Hz, 1H), 3.84 (s, 3H), 1.66 (s, 6H); MS (ESI) m/z: 406.1 (M+H$^+$).

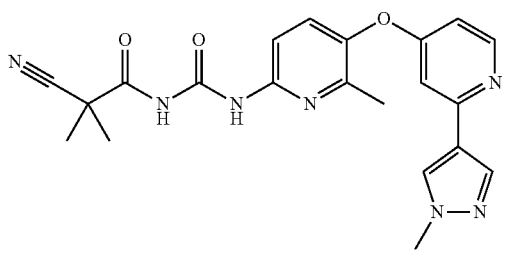 [SMILES: Cc1nc(NC(=O)NC(=O)C(C)(C)C#N)ccc1Oc1ccnc(-c2cnn(C)c2)c1]

Example 29

A suspension of Example B9 (0.072 g, 0.640 mmol) in DCE (4 mL) was treated with oxalyl chloride (0.056 mL, 0.640 mmol), stirred at RT for 1 h, then heated to 80° C. for 1.5 h. The mixture was cooled to RT, added drop-wise to a solution of Example A6 (0.15 g, 0.533 mmol) and pyridine (0.215 mL, 2.67 mmol) in THF (4 mL) and stirred at RT overnight. The mixture was treated with satd. Na$_2$CO$_3$, extracted with EtOAc (4×) and the combined organics were dried over Na$_2$SO$_4$, concentrated to dryness and purified via silica gel chromatography (MeOH/DCM) to afford 2-cyano-2-methyl-N-((6-methyl-5-((2-(1-methyl-1H-pyrazol-4-yl)pyridin-4-yl)oxy)pyridin-2-yl)carbamoyl)propanamide (93 mg, 42%) as a white solid. $^1$H NMR (400 MHz, DMSO-d$_6$): δ 11.10 (s, 1H), 10.65 (s, 1H), 8.36 (d, J=5.7 Hz, 1H), 8.25 (s, 1H), 7.96 (s, 1H), 7.87 (m, 1H), 7.65 (d, J=8.8 Hz, 1H), 7.18 (d, J=2.4 Hz, 1H), 6.61 (dd, J=5.7, 2.4 Hz, 1H), 3.84 (s, 3H), 2.28 (s, 3H), 1.66 (s, 6H); MS (ESI) m/z: 420.1 (M+H$^+$).

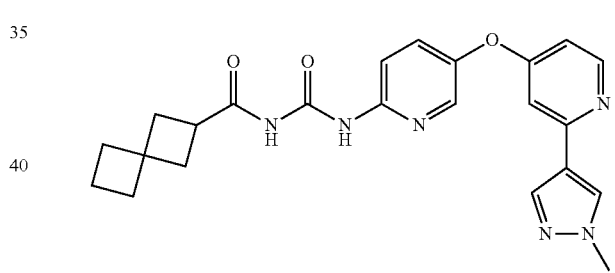

Example 31

A solution of Example B10 (0.060 g, 0.431 mmol) in DCE (4 mL) was treated with oxalyl chloride (0.038 mL, 0.431 mmol), heated at 80° C. for 2 h, cooled to RT, added drop-wise to a solution of Example A2 (0.096 g, 0.359 mmol) and pyridine (0.145 mL, 1.796 mmol) in THF (4 mL) and stirred at RT overnight. The mixture was treated with satd. NaHCO$_3$, extracted with EtOAc (4×) and the combined organics were dried over Na$_2$SO$_4$, concentrated to dryness and purified via silica gel chromatography (EtOAc/DCM). The material was treated with MeCN, and the solid collected via filtration and dried to afford N-((5-((2-(1-methyl-1H-pyrazol-4-yl)pyridin-4-yl)oxy)pyridin-2-yl)carbamoyl)spiro[3.3]heptane-2-carboxamide (75 mg, 48%) as a white solid. $^1$H NMR (400 MHz, DMSO-d$_6$): δ 11.07 (s, 1H), 10.70 (s, 1H), 8.36 (d, J=5.7 Hz, 1H), 8.25-8.24 (m, 2H), 8.06 (d, J=9.0 Hz, 1H), 7.95 (s, 1H), 7.71 (dd, J=9.0, 2.9 Hz, 1H), 7.21 (d, J=2.4 Hz, 1H), 6.69 (dd, J=5.7, 2.4 Hz, 1H), 3.83 (s, 3H), 3.13 (m, 1H), 2.15 (d, J=8.4 Hz, 4H), 2.01-1.95 (m, 2H), 1.86 (m, 2H), 1.77-1.71 (m, 2H); MS (ESI) m/z: 433.1 (M+H$^+$).

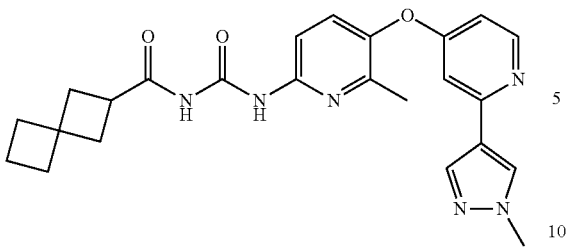

Example 32

A solution of Example B10 (0.060 g, 0.431 mmol) in DCE (4 mL) was treated with oxalyl chloride (0.038 mL, 0.431 mmol), heated at 80° C. for 2 h, cooled to RT, added dropwise to a solution of Example A6 (0.101 g, 0.359 mmol) and pyridine (0.145 mL, 1.796 mmol) in THF (4 mL) and stirred at RT overnight. The mixture was treated with satd. NaHCO$_3$, extracted with EtOAc (4×) and the combined organics were dried over Na$_2$SO$_4$, concentrated to dryness and purified via silica gel chromatography (EtOAc/DCM). The material was treated with MeCN, and the solid collected via filtration and dried to afford N-((6-methyl-5-((2-(1-methyl-1H-pyrazol-4-yl)pyridin-4-yl)oxy)pyridin-2-yl)carbamoyl)spiro[3.3]heptane-2-carboxamide (78 mg, 49%) as a white solid. $^1$H NMR (400 MHz, DMSO-d$_6$): δ 11.02 (s, 1H), 10.68 (s, 1H), 8.34 (d, J=5.7 Hz, 1H), 8.24 (s, 1H), 7.94 (s, 1H), 7.88 (d, J=8.8 Hz, 1H), 7.60 (d, J=8.8 Hz, 1H), 7.15 (d, J=2.4 Hz, 1H), 6.59 (dd, J=5.7, 2.4 Hz, 1H), 3.82 (s, 3H), 3.12 (m, 1H), 2.24 (s, 3H), 2.15 (d, J=8.3 Hz, 4H), 2.00-1.96 (m, 2H), 1.87 (m, 2H), 1.77-1.70 (m, 2H); MS (ESI) m/z: 447.2 (M+H$^+$).

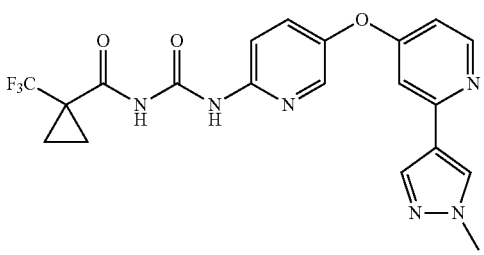 [SMILES: Cn1cc(-c2cc(Oc3ccc(NC(=O)NC(=O)C4(C(F)(F)F)CC4)nc3)ccn2)cn1]

Example 33

A solution of Example B11 (0.060 g, 0.392 mmol) in DCE (4 mL) was treated with oxalyl chloride (0.034 mL, 0.392 mmol), heated at 80° C. for 2 h, cooled to RT, added dropwise to a solution of Example A2 (0.087 g, 0.327 mmol) and pyridine (0.132 mL, 1.633 mmol) in THF (4 mL) and stirred at RT overnight. The mixture was treated with satd. NaHCO$_3$, extracted with EtOAc (4×) and the combined organics were dried over Na$_2$SO$_4$ and concentrated to dryness. The material was treated with MeCN, the solid collected via filtration and dried to afford N-((5-((2-(1-methyl-1H-pyrazol-4-yl)pyridin-4-yl)oxy)pyridin-2-yl)carbamoyl)-1-(trifluoromethyl)cyclopropanecarboxamide (127 mg, 87%) as a white solid. $^1$H NMR (400 MHz, DMSO-d$_6$): δ 10.80 (s, 1H), 10.62 (s, 1H), 8.36 (d, J=5.7 Hz, 1H), 8.26 (d, J=2.9 Hz, 1H), 8.24 (s, 1H), 8.01 (m, 1H), 7.95 (s, 1H), 7.73 (dd, J=9.0, 2.9 Hz, 1H), 7.22 (d, J=2.4 Hz, 1H), 6.69 (dd, J=5.7, 2.4 Hz, 1H), 3.83 (s, 3H), 1.61 (m, 2H), 1.38 (m, 2H); MS (ESI) m/z: 447.1 (M+H$^+$).

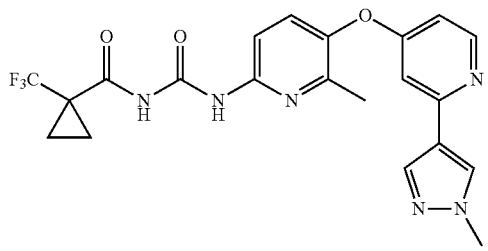 [SMILES: Cc1nc(NC(=O)NC(=O)C2(C(F)(F)F)CC2)ccc1Oc1ccnc(-c2cnn(C)c2)c1]

Example 34

A solution of Example B11 (0.06 g, 0.392 mmol) in DCE (4 mL) was treated with oxalyl chloride (0.041 mL, 0.470 mmol), heated at 80° C. for 2 h, cooled to RT, added dropwise to a solution of Example A6 (0.110 g, 0.392 mmol) and pyridine (0.158 mL, 1.959 mmol) in THF (4 mL) and stirred at RT overnight. The mixture was treated with satd. NaHCO$_3$, extracted with EtOAc (4×) and the combined organics were dried over Na$_2$SO$_4$ and concentrated to dryness. The material was treated with MeCN, the solid collected via filtration and dried to afford N-((6-methyl-5-((2-(1-methyl-1H-pyrazol-4-yl)pyridin-4-yl)oxy)pyridin-2-yl)carbamoyl)-1-(trifluoromethyl)cyclopropanecarboxamide (124 mg, 69%) as a white solid. $^1$H NMR (400 MHz, DMSO-d$_6$): δ 10.75 (s, 1H), 10.54 (s, 1H), 8.34 (d, J=5.7 Hz, 1H), 8.24 (s, 1H), 7.94 (s, 1H), 7.84 (m, 1H), 7.62 (d, J=8.8 Hz, 1H), 7.16 (d, J=2.4 Hz, 1H), 6.59 (dd, J=5.7, 2.4 Hz, 1H), 3.83 (s, 3H), 2.25 (s, 3H), 1.62 (m, 2H), 1.38 (m, 2H); MS (ESI) m/z: 461.1 (M+H$^+$).

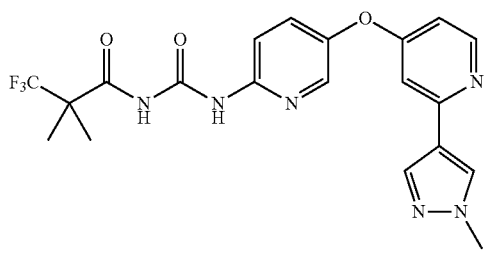 [SMILES: Cn1cc(-c2cc(Oc3ccc(NC(=O)NC(=O)C(C)(C)C(F)(F)F)nc3)ccn2)cn1]

Example 35

A solution of Example B12 (0.060 g, 0.387 mmol) in DCE (4 mL) was treated with oxalyl chloride (0.034 mL, 0.387 mmol), heated at 80° C. for 2 h, cooled to RT, added dropwise to a solution of Example A2 (0.086 g, 0.322 mmol) and pyridine (0.130 mL, 1.612 mmol) in THF (4 mL) and stirred at RT overnight. The mixture was treated with satd. NaHCO$_3$, extracted with EtOAc (4×) and the combined organics were dried over Na$_2$SO$_4$ and concentrated to dryness. The material was treated with MeCN, the solid collected via filtration and dried to afford 3,3,3-trifluoro-2,2-dimethyl-N-((5-((2-(1-methyl-1H-pyrazol-4-yl)pyridin-4-yl)oxy)pyridin-2-yl)carbamoyl)propanamide (101 mg, 70%) as a white solid. $^1$H NMR (400 MHz, DMSO-d$_6$): δ 10.84-10.67 (br m, 2H), 8.37 (d, J=5.7 Hz, 1H), 8.27 (d, J=2.9 Hz, 1H), 8.24 (s, 1H), 8.03 (m, 1H), 7.95 (d, J=0.7 Hz, 1H), 7.75 (dd, J=9.0, 2.9 Hz, 1H), 7.22 (d, J=2.4 Hz, 1H), 6.69 (dd, J=5.7, 2.4 Hz, 1H), 3.83 (s, 3H), 1.49 (s, 6H); MS (ESI) m/z: 449.1 (M+H$^+$).

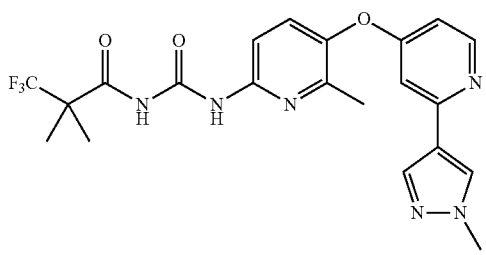 [SMILES: Cc1nc(NC(=O)NC(=O)C(C)(C)C(F)(F)F)ccc1Oc1ccnc(-c2cnn(C)c2)c1]

Example 36

A solution of Example B12 (0.060 g, 0.387 mmol) in DCE (4 mL) was treated with oxalyl chloride (0.041 mL, 0.464 mmol), heated at 80° C. for 2 h, cooled to RT, added dropwise to a solution of Example A6 (0.109 g, 0.387 mmol) and pyridine (0.156 mL, 1.934 mmol) in THF (4 mL) and stirred at RT overnight. The mixture was treated with satd. NaHCO$_3$, extracted with EtOAc (4×) and the combined organics were dried over Na$_2$SO$_4$ and concentrated to dryness. The material was treated with MeCN, the solid collected via filtration and dried to afford 3,3,3-trifluoro-2,2-dimethyl-N-((6-methyl-5-((2-(1-methyl-1H-pyrazol-4-yl)pyridin-4-yl)oxy)pyridin-2-yl)carbamoyl)propanamide (77 mg, 43%) as a white solid. $^1$H NMR (400 MHz, DMSO-d$_6$): δ 10.77 (s, 1H), 10.69 (br m, 1H), 8.34 (d, J=5.7 Hz, 1H), 8.24 (s, 1H), 7.95 (s, 1H), 7.86 (m, 1H), 7.64 (d, J=8.8 Hz, 1H), 7.16 (d, J=2.4 Hz, 1H), 6.60 (dd, J=5.7, 2.4 Hz, 1H), 3.83 (s, 3H), 2.26 (s, 3H), 1.49 (s, 6H); MS (ESI) m/z: 463.1 (M+H$^+$).

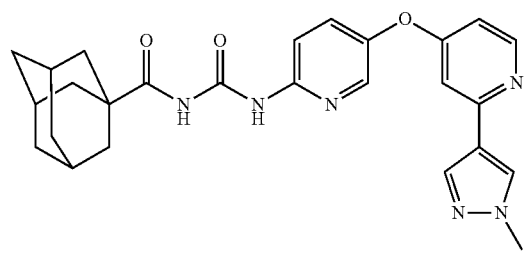

Example 38

A solution of Example B13 (0.150 g, 0.837 mmol) in dioxane (10 mL) was treated with oxalyl chloride (0.150 g, 1.182 mmol), heated at 100° C. for 2 h, cooled to RT and concentrated to dryness. The residue was treated with a solution of Example A2 (0.150 g, 0.561 mmol) and pyridine (0.080 g, 1.011 mmol) in DCM (10 mL) and stirred at RT for 2 days. The mixture was concentrated to dryness and purified via silica gel chromatography (MeOH/DCM) to afford N-((5-((2-(1-methyl-1H-pyrazol-4-yl)pyridin-4-yl)oxy)pyridin-2-yl)carbamoyl)adamantane-1-carboxamide (80 mg, 29%) as a white solid. $^1$H NMR (400 MHz, DMSO-d$_6$): δ 11.24 (s, 1H), 10.38 (s, 1H), 8.36 (d, J=5.7 Hz, 1H) 8.25-8.24 (m, 2H) 8.07 (br d, J=9.0 Hz, 1H) 7.95 (s, 1H) 7.72 (dd, J=9.0, 2.9 Hz, 1H) 7.21 (d, J=2.4 Hz, 1H), 6.69 (dd, J=5.7, 2.4 Hz, 1H), 3.83 (s, 3H), 1.98 (m, 3H), 1.89 (m, 6H), 1.66 (m, 6H); MS (ESI) m/z: 473.2 (M+H$^+$).

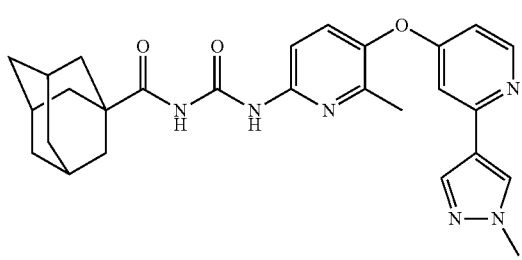 [SMILES: Cc1nc(NC(=O)NC(=O)C23CC4CC(CC(C4)C2)C3)ccc1Oc1ccnc(-c2cnn(C)c2)c1]

Example 37

A solution of Example B13 (0.150 g, 0.837 mmol) in dioxane (10 mL) was treated with oxalyl chloride (0.150 g, 1.182 mmol), heated at 100° C. for 2 h, cooled to RT and concentrated to dryness. The residue was treated with a solution of Example A6 (0.150 g, 0.533 mmol) and pyridine (0.080 g, 1.011 mmol) in DCM (10 mL) and stirred at RT for 2 days. The mixture was concentrated to dryness, the residue treated with MeCN and the resulting solid collected via filtration and dried to afford N-((6-methyl-5-((2-(1-methyl-1H-pyrazol-4-yl)pyridin-4-yl)oxy)pyridin-2-yl)carbamoyl)adamantane-1-carboxamide (200 mg, 77%) as a white solid. $^1$H NMR (400 MHz, DMSO-d$_6$): δ 11.18 (s, 1H), 10.32 (s, 1H), 8.35 (d, J=5.7 Hz, 1H), 8.24 (s, 1H), 7.95 (d, J=0.7 Hz, 1H), 7.90 (s, 1H), 7.61 (d, J=8.8 Hz, 1H), 7.16 (d, J=2.4 Hz, 1H), 6.60 (dd, J=5.7, 2.4 Hz, 1H), 3.83 (s, 3H), 2.25 (s, 3H), 1.98 (m, 3H), 1.89 (m, 6H), 1.66 (m, 6H); MS (ESI) m/z: 487.2 (M+H$^+$).

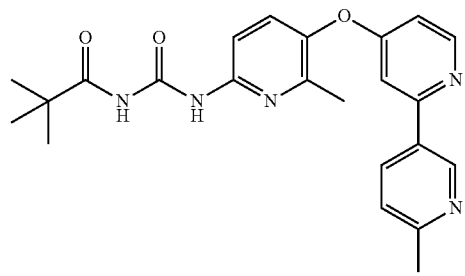 [SMILES: Cc1ccc(-c2cc(Oc3ccc(NC(=O)NC(=O)C(C)(C)C)nc3C)ccn2)cn1]

Example 39

A suspension of Example C1 (0.20 g, 0.551 mmol), Example C2 (0.254 g, 1.158 mmol) and satd. NaHCO$_3$ (1.1 mL) in dioxane (4.4 mL) was sparged with Ar under sonication, treated with Pd(PPh$_3$)$_4$ (0.064 g, 0.055 mmol), sparged again with Ar, heated at 80° C. for 3 h, then 90° C. for 1.5 h. The mixture was cooled to RT, diluted with EtOAc and filtered through diatomaceous earth. The filtrate was concentrated to dryness and purified via silica gel chromatography (MeOH/DCM). The material was further purified via reverse-phase silica gel chromatography (MeCN/H$_2$O with 0.1% TFA). Pure fractions were combined and concentrated under reduced pressure. The aqueous residue was neutralized with satd. Na$_2$CO$_3$ and the solid collected via filtration, dissolved in MeCN/H$_2$O, frozen and lyophilized to afford N-((6-methyl-5-((6'-methyl-[2,3'-bipyridin]-4-yl)oxy)pyridin-2-yl)carbamoyl)pivalamide (150 mg, 65%) as a white solid. $^1$H NMR (400 MHz, DMSO-d$_6$): δ 11.15 (s, 1H), 10.39 (s, 1H), 9.08 (d, J=2.4 Hz, 1H), 8.52 (d, J=5.7 Hz, 1H), 8.26 (dd, J=8.1, 2.4 Hz, 1H), 7.91 (m, 1H), 7.65 (d, J=8.8 Hz, 1H), 7.57 (d, J=2.4 Hz, 1H), 7.32 (d, J=8.2 Hz, 1H), 6.78 (dd, J=5.7, 2.4 Hz, 1H), 2.49 (s, 3H), 2.26 (s, 3H), 1.20 (s, 9H); MS (ESI) m/z: 420.2 (M+H$^+$).

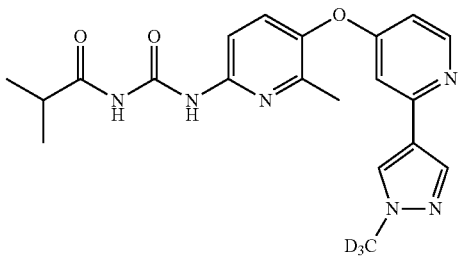

Example 41

A suspension of Example B7 (0.074 g, 0.844 mmol) in DCE (5.25 mL) was treated with oxalyl chloride (0.074 mL, 0.844 mmol), stirred at RT for 1 h, warmed to 80° C. for 1.5 h, cooled to RT, added drop-wise to a solution of Example A10 (0.200 g, 0.703 mmol) and pyridine (0.284 mL, 3.52 mmol) in THF (8 mL) and stirred at RT overnight. The mixture was treated with satd. Na$_2$CO$_3$, extracted with EtOAc (6×) and the combined organics were dried over Na$_2$SO$_4$, concentrated to dryness and purified via silica gel chromatography (MeOH/DCM). The material was dissolved in MeCN/H$_2$O, frozen and lyophilized to afford N-((6-methyl-5-((2-(1-(trideuteromethyl)-1H-pyrazol-4-yl)pyridin-4-yl)oxy)pyridin-2-yl)carbamoyl)isobutyramide (202 mg, 72%) as a white solid. $^1$H NMR (400 MHz, DMSO-d$_6$): δ 11.04 (s, 1H), 10.82 (s, 1H), 8.34 (d, J=5.7 Hz, 1H), 8.24 (d, J=0.7 Hz, 1H), 7.94 (d, J=0.7 Hz, 1H), 7.90 (d, J=8.8 Hz, 1H), 7.61 (d, J=8.8 Hz, 1H), 7.15 (d, J=2.4 Hz, 1H), 6.59 (dd, J=5.7, 2.5 Hz, 1H), 2.65 (m, 1H), 2.24 (s, 3H), 1.08 (d, J=6.8 Hz, 6H); MS (ESI) m/z: 398.2 (M+H$^+$).

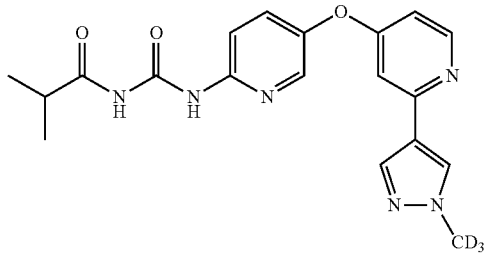 [SMILES: [2H]C([2H])([2H])n1cc(-c2cc(Oc3ccc(NC(=O)NC(=O)C(C)C)nc3)ccn2)cn1]

Example 40

A suspension of Example A9 (1.103 g, 4.97 mmol), Example C3 (1.05 g, 4.97 mmol), K$_2$CO$_3$ (1.375 g, 9.95 mmol) and Pd(PPh$_3$)$_4$ (0.200 g, 0.173 mmol) in dioxane (20 mL) and H$_2$O (4 mL) was heated under argon at 90° C. overnight. The mixture was concentrated to dryness and treated with DCM. The solids were removed via filtration and washed with DCM and THF. The combined filtrate was concentrated to dryness and purified via silica gel chromatography (MeOH/DCM) to afford 5-((2-(1-(trideuteromethyl)-1H-pyrazol-4-yl)pyridin-4-yl)oxy)pyridin-2-amine (290 mg, 22%) as a pink solid. $^1$H NMR (400 MHz, DMSO-d$_6$): δ 8.30 (d, J=5.7 Hz, 1H), 8.21 (s, 1H), 7.91 (s, 1H), 7.79 (d, J=2.9 Hz, 1H), 7.27 (dd, J=8.8, 2.9 Hz, 1H), 7.12 (d, J=2.4 Hz, 1H), 6.56 (dd, J=5.7, 2.4 Hz, 1H), 6.50 (d, J=8.9 Hz, 1H), 5.99 (s, 2H); MS (ESI) m/z: 271.1 (M+H$^+$).

A suspension of Example B7 (0.077 g, 0.888 mmol) in DCE (5.5 mL) was treated with oxalyl chloride (0.078 mL, 0.888 mmol), stirred at RT for 1 h, warmed to 80° C. for 1.5 h, cooled to RT, added drop-wise to a solution of 5-((2-(1-(trideuteromethyl)-1H-pyrazol-4-yl)pyridin-4-yl)oxy)pyridin-2-amine (0.200 g, 0.740 mmol) and pyridine (0.299 mL, 3.70 mmol) in THF (8 mL) and stirred at RT overnight. The mixture was treated with satd. Na$_2$CO$_3$, extracted with EtOAc (6×) and the combined organics were dried over Na$_2$SO$_4$, concentrated to dryness and purified via silica gel chromatography (MeOH/DCM). The material was dissolved in MeCN/H$_2$O, frozen and lyophilized to afford N-((5-((2-(1-(trideuteromethyl)-1H-pyrazol-4-yl)pyridin-4-yl)oxy)pyridin-2-yl)carbamoyl)isobutyramide (199 mg, 70%) as a white solid. $^1$H NMR (400 MHz, DMSO-d$_6$): δ 11.10 (s, 1H), 10.84 (s, 1H), 8.36 (d, J=5.7 Hz, 1H), 8.25-8.24 (m, 2H), 8.07 (d, J=9.0 Hz, 1H), 7.95 (d, J=0.7 Hz, 1H), 7.72 (dd, J=9.0, 2.9 Hz, 1H), 7.21 (d, J=2.4 Hz, 1H), 6.69 (dd, J=5.7, 2.4 Hz, 1H), 2.66 (m, 1H), 1.08 (d, J=6.8 Hz, 6H); MS (ESI) m/z: 384.2 (M+H$^+$).

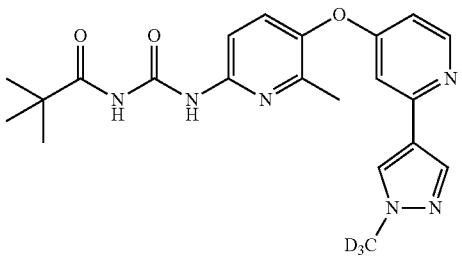 [SMILES: [2H]C([2H])([2H])n1cc(-c2cc(Oc3ccc(NC(=O)NC(=O)C(C)(C)C)nc3C)ccn2)cn1]

Example 42

A mixture of Example C1 (0.18 g, 0.496 mmol), Example C3 (0.115 g, 0.546 mmol) and K$_2$CO$_3$ (0.206 g, 1.488 mmol) in dioxane (4 mL) and H$_2$O (1 mL) was sparged with Ar, treated with Pd(PPh$_3$)$_4$ (0.029 g, 0.025 mmol), sparged again with Ar and heated at 80° C. overnight. The mixture was cooled to RT, treated with brine, extracted with EtOAc (2×) and the combined organics were dried over Na$_2$SO$_4$, concentrated to dryness and purified via silica gel chromatography (MeOH/DCM). The material was treated with 1:1 MeCN/H$_2$O, frozen, lyophilized and the resulting solid treated with MeCN, the solid collected via filtration and dried to afford N-((6-methyl-5-((2-(1-(trideuteromethyl)-1H-pyrazol-4-yl)pyridin-4-yl)oxy)pyridin-2-yl)carbamoyl)pivalamide (110 mg, 54%) as a white solid. $^1$H NMR (400 MHz, DMSO-d$_6$): δ 11.16 (s, 1H), 10.40 (s, 1H), 8.35 (d, J=5.7 Hz, 1H), 8.25 (s, 1H), 7.95 (s, 1H), 7.90 (m, 1H), 7.63 (d, J=8.8 Hz, 1H), 7.16

(d, J=2.4 Hz, 1H), 6.60 (dd, J=5.7, 2.5 Hz, 1H), 2.26 (s, 3H), 1.21 (s, 9H); MS (ESI) m/z: 412.2 (M+H⁺).

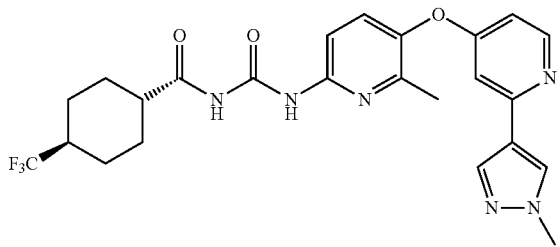

Example 43

A mixture of Example B14 (0.190 g, 0.97 mmol) in DCE (4.8 mL) was treated with oxalyl chloride (0.125 mL, 1.46 mmol), stirred at RT for 5 minutes, heated at 80° C. for 1 h, cooled to RT, added to a solution of Example A6 (0.200 g, 0.711 mmol) and pyridine (0.057 mL, 0.711 mmol) in DCE (5 mL) and stirred at RT overnight. The mixture was treated with H₂O, the layers separated, the organic layer washed with satd. NaHCO₃, dried over Na₂SO₄ and concentrated to dryness. The material was suspended in MeCN, sonicated, the solid collected via filtration, purified via silica gel chromatography (MeOH/DCM) and dried thoroughly to afford trans-N-((6-methyl-5-((2-(1-methyl-1H-pyrazol-4-yl)pyridin-4-yl)oxy)pyridin-2-yl)carbamoyl)-4-(trifluoromethyl)cyclohexanecarboxamide (85 mg, 24%) as a white solid. ¹H NMR (400 MHz, DMSO-d₆): δ 10.98 (s, 1H), 10.85 (s, 1H), 8.35 (d, J=5.7 Hz, 1H), 8.25 (s, 1H), 7.95 (s, 1H), 7.90 (d, J=8.8 Hz, 1H), 7.62 (d, J=8.8 Hz, 1H), 7.16 (d, J=2.4 Hz, 1H), 6.60 (dd, J=5.7, 2.4 Hz, 1H), 3.84 (s, 3H), 2.40 (m, 1H), 2.25 (s, 3H), 1.94 (m, 4H), 1.71-1.59 (m, 1H), 1.52-1.40 (m, 2H), 1.29-1.17 (m, 2H); MS (ESI) m/z: 503.2 (M+H⁺).

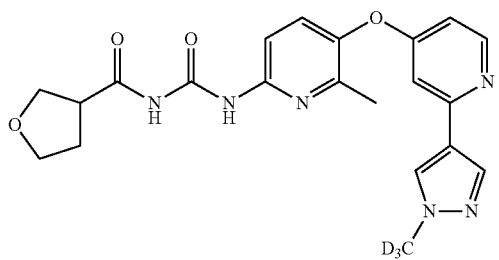 [SMILES: [2H]C([2H])([2H])n1cc(-c2cc(Oc3ccc(NC(=O)NC(=O)C4CCOC4)nc3C)ccn2)cn1]

Example 44

A solution of Example B3 (0.970 g, 8.43 mmol) in dioxane (10 mL) was treated with oxalyl chloride (0.400 g, 3.15 mmol), heated at 100° C. for 1 h, cooled to RT, concentrated to dryness, dissolved in DCM (15 mL), added to a solution of Example A10 (0.470 g, 1.653 mmol) and pyridine (0.392 g, 4.96 mmol) in DCM (8 mL) and stirred at RT overnight. The mixture was concentrated to dryness, purified via silica gel chromatography (THF/DCM) and re-purified via silica gel chromatography (MeOH/DCM) to afford N-((6-methyl-5-((2-(1-(trideuteromethyl)-1H-pyrazol-4-yl)pyridin-4-yl)oxy)pyridin-2-yl)carbamoyl)tetrahydrofuran-3-carboxamide (98 mg, 14%) as a white amorphous solid. ¹H NMR (400 MHz, DMSO-d₆): δ 10.96 (s, 1H), 10.93 (s, 1H), 8.35 (d, J=5.7 Hz, 1H), 8.25 (s, 1H), 7.95 (s, 1H), 7.90 (d, J=8.8 Hz, 1H), 7.62 (d, J=8.8 Hz, 1H), 7.16 (d, J=2.4 Hz, 1H), 6.60 (dd, J=5.7, 2.4 Hz, 1H), 3.87 (t, J=8.3 Hz, 1H), 3.79-3.73 (m, 2H), 3.67 (m, 1H), 3.23 (m, 1H), 2.25 (s, 3H), 2.07 (m, 2H); MS (ESI) m/z: 426.2 (M+H⁺).

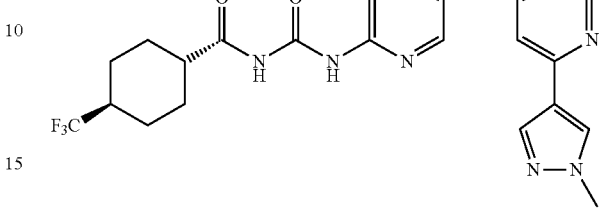

Example 45

A mixture of Example B14 (0.190 g, 0.97 mmol) in DCE (4.8 mL) was treated with oxalyl chloride (0.125 mL, 1.46 mmol), stirred at RT for 5 minutes, heated at 80° C. for 1 h, cooled to RT, added to a solution of Example A2 (0.200 g, 0.748 mmol) and pyridine (0.060 mL, 0.748 mmol) in DCE (5 mL) and stirred at RT overnight. The mixture was treated with H₂O, the layers separated, the organic layer washed with satd. NaHCO₃, dried over Na₂SO₄ and concentrated to dryness. The material was suspended in MeCN and briefly sonicated. The solid was collected via filtration, then purified via silica gel chromatography (MeOH/EtOAc) to afford trans-N-((5-((2-(1-methyl-1H-pyrazol-4-yl)pyridin-4-yl)oxy)pyridin-2-yl)carbamoyl)-4-(trifluoromethyl)cyclohexanecarboxamide (64 mg, 17%) as a white solid. ¹H NMR (400 MHz, DMSO-d₆): δ 11.04 (s, 1H), 10.86 (s, 1H), 8.36 (d, J=5.7 Hz, 1H), 8.25-8.23 (m, 2H), 8.07 (d, J=9.0 Hz, 1H), 7.95 (s, 1H), 7.72 (dd, J=9.0, 2.9 Hz, 1H), 7.21 (d, J=2.4 Hz, 1H), 6.69 (dd, J=5.7, 2.4 Hz, 1H), 3.83 (s, 3H), 2.30 (m, 1H), 1.93 (m, 4H), 1.69-1.59 (m, 1H), 1.46 (m, 2H), 1.28-1.15 (m, 2H); MS (ESI) m/z: 489.2 (M+H⁺).

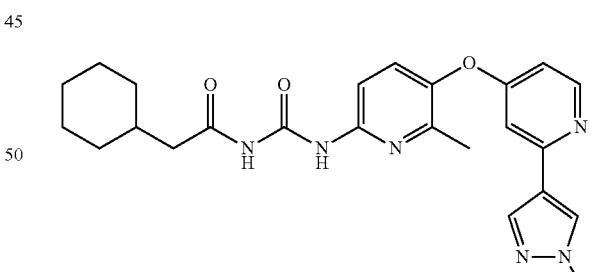

Example 46

Cyclohexylacetyl chloride (1 mL, 6.52 mmol) was added to solution of NH₄OH (~15M, 5 mL, ~75 mmol) in EtOAc (5 mL) and satd. NaHCO₃ (5 mL) and stirred at RT for 20 minutes. The layers were separated, the aqueous layer extracted with EtOAc (2×) and the combined organics were dried over Na₂SO₄ and concentrated to dryness to afford 2-cyclohexylacetamide (481 mg, 52%) as a white solid.

A mixture of 2-cyclohexylacetamide (0.151 g, 1.066 mmol) in DCE (5 mL) was treated with oxalyl chloride (0.15 mL, 1.747 mmol), heated at 80° C. for 0.5 h, cooled to RT, concentrated to dryness, dissolved in DCM (5 mL), added to a solution of Example A6 (0.200 g, 0.711 mmol) and pyridine (0.100 mL, 1.244 mmol) in DCM (1 mL) and stirred at RT for 0.5 h. The mixture was treated with H₂O, the layers separated, the organic layer washed with satd. NaHCO₃, dried over Na₂SO₄, concentrated to dryness and purified via silica gel chromatography (MeOH/EtOAc) to afford 2-cyclohexyl-N-((6-methyl-5-((2-(1-methyl-1H-pyrazol-4-yl)pyridin-4-yl)oxy)pyridin-2-yl)carbamoyl)acetamide (218 mg, 67%) as a white solid. ¹H NMR (400 MHz, DMSO-d₆): δ 11.05 (s, 1H), 10.82 (s, 1H), 8.35 (d, J=5.7 Hz, 1H), 8.25 (s, 1H), 7.95 (d, J=0.7 Hz, 1H), 7.91 (d, J=8.8 Hz, 1H), 7.61 (d, J=8.8 Hz, 1H), 7.15 (d, J=2.4 Hz, 1H), 6.60 (dd, J=5.7, 2.4 Hz, 1H), 3.84 (s, 3H), 2.27 (d, J=7.0 Hz, 2H), 2.25 (s, 3H), 1.74 (m, 1H), 1.69-1.56 (m, 5H), 1.27-1.08 (m, 3H), 1.00-0.89 (m, 2H); MS (ESI) m/z: 449.2 (M+H⁺).

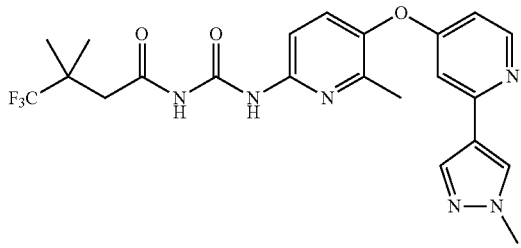 [SMILES: Cc1nc(NC(=O)NC(=O)CC(C)(C)C(F)(F)F)ccc1Oc1ccnc(-c2cnn(C)c2)c1]

Example 47

A solution of Example B15 (0.07 g, 0.414 mmol) in DCE (4 mL) was treated with oxalyl chloride (0.036 mL, 0.414 mmol) and heated at 80° C. for 1 h. The mixture was cooled to RT, added to a solution of Example A6 (0.090 g, 0.318 mmol) and pyridine (0.154 mL, 1.910 mmol) in THF (4 mL) and stirred at RT overnight. The mixture was treated with satd. NaHCO₃, extracted with EtOAc (4×) and the combined organics were dried over Na₂SO₄, concentrated and purified via silica gel chromatography (MeOH/DCM). The material was further purified via reverse-phase silica gel chromatography (MeCN/H₂O with 0.1% TFA). Pure fractions were combined and concentrated under reduced pressure. The aqueous residue was neutralized with satd. NaHCO₃, extracted with EtOAc (3×) and the combined organics dried over Na₂SO₄ and concentrated to dryness. The material was dissolved in MeCN, treated with H₂O, frozen and lyophilized to afford 4,4,4-trifluoro-3,3-dimethyl-N-((6-methyl-5-((2-(1-methyl-1H-pyrazol-4-yl)pyridin-4-yl)oxy)pyridin-2-yl)carbamoyl)butanamide (26 mg, 17%) as a white solid. ¹H NMR (400 MHz, DMSO-d₆): δ 11.01 (s, 1H), 10.92 (s, 1H), 8.35 (d, J=5.7 Hz, 1H), 8.25 (s, 1H), 7.95 (s, 1H), 7.91 (d, J=8.8 Hz, 1H), 7.63 (d, J=8.8 Hz, 1H), 7.16 (d, J=2.4 Hz, 1H), 6.61 (dd, J=5.7, 2.4 Hz, 1H), 3.84 (s, 3H), 2.62 (s, 2H), 2.26 (s, 3H), 1.24 (s, 6H); MS (ESI) m/z: 477.1 (M+H⁺).

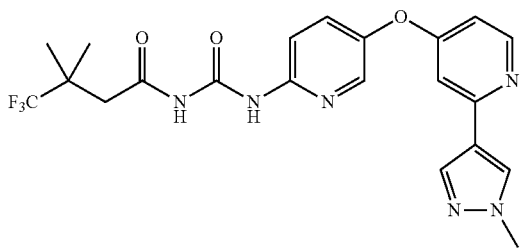 [SMILES: Cn1cc(-c2cc(Oc3ccc(NC(=O)NC(=O)CC(C)(C)C(F)(F)F)nc3)ccn2)cn1]

Example 48

A solution of Example B15 (0.07 g, 0.414 mmol) in DCE (4 mL) was treated with oxalyl chloride (0.036 mL, 0.414 mmol) and heated at 80° C. for 1 h. The mixture was cooled to RT, added to a solution Example A2 (0.085 g, 0.318 mmol) and pyridine (0.154 mL, 1.910 mmol) in THF (4 mL) and stirred at RT overnight. The mixture was treated with satd. NaHCO₃, extracted with EtOAc (4×) and the combined organics were dried over Na₂SO₄, concentrated and purified via silica gel chromatography (MeOH/DCM). The material was further purified via reverse-phase silica gel chromatography (MeCN/H₂O with 0.1% TFA), the organics removed under reduced pressure and the aqueous residue neutralized with satd. NaHCO₃, extracted with EtOAc (3×) and the combined organics dried over Na₂SO₄ and concentrated to dryness. The material was dissolved in MeCN, treated with H₂O, frozen and lyophilized to afford 4,4,4-trifluoro-3,3-dimethyl-N-((5-((2-(1-methyl-1H-pyrazol-4-yl)pyridin-4-yl)oxy)pyridin-2-yl)carbamoyl)butanamide (13 mg, 9%) as a white solid. ¹H NMR (400 MHz, DMSO-d₆): δ 11.02 (s, 1H), 10.99 (s, 1H), 8.37 (d, J=5.7 Hz, 1H), 8.27-8.25 (m, 2H), 8.08 (d, J=9.0 Hz, 1H), 7.96 (s, 1H), 7.74 (dd, J=9.0, 2.9 Hz, 1H), 7.22 (d, J=2.4 Hz, 1H), 6.71 (dd, J=5.7, 2.4 Hz, 1H), 3.84 (s, 3H), 2.63 (s, 2H), 1.24 (s, 6H); MS (ESI) m/z: 463.1 (M+H⁺).

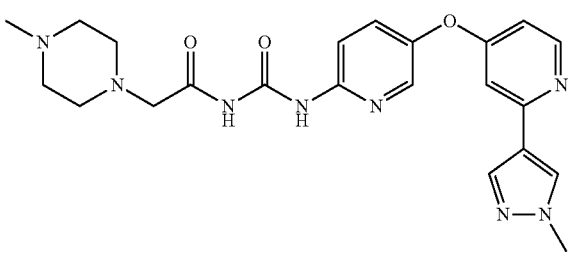

Example 49

A solution of Example A2 (0.15 g, 0.561 mmol) in THF (3 mL) was treated with TEA (0.114 g, 1.122 mmol) and 2-chloroacetyl isocyanate (0.107 g, 0.898 mmol), stirred at RT for 2 h, treated with N-methylpiperazine (0.112 g, 1.122 mmol) and stirred at RT for 4 h. The mixture was diluted with EtOAc, stirred for several minutes, the solids removed via filtration and the filtrate concentrated to dryness and purified via silica gel chromatography (NH₄OH/MeOH/DCM). The material was suspended in 2:1 EtOAc/DCM and the solid was removed via filtration and discarded. The filtrate was concentrated to dryness and treated with 3:2 EtOAc/Hex. The mixture was briefly sonicated. The solid was collected via filtration, dissolved in MeCN/H₂O, frozen and lyophilized to afford N-((5-((2-(1-methyl-1H-pyrazol-4-yl)pyridin-4-yl)oxy)pyridin-2-yl)carbamoyl)-2-(4-methylpiperazin-1-yl)acetamide (76 mg, 30%) as a white solid. $^1$H NMR (400 MHz, DMSO-d$_6$): δ 10.88 (s, 1H), 10.48 (br s, 1H), 8.37 (d, J=5.7 Hz, 1H), 8.27-8.24 (m, 2H), 8.07-8.00 (m, 1H), 7.96 (d, J=0.7 Hz, 1H), 7.74 (dd, J=9.0, 2.9 Hz, 1H), 7.23 (d, J=2.4 Hz, 1H), 6.70 (dd, J=5.7, 2.4 Hz, 1H), 3.84 (s, 3H), 3.22 (s, 2H), 2.51 (m, 4H), 2.35 (m, 4H), 2.15 (s, 3H); MS (ESI) m/z: 451.2 (M+H$^+$).

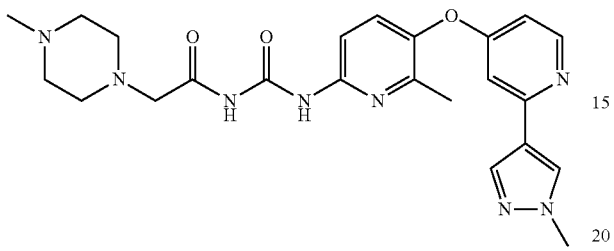

Example 50

A solution of Example A6 (0.15 g, 0.533 mmol) in THF (4 mL) was treated with TEA (0.108 g, 1.066 mmol) and 2-chloro acetylisocyanate (0.096 g, 0.800 mmol) stirred at RT for 2 h, treated with N-methyl piperazine (0.107 g, 1.066 mmol) and stirred at RT for 20 h. The mixture was concentrated to dryness, purified via silica gel chromatography (NH$_4$OH/MeOH/DCM), then further purified via reverse-phase silica gel chromatography (MeCN/H$_2$O with 0.1% TFA). The combined fractions were neutralized with satd. NaHCO$_3$, treated with solid NaCl and extracted with THF (2×). The combined organics were washed with brine, dried over Na$_2$SO$_4$, concentrated to dryness, dissolved in MeCN/H$_2$O, frozen and lyophilized to afford N-((6-methyl-5-((2-(1-methyl-1H-pyrazol-4-yl)pyridin-4-yl)oxy)pyridin-2-yl)carbamoyl)-2-(4-methylpiperazin-1-yl)acetamide (26 mg, 10.5%) as a white solid. MS (ESI) m/z: 465.2 (M+H$^+$).

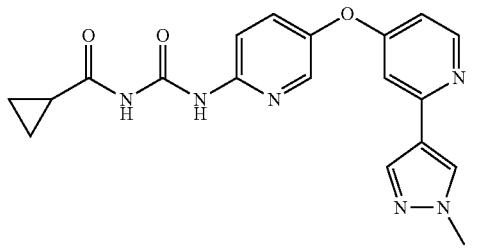 [SMILES: Cn1cc(-c2cc(Oc3ccc(NC(=O)NC(=O)C4CC4)nc3)ccn2)cn1]

Example 51

A solution of cyclopropanecarbonyl chloride (0.200 g, 1.913 mmol) in dioxane (10 mL) was treated with silver cyanate (0.280 g, 1.871 mmol) and heated at 80° C. for 1 h. The mixture was cooled to RT, treated with Example A2 (0.250 g, 0.935 mmol) and stirred at RT for 1 h. The solids were removed via filtration, the filtrate concentrated to dryness and the resulting residue triturated with MeCN to afford N-((5-((2-(1-methyl-1H-pyrazol-4-yl)pyridin-4-yl)oxy)pyridin-2-yl)carbamoyl)cyclopropanecarboxamide (323 mg, 91%) as a white solid. $^1$H NMR (400 MHz, DMSO-d$_6$): δ 11.19 (s, 1H), 11.10 (s, 1H), 8.37 (d, J=5.7 Hz, 1H), 8.25 (s, 1H), 8.24 (d, J=2.9 Hz, 1H), 8.09 (d, J=9.0 Hz, 1H), 7.96 (s, 1H), 7.72 (dd, J=9.0, 2.9 Hz, 1H), 7.22 (d, J=2.4 Hz, 1H), 6.70 (dd, J=5.7, 2.4 Hz, 1H), 3.84 (s, 3H), 1.88 (m, 1H), 0.93 (t, J=5.7 Hz, 4H); MS (ESI) m/z: 379.1 (M+H$^+$).

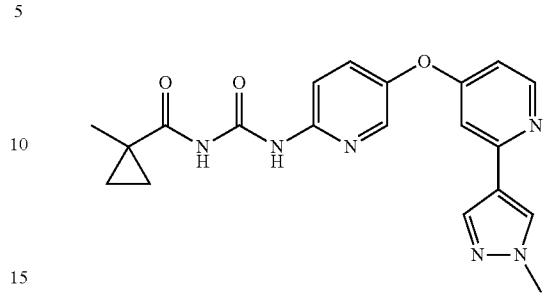

Example 52

A solution of 1-methylcyclopropanecarboxylic acid (0.300 g, 3.00 mmol) in DCM (10 mL) was treated with oxalyl chloride (0.571 g, 4.49 mmol) followed by a catalytic amount of DMF (0.022 g, 0.300 mmol) and stirred at RT for 2 h. The mixture was concentrated to dryness, dissolved in dioxane (10 mL), treated with silver cyanate (0.280 g, 1.871 mmol) and heated at 80° C. for 1 h. The mixture was cooled to RT, treated with Example A2 (0.250 g, 0.935 mmol) and stirred at RT for 1 h. The solids were removed via filtration, the filtrate concentrated to dryness and the resulting residue triturated with MeCN to afford 1-methyl-N-((5-((2-(1-methyl-1H-pyrazol-4-yl)pyridin-4-yl)oxy)pyridin-2-yl)carbamoyl)cyclopropanecarboxamide (251 mg, 69%) as a white solid. $^1$H NMR (400 MHz, DMSO-d$_6$): δ 11.24 (s, 1H), 10.06 (s, 1H), 8.37 (d, J=5.7 Hz, 1H), 8.26-8.24 (m, 2H), 8.07 (br m, 1H), 7.96 (s, 1H), 7.73 (dd, J=9.0, 2.9 Hz, 1H), 7.23 (d, J=2.4 Hz, 1H), 6.70 (dd, J=5.7, 2.4 Hz, 1H), 3.84 (s, 3H), 1.35 (s, 3H), 1.20 (m, 2H), 0.75 (m, 2H); MS (ESI) m/z: 393.1 (M+H$^+$).

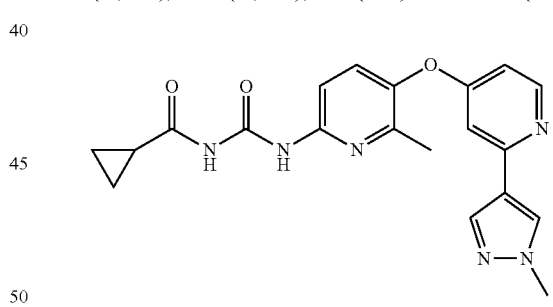

Example 53

A solution of cyclopropanecarbonyl chloride (0.200 g, 1.913 mmol) in dioxane (10 mL) was treated with silver cyanate (0.300 g, 2.002 mmol) and heated at 80° C. for 1 h. The mixture was cooled to RT, treated with Example A6 (0.120 g, 0.427 mmol) and stirred at RT for 1 h. The solids were removed via filtration, rinsed with THF and the filtrate concentrated to dryness and purified via silica gel chromatography (EtOAc/DCM) to afford N-((6-methyl-5-((2-(1-methyl-1H-pyrazol-4-yl)pyridin-4-yl)oxy)pyridin-2-yl)carbamoyl)cyclopropanecarboxamide (53 mg, 30%) as a white solid. $^1$H NMR (400 MHz, DMSO-d$_6$): δ 11.17 (s, 1H), 11.05 (s, 1H), 8.35 (d, J=5.7 Hz, 1H), 8.25 (s, 1H), 7.96 (s, 1H), 7.91 (d, J=8.8 Hz, 1H), 7.61 (d, J=8.8 Hz, 1H), 7.17 (d, J=2.4 Hz, 1H), 6.61 (dd, J=5.7, 2.5 Hz, 1H), 3.84 (s, 3H), 2.24 (s, 3H), 1.91 (d, J=6.4 Hz, 1H), 0.92 (m, 4H); MS (ESI) m/z: 393.1 (M+H⁺).

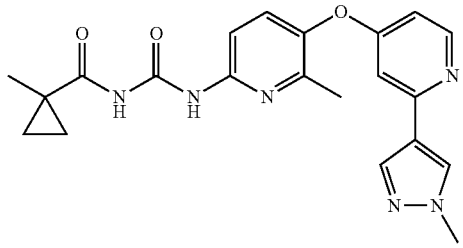

Example 54

A solution of 1-methylcyclopropane carboxylic acid (0.200 g, 1.998 mmol) in DCM (10 mL) was treated with oxalyl chloride (0.200 g, 1.576 mmol) followed by a catalytic amount of DMF (3.90 mg, 0.053 mmol) and stirred at RT for 2 h. The mixture was concentrated to dryness, dissolved in dioxane (10 mL), treated with silver cyanate (0.160 g, 1.066 mmol) and heated at 80° C. for 1 h. The mixture was cooled to RT, treated with Example A6 (0.150 g, 0.533 mmol) and stirred at RT for 1 h. The solids were removed via filtration, rinsed with THF and the filtrate concentrated to dryness and purified via silica gel chromatography (EtOAc/DCM) to afford 1-methyl-N-((6-methyl-5-((2-(1-methyl-1H-pyrazol-4-yl)pyridin-4-yl)oxy)pyridin-2-yl)carbamoyl)cyclopropanecarboxamide (80 mg, 35%) as a white solid. ¹H NMR (400 MHz, DMSO-d₆): δ 11.19 (s, 1H), 10.05 (s, 1H), 8.35 (d, J=5.7 Hz, 1H), 8.20 (s, 1H), 7.95 (s, 1H), 7.90 (s, 1H), 7.62 (d, J=8.8 Hz, 1H), 7.17 (d, J=2.4 Hz, 1H), 6.60 (dd, J=5.7, 2.4 Hz, 1H), 3.84 (s, 3H), 2.25 (s, 3H), 1.35 (s, 3H), 1.19 (m, 2H), 0.75 (m, 2H); MS (ESI) m/z: 407.2 (M+H⁺).

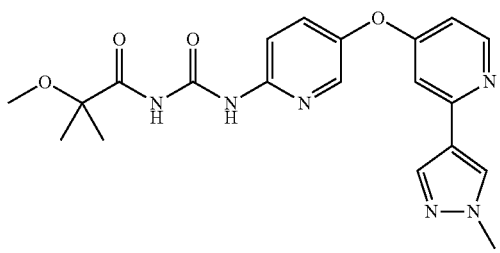

Example 55

A solution of Example B16 (0.200 g, 0.994 mmol) and Example A2 (0.166 g, 0.621 mmol) in dioxane (4 mL) was treated with 1-methylpyrrolidine (0.065 mL, 0.621 mmol) and heated at 80° C. for 4 h. The mixture was cooled to RT, treated with satd. NaHCO₃, extracted with EtOAc (3×) and the combined organics were dried over Na₂SO₄, concentrated to dryness and purified via silica gel chromatography (MeOH/DCM). The resulting material was dissolved in MeCN/H₂O, frozen and lyophilized to afford 2-methoxy-2-methyl-N-((5-((2-(1-methyl-1H-pyrazol-4-yl)pyridin-4-yl)oxy)pyridin-2-yl)carbamoyl)propanamide (114 mg, 45%) as a white solid. ¹H NMR (400 MHz, DMSO-d₆): δ 10.81 (s, 1H), 10.23 (s, 1H), 8.37 (d, J=5.7 Hz, 1H), 8.27-8.24 (m, 2H), 8.02 (br s, 1H), 7.96 (d, J=0.7 Hz, 1H), 7.74 (dd, J=9.0, 2.9 Hz, 1H), 7.22 (d, J=2.4 Hz, 1H), 6.70 (dd, J=5.7, 2.4 Hz, 1H), 3.84 (s, 3H), 3.20 (s, 3H), 1.35 (s, 6H); MS (ESI) m/z: 411.2 (M+H⁺).

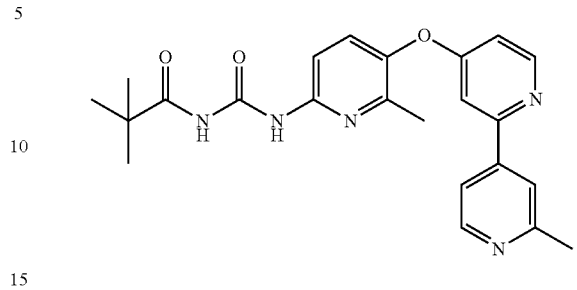

Example 56

A solution of 2,2,2-trimethylacetamide (0.034 g, 0.332 mmol) in DCE (1.4 mL) was treated drop-wise with oxalyl chloride (0.032 mL, 0.360 mmol), stirred for 0.5 h at RT, then heated at 80° C. for 1 h. The mixture was cooled to RT, treated with a solution of Example A11 (0.081 g, 0.277 mmol) and pyridine (0.112 mL, 1.385 mmol) in THF (1.4 mL) and stirred at RT overnight. The mixture was treated with satd. NaHCO₃, extracted with EtOAc (4×) and the combined organics were dried over Na₂SO₄, concentrated to dryness and purified via silica gel chromatography (MeOH/DCM). The resulting material was dissolved in MeCN and H₂O, frozen and lyophilized to afford N-((6-methyl-5-((2'-methyl-[2,4'-bipyridin]-4-yl)oxy)pyridin-2-yl)carbamoyl)pivalamide (39 mg, 34%) as a white solid. ¹H NMR (400 MHz, DMSO-d₆): δ 11.16 (s, 1H), 10.40 (s, 1H), 8.57 (d, J=5.6 Hz, 1H), 8.52 (d, J=5.2 Hz, 1H), 7.94-7.88 (m, 2H), 7.80 (m, 1H), 7.68-7.65 (m, 2H), 6.88 (dd, J=5.7, 2.4 Hz, 1H), 2.53 (s, 3H), 2.28 (s, 3H), 1.21 (s, 9H); MS (ESI) m/z: 420.2 (M+H⁺).

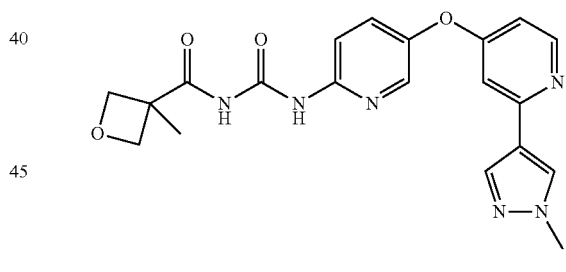

Example 57

A solution of 3-methyloxetane-3-carboxylic acid (0.400 g, 3.44 mmol) in DCM (10 mL) was treated with oxalyl chloride (0.400 g, 3.15 mmol) followed by a catalytic amount of DMF (6.84 mg, 0.094 mmol) and stirred at RT for 2 h. Silver cyanate (0.500 g, 3.34 mmol) was added, the mixture sonicated for 10 minutes, treated with Example A2 (0.250 g, 0.935 mmol) and sonicated for another 10 minutes. MeCN (10 mL) was added, the mixture heated to 60° C. for 1 h, then cooled to RT. The solids were removed via filtration, rinsed with DCM, then THF, the filtrate concentrated to dryness and purified via silica gel chromatography (MeOH/DCM) to afford 3-methyl-N-((5-((2-(1-methyl-1H-pyrazol-4-yl)pyridin-4-yl)oxy)pyridin-2-yl)carbamoyl)oxetane-3-carboxamide (82 mg, 19%) as a white amorphous solid. ¹H NMR (400 MHz, DMSO-d₆): δ 10.97 (s, 1H), 10.91 (s, 1H), 8.38 (d, J=5.7 Hz, 1H), 8.28 (d, J=2.9 Hz, 1H), 8.26 (s, 1H), 8.08 (d, J=9.0 Hz, 1H), 7.97 (s, 1H), 7.74 (dd, J=9.0, 2.9 Hz, 1H), 7.24 (d, J=2.4 Hz, 1H), 6.72 (dd, J=5.7, 2.4 Hz, 1H), 4.80 (d, J=6.3 Hz, 2H), 4.31 (d, J=6.3 Hz, 2H), 3.84 (s, 3H), 1.60 (s, 3H); MS (ESI) m/z: 409.1 (M+H⁺).

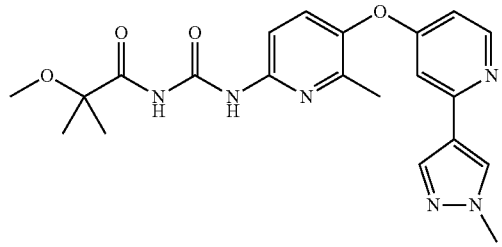

Example 58

A solution of Example B16 (0.200 g, 0.994 mmol) and Example A6 (0.112 g, 0.398 mmol) in dioxane (4 mL) was treated with 1-methylpyrrolidine (0.041 mL, 0.398 mmol), heated at 80° C. for 4 h, then cooled to RT and stirred overnight. The mixture was treated with satd. NaHCO₃, extracted with EtOAc (4×) and the combined organics were dried over Na₂SO₄, concentrated to dryness and purified via silica gel chromatography (MeOH/EtOAc). The material was dissolved in 1:1 MeCN/H₂O, frozen and lyophilized to afford 2-methoxy-2-methyl-N-((6-methyl-5-((2-(1-methyl-1H-pyrazol-4-yl)pyridin-4-yl)oxy)pyridin-2-yl)carbamoyl)propanamide (84 mg, 50%) as an off-white solid. ¹H NMR (400 MHz, DMSO-d₆): δ 10.78 (s, 1H), 10.15 (s, 1H), 8.35 (d, J=5.7 Hz, 1H), 8.25 (s, 1H), 7.96 (d, J=0.7 Hz, 1H), 7.87 (s, 1H), 7.64 (d, J=8.8 Hz, 1H), 7.17 (d, J=2.4 Hz, 1H), 6.61 (dd, J=5.7, 2.4 Hz, 1H), 3.84 (s, 3H), 3.20 (s, 3H), 2.27 (s, 3H), 1.35 (s, 6H); MS (ESI) m/z: 424.9 (M+H⁺).

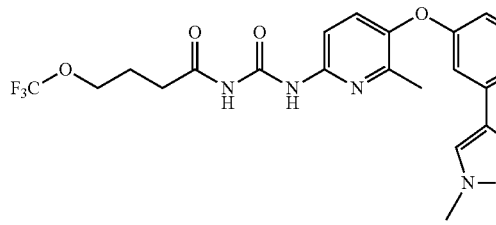

Example 59

A mixture of 4-(trifluoromethoxy)butanoic acid (1.0 g, 5.81 mmol) and HOBt (1.157 g, 7.55 mmol) in MeCN (20 mL) was treated with EDC (1.448 g, 7.55 mmol) and stirred at RT for 2 h. Ammonium hydroxide (~15M, 0.7 mL, ~10.5 mmol) was added and the mixture stirred at RT for 20 h. The mixture was treated with Et₂O, water and brine, the layers separated and the organic layer dried over Na₂SO₄ and concentrated to afford 4-(trifluoromethoxy)butanamide (1.024 g, 103%) as a white solid. ¹H NMR (400 MHz, DMSO-d₆): δ 7.30 (s, 1H), 6.78 (s, 1H), 4.04 (t, J=6.4 Hz, 2H), 2.13 (t, J=7.4 Hz, 2H), 1.82 (m, 2H).

A −78° C. mixture of 4-(trifluoromethoxy)butanamide (175 mg, 1.023 mmol) in THF (5 mL) was treated drop wise with LiHMDS (1.0M in THF, 1.33 mL, 1.33 mmol), stirred for 0.5 h, then treated drop wise with a solution of isopropenyl chloroformate (0.129 mL, 1.176 mmol) in THF (1 mL). The mixture was allowed to warm to RT, treated with satd. NaHCO₃ and extracted with EtOAc (3×). The combined organics were dried over Na₂SO₄ and concentrated to afford prop-1-en-2-yl (4-(trifluoromethoxy)butanoyl)carbamate (100% yield assumed).

A mixture of prop-1-en-2-yl (4-(trifluoromethoxy)butanoyl)carbamate (261 mg, 1.023 mmol) and Example A6 (180 mg, 0.639 mmol) in dioxane (5 mL) was treated with 1-methylpyrrolidine (54 mg, 0.639 mmol) and heated at 80° C. for 16 h. The mixture was cooled to RT, treated with EtOAc, washed with water, then brine, dried over Na₂SO₄, concentrated and purified via reverse-phase silica gel chromatography (MeCN/H₂O with 0.1% TFA). The combined pure fractions were concentrated to remove organics and the resulting aqueous mixture was neutralized with satd. NaHCO₃ and extracted with EtOAc (3×). The combined organics were washed with brine, dried over Na₂SO₄ and concentrated to dryness. The residue was dissolved in MeCN, treated with water, frozen and lyophilized to afford N-((6-methyl-5-((2-(1-methyl-1H-pyrazol-4-yl)pyridin-4-yl)oxy)pyridin-2-yl)carbamoyl)-4-(trifluoromethoxy)butanamide (38 mg, 12%) as a white solid. ¹H NMR (400 MHz, DMSO-d₆): δ 10.92 (s, 1H), 10.88 (s, 1H), 8.35 (d, J=5.8 Hz, 1H), 8.26 (s, 1H), 7.96 (s, 1H), 7.90 (d, J=8.8 Hz, 1H), 7.62 (d, J=8.8 Hz, 1H), 7.18 (s, 1H), 6.63 (s, 1H), 4.11 (t, J=6.4 Hz, 2H), 3.84 (s, 3H), 2.53 (t, J=7.3 Hz, 2H), 2.25 (s, 3H), 1.95 (t, J=6.8 Hz, 2H); MS (ESI) m/z: 479.2 (M+H⁺).

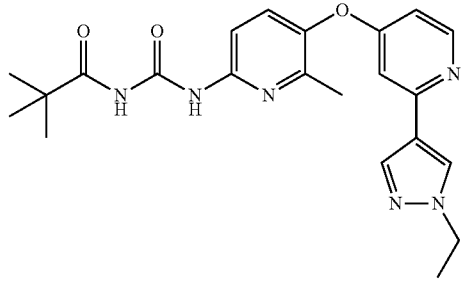 [SMILES: CCn1cc(-c2cc(Oc3ccc(NC(=O)NC(=O)C(C)(C)C)nc3C)ccn2)cn1]

Example 60

A solution of 2,2,2-trimethylacetamide (0.053 g, 0.528 mmol) in DCE (3 mL) was treated with oxalyl chloride (0.046 mL, 0.528 mmol), heated at 80° C. for 0.5 h, then cooled to RT and treated drop wise with a solution of Example A12 (0.12 g, 0.406 mmol) and pyridine (0.164 mL, 2.032 mmol) in THF (3 mL). The mixture was stirred at RT overnight, treated with satd. NaHCO₃ and extracted with EtOAc (4×). The combined organics were dried over Na₂SO₄, concentrated and purified via silica gel chromatography (MeOH/EtOAc). The residue was dissolved in 1:1 MeCN/H₂O, frozen and lyophilized to afford N-((5-((2-(1-ethyl-1H-pyrazol-4-yl)pyridin-4-yl)oxy)-6-methylpyridin-2-yl)carbamoyl)pivalamide (124 mg, 72%) as a white solid. ¹H NMR (400 MHz, DMSO-d₆): δ 11.15 (s, 1H), 10.39 (s, 1H), 8.35 (d, J=5.7 Hz, 1H), 8.29 (s, 1H), 7.96 (s, 1H), 7.91 (m, 1H), 7.62 (d, J=8.8 Hz, 1H), 7.17 (d, J=2.4 Hz, 1H), 6.60 (dd, J=5.7, 2.4 Hz, 1H), 4.12 (q, J=7.3 Hz, 2H), 2.25 (s, 3H), 1.36 (t, J=7.3 Hz, 3H), 1.21 (s, 9H); MS (ESI) m/z: 423.2 (M+H⁺+).

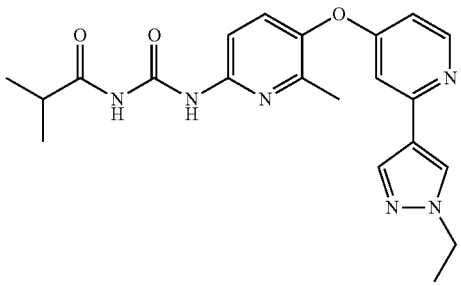 [SMILES: CCn1cc(-c2cc(Oc3ccc(NC(=O)NC(=O)C(C)C)nc3C)ccn2)cn1]

Example 61

A solution of Example B7 (0.046 g, 0.528 mmol) in DCE (3 mL) was treated with oxalyl chloride (0.046 mL, 0.528 mmol), heated at 80° C. for 0.5 h, then cooled to RT and treated drop wise with a solution of Example A12 (0.12 g, 0.406 mmol) and pyridine (0.164 mL, 2.032 mmol) in THF (3 mL). The mixture was stirred at RT overnight, treated with satd. NaHCO$_3$ and extracted with EtOAc (4×). The combined organics were dried over Na$_2$SO$_4$, concentrated and purified via silica gel chromatography (MeOH/EtOAc). The residue was dissolved in 1:1 MeCN/H$_2$O, frozen and lyophilized to afford N-((5-((2-(1-ethyl-1H-pyrazol-4-yl)pyridin-4-yl)oxy)-6-methylpyridin-2-yl)carbamoyl)isobutyramide (89 mg, 54%) as a white solid. $^1$H NMR (400 MHz, DMSO-d$_6$): δ 11.05 (s, 1H), 10.83 (s, 1H), 8.35 (d, J=5.7 Hz, 1H), 8.29 (s, 1H), 7.96 (s, 1H), 7.90 (d, J=8.8 Hz, 1H), 7.61 (d, J=8.8 Hz, 1H), 7.17 (d, J=2.4 Hz, 1H), 6.60 (dd, J=5.7, 2.4 Hz, 1H), 4.12 (q, J=7.3 Hz, 2H), 2.66-2.65 (m, 1H), 2.25 (s, 3H), 1.36 (t, J=7.3 Hz, 3H), 1.09 (d, J=6.8 Hz, 6H); MS (ESI) m/z: 409.2 (M+H$^+$).

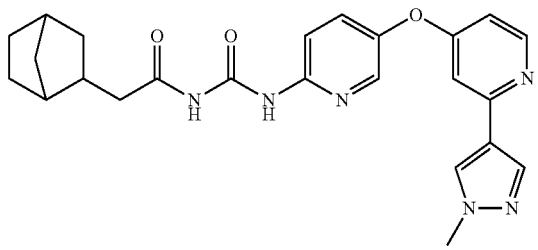 [SMILES: Cn1cc(-c2cc(Oc3ccc(NC(=O)NC(=O)CC4CC5CCC4C5)nc3)ccn2)cn1]

Example 62

A solution of 2-(bicyclo[2.2.1]heptan-2-yl)acetic acid (0.50 g, 3.24 mmol) in DCM (30 mL) was treated with oxalyl chloride (0.426 mL, 4.86 mmol), followed by a catalytic amount of DMF (1 drop) and stirred at RT for 2 h. A solution of NH$_4$OH (~15M, 2 mL, ~30 mmol) in THF (5 mL) was added drop wise and the mixture stirred at RT overnight. The mixture was concentrated to dryness and the residue was dissolved in EtOAc, washed with brine, dried over MgSO$_4$ and concentrated to dryness to afford 2-(bicyclo[2.2.1]heptan-2-yl)acetamide (480 mg, 97%). $^1$H NMR (400 MHz, DMSO-d$_6$): δ 7.19 (s, 1H), 6.65 (s, 1H), 2.14 (s, 1H), 1.91 (m, 3H), 1.75 (m, 1H), 1.35 (m, 4H), 1.11 (m, 4H); MS (ESI) m/z: 154.2 (M+H$^+$).

A suspension of 2-(bicyclo[2.2.1]heptan-2-yl)acetamide (0.069 g, 0.449 mmol) in DCE (3 mL) was treated with oxalyl chloride (0.039 mL, 0.449 mmol) and heated at 80° C. for 3 h. The mixture was cooled to RT, added drop wise to a solution of Example A2 (0.10 g, 0.374 mmol) and pyridine (0.151 mL, 1.871 mmol) in THF (3 mL) and stirred at RT for 3 days. The mixture was concentrated to dryness and purified via silica gel chromatography (EtOAc, MeOH/DCM). The material was treated with MeCN, the solid collected via filtration and dried to afford 2-(bicyclo[2.2.1]heptan-2-yl)-N-((5-((2-(1-methyl-1H-pyrazol-4-yl)pyridin-4-yl)oxy)pyridin-2-yl)carbamoyl)acetamide (138 mg, 81%) as a white solid. $^1$H NMR (400 MHz, DMSO-d$_6$): δ 11.10 (s, 1H), 10.82 (s, 1H), 8.37 (d, J=5.7 Hz, 1H), 8.26-8.25 (m, 2H), 8.08 (d, J=9.0 Hz, 1H), 7.95 (d, J=0.7 Hz, 1H), 7.72 (dd, J=9.0, 2.9 Hz, 1H), 7.22 (d, J=2.4 Hz, 1H), 6.70 (dd, J=5.7, 2.4 Hz, 1H), 3.83 (s, 3H), 2.36 (dd, J=14.7, 7.8 Hz, 1H), 2.23 (dd, J=14.7, 7.8 Hz, 1H), 2.21 (m, 1H), 1.94 (m, 1H), 1.85 (m, 1H), 1.45-1.38 (m, 3H), 1.31 (m, 1H), 1.11-1.07 (m, 4H); MS (ESI) m/z: 447.3 (M+H$^+$).

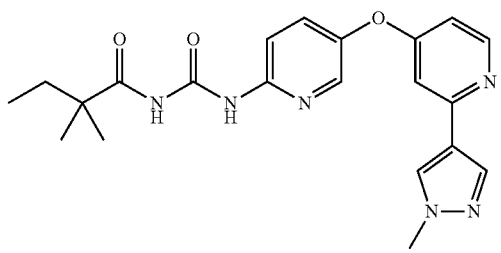 [SMILES: CCC(C)(C)C(=O)NC(=O)Nc1ccc(Oc2ccnc(-c3cnn(C)c3)c2)cn1]

Example 63

A suspension of Example B17 (0.052 g, 0.449 mmol) in DCE (3 mL) was treated with oxalyl chloride (0.039 mL, 0.449 mmol) and heated at 80° C. for 3 h. The mixture was cooled to RT and added drop wise to a solution of Example A2 (0.10 g, 0.374 mmol) and pyridine (0.151 mL, 1.871 mmol) in THF (3 mL) and stirred at RT for 3 days. The mixture was concentrated to dryness and purified via silica gel chromatography (EtOAc, MeOH/DCM). The material was treated with MeCN and the white solid was collected via filtration and dried to afford 2,2-dimethyl-N-((5-((2-(1-methyl-1H-pyrazol-4-yl)pyridin-4-yl)oxy)pyridin-2-yl)carbamoyl)butanamide (104 mg, 68%). $^1$H NMR (400 MHz, DMSO-d$_6$): δ 11.25 (s, 1H), 10.4 (s, 1H), 8.38 (d, J=5.7 Hz, 1H), 8.27 (d, J=3.1 Hz, 1H), 8.26 (s, 1H), 8.10 (d, J=9.0 Hz, 1H), 7.97 (d, J=0.7 Hz, 1H), 7.74 (dd, J=9.0, 2.9 Hz, 1H), 7.23 (d, J=2.4 Hz, 1H), 6.71 (dd, J=5.7, 2.4 Hz, 1H), 3.85 (s, 3H), 1.64 (q, J=7.5 Hz, 2H), 1.17 (s, 6H), 0.78 (t, J=7.4 Hz, 3H); MS (ESI) m/z: 409.2 (M+H$^+$).

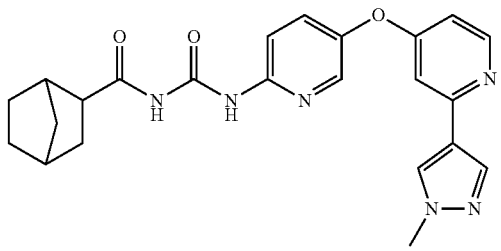 [SMILES: Cn1cc(-c2cc(Oc3ccc(NC(=O)NC(=O)C4CC5CCC4C5)nc3)ccn2)cn1]

Example 64

A solution of endo-norbornane-2-carboxylic acid (0.200 g, 1.427 mmol) in DCM (10 mL) was treated with oxalyl chloride (0.200 g, 1.576 mmol), followed by catalytic DMF (5.47 mg, 0.075 mmol) and stirred at RT for 4 h. The mixture was concentrated to dryness, treated with DCM (10 mL) and silver cyanate (0.250 g, 1.668 mmol) and stirred at RT for 2 h. Example A2 (0.200 g, 0.748 mmol) was added and the mixture stirred at RT overnight. The solids were removed via filtration through diatomaceous earth, washed with DCM and THF and the filtrate concentrated to dryness and purified via silica gel chromatography (EtOAc/Hex). The resulting material was treated with MeOH and the solids were collected via filtration and dried in vacuo to afford N-((5-((2-(1-methyl-1H-pyrazol-4-yl)pyridin-4-yl)oxy)pyridin-2-yl)carbamoyl)bicyclo[2.2.1]heptane-2-carboxamide (185 mg, 35%) as a white solid. $^1$H NMR (400 MHz, DMSO-d$_6$): δ 11.15 (s, 1H), 10.82 (s, 1H), 8.37 (d, J=5.7 Hz, 1H), 8.25 (s, 2H), 8.09 (d, J=9.0 Hz, 1H), 7.96 (s, 1H), 7.72 (dd, J=9.0, 2.9 Hz, 1H), 7.22 (d, J=2.4 Hz, 1H), 6.70 (dd, J=5.7, 2.5 Hz, 1H), 3.84 (s, 3H), 2.91-2.86 (m, 1H), 2.63 (s, 1H), 2.21 (s, 1H), 1.45-1.38 (m, 8H); MS (ESI) m/z: 433.2 (M+H$^+$).

(0.450 g, 3.55 mmol), followed by catalytic DMF (8.20 mg, 0.112 mmol) and stirred at RT for 2 h. The mixture was concentrated to dryness, dissolved in DCM (10 mL), treated with silver cyanate (0.550 g, 3.67 mmol), stirred for 2 h, treated with Example A2 (0.300 g, 1.122 mmol) and stirred at RT overnight. The solids were removed via filtration through diatomaceous earth, washed with DCM and THF and the filtrate concentrated to dryness. The material was treated with MeCN and the solid was collected via filtration and dried to afford N-((5-((2-(1-methyl-1H-pyrazol-4-yl)pyridin-4-yl)oxy)pyridin-2-yl)carbamoyl)tetrahydrofuran-3-carboxamide (115 mg, 25%) as a white solid. $^1$H NMR (400 MHz, DMSO-d$_6$): δ 10.98 (s, 2H), 8.37 (d, J=5.7 Hz, 1H), 8.26-8.24 (m, 2H), 8.08 (d, J=9.0 Hz, 1H), 7.95 (s, 1H), 7.73 (dd, J=9.0, 2.9 Hz, 1H), 7.22 (d, J=2.4 Hz, 1H), 6.70 (dd, J=5.7, 2.4 Hz, 1H), 3.92 (m, 1H), 3.84 (s, 3H), 3.77-3.75 (m, 2H), 3.67 (q, J=7.5 Hz, 1H), 3.21-3.19 (m, 1H), 2.08-2.06 (m, 2H); MS (ESI) m/z: 409.2 (M+H$^+$).

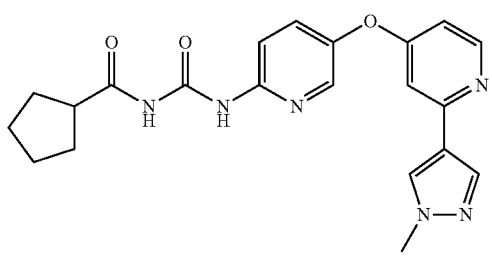 [SMILES: Cn1cc(-c2cc(Oc3ccc(NC(=O)NC(=O)C4CCCC4)nc3)ccn2)cn1]

Example 65

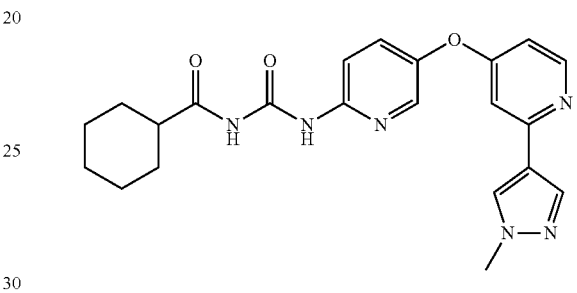

Example 67

A solution of cyclopentanecarbonyl chloride (0.400 g, 3.02 mmol) in DCM (10 mL) was treated with silver cyanate (0.500 g, 3.34 mmol), stirred at RT for 4 h, treated with Example A2 (0.300 g, 1.122 mmol) and stirred at RT overnight. The solids were removed via filtration through diatomaceous earth, washed with DCM and THF and the filtrate concentrated to dryness. The residue was treated with MeCN and the solid was collected via filtration and dried to afford N-((5-((2-(1-methyl-1H-pyrazol-4-yl)pyridin-4-yl)oxy)pyridin-2-yl)carbamoyl)cyclopentanecarboxamide (310 mg, 67%) as a white solid. $^1$H NMR (400 MHz, DMSO-d$_6$): δ 11.11 (s, 1H), 10.85 (s, 1H), 8.37 (d, J=5.7 Hz, 1H), 8.25 (br s, 2H), 8.08 (d, J=9.0 Hz, 1H), 7.95 (s, 1H), 7.72 (dd, J=9.0, 2.9 Hz, 1H), 7.22 (d, J=2.4 Hz, 1H), 6.69 (dd, J=5.7, 2.4 Hz, 1H), 3.84 (s, 3H), 2.84 (m, 1H), 1.83 (m, 2H), 1.63-1.60 (m, 6H); MS (ESI) m/z: 407.2 (M+H$^+$).

A solution of cyclohexane carbonylchloride (0.400 g, 2.73 mmol) in DCM (10 mL) was treated with silver cyanate (0.500 g, 3.34 mmol), stirred at RT for 4 h, treated with Example A2 (0.300 g, 1.122 mmol) and stirred at RT overnight. The solids were removed via filtration through diatomaceous earth, washed with DCM and THF and the filtrate concentrated to dryness. The material was treated with MeCN, the solid collected via filtration and dried to afford N-((5-((2-(1-methyl-1H-pyrazol-4-yl)pyridin-4-yl)oxy)pyridin-2-yl)carbamoyl)cyclohexanecarboxamide (308 mg, 65%) as a white solid. $^1$H NMR (400 MHz, DMSO-d$_6$): δ 11.11 (s, 1H), 10.79 (s, 1H), 8.37 (d, J=5.7 Hz, 1H), 8.25 (br s, 2H), 8.08 (d, J=9.0 Hz, 1H), 7.95 (s, 1H), 7.72 (dd, J=9.0, 2.9 Hz, 1H), 7.21 (d, J=2.4 Hz, 1H), 6.69 (dd, J=5.7, 2.4 Hz, 1H), 3.84 (s, 3H), 2.41 (s, 1H), 1.76-1.70 (m, 5H), 1.31-1.25 (m, 5H); MS (ESI) m/z: 421.2 (M+H$^+$).

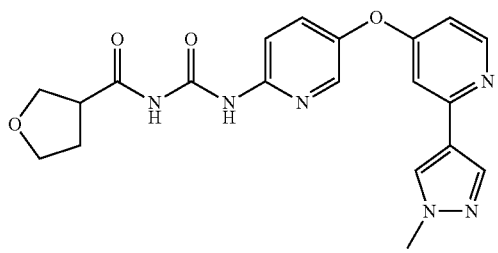 [SMILES: Cn1cc(-c2cc(Oc3ccc(NC(=O)NC(=O)C4CCOC4)nc3)ccn2)cn1]

Example 66

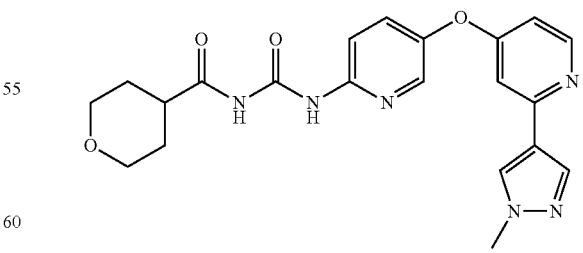

Example 68

A solution of tetrahydrofuran-3-carboxylic acid (0.400 g, 3.44 mmol) in DCM (10 mL) was treated with oxalyl chloride A solution of tetrahydro-2H-pyran-4-carboxylic acid (0.400 g, 3.07 mmol) in DCM (10 mL) was treated with oxalyl chloride (0.450 g, 3.55 mmol), followed by catalytic DMF (8.20 mg, 0.112 mmol) and stirred at RT for 2 h. The mixture was concentrated to dryness, the residue dissolved in DCM (10 mL), treated with silver cyanate (0.550 g, 3.67 mmol), stirred at RT for 2 h, treated with Example A2 (0.300 g, 1.122 mmol) and stirred at RT overnight. The solids were removed via filtration through diatomaceous earth, washed with DCM and THF and the filtrate was concentrated to dryness. The residue was treated with MeCN and the solid was collected via filtration and dried to afford N-((5-((2-(1-methyl-1H-pyrazol-4-yl)pyridin-4-yl)oxy)pyridin-2-yl)carbamoyl)tetrahydro-2H-pyran-4-carboxamide (170 mg, 35%) as a white solid. $^1$H NMR (400 MHz, DMSO-d$_6$): δ 11.05 (s, 1H), 10.88 (s, 1H), 8.37 (d, J=5.7 Hz, 1H), 8.26-8.24 (m, 2H), 8.08 (d, J=9.0 Hz, 1H), 7.95 (s, 1H), 7.72 (dd, J=9.0, 2.9 Hz, 1H), 7.22 (d, J=2.4 Hz, 1H), 6.70 (dd, J=5.7, 2.4 Hz, 1H), 3.88 (m, 2H), 3.83 (s, 3H), 3.31 (m, 2H), 2.68 (t, J=11.3 Hz, 1H), 1.71 (d, J=13.0 Hz, 2H), 1.64-1.60 (m, 2H); MS (ESI) m/z: 423.2 (M+H$^+$).

Example 69

A suspension of Example B17 (0.049 g, 0.427 mmol) in DCE (3 mL) was treated with oxalyl chloride (0.037 mL, 0.427 mmol) and heated at 80° C. for 3 h. The mixture was cooled to RT, added drop wise to a solution of Example A6 (0.10 g, 0.355 mmol) and pyridine (0.143 mL, 1.777 mmol) in THF (3 mL) and stirred at RT for 3 days. The mixture was concentrated to dryness and purified via silica gel chromatography (MeOH/DCM). The material was treated with MeCN and the solid collected via filtration and dried under vacuum to afford 2,2-dimethyl-N-((6-methyl-5-((2-(1-methyl-1H-pyrazol-4-yl)pyridin-4-yl)oxy)pyridin-2-yl)carbamoyl)butanamide (130 mg, 86%) as a peach-colored solid. $^1$H NMR (400 MHz, DMSO-d$_6$): δ 11.19 (s, 1H), 10.37 (br s, 1H), 8.36 (d, J=5.7 Hz, 1H), 8.26 (s, 1H), 7.96 (s, 1H), 7.92 (m, 1H), 7.63 (d, J=8.8 Hz, 1H), 7.17 (d, J=2.4 Hz, 1H), 6.62 (dd, J=5.7, 2.4 Hz, 1H), 3.84 (s, 3H), 2.26 (s, 3H), 1.63 (t, J=7.5 Hz, 2H), 1.17 (s, 6H), 0.78 (t, J=7.4 Hz, 3H); MS (ESI) m/z: 423.2 (M+H$^+$).

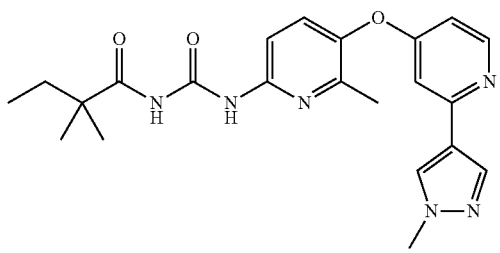 [SMILES: CCC(C)(C)C(=O)NC(=O)Nc1ccc(Oc2ccnc(-c3cnn(C)c3)c2)c(C)n1]

Example 70

A solution of 2,2,2-trimethylacetamide (0.038 g, 0.375 mmol) in DCE (4 mL) was treated with oxalyl chloride (0.033 mL, 0.375 mmol), stirred for 5 min, then heated to 80° C. for 0.5 h. The mixture was cooled to RT, added to a mixture of Example A13 (0.082 g, 0.288 mmol) and pyridine (0.140 mL, 1.730 mmol) in dioxane (4 mL) and stirred at RT overnight. The mixture was treated with satd. NaHCO$_3$, extracted with EtOAc (3×) and the combined organics were dried over Na$_2$SO$_4$ and concentrated to dryness. The residue was treated with MeCN, the solid collected via filtration and dried to afford N-((5-((2-(2-methylthiazol-5-yl)pyridin-4-yl)oxy)pyridin-2-yl)carbamoyl)pivalamide (75 mg, 63%) as a white solid. $^1$H NMR (400 MHz, DMSO-d$_6$): δ 11.22 (s, 1H), 10.43 (s, 1H), 8.41 (d, J=5.8 Hz, 1H), 8.32 (s, 1H), 8.28 (d, J=2.9 Hz, 1H), 8.09 (d, J=9.0 Hz, 1H), 7.76 (dd, J=9.0, 2.9 Hz, 1H), 7.60 (d, J=2.4 Hz, 1H), 6.82 (dd, J=5.8, 2.4 Hz, 1H), 2.65 (s, 3H), 1.21 (s, 9H); MS (ESI) m/z: 412.2 (M+H$^+$).

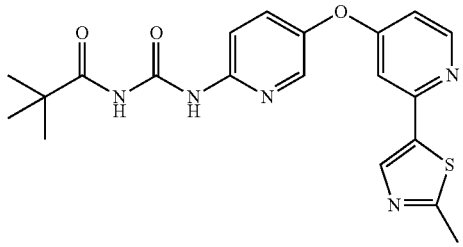 [SMILES: Cc1ncc(-c2cc(Oc3ccc(NC(=O)NC(=O)C(C)(C)C)nc3)ccn2)s1]

Example 71

A solution of Example B7 (0.036 g, 0.410 mmol) in DCE (1.7 mL) was treated drop wise with oxalyl chloride (0.039 mL, 0.445 mmol), stirred at RT for 0.5 h then heated at 80° C. for 1 h. The mixture was cooled to RT, added to a solution of Example A14 (0.1 g, 0.342 mmol) and pyridine (0.138 mL, 1.710 mmol) in THF (1.7 mL) and stirred at RT overnight. The mixture was treated with satd. NaHCO$_3$, extracted with EtOAc (4×) and the combined organics were dried over Na$_2$SO$_4$ and concentrated to dryness. The resulting oil was treated with MeCN and the solid collected via filtration. The solid was again triturated with MeCN and collected via filtration to afford N-((6-methyl-5-((6'-methyl-[2,3'-bipyridin]-4-yl)oxy)pyridin-2-yl)carbamoyl)isobutyramide (30 mg, 22%) as a white solid. $^1$H NMR (400 MHz, DMSO-d$_6$): δ 11.05 (s, 1H), 10.84 (s, 1H), 9.09 (d, J=2.4 Hz, 1H), 8.53 (d, J=5.7 Hz, 1H), 8.27 (dd, J=8.1, 2.4 Hz, 1H), 7.91 (d, J=8.8 Hz, 1H), 7.65 (d, J=8.8 Hz, 1H), 7.58 (d, J=2.4 Hz, 1H), 7.33 (d, J=8.2 Hz, 1H), 6.78 (dd, J=5.7, 2.4 Hz, 1H), 2.65 (m, 1H), 2.50 (s, 3H), 2.27 (s, 3H), 1.09 (d, J=6.8 Hz, 6H); MS (ESI) m/z: 406.2 (M+H$^+$).

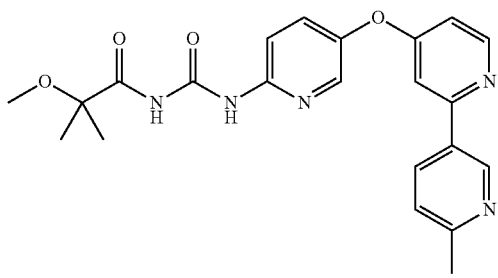 [SMILES: COC(C)(C)C(=O)NC(=O)Nc1ccc(Oc2ccnc(-c3ccc(C)nc3)c2)cn1]

Example 72

A solution of Example B16 (0.200 g, 0.994 mmol) and Example A15 (0.111 g, 0.398 mmol in dioxane (4 mL) was treated with 1-methylpyrrolidine (0.041 mL, 0.398 mmol) heated at 80° C. for 4 h, then cooled to RT and stirred overnight. The mixture was treated with satd. NaHCO$_3$, extracted with EtOAc (4×) and the combined organics were dried over Na$_2$SO$_4$, concentrated to dryness and purified via silica gel chromatography (MeOH/DCM). The resulting oil was dissolved in MeCN/H$_2$O, frozen and lyophilized to afford 2-methoxy-2-methyl-N-((5-((6'-methyl-[2,3'-bipyridin]-4-yl)oxy)pyridin-2-yl)carbamoyl)propanamide (75 mg, 45%) as an off-white solid. $^1$H NMR (400 MHz, DMSO-d$_6$): δ 10.80 (s, 1H), 9.10 (d, J=2.4 Hz, 1H), 8.55 (d, J=5.7 Hz, 1H), 8.30-8.26 (m, 2H), 8.03 (m, 1H), 7.78 (dd, J=9.0, 2.9 Hz, 1H), 7.64 (d, J=2.4 Hz, 1H), 7.33 (d, J=8.2 Hz, 1H), 6.89 (dd, J=5.7, 2.4 Hz, 1H), 3.20 (s, 3H), 2.50 (s, 3H), 1.35 (s, 6H); MS (ESI) m/z: 422.2 (M+H$^+$).

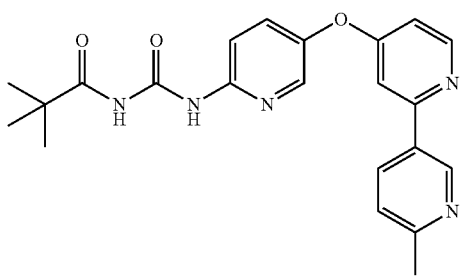 [SMILES: Cc1ccc(-c2cc(Oc3ccc(NC(=O)NC(=O)C(C)(C)C)nc3)ccn2)cn1]

Example 73

A solution of 2,2,2-trimethylacetamide (0.044 g, 0.431 mmol) in DCE (1.8 mL) was treated drop wise with oxalyl chloride (0.041 mL, 0.467 mmol), stirred at RT for 0.5 h, then heated to 80° C. for 1 h. The mixture was cooled to RT, added to a solution of Example A15 (0.1 g, 0.359 mmol) and pyridine (0.145 mL, 1.797 mmol) in THF (1.8 mL) and stirred at RT for 2 h. The mixture was treated with satd. NaHCO$_3$, extracted with EtOAc (4×) and the combined organics were dried over Na$_2$SO$_4$, concentrated to dryness and purified via silica gel chromatography (MeOH/DCM). The resulting solid was treated with MeCN, the solid collected via filtration and dried to afford N-((5-((6'-methyl-[2,3'-bipyridin]-4-yl)oxy)pyridin-2-yl)carbamoyl)pivalamide (33 mg, 23%) as an off-white solid. $^1$H NMR (400 MHz, DMSO-d$_6$): δ 11.22 (s, 1H), 10.44 (m, 1H), 9.10 (d, J=2.3 Hz, 1H), 8.55 (d, J=5.7 Hz, 1H), 8.29-8.26 (m, 2H), 8.09 (m, 1H), 7.77 (dd, J=9.0, 3.0 Hz, 1H), 7.64 (d, J=2.4 Hz, 1H), 7.33 (d, J=8.2 Hz, 1H), 6.89 (dd, J=5.7, 2.4 Hz, 1H), 2.50 (s, 3H), 1.21 (s, 9H); MS (ESI) m/z: 406.2 (M+H$^+$).

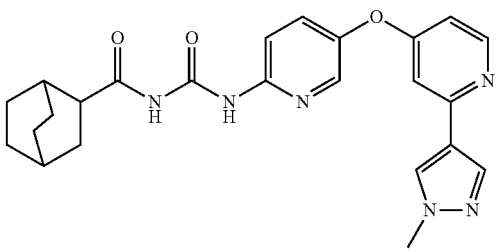 [SMILES: Cn1cc(-c2cc(Oc3ccc(NC(=O)NC(=O)C4CC5CCC4CC5)nc3)ccn2)cn1]

Example 74

A solution of bicyclo(2.2.2)octane-2-carboxylic acid (0.100 g, 0.648 mmol) in DCM (6 mL) was treated with oxalyl chloride (0.100 g, 0.788 mmol) followed by catalytic DMF (4.74 mg, 0.065 mmol) and stirred at RT for 2 h. The mixture was concentrated to dryness, treated with silver cyanate (0.120 g, 0.801 mmol) in DCM (6 mL), stirred at RT for 2 h, treated with Example A2 (0.150 g, 0.561 mmol) and stirred at RT overnight. The solids were removed via filtration through diatomaceous earth, washed with DCM and THF and the filtrate concentrated to dryness and purified via silica gel chromatography (EtOAc/Hex) to afford N-((5-((2-(1-methyl-1H-pyrazol-4-yl)pyridin-4-yl)oxy)pyridin-2-yl)carbamoyl)bicyclo[2.2.2]octane-2-carboxamide (118 mg, 38%) as a white solid. $^1$H NMR (400 MHz, DMSO-d$_6$): δ 11.15 (s, 1H), 10.81 (s, 1H), 8.37 (d, J=5.7 Hz, 1H), 8.25-8.24 (m, 2H), 8.08 (d, J=9.0 Hz, 1H), 7.95 (s, 1H), 7.72 (dd, J=9.0, 2.9 Hz, 1H), 7.22 (d, J=2.4 Hz, 1H), 6.70 (dd, J=5.7, 2.5 Hz, 1H), 3.83 (s, 3H), 2.72 (t, J=7.9 Hz, 1H), 1.92 (dd, J=12.9, 6.2 Hz, 1H), 1.81 (s, 1H), 1.51-1.43 (m, 10H); MS (ESI) m/z: 447.5 (M+H$^+$).

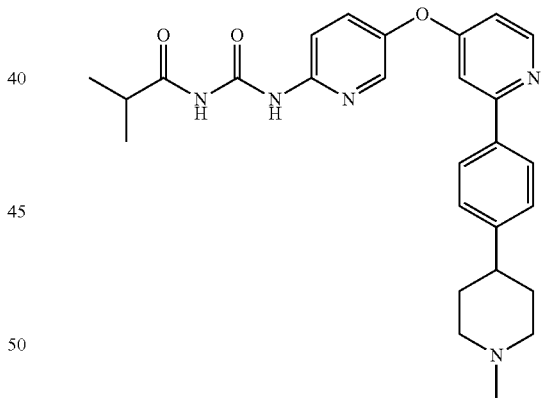

Example 75

A solution of Pd(PPh$_3$)$_4$ (0.105 g, 0.091 mmol), K$_2$CO$_3$ (0.377 g, 2.73 mmol), Example A1 (0.229 g, 0.909 mmol) and Example C4 (0.356 g, 1.182 mmol) in dioxane (8 mL) and water (2 mL) was sparged with Ar and heated at 90° C. overnight. The mixture was cooled to RT, treated with EtOAc and brine and filtered through diatomaceous earth. The layers of the filtrate were separated, the aqueous extracted with additional EtOAc (2×) and the combined organics were dried over Na$_2$SO$_4$, concentrated to dryness and purified via silica gel chromatography (MeOH/DCM) to afford 2-(4-(1-methylpiperidin-4-yl)phenyl)-4-((6-nitropyridin-3-yl)oxy)pyridine (199 mg, 54%). ¹H NMR (400 MHz, DMSO-d): δ 8.64 (d, J=5.6 Hz, 1H), 8.61 (d, J=2.8 Hz, 1H), 8.40 (d, J=8.9 Hz, 1H), 8.01-7.97 (m, 3H), 7.72 (d, J=2.3 Hz, 1H), 7.34 (s, 1H), 7.32 (s, 1H), 7.13 (dd, J=5.6, 2.3 Hz, 1H), 2.87 (m, 2H), 2.19 (s, 3H), 1.98 (m, 2H), 1.77-1.60 (m, 5H); MS (ESI) m/z: 391.2 (M+H⁺).

A solution of 2-(4-(1-methylpiperidin-4-yl)phenyl)-4-((6-nitropyridin-3-yl)oxy)pyridine (0.199 g, 0.510 mmol) in EtOAc (10 mL) and EtOH (10 mL) was treated with tin(II) chloride dehydrate (0.575 g, 2.55 mmol), heated at 65° C. for 4 h, then heated 75° C. overnight. Additional tin(II) chloride dehydrate (300 mg) was added, the mixture heated at 80° C. for 6 h, treated with another portion of tin(II) chloride dehydrate (300 mg) and heated at 80° C. for 3 days. Additional tin(II) chloride dehydrate (300 mg) was added and the mixture heated at 80° C. overnight. The mixture was cooled to RT, concentrated to dryness, treated with EtOAc and satd. NaHCO₃, filtered through diatomaceous earth and the filter cake rinsed with EtOAc/THF. The filtrate was treated with solid NaOH (2 g) and NaCl until the aqueous layer was saturated, extracted with 3:1 EtOAc/THF (2×) and the combined organics were washed with brine, dried over Na₂SO₄ and concentrated to dryness to afford 5-((2-(4-(1-methylpiperidin-4-yl)phenyl)pyridin-4-yl)oxy)pyridin-2-amine (250 mg, >100%). MS (ESI) m/z: 361.2 (M+H⁺).

A solution of Example B7 (0.045 g, 0.520 mmol) in DCE (3 mL) was treated with oxalyl chloride (0.046 mL, 0.520 mmol), stirred at RT for 5 min, then warmed to 80° C. for 0.5 h. The mixture was cooled to RT, added drop wise to a solution of 5-((2-(4-(1-methylpiperidin-4-yl)phenyl)pyridin-4-yl)oxy)pyridin-2-amine (0.125 g, 0.347 mmol) and DIEA (0.363 mL, 2.081 mmol) in THF (3 mL) and stirred at RT overnight. The mixture was treated with 1:1 1 N NaOH/brine, extracted with EtOAc (3×) and the combined organics were dried over Na₂SO₄, concentrated to dryness and purified via reverse-phase silica gel chromatography (MeCN/H₂O with 0.1% TFA). The organics were removed under reduced pressure. The remaining aqueous layer was neutralized with 1N NaOH, extracted with EtOAc (3×) and the combined organics were dried over Na₂SO₄ and concentrated to dryness. The material was suspended in 1:1 MeCN/H₂O, frozen and lyophilized to afford N-((5-((2-(4-(1-methylpiperidin-4-yl)phenyl)pyridin-4-yl)oxy)pyridin-2-yl)carbamoyl)isobutyramide (23 mg, 14%) as a white solid. ¹H NMR (400 MHz, DMSO-d₆): δ 11.10 (s, 1H), 10.85 (s, 1H), 8.51 (d, J=5.7 Hz, 1H), 8.28 (d, J=2.9 Hz, 1H), 8.09 (d, J=9.0 Hz, 1H), 7.93 (d, J=8.2 Hz, 2H), 7.75 (dd, J=9.0, 2.9 Hz, 1H), 7.46 (d, J=2.4 Hz, 1H), 7.31 (d, J=8.2 Hz, 2H), 6.84 (dd, J=5.6, 2.4 Hz, 1H), 2.84 (m, 2H), 2.66 (m, 1H), 2.17 (s, 3H), 1.94 (m, 2H), 1.75-1.59 (m, 5H), 1.08 (d, J=6.8 Hz, 6H); MS (ESI) m/z: 474.3 (M+H⁺).

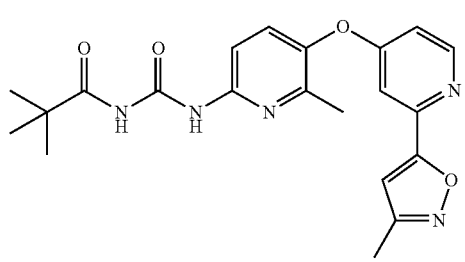 [SMILES: Cc1cc(-c2cc(Oc3ccc(NC(=O)NC(=O)C(C)(C)C)nc3C)ccn2)on1]

Example 76

A suspension of 2,2,2-trimethylacetamide (0.086 g, 0.850 mmol) in DCE (3.5 mL) was treated drop-wise with oxalyl chloride (0.074 mL, 0.850 mmol), stirred at RT for 0.5 h, then warmed to 85° C. for 1 h. The solution was cooled to RT, added drop-wise to a solution of Example A7 (0.2 g, 0.708 mmol) and pyridine (0.069 mL, 0.850 mmol) in THF (3.5 mL) and stirred at RT for 2.5 days. Satd. NaHCO₃ was added, the mixture extracted with EtOAc (4×) and the combined organics were dried over Na₂SO₄, concentrated to dryness and purified via silica gel chromatography (MeOH/DCM). The white solid was dissolved in MeOH, treated with water until a precipitate formed and the solid was collected via filtration, dissolved in MeCN/H₂O, frozen and lyophilized to afford N-((6-methyl-5-((2-(3-methylisoxazol-5-yl)pyridin-4-yl)oxy)pyridin-2-yl)carbamoyl)pivalamide (51 mg, 18%) as a white solid. ¹H NMR (400 MHz, DMSO-d₆): δ 11.16 (s, 1H), 10.41 (s, 1H), 8.55 (d, J=5.7 Hz, 1H), 7.93-7.91 (m, 1H), 7.69 (d, J=8.8 Hz, 1H), 7.34 (d, J=2.5 Hz, 1H), 6.97-6.95 (m, 2H), 2.28 (s, 3H), 2.25 (s, 3H), 1.20 (s, 9H); MS (ESI) m/z: 410.2 (M+H⁺).

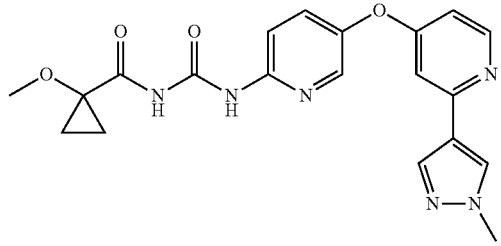

Example 77

A solution of Example A2 (0.113 g, 0.424 mmol) and Example B18 (0.211 g, 1.059 mmol) in dioxane (4 mL) was treated with 1-methylpyrrolidine (0.138 mL, 1.27 mmol), heated at 80° C. for 3 h, cooled to RT and stirred overnight. The mixture was concentrated to dryness and purified via silica gel chromatography (MeOH/DCM). The resulting material was suspended in 1:1 MeCN/H₂O, frozen and lyophilized to afford 1-methoxy-N-((5-((2-(1-methyl-1H-pyrazol-4-yl)pyridin-4-yl)oxy)pyridin-2-yl)carbamoyl)cyclopropanecarboxamide (131 mg, 76%) as a white solid. ¹H NMR (400 MHz, DMSO-d₆): δ 10.86 (s, 1H), 10.44 (br s, 1H), 8.37 (d, J=5.7 Hz, 1H), 8.26-8.24 (m, 2H), 8.01 (m, 1H), 7.95 (d, J=0.7 Hz, 1H), 7.73 (dd, J=9.0, 2.9 Hz, 1H), 7.22 (d, J=2.4 Hz, 1H), 6.69 (dd, J=5.7, 2.4 Hz, 1H), 3.83 (s, 3H), 3.31 (s, 3H), 1.23 (s, 4H); MS (ESI) m/z: 409.2 (M+H⁺).

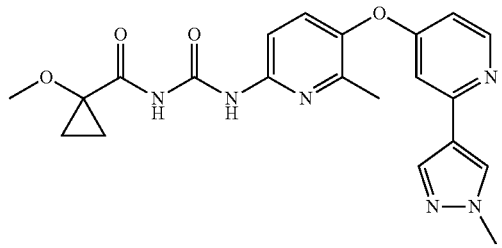

Example 78

A solution of Example A6 (0.119 g, 0.424 mmol) and Example B18 (0.211 g, 1.059 mmol) in dioxane (4 mL) was treated with 1-methylpyrrolidine (0.138 mL, 1.271 mmol), heated at 80° C. for 3 h, cooled to RT and stirred overnight. The mixture was concentrated to dryness and purified via silica gel chromatography (MeOH/DCM). The resulting material was suspended in 1:1 MeCN/H$_2$O, frozen and lyophilized to afford 1-methoxy-N-((6-methyl-5-((2-(1-methyl-1H-pyrazol-4-yl)pyridin-4-yl)oxy)pyridin-2-yl)carbamoyl)cyclopropanecarboxamide (156 mg, 87%) as a white solid. $^1$H NMR (400 MHz, DMSO-d$_6$): δ 10.86 (br s, 1H), 10.37 (br s, 1H), 8.36 (d, J=5.7 Hz, 1H), 8.26 (s, 1H), 7.96 (s, 1H), 7.89 (br s, 1H), 7.64 (d, J=8.8 Hz, 1H), 7.17 (d, J=2.4 Hz, 1H), 6.62 (dd, J=5.7, 2.4 Hz, 1H), 3.85 (s, 3H), 3.32 (s, 3H), 2.27 (s, 3H), 1.24 (s, 4H); MS (ESI) m/z: 423.2 (M+H$^+$).

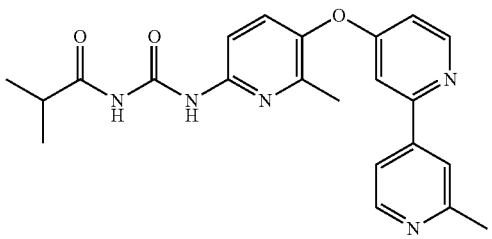 [SMILES: Cc1cc(-c2cc(Oc3ccc(NC(=O)NC(=O)C(C)C)nc3C)ccn2)ccn1]

Example 79

A solution of Example B7 (0.036 g, 0.410 mmol) in DCE (1.7 mL) was treated drop-wise with oxalyl chloride (0.036 mL, 0.410 mmol), stirred at RT for 20 minutes, then heated at 80° C. for 1 h. The mixture was cooled to RT, added drop-wise to a solution of Example A11 (0.1 g, 0.342 mmol) and pyridine (0.138 mL, 1.710 mmol) in THF (1.7 mL), and the resulting mixture was stirred at RT overnight. The mixture was treated with satd. NaHCO$_3$, extracted with EtOAc (4×) and the combined organics were dried over Na$_2$SO$_4$, concentrated to dryness and purified via silica gel chromatography (MeOH/DCM). The resulting oil was treated with Et$_2$O, allowed to stand overnight, the Et$_2$O decanted from the solid and the solid was dissolved in MeCN/H$_2$O, frozen and lyophilized to afford N-((6-methyl-5-((2'-methyl-[2,4'-bipyridin]-4-yl)oxy)pyridin-2-yl)carbamoyl)isobutyramide (43 mg, 30%) as an off-white solid. $^1$H NMR (400 MHz, DMSO-d$_6$): δ 11.05 (s, 1H), 10.83 (s, 1H), 8.57 (d, J=5.6 Hz, 1H), 8.51 (d, J=5.2 Hz, 1H), 7.91 (d, J=8.8 Hz, 1H), 7.89 (s, 1H), 7.79 (dd, J=5.3, 1.7 Hz, 1H), 7.65-7.64 (m, 2H), 6.87 (dd, J=5.6, 2.4 Hz, 1H), 2.65-2.64 (m, 1H), 2.52 (s, 3H), 2.27 (s, 3H), 1.08 (d, J=6.8 Hz, 6H); MS (ESI) m/z: 406.2 (M+H$^+$).

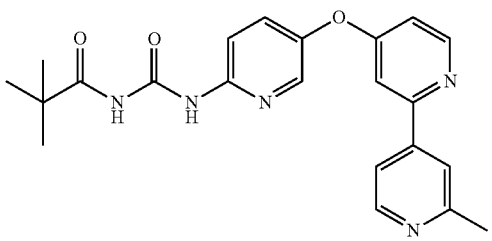 [SMILES: Cc1cc(-c2cc(Oc3ccc(NC(=O)NC(=O)C(C)(C)C)nc3)ccn2)ccn1]

Example 80

A solution of 2,2,2-trimethylacetamide (0.052 g, 0.517 mmol) in DCE (2 mL) was treated drop-wise with oxalyl chloride (0.045 mL, 0.517 mmol), stirred at RT for 0.5 h, then heated at 80° C. for 1 h. The mixture was cooled to RT, added drop-wise to a solution of Example A16 (0.12 g, 0.431 mmol) and pyridine (0.174 mL, 2.156 mmol) in THF (2 mL) and stirred at RT for 1.5 h. The mixture was treated with satd. NaHCO$_3$, extracted with EtOAc (5×) and the combined organics were dried over Na$_2$SO$_4$, concentrated to dryness and purified via silica gel chromatography (MeOH/DCM) to afford N-((5-((2'-methyl-[2,4'-bipyridin]-4-yl)oxy)pyridin-2-yl)carbamoyl)pivalamide (88 mg, 49%) as a white solid. $^1$H NMR (400 MHz, DMSO-d$_6$): δ 11.23 (s, 1H), 10.44 (s, 1H), 8.60 (d, J=5.6 Hz, 1H), 8.52 (d, J=5.2 Hz, 1H), 8.31 (d, J=2.9 Hz, 1H), 8.10 (d, J=9.0 Hz, 1H), 7.90 (s, 1H), 7.81-7.76 (m, 2H), 7.71 (d, J=2.4 Hz, 1H), 6.98 (dd, J=5.6, 2.4 Hz, 1H), 2.53 (s, 3H), 1.21 (s, 9H); MS (ESI) m/z: 406.2 (M+H$^+$).

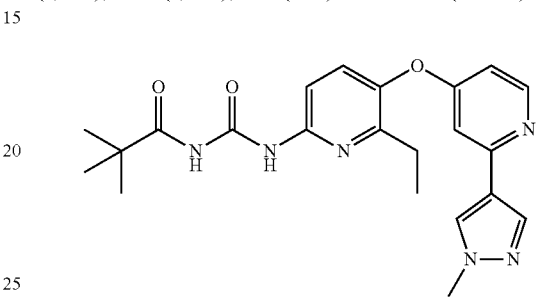

Example 81

A solution of 2,2,2-trimethylacetamide (45 mg, 0.447 mmol) in DCE (1.5 mL) was treated drop-wise with oxalyl chloride (42 μL, 0.484 mmol), stirred at RT for 0.5 h, then warmed to 80° C. for 1 h. The mixture was cooled to RT, treated with a solution of Example A17 (110 mg, 0.372 mmol) and pyridine (147 mg, 1.862 mmol) in THF (1.5 mL) and stirred at RT overnight. The mixture was treated with EtOAc, washed with satd. NaHCO$_3$ (1×), then brine (1×), dried over Na$_2$SO$_4$, concentrated to dryness and purified via silica gel chromatography (MeOH/EtOAc) to afford N-((6-ethyl-5-((2-(1-methyl-1H-pyrazol-4-yl)pyridin-4-yl)oxy)pyridin-2-yl)carbamoyl)pivalamide (76 mg, 48%) as a white solid. $^1$H NMR (400 MHz, DMSO-d$_6$): δ 11.17 (s, 1H), 10.40 (s, 1H), 8.35 (d, J=5.7 Hz, 1H), 8.25 (s, 1H), 7.93-7.92 (m, 2H), 7.63 (d, J=8.8 Hz, 1H), 7.18 (d, J=2.4 Hz, 1H), 6.60 (dd, J=5.7, 2.4 Hz, 1H), 3.84 (s, 3H), 2.58 (q, J=7.5 Hz, 2H), 1.21 (s, 9H), 1.12 (t, J=7.5 Hz, 3H); MS (ESI) m/z: 423.2 (M+H$^+$).

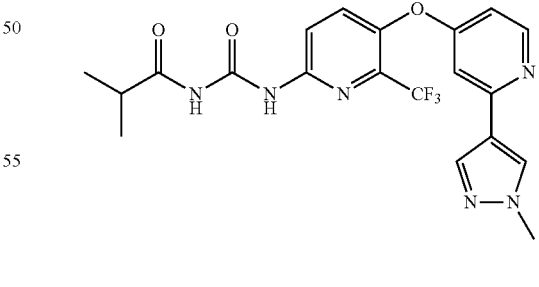

Example 82

A suspension of 2-amino-5-bromo-6-trifluoromethyl-pyridine (0.5 g, 2.075 mmol), PdCl$_2$(dppf)-DCM adduct (0.085 g, 0.104 mmol), bis(pinacolato)diboron (0.685 g, 2.70 mmol) and KOAc (0.611 g, 6.22 mmol) in dioxane (8 mL) was sparged with Ar and heated at 105° C. overnight. The mixture was cooled to RT, treated with EtOAc, the solids removed via filtration through diatomaceous earth, rinsed well with EtOAc and the filtrate concentrated to dryness to afford 5-(4,4,5,5-tetramethyl-1,3,2-dioxaborolan-2-yl)-6-(trifluoromethyl)pyridin-2-amine (100% yield assumed). MS (ESI) m/z: 289.1 (M+H⁺).

A solution of 5-(4,4,5,5-tetramethyl-1,3,2-dioxaborolan-2-yl)-6-(trifluoromethyl)pyridin-2-amine (0.598 g, 2.076 mmol) in THF (10 mL) and water (10 mL) was treated with sodium perborate monohydrate (0.332 g, 3.32 mmol) and stirred at RT overnight. The mixture was treated with EtOAc and the solids removed via filtration through diatomaceous earth. The filtrate was treated with brine, extracted with EtOAc (3×) and the combined organics were dried over Na₂SO₄, concentrated to dryness and purified via silica gel chromatography (EtOAc/Hex) to afford 6-amino-2-(trifluoromethyl)pyridin-3-ol (92 mg, 25%). $^1$H NMR (400 MHz, DMSO-$d_6$): δ 9.47 (s, 1H), 7.15 (d, J=8.9 Hz, 1H), 6.58 (d, J=8.9 Hz, 1H), 5.70 (s, 2H); MS (ESI) m/z: 179.1 (M+H⁺).

A solution of 6-amino-2-(trifluoromethyl)pyridin-3-ol (0.092 g, 0.517 mmol) in DMA (5 mL) was sparged with Ar, treated with potassium t-butoxide (0.087 g, 0.775 mmol), stirred for 1 minute, treated with 2,4-dichloropyridine (0.092 g, 0.620 mmol), flushed with Ar and heated at 95° C. overnight. The mixture was cooled to RT, treated with EtOAc, washed with satd. NaHCO₃ (2×), dried over Na₂SO₄, concentrated to dryness and purified via silica gel chromatography (EtOAc/Hex) to afford 5-((2-chloropyridin-4-yl)oxy)-6-(trifluoromethyl)pyridin-2-amine (62 mg, 41%). $^1$H NMR (400 MHz, DMSO-$d_6$): δ 8.27-8.24 (m, 1H), 7.52-7.49 (m, 1H), 7.04 (s, 1H), 6.94-6.91 (m, 1H), 6.76 (d, J=9.1 Hz, 1H), 6.66 (s, 2H); MS (ESI) m/z: 290.1 (M+H⁺).

A suspension of triphenylphosphine (0.033 g, 0.125 mmol), K₂CO₃ (0.118 g, 0.856 mmol), Pd(OAc)₂ (0.007 g, 0.031 mmol), 1-methyl-4-(4,4,5,5-tetramethyl-1,3,2-dioxaborolan-2-yl)-pyrazole (0.089 g, 0.428 mmol) and 5-((2-chloropyridin-4-yl)oxy)-6-(trifluoromethyl)pyridin-2-amine (0.062 g, 0.214 mmol) in dioxane (6 mL) and water (1.5 mL) was sparged with Ar and heated at 85° C. overnight. The mixture was cooled to RT, treated with brine, extracted with EtOAc (3×) and the combined organics were dried over Na₂SO₄, concentrated and purified via silica gel chromatography (MeOH/EtOAc) to afford 5-((2-(1-methyl-1H-pyrazol-4-yl)pyridin-4-yl)oxy)-6-(trifluoromethyl)pyridin-2-amine (55 mg, 77%). MS (ESI) m/z: 336.1 (M+H⁺).

A suspension of Example B7 (0.021 g, 0.246 mmol) in DCE (3 mL) was treated with oxalyl chloride (0.022 mL, 0.246 mmol), stirred at RT for 5 min, then heated at 80° C. for 1 h. The mixture was cooled to RT, added drop-wise to a solution of 5-((2-(1-methyl-1H-pyrazol-4-yl)pyridin-4-yl)oxy)-6-(trifluoromethyl)pyridin-2-amine (0.055 g, 0.164 mmol) and DIEA (0.172 mL, 0.984 mmol) in dioxane (3 mL) and stirred at RT overnight. A solution of silver cyanate (0.246 g, 1.640 mmol) in DCM (3 mL) was treated with isobutyryl chloride (0.035 g, 0.328 mmol), stirred at RT for 2 h, then added to the DCE mixture and stirred at RT for 2 h. A second suspension of Example B7 (140 mg) in DCE (4 mL) was treated with oxalyl chloride (0.15 mL), heated at 80° C. for 2 h, cooled to RT, added to the original reaction mixture and stirred at RT overnight. The mixture was treated with EtOAc and the solids removed via filtration through diatomaceous earth. The filtrate was washed with satd. NaHCO₃ (2×) and the combined organics were dried over Na₂SO₄, concentrated to dryness and purified via silica gel chromatography (MeOH/EtOAc) to afford N-((5-((2-(1-methyl-1H-pyrazol-4-yl)pyridin-4-yl)oxy)-6-(trifluoromethyl)pyridin-2-yl)carbamoyl)isobutyramide (33 mg, 45%) as a light brown solid. $^1$H NMR (400 MHz, DMSO-$d_6$): δ 11.28 (s, 1H), 10.97 (s, 1H), 8.40 (d, J=5.7 Hz, 1H), 8.34 (d, J=9.1 Hz, 1H), 8.28 (s, 1H), 7.98-7.97 (m, 2H), 7.29 (d, J=2.5 Hz, 1H), 6.78 (dd, J=5.7, 2.5 Hz, 1H), 3.84 (s, 3H), 2.72-2.63 (m, 1H), 1.10 (d, J=6.8 Hz, 6H); MS (ESI) m/z: 449.2 (M+H⁺).

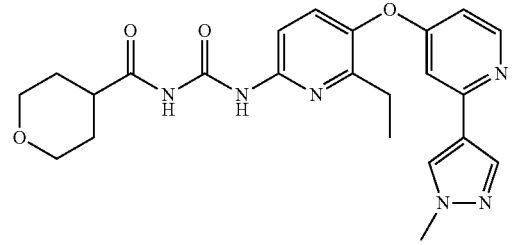 [SMILES: CCc1nc(NC(=O)NC(=O)C2CCOCC2)ccc1Oc1ccnc(-c2cnn(C)c2)c1]

Example 83

A solution of Example B5 (58 mg, 0.447 mmol) in DCE (1.5 mL) was treated drop-wise with oxalyl chloride (42 µL, 0.484 mmol), stirred at RT for 0.5 h, then heated at 80° C. for 1 h. The mixture was cooled to RT, treated with a mixture of Example A17 (110 mg, 0.372 mmol) and pyridine (147 mg, 1.862 mmol) in THF (3 mL) and stirred at RT for 2 h. The mixture was treated with EtOAc, washed with satd. NaHCO₃, then brine, dried over Na₂SO₄, concentrated to dryness and purified via silica gel chromatography (MeOH/EtOAc). The material was re-purified via reverse-phase silica gel chromatography (MeCN/H₂O with 0.1% TFA). The pure fractions were concentrated under reduced pressure and the aqueous material neutralized with satd. NaHCO₃. The material was extracted with EtOAc (3×) and the combined organics were washed with brine, dried over Na₂SO₄ and concentrated to dryness to afford N-((6-ethyl-5-((2-(1-methyl-1H-pyrazol-4-yl)pyridin-4-yl)oxy)pyridin-2-yl)carbamoyl)tetrahydro-2H-pyran-4-carboxamide (22 mg, 13%) as a white solid. $^1$H NMR (400 MHz, DMSO-$d_6$): δ 11.02 (s, 1H), 10.88 (s, 1H), 8.36 (d, J=5.7 Hz, 1H), 8.26 (s, 1H), 7.96 (d, J=0.7 Hz, 1H), 7.92 (d, J=8.8 Hz, 1H), 7.63 (d, J=8.8 Hz, 1H), 7.18 (d, J=2.4 Hz, 1H), 6.61 (dd, J=5.7, 2.5 Hz, 1H), 3.89 (d, J=11.3 Hz, 2H), 3.84 (s, 3H), 3.32 (s, 2H), 2.70-2.64 (m, 1H), 2.59 (q, J=7.5 Hz, 2H), 1.73 (d, J=13.0 Hz, 2H), 1.64-1.62 (m, 2H), 1.12 (t, J=7.5 Hz, 3H); MS (ESI) m/z: 451.2 (M+H⁺).

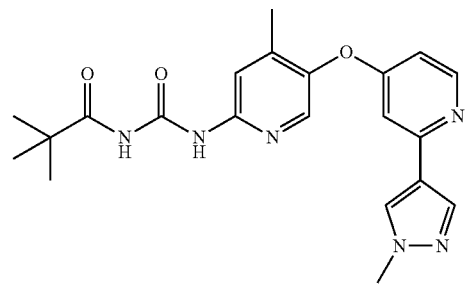 [SMILES: Cc1cc(NC(=O)NC(=O)C(C)(C)C)ncc1Oc1ccnc(-c2cnn(C)c2)c1]

Example 84

A solution of trimethylacetamide (0.054 g, 0.533 mmol) in DCE (3 mL) was treated with oxalyl chloride (0.062 mL, 0.711 mmol), stirred at RT for 1 h, then heated at 75° C. for 1 h. The mixture was cooled to RT, treated with a solution of Example A19 (0.1 g, 0.355 mmol) and TEA (0.149 mL, 1.066 mmol) in DCM (3 mL) and stirred at RT for 1 h. The mixture was treated with water, extracted with DCM (2×) and the combined organics were washed with brine, dried over Na$_2$SO$_4$, concentrated to dryness and purified via silica gel chromatography (EtOAc/Hex) to afford N-((4-methyl-5-((2-(1-methyl-1H-pyrazol-4-yl)pyridin-4-yl)oxy)pyridin-2-yl)carbamoyl)pivalamide (93 mg, 64%) as a white solid. $^1$H NMR (400 MHz, DMSO-d$_6$): δ 11.18 (s, 1H), 10.24 (s, 1H), 8.35 (d, J=5.7 Hz, 1H), 8.25 (s, 1H), 8.14 (s, 1H), 8.01 (s, 1H), 7.96 (s, 1H), 7.16 (d, J=2.4 Hz, 1H), 6.60 (dd, J=5.7, 2.5 Hz, 1H), 3.84 (s, 3H), 2.16 (s, 3H), 1.21 (s, 9H); MS (ESI) m/z: 409.2 (M+H$^+$).

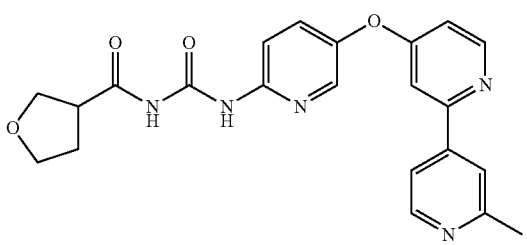 [SMILES: Cc1cc(-c2cc(Oc3ccc(NC(=O)NC(=O)C4CCOC4)nc3)ccn2)ccn1]

Example 85

A solution of tetrahydrofuran-3-carboxylic acid (0.250 g, 2.156 mmol) in DCM (10 mL) was treated drop-wise with oxalyl chloride (0.185 mL, 2.156 mmol), then DMF (0.0056 mL, 0.072 mmol), stirred at RT for 2 h, then concentrated to dryness. The residue was dissolved in DCM (10 mL), treated with silver cyanate (0.480 g, 3.20 mmol), stirred at RT for 2 h, treated with a solution of Example A16 (0.2 g, 0.719 mmol) in THF (5 mL) and stirred at RT overnight. The mixture was treated with solid NaHCO$_3$, then EtOAc; the solids were removed via filtration through diatomaceous earth and the filtrate was concentrated to dryness and purified via silica gel chromatography (MeOH/DCM). The material was re-purified via preparative TLC (TEA/MeOH/DCM); the resulting solid was treated with hot EtOAc/Hex and the solids collected via filtration to afford N-((5-((2'-methyl-[2,4'-bipyridin]-4-yl)oxy)pyridin-2-yl)carbamoyl)tetrahydrofuran-3-carboxamide (51 mg, 17%) as a white solid. $^1$H NMR (400 MHz, DMSO-d$_6$): δ 11.0 (br s, 2H), 8.60 (d, J=5.6 Hz, 1H), 8.53 (d, J=5.3 Hz, 1H), 8.31 (d, J=2.9 Hz, 1H), 8.10 (d, J=9.1 Hz, 1H), 7.90 (s, 1H), 7.80 (s, 2H), 7.72 (d, J=2.4 Hz, 1H), 6.99 (dd, J=5.6, 2.4 Hz, 1H), 3.87 (m, 1H), 3.77 (m, 2H), 3.68 (m, 1H), 3.31 (m, 1H), 2.53 (s, 3H), 2.07 (d, J=7.3 Hz, 2H); MS (ESI) m/z: 420.2 (M+H$^+$).

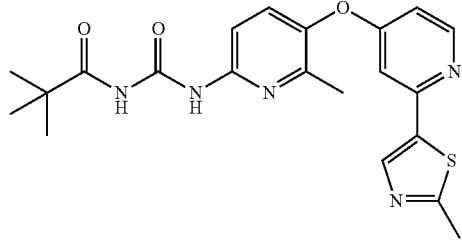 [SMILES: Cc1ncc(-c2cc(Oc3ccc(NC(=O)NC(=O)C(C)(C)C)nc3C)ccn2)s1]

Example 86

A solution of 2,2,2-trimethylacetamide (0.031 g, 0.302 mmol) in DCE (2 mL) was treated with oxalyl chloride (0.026 mL, 0.302 mmol), stirred at RT for 5 min, then heated at 80° C. for 0.5 h. The solution was cooled to RT, added to a mixture of Example A20 (0.060 g, 0.201 mmol) and pyridine (0.130 mL, 1.609 mmol) in dioxane (4 mL) and stirred at RT for 3 h. The mixture was treated with satd. NaHCO$_3$, extracted with EtOAc (3×) and the combined organics were dried over Na$_2$SO$_4$ and concentrated to dryness. The material was treated with MeCN, the solid collected via filtration and dried to afford N-((6-methyl-5-((2-(2-methylthiazol-5-yl)pyridin-4-yl)oxy)pyridin-2-yl)carbamoyl)pivalamide (55 mg, 64%) as a white solid. $^1$H NMR (400 MHz, DMSO-d$_6$): δ 11.16 (br s, 1H), 10.40 (br s, 1H), 8.39 (d, J=5.8 Hz, 1H), 8.32 (s, 1H), 7.91-7.90 (m, 1H), 7.65 (d, J=8.8 Hz, 1H), 7.56 (d, J=2.4 Hz, 1H), 6.71 (dd, J=5.8, 2.4 Hz, 1H), 2.65 (s, 3H), 2.27 (s, 3H), 1.21 (s, 9H); MS (ESI) m/z: 426.2 (M+H$^+$).

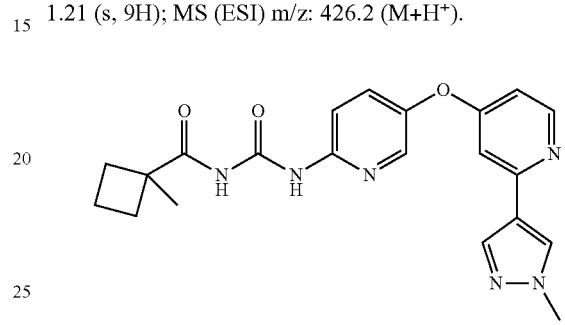

Example 87

A solution of Example B19 (0.800 g, 7.01 mmol) in DCM was treated with oxalyl chloride (0.800 g, 6.30 mmol) and catalytic DMF (8.20 mg, 0.112 mmol) and stirred at RT for 2 h. The mixture was concentrated to dryness, re-dissolved in DCM, treated with silver cyanate (0.800 g, 5.34 mmol), stirred for 2 h, treated with Example A2 (0.300 g, 1.122 mmol) and stirred at RT for 7 h. The solids were removed via filtration through diatomaceous earth and the filtrate concentrated to dryness. The residue was purified via reverse-phase silica gel chromatography (MeCN/H$_2$O with 0.1% TFA) to afford 1-methyl-N-((5-((2-(1-methyl-1H-pyrazol-4-yl)pyridin-4-yl)oxy)pyridin-2-yl)carbamoyl)cyclobutanecarboxamide (132 mg, 28%) as a white solid. $^1$H NMR (400 MHz, DMSO-d$_6$): δ 11.18 (s, 1H), 10.57 (s, 1H), 8.37 (d, J=5.7 Hz, 1H), 8.27-8.25 (m, 2H), 8.09 (d, J=9.0 Hz, 1H), 7.96 (s, 1H), 7.73 (dd, J=9.0, 2.9 Hz, 1H), 7.22 (d, J=2.4 Hz, 1H), 6.70 (dd, J=5.7, 2.4 Hz, 1H), 3.84 (s, 3H), 2.41 (m, 2H), 1.90 (m, 4H), 1.43 (s, 3H); MS (ESI) m/z: 407.1 (M+H$^+$).

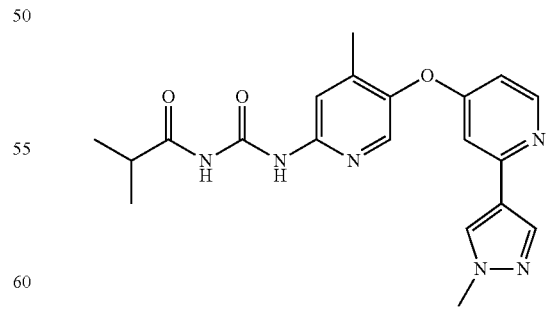

Example 88

A solution of Example B7 (0.062 g, 0.711 mmol) in DCE (3 mL) was treated with oxalyl chloride (0.090 g, 0.711 mmol), stirred at RT for 1 h, then heated at 75° C. for 1 h. The mixture was cooled to RT, treated with a solution of Example A19 (0.1 g, 0.355 mmol) and TEA (0.108 g, 1.066 mmol) in DCM (3 mL) and stirred at RT for 1 h. The mixture was treated with water, extracted with DCM (2×) and the combined organics were washed with brine, dried over Na$_2$SO$_4$, concentrated to dryness and purified via silica gel chromatography (MeOH/DCM). The material was dissolved in MeCN/H$_2$O, frozen and lyophilized to afford N-((4-methyl-5-((2-(1-methyl-1H-pyrazol-4-yl)pyridin-4-yl)oxy)pyridin-2-yl)carbamoyl)isobutyramide (58 mg, 41%) as a white solid. $^1$H NMR (400 MHz, DMSO-d$_6$): δ 11.06 (s, 1H), 10.85 (s, 1H), 8.34 (d, J=5.7 Hz, 1H), 8.25 (s, 1H), 8.13 (s, 1H), 8.02 (s, 1H), 7.95 (s, 1H), 7.16 (d, J=2.5 Hz, 1H), 6.60 (dd, J=5.7, 2.5 Hz, 1H), 3.84 (s, 3H), 2.67-2.66 (m, 1H), 2.16 (s, 3H), 1.09 (d, J=6.8 Hz, 6H); MS (ESI) m/z: 395.2 (M+H$^+$).

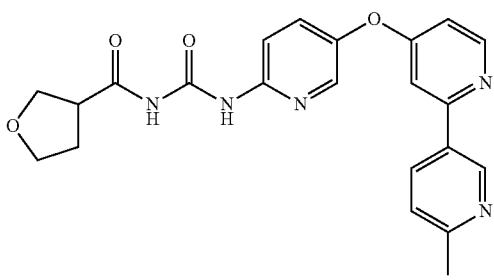 [SMILES: Cc1ccc(-c2cc(Oc3ccc(NC(=O)NC(=O)C4CCOC4)nc3)ccn2)cn1]

Example 89

A solution of tetrahydrofuran-3-carboxylic acid (0.250 g, 2.156 mmol) in DCM (10 mL) was treated drop-wise with oxalyl chloride (0.185 mL, 2.156 mmol), followed by DMF (5.6 µL, 0.072 mmol) and stirred at RT for 2 h. The solution was concentrated to dryness, the residue dissolved in DCM (10 mL), treated with and silver cyanate (0.480 g, 3.20 mmol) and stirred at RT for 2 h. A solution of Example A15 (0.2 g, 0.719 mmol) in THF (5 mL) was added and the mixture was stirred at RT for 3 h. Solid NaHCO$_3$ was added, the mixture diluted with EtOAc and the solids removed via filtration through diatomaceous earth. The filtrate was concentrated to dryness and purified via silica gel chromatography (MeOH/DCM). The material was further purified via preparative TLC (MeOH/DCM), then via reverse-phase silica gel chromatography (MeCN/H$_2$O, with 0.1% TFA). The organics were removed under reduced pressure, the aqueous residue neutralized with satd. NaHCO$_3$ and extracted with EtOAc (4×). The combined organics were dried over Na$_2$SO$_4$ and concentrated to dryness. The solid was dissolved in hot MeOH, cooled to RT and allowed to stand for several hours. The resulting solid was collected via filtration and dried to afford N-((5-((6'-methyl-[2,3'-bipyridin]-4-yl)oxy)pyridin-2-yl)carbamoyl)tetrahydrofuran-3-carboxamide (8 mg, 2.7%) as a white solid. $^1$H NMR (400 MHz, DMSO-d$_6$): δ 10.99 (br s, 2H), 9.10 (d, J=2.4 Hz, 1H), 8.56 (d, J=5.7 Hz, 1H), 8.30-8.27 (m, 2H), 8.09 (d, J=9.0 Hz, 1H), 7.77 (dd, J=9.0, 2.9 Hz, 1H), 7.64 (d, J=2.4 Hz, 1H), 7.34 (d, J=8.2 Hz, 1H), 6.90 (dd, J=5.7, 2.4 Hz, 1H), 3.86 (m, 1H), 3.79-3.73 (m, 2H), 3.67 (m, 1H), 3.23 (m, 1H), 2.51 (s, 3H), 2.07 (m, 2H); MS (ESI) m/z: 420.2 (M+H$^+$).

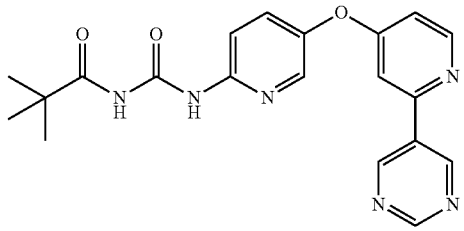 [SMILES: CC(C)(C)C(=O)NC(=O)Nc1ccc(Oc2ccnc(-c3cncnc3)c2)cn1]

Example 90

A solution of Example A9 (0.25 g, 1.128 mmol) and pyrimidinyl-5-boronic acid (0.196 g, 1.579 mmol) in dioxane (8 mL) was treated with a solution of K$_2$CO$_3$ (0.156 g, 1.128 mmol) in water (2 mL), Pd(PPh$_3$)$_4$ (0.130 g, 0.113 mmol) and heated at 95° C. for 20 h. The mixture was cooled to RT, treated with water and extracted with EtOAc (2×). The combined organics were washed with brine, dried over Na$_2$SO$_4$, concentrated to dryness and purified via silica gel chromatography (MeOH/DCM) to afford 5-((2-(pyrimidin-5-yl)pyridin-4-yl)oxy)pyridin-2-amine (65 mg, 22%) as a white solid. $^1$H NMR (400 MHz, DMSO-d$_6$): δ 9.39 (s, 2H), 9.24 (s, 1H), 8.55 (d, J=5.7 Hz, 1H), 7.84 (d, J=3.0 Hz, 1H), 7.75 (d, J=2.4 Hz, 1H), 7.32 (dd, J=8.9, 3.0 Hz, 1H), 6.83 (dd, J=5.7, 2.4 Hz, 1H), 6.53 (d, J=8.9 Hz, 1H), 6.04 (s, 2H); MS (ESI) m/z: 266.1 (M+H$^+$).

A solution of 2,2,2-trimethylacetamide (0.048 g, 0.475 mmol) in DCE (3 mL) was treated with oxalyl chloride (0.042 mL, 0.475 mmol), stirred at RT for 1 h, then heated at 75° C. for 1 h. The mixture was cooled to RT, treated with a solution 5-((2-(pyrimidin-5-yl)pyridin-4-yl)oxy)pyridin-2-amine (0.063 g, 0.237 mmol) and TEA (0.099 mL, 0.712 mmol) in THF (3 mL) and stirred at RT for 1 h. The mixture was treated with water, extracted with DCM (2×) and the combined organics were washed with brine, dried over Na$_2$SO$_4$, concentrated to dryness and purified via silica gel chromatography (MeOH/DCM) to afford N-((5-((2-(pyrimidin-5-yl)pyridin-4-yl)oxy)pyridin-2-yl)carbamoyl)pivalamide (65 mg, 70%) as a white solid. $^1$H NMR (400 MHz, DMSO-d$_6$): δ 11.23 (s, 1H), 10.44 (s, 1H), 9.41 (s, 2H), 9.24 (s, 1H), 8.62 (d, J=5.7 Hz, 1H), 8.30 (d, J=2.9 Hz, 1H), 8.11 (d, J=9.0 Hz, 1H), 7.83 (d, J=2.4 Hz, 1H), 7.78 (dd, J=9.0, 2.9 Hz, 1H), 6.99 (dd, J=5.7, 2.4 Hz, 1H), 1.21 (s, 9H); MS (ESI) m/z: 393.2 (M+H$^+$).

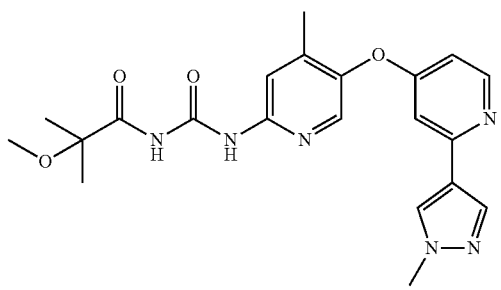 [SMILES: COC(C)(C)C(=O)NC(=O)Nc1cc(C)c(Oc2ccnc(-c3cnn(C)c3)c2)cn1]

Example 91

A mixture of Example B16 (0.107 g, 0.533 mmol), Example A19 (0.1 g, 0.355 mmol) and 1-methylpyrrolidine (9.08 mg, 0.107 mmol) in THF (3 mL) was heated at 55° C.

for 16 h. The mixture was concentrated to dryness and purified via silica gel chromatography (MeOH/DCM) to afford 2-methoxy-2-methyl-N-((4-methyl-5-((2-(1-methyl-1H-pyrazol-4-yl)pyridin-4-yl)oxy)pyridin-2-yl)carbamoyl)propanamide (106 mg, 70%) as a white solid. ¹H NMR (400 MHz, DMSO-d₆): δ 10.76 (s, 1H), 10.20 (br s, 1H), 8.35 (d, J=5.7 Hz, 1H), 8.25 (s, 1H), 8.14 (s, 1H), 7.97 (br s, 1H), 7.96 (d, J=0.7 Hz, 1H), 7.16 (d, J=2.4 Hz, 1H), 6.60 (dd, J=5.7, 2.5 Hz, 1H), 3.84 (s, 3H), 3.20 (s, 3H), 2.16 (s, 3H), 1.35 (s, 6H); MS (ESI) m/z: 425.2 (M+H⁺).

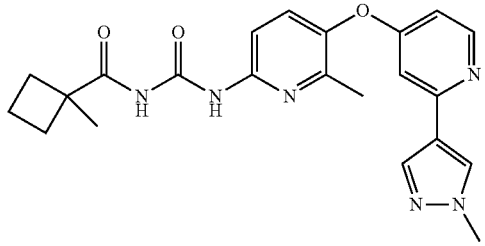 [SMILES: Cc1nc(NC(=O)NC(=O)C2(C)CCC2)ccc1Oc1ccnc(-c2cnn(C)c2)c1]

Example 92

A solution of Example B19 (0.300 g, 2.63 mmol) in DCM was treated with oxalyl chloride (0.500 g, 3.94 mmol) followed by DMF (9.9 mg, 0.14 mmol) and stirred at RT for 2 h. The mixture was concentrated to dryness, re-dissolved in DCM, treated with silver cyanate (0.600 g, 4.00 mmol), stirred at RT for 2 h, treated with Example A6 (0.380 g, 1.351 mmol) and stirred at RT overnight. The solids were removed via filtration through diatomaceous earth and the filtrate concentrated to dryness and purified via silica gel chromatography (EtOAc/Hex) to afford 1-methyl-N-((6-methyl-5-((2-(1-methyl-1H-pyrazol-4-yl)pyridin-4-yl)oxy)pyridin-2-yl)carbamoyl)cyclobutanecarboxamide (19 mg, 3.2%). MS (ESI) m/z: 421.2 (M+H⁺).

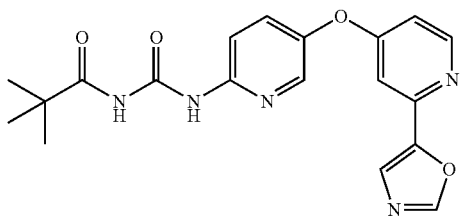 [SMILES: CC(C)(C)C(=O)NC(=O)Nc1ccc(Oc2ccnc(-c3cnco3)c2)cn1]

Example 93

A suspension of Pd(PPh₃)₄ (0.034 g, 0.030 mmol), K₂CO₃ (0.330 g, 2.384 mmol), 5-(4,4,5,5-tetramethyl-1,3,2-dioxaborolan-2-yl)oxazole (0.140 g, 0.715 mmol), and Example A1 (0.15 g, 0.596 mmol) in dioxane (6 mL) and water (1.5 mL) was sparged with Ar and heated at 90° C. overnight. The mixture was cooled to RT, treated with satd NaHCO₃ and EtOAc and the solids removed via filtration through diatomaceous earth. The layers of the filtrate were separated, the aqueous layer extracted with EtOAc (3×) and the combined organics were dried over Na₂SO₄, concentrated to dryness and purified via silica gel chromatography (EtOAc/Hex) to afford 5-(4-((6-nitropyridin-3-yl)oxy)pyridin-2-yl)oxazole (92 mg, 54%). MS (ESI) m/z: 285.1 (M+H⁺).

A solution of 5-(4-((6-nitropyridin-3-yl)oxy)pyridin-2-yl)oxazole (0.092 g, 0.324 mmol) in MeOH (10 mL) was treated with 10% Pd/C (50% wet, 0.034 g, 0.032 mmol) and hydrogenated (1 atm) for 5 h. The solid was removed via filtration through diatomaceous earth and the filtrate concentrated to dryness to afford 5-((2-(oxazol-5-yl)pyridin-4-yl)oxy)pyridin-2-amine (73 mg, 89%). ¹H NMR (400 MHz, DMSO-d₆): δ 8.47 (s, 1H), 8.46 (d, J=5.7 Hz, 1H), 7.84 (d, J=2.9 Hz, 1H), 7.76 (s, 1H), 7.32 (dd, J=8.9, 3.0 Hz, 1H), 7.15 (d, J=2.5 Hz, 1H), 6.86 (dd, J=5.7, 2.5 Hz, 1H), 6.53 (d, J=8.9 Hz, 1H), 6.06 (s, 2H); MS (ESI) m/z: 255.1 (M+H⁺).

A solution of 2,2,2-trimethylacetamide (0.044 g, 0.431 mmol) in DCE (2 mL) was treated with oxalyl chloride (0.038 mL, 0.431 mmol), stirred at RT for 5 min, then heated at 80° C. for 0.5 h. The mixture was cooled to RT, added to a mixture of 5-((2-(oxazol-5-yl)pyridin-4-yl)oxy)pyridin-2-amine (0.073 g, 0.287 mmol) and pyridine (0.186 mL, 2.297 mmol) in dioxane (4 mL) and stirred at RT for 3 h. The mixture was treated with satd. NaHCO₃, extracted with EtOAc (3×) and the combined organics were dried over Na₂SO₄ and concentrated to dryness. The material was treated with MeCN and the solid collected via filtration to afford N-((5-((2-(oxazol-5-yl)pyridin-4-yl)oxy)pyridin-2-yl)carbamoyl)pivalamide (44 mg, 40%) as a white solid. ¹H NMR (400 MHz, DMSO-d₆): δ 11.24 (s, 1H), 10.45 (s, 1H), 8.52 (d, J=5.7 Hz, 1H), 8.49 (s, 1H), 8.31 (d, J=2.9 Hz, 1H), 8.11 (d, J=9.0 Hz, 1H), 7.81-7.77 (m, 2H), 7.27 (d, J=2.5 Hz, 1H), 6.95 (dd, J=5.7, 2.5 Hz, 1H), 1.21 (s, 9H); MS (ESI) m/z: 382.2 (M+H⁺).

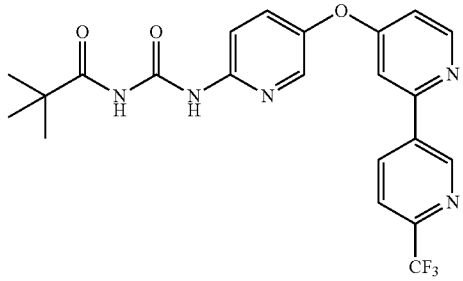 [SMILES: CC(C)(C)C(=O)NC(=O)Nc1ccc(Oc2ccnc(-c3ccc(C(F)(F)F)nc3)c2)cn1]

Example 94

A suspension of Pd(PPh₃)₄ (0.034 g, 0.030 mmol), K₂CO₃ (0.330 g, 2.384 mmol), 2-trifluoromethylpyridine-5-boronic acid (0.137 g, 0.715 mmol), and Example A1 (0.15 g, 0.596 mmol) in dioxane (6 mL) and water (1.5 mL) was sparged with Ar and heated at 90° C. overnight. The mixture was cooled to RT, treated with satd. NaHCO₃ and EtOAc and the solids were removed by filtration through diatomaceous earth. The layers of the filtrate were separated, the aqueous layer extracted with EtOAc (3×) and the combined organics were dried over Na₂SO₄, concentrated to dryness and purified via silica gel chromatography (EtOAc/Hex) to afford 4-((6-nitropyridin-3-yl)oxy)-6'-(trifluoromethyl)-2,3'-bipyridine (177 mg, 82%). ¹H NMR (400 MHz, DMSO-d₆): δ 9.43 (s, 1H), 8.77-8.69 (m, 2H), 8.64 (m, 1H), 8.42 (m, 1H), 8.08-8.00 (m, 3H), 7.30 (m, 1H); MS (ESI) m/z: 363.1 (M+H⁺).

A solution of 4-((6-nitropyridin-3-yl)oxy)-6'-(trifluoromethyl)-2,3'-bipyridine (0.177 g, 0.489 mmol) in MeOH (10 mL) was treated with 10% Pd/C (50% wet, 0.052 g, 0.049 mmol) and hydrogenated (1 atm) for 5 h. The solid was removed via filtration through diatomaceous earth, and the filtrate was concentrated to dryness and purified via silica gel chromatography (MeOH/EtOAc) to afford 5-((6'-(trifluoromethyl)-[2,3'-bipyridin]-4-yl)oxy)pyridin-2-amine (63 mg, 39%). ¹H NMR (400 MHz, DMSO-d₆): δ 9.39 (s, 1H), 8.66 (d, J=8.4 Hz, 1H), 8.57 (d, J=5.7 Hz, 1H), 8.00 (d, J=8.2 Hz, 1H), 7.85 (d, J=2.9 Hz, 1H), 7.75 (d, J=2.4 Hz, 1H), 7.33 (dd, J=8.9, 3.0 Hz, 1H), 6.86 (dd, J=5.7, 2.4 Hz, 1H), 6.53 (d, J=8.9 Hz, 1H), 6.05 (s, 2H); MS (ESI) m/z: 333.1 (M+H⁺).

A solution of 2,2,2-trimethylacetamide (0.029 g, 0.284 mmol) in DCE (2 mL) was treated with oxalyl chloride (0.025 mL, 0.284 mmol), stirred at RT for 5 min, then heated at 80° C. for 0.5 h. The mixture was cooled to RT, added to a mixture of 5-((6'-(trifluoromethyl)-[2,3'-bipyridin]-4-yl)oxy)pyridin-2-amine (0.063 g, 0.190 mmol) and pyridine (0.123 mL, 1.517 mmol) in dioxane (4 mL) and stirred at RT for 3 h. The mixture was treated with satd. NaHCO₃, extracted with EtOAc (3×) and the combined organics were dried over Na₂SO₄ and concentrated to dryness. The material was treated with MeCN and the solid collected via filtration to afford N-((5-((6'-(trifluoromethyl)-[2,3'-bipyridin]-4-yl)oxy)pyridin-2-yl)carbamoyl)pivalamide (57 mg, 65%) as a white solid. ¹H NMR (400 MHz, DMSO-d₆): δ 11.24 (s, 1H), 10.47 (s, 1H); 9.41 (s, 1H); 8.67-8.66 (m, 2H), 8.31-8.30 (m, 1H), 8.11 (d, J=9.0 Hz, 1H); 8.00 (d, J=8.3 Hz, 1H); 7.84 (d, J=2.4 Hz, 1H); 7.79 (dd, J=9.0, 2.9 Hz, 1H); 7.01 (dd, J=5.7, 2.4 Hz, 1H); 1.21 (s, 9H); MS (ESI) m/z: 460.2 (M+H⁺).

J=2.4 Hz, 1H), 7.85 (d, J=2.9 Hz, 1H), 7.33 (dd, J=8.9, 3.0 Hz, 1H), 6.91 (dd, J=5.7, 2.4 Hz, 1H), 6.53 (d, J=8.9 Hz, 1H), 6.05 (s, 2H); MS (ESI) m/z: 333.1 (M+H⁺).

A solution of 2,2,2-trimethylacetamide (0.019 g, 0.190 mmol) in DCE (2 mL) was treated with oxalyl chloride (0.017 mL, 0.190 mmol), stirred at RT for 5 min, then heated at 80° C. for 0.5 h. The mixture was cooled to RT, added to a solution of 5-((2'-(trifluoromethyl)-[2,4'-bipyridin]-4-yl)oxy)pyridin-2-amine (0.042 g, 0.126 mmol) and pyridine (0.082 mL, 1.011 mmol) in dioxane (4 mL) and stirred at RT for 3 h. The mixture was treated with satd. NaHCO₃, extracted with EtOAc (3×) and the combined organics were dried over Na₂SO₄ and concentrated to dryness. The material was treated with MeCN and the solid collected via filtration to afford N-((5-((2'-(trifluoromethyl)-[2,4'-bipyridin]-4-yl)oxy)pyridin-2-yl)carbamoyl)pivalamide (34 mg, 59%) as a white solid. ¹H NMR (400 MHz, DMSO-d₆): δ 11.24 (s, 1H), 10.45 (s, 1H), 8.87 (d, J=5.1 Hz, 1H), 8.65 (d, J=5.6 Hz, 1H), 8.51 (s, 1H), 8.37 (d, J=5.2 Hz, 1H), 8.32 (d, J=2.9 Hz, 1H), 8.11 (d, J=9.0 Hz, 1H), 7.97 (d, J=2.4 Hz, 1H), 7.79 (dd, J=9.0, 2.9 Hz, 1H), 7.05 (dd, J=5.6, 2.4 Hz, 1H), 1.21 (s, 9H); MS (ESI) m/z: 460.2 (M+H⁺).

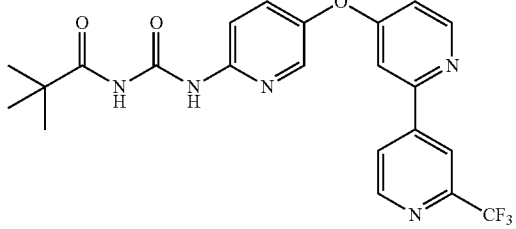

Example 95

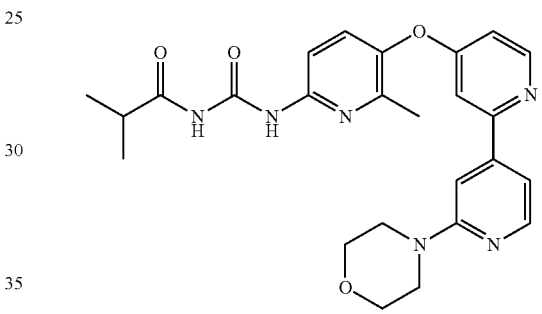

Example 96

A suspension of Example A1 (0.125 g, 0.497 mmol), Pd(PPh₃)₄ (0.029 g, 0.025 mmol), K₂CO₃ (0.275 g, 1.987 mmol) and 2-(trifluoromethyl)pyridine-4-boronic acid (0.104 g, 0.546 mmol) in dioxane (6 mL) and water (1.5 mL) was sparged with Ar and heated at 90° C. overnight. The mixture was cooled to RT, treated with satd. NaHCO₃ and EtOAc and the solids were removed via filtration through diatomaceous earth. The layers of the filtrate were separated, the aqueous layer extracted with EtOAc (3×) and the combined organics were dried over Na₂SO₄, concentrated to dryness and purified via silica gel chromatography (EtOAc/Hex) to afford 4-((6-nitropyridin-3-yl)oxy)-2'-(trifluoromethyl)-2,4'-bipyridine (139 mg, 77%). ¹H NMR (400 MHz, DMSO-d₆): δ 8.89 (d, J=5.2 Hz, 1H), 8.78 (m, 1H), 8.64 (m, 1H), 8.53 (s, 1H), 8.44-8.38 (m, 2H), 8.17 (d, J=2.3 Hz, 1H), 8.03 (m, 1H), 7.36 (dd, J=5.5, 2.3 Hz, 1H); MS (ESI) m/z: 363.1 (M+H⁺).

A solution of 4-((6-nitropyridin-3-yl)oxy)-2'-(trifluoromethyl)-2,4'-bipyridine (0.139 g, 0.384 mmol) in MeOH (10 mL) was treated with 10% Pd/C (50% wet, 0.041 g, 0.038 mmol) and hydrogenated (1 atm) for 5 h. The solids were removed via filtration through diatomaceous earth, the filtrate concentrated to dryness and purified via silica gel chromatography (MeOH/EtOAc) to afford 5-((2'-(trifluoromethyl)-[2,4'-bipyridin]-4-yl)oxy)pyridin-2-amine (42 mg, 33%). ¹H NMR (400 MHz, DMSO-d₆): δ 8.87 (d, J=5.1 Hz, 1H), 8.59 (d, J=5.7 Hz, 1H), 8.49 (s, 1H), 8.35-8.33 (m, 1H), 7.87 (d, A mixture of Example B7 (0.281 g, 3.22 mmol) in DCE (10 mL) was treated with oxalyl chloride (0.300 mL, 3.49 mmol) and heated at 100° C. for 1 h. The mixture was cooled to RT and concentrated to dryness. The residue was dissolved in DCM (5 mL), added to a solution of Example A8 (0.506 g, 2.147 mmol) and pyridine (0.200 mL, 2.478 mmol) in DCM (10 mL) and stirred at RT for 2 days. Additional Example B7 (0.281 g) in DCE (5 mL) was treated with oxalyl chloride (0.280 mL), stirred at RT for 15 min, heated at 80° C. for 1 h, cooled to RT, added to the above solution and stirred at RT for 2 days. The mixture was concentrated to dryness, treated with satd. NaHCO₃ and extracted with DCM (3×). The combined organics were dried over Na₂SO₄ and concentrated to dryness. The material was suspended in MeCN, sonicated and the resulting solid collected via filtration to afford N-((5-((2-chloropyridin-4-yl)oxy)-6-methylpyridin-2-yl)carbamoyl)isobutyramide (136 mg, 18%) as a light brown solid. MS (ESI) m/z: 349.1 (M+H⁺).

A mixture of N-((5-((2-chloropyridin-4-yl)oxy)-6-methylpyridin-2-yl)carbamoyl)isobutyramide (0.136 g, 0.390 mmol), K₂CO₃ (0.108 g, 0.780 mmol) and 4-(4-(4,4,5,5-tetramethyl-1,3,2-dioxaborolan-2-yl)pyridin-2-yl)morpholine (0.136 g, 0.468 mmol) in dioxane (8 mL) and water (2 mL) was sparged with Ar, treated with Pd(PPh₃)₄ (0.045 g, 0.039 mmol), sparged again with Ar and heated at 95° C. overnight. The mixture was cooled to RT, treated with EtOAc and the solids removed via filtration through a pad of diatomaceous earth and Na$_2$SO$_4$. The filtrate was concentrated to dryness and purified via silica gel chromatography (MeOH/DCM). The material was purified twice more via silica gel chromatography (MeOH/EtOAc). The resulting material was treated with Et$_2$O, sonicated and the solid collected via filtration to afford N-((6-methyl-5-((2'-morpholino-[2,4'-bipyridin]-4-yl)oxy)pyridin-2-yl)carbamoyl)isobutyramide (52 mg, 28%) as a white solid. $^1$H NMR (400 MHz, DMSO-d$_6$): δ 11.05 (s, 1H), 10.84 (s, 1H), 8.54 (d, J=5.6 Hz, 1H), 8.21 (d, J=5.2 Hz, 1H), 7.92 (d, J=8.8 Hz, 1H), 7.73 (d, J=2.4 Hz, 1H), 7.65 (d, J=8.8 Hz, 1H), 7.44 (s, 1H), 7.30 (dd, J=5.2, 1.3 Hz, 1H), 6.80 (dd, J=5.6, 2.4 Hz, 1H), 3.70 (m, 4H), 3.51 (m, 4H), 2.66 (m, 1H), 2.27 (s, 3H), 1.09 (d, J=6.8 Hz, 6H); MS (ESI) m/z: 477.3 (M+H$^+$).

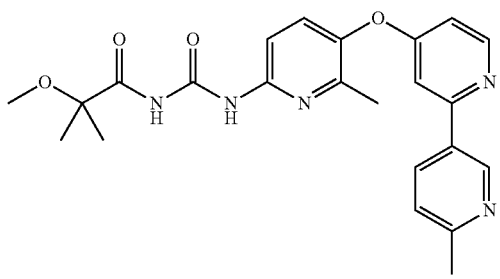 [SMILES: COC(C)(C)C(=O)NC(=O)Nc1ccc(Oc2ccnc(-c3ccc(C)nc3)c2)c(C)n1]

Example 97

A solution of Example A14 (0.15 g, 0.513 mmol) and Example B16 (0.15 g, 0.745 mmol) in dioxane (5 mL) was treated with 1-methylpyrrolidine (0.054 mL, 0.513 mmol) and heated at 80° C. for 4 h. The mixture was cooled to RT, treated with satd. NaHCO$_3$ and extracted with EtOAc (4×). The combined organics were dried over Na$_2$SO$_4$, concentrated to dryness and purified via silica gel chromatography (MeOH/DCM). The material was treated with MeCN and the resulting solid collected via filtration to afford 2-methoxy-2-methyl-N-((6-methyl-5-((6'-methyl-[2,3'-bipyridin]-4-yl)oxy)pyridin-2-yl)carbamoyl)propanamide (32 mg, 14%). $^1$H NMR (400 MHz, acetone-d$_6$): δ 10.93 (s, 1H), 9.17 (s, 1H), 9.13 (d, J=2.4 Hz, 1H), 8.56-8.55 (m, 1H), 8.28 (dd, J=8.1, 2.4 Hz, 1H), 8.04-8.02 (m, 1H), 7.63 (d, J=8.8 Hz, 1H), 7.50 (d, J=2.4 Hz, 1H), 7.31 (d, J=8.1 Hz, 1H), 6.84 (dd, J=5.6, 2.4 Hz, 1H), 3.38 (s, 3H), 2.53 (s, 3H), 2.34 (s, 3H), 1.47 (s, 6H); MS (ESI) m/z: 436.2 (M+H$^+$).

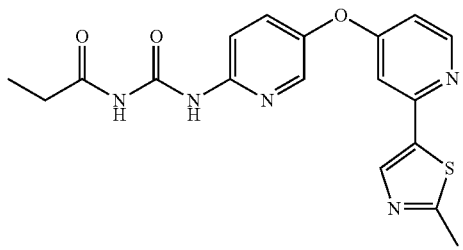 [SMILES: CCC(=O)NC(=O)Nc1ccc(Oc2ccnc(-c3cnc(C)s3)c2)cn1]

Example 98

A solution of propionamide (0.103 g, 1.407 mmol) in DCE (5 mL) was treated with oxalyl chloride (0.100 mL, 1.161 mmol) and heated at 80° C. for 1 h. The mixture was cooled to RT, added to a solution of Example A13 (0.200 g, 0.703 mmol) and pyridine (0.057 mL, 0.703 mmol) in DCM (10 mL) and stirred at RT overnight. The mixture was treated with satd. NaHCO$_3$, extracted with EtOAc (3×) and the combined organics were dried over Na$_2$SO$_4$ and concentrated to dryness. The material was treated with MeCN, sonicated and the resulting solid was collected via filtration to afford N-((5-((2-(2-methylthiazol-5-yl)pyridin-4-yl)oxy)pyridin-2-yl)carbamoyl)propionamide (71 mg, 26%) as a white solid. $^1$H NMR (400 MHz, DMSO-d$_6$): δ 11.07 (s, 1H), 10.82 (s, 1H), 8.40 (d, J=5.8 Hz, 1H), 8.32 (s, 1H), 8.27 (d, J=2.9 Hz, 1H), 8.08 (d, J=9.0 Hz, 1H), 7.74 (dd, J=9.0, 2.9 Hz, 1H), 7.60 (d, J=2.4 Hz, 1H), 6.81 (dd, J=5.8, 2.4 Hz, 1H), 2.64 (s, 3H), 2.41 (q, J=7.5 Hz, 2H), 1.04 (t, J=7.5 Hz, 3H); MS (ESI) m/z: 384.2 (M+H$^+$).

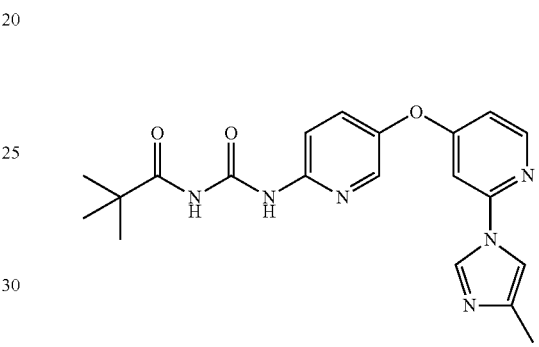

Example 99

A solution of 2,2,2-trimethylacetamide (0.596 g, 5.89 mmol) in DCE (20 mL) was treated with oxalyl chloride (0.516 mL, 5.89 mmol), stirred at RT for 1 h, then heated to 80° C. for 2 h. The mixture was cooled to RT, treated with a suspension of Example A21 (1.05 g, 3.93 mmol) and TEA (1.64 mL, 11.8 mmol) in THF (20 mL) and stirred at RT for 2 h. The reaction was partitioned into EtOAc (50 mL) and water (60 mL). The aqueous layer was separated and extracted with EtOAc (30 mL). The combined organics were washed with brine, dried (Na$_2$SO$_4$) and concentrated to afford a foam. This material was suspended in MeCN (15 mL), briefly sonicated and then stirred for 15 minutes. The solids were collected by filtration, washed with MeCN (2×1 mL) and dried under vacuum to afford crop 1. The filtrate was concentrated and purified by silica gel chromatography (1-5% MeOH/EtOAc) to provide a second crop. Both crops were combined, suspended in MeCN-water (10 mL) and lyophilized to afford N-((5-((2-(4-methyl-1H-imidazol-1-yl)pyridin-4-yl)oxy)pyridin-2-yl)carbamoyl)pivalamide (0.984 g, 63%) as a white solid. $^1$H NMR (400 MHz, DMSO-d$_6$): δ 11.23 (s, 1H), 10.45 (s, 1H), 8.40 (d, J=1.4 Hz, 1H), 8.34 (d, J=5.8 Hz, 1H), 8.30 (dd, J=2.9, 0.6 Hz, 1H), 8.10 (d, J=9.1 Hz, 1H), 7.78 (dd, J=9.0, 2.9 Hz, 1H), 7.64 (t, J=1.3 Hz, 1H), 7.39 (d, J=2.2 Hz, 1H), 6.84 (dd, J=5.8, 2.2 Hz, 1H), 2.13 (d, J=1.0 Hz, 3H), 1.21 (s, 9H); MS (ESI) m/z: 395.1 (M+H$^+$).

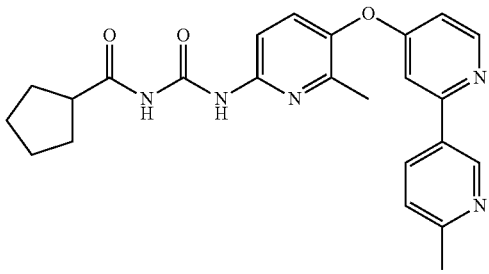 [SMILES: Cc1ccc(-c2cc(Oc3ccc(NC(=O)NC(=O)C4CCCC4)nc3C)ccn2)cn1]

Example 100

A suspension of cyclopentanecarbonyl chloride (0.1 mL, 0.869 mmol) in DCE (1.5 mL) under Ar was treated with silver cyanate (0.15 g, 1.00 mmol) and heated at 50° C. for 2 h. The mixture was cooled to RT, treated drop-wise with a solution of Example A14 (0.15 g, 0.513 mmol) and pyridine (0.25 mL, 3.09 mmol) in THF (4 mL) and stirred at RT overnight. The mixture was treated with satd. NaHCO$_3$, extracted with EtOAc (4×) and the combined organics were dried over Na$_2$SO$_4$, concentrated to dryness and purified via silica gel chromatography (MeOH/DCM) to afford N-((6-methyl-5-((6'-methyl-[2,3'-bipyridin]-4-yl)oxy)pyridin-2-yl)carbamoyl)cyclopentanecarboxamide (163 mg, 72%) as an off-white solid. $^1$H NMR (400 MHz, DMSO-d$_6$): δ 11.07 (s, 1H), 10.85 (s, 1H), 9.10 (br s, 1H), 8.54 (br s, 1H), 8.28 (d, J=2.4 Hz, 1H), 7.93 (s, 1H), 7.66 (s, 1H), 7.58 (s, 1H), 7.35 (s, 1H), 6.79 (d, J=2.8 Hz, 1H), 2.86 (m, 1H), 2.51 (s, 3H), 2.27 (s, 3H), 1.89 (m, 2H), 1.76-1.71 (m, 6H); MS (ESI) m/z: 432.2 (M+H$^+$).

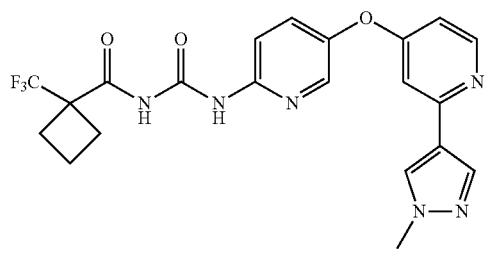 [SMILES: Cn1cc(-c2cc(Oc3ccc(NC(=O)NC(=O)C4(C(F)(F)F)CCC4)nc3)ccn2)cn1]

Example 101

A solution of 1-(trifluoromethyl)cyclobutanecarboxylic acid (0.250 g, 1.487 mmol) in DCM (10 mL) was treated with oxalyl chloride (0.180 g, 1.418 mmol) followed by a catalytic amount of DMF and stirred at RT for 1 h. The mixture was treated with silver cyanate (0.250 g, 1.668 mmol), stirred at RT for 2 h, treated with Example A2 (0.200 g, 0.748 mmol) and stirred at RT overnight. The solids were removed via filtration through diatomaceous earth, rinsed well with DCM, then THF and the filtrate was concentrated to dryness and purified via silica gel chromatography (EtOAc/Hex) to afford N-((5-((2-(1-methyl-1H-pyrazol-4-yl)pyridin-4-yl)oxy)pyridin-2-yl)carbamoyl)-1-(trifluoromethyl)cyclobutanecarboxamide (175 mg, 51%) as an off-white solid. $^1$H NMR (400 MHz, DMSO-d$_6$): δ 11.34 (br s, 1H), 10.84 (s, 1H), 8.38 (d, J=5.7 Hz, 1H), 8.28 (d, J=2.9 Hz, 1H), 8.25 (s, 1H), 8.05 (br d, J=9.0 Hz, 1H), 7.96 (d, J=0.7 Hz, 1H), 7.75 (dd, J=9.0, 2.9 Hz, 1H), 7.23 (d, J=2.4 Hz, 1H), 6.71 (dd, J=5.7, 2.4 Hz, 1H), 3.84 (s, 3H), 2.68 (m, 2H), 2.41 (m, 2H), 1.97-1.83 (m, 2H); MS (ESI) m/z: 461.1 (M+H$^+$).

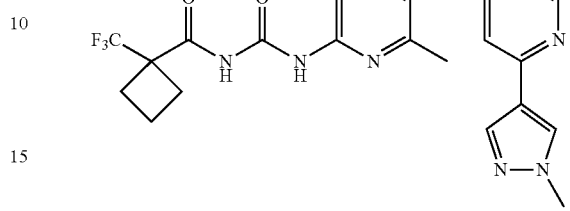

Example 102

A solution of 1-(trifluoromethyl)cyclobutanecarboxylic acid (0.250 g, 1.487 mmol) in DCM (10 mL) was treated with oxalyl chloride (0.180 g, 1.418 mmol) followed by a catalytic amount of DMF and stirred at RT for 1 h. The mixture was treated with silver cyanate (0.250 g, 1.668 mmol), stirred at RT for 2 h, treated with Example A6 (0.200 g, 0.711 mmol) and stirred at RT overnight. The solids were removed via filtration through diatomaceous earth, rinsed well with DCM, then THF and the filtrate concentrated to dryness and purified via silica gel chromatography (EtOAc/Hex) to afford N-((6-methyl-5-((2-(1-methyl-1H-pyrazol-4-yl)pyridin-4-yl)oxy)pyridin-2-yl)carbamoyl)-1-(trifluoromethyl)cyclobutanecarboxamide (200 mg, 56%) as a white solid. $^1$H NMR (400 MHz, DMSO-d$_6$): δ 11.14 (br s, 1H), 10.78 (s, 1H), 8.36 (d, J=5.7 Hz, 1H), 8.25 (s, 1H), 7.96 (s, 1H), 7.87 (br s, 1H), 7.65 (d, J=8.8 Hz, 1H), 7.16 (d, J=2.4 Hz, 1H), 6.61 (dd, J=5.7, 2.4 Hz, 1H), 3.84 (s, 3H), 2.68 (m, 2H), 2.42 (m, 2H), 2.27 (s, 3H), 1.98-1.82 (m, 2H); MS (ESI) m/z: 475.1 (M+H$^+$).

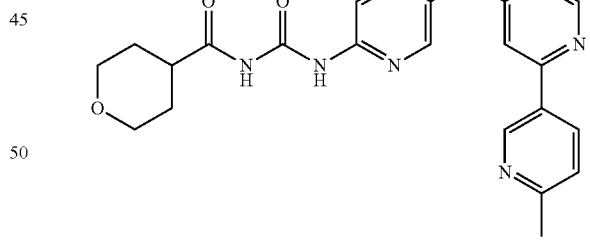

Example 103

A mixture of Example B5 (0.568 g, 4.40 mmol) and oxalyl chloride (0.400 mL, 4.66 mmol) in DCE (10 mL) was heated at 100° C. for 1 h, cooled to RT, added to a solution of Example A9 (0.650 g, 2.93 mmol) and pyridine (0.400 mL, 4.96 mmol) in DCM (10 mL) and stirred at RT for 2 days. The mixture was treated with satd. NaHCO$_3$, extracted with EtOAc (3×) and the combined organics were dried over Na$_2$SO$_4$ and concentrated to dryness. The material was treated with MeCN, sonicated, the solid collected via filtration and purified via silica gel chromatography (MeOH/DCM) to afford N-((5-((2-chloropyridin-4-yl)oxy)pyridin-2-yl)carbamoyl)tetrahydro-2H-pyran-4-carboxamide (335 mg, 30%) as a white solid. MS (ESI) m/z: 377.1 (M+H⁺).

A mixture of N-((5-((2-chloropyridin-4-yl)oxy)pyridin-2-yl)carbamoyl)tetrahydro-2H-pyran-4-carboxamide (0.334 g, 0.886 mmol), NaHCO₃ (0.149 g, 1.773 mmol) and 2-methyl-5-(4,4,5,5-tetramethyl-1,3,2-dioxaborolan-2-yl)pyridine (0.233 g, 1.064 mmol) in dioxane (4 mL) and water (1 mL) was sparged with Ar under sonication for 5 minutes, treated with Pd(PPh₃)₄ (0.102 g, 0.089 mmol), sparged again with Ar and heated at 95° C. overnight. The mixture was cooled to RT, diluted with THF and washed with brine. The aqueous layer was back-extracted with THF (3×) and the combined organics were dried over Na₂SO₄ and concentrated to dryness. The material was treated with MeCN and sonicated. The solids were collected via filtration and purified via silica gel chromatography (MeOH/EtOAc) to afford N-((5-(((6'-methyl-[2,3'-bipyridin]-4-yl)oxy)pyridin-2-yl)carbamoyl)tetrahydro-2H-pyran-4-carboxamide (50 mg, 13%) as a white solid. $^1$H NMR (400 MHz, DMSO-d₆): δ 11.06 (s, 1H), 10.88 (s, 1H), 9.10 (d, J=2.3 Hz, 1H), 8.55 (d, J=5.7 Hz, 1H), 8.30-8.26 (m, 2H), 8.09 (d, J=9.0 Hz, 1H), 7.76 (dd, J=9.0, 2.9 Hz, 1H), 7.63 (d, J=2.4 Hz, 1H), 7.33 (d, J=8.2 Hz, 1H), 6.89 (dd, J=5.7, 2.4 Hz, 1H), 3.91-3.85 (m, 2H), 3.33-3.26 (m, 2H), 2.73-2.64 (m, 1H), 2.50 (s, 3H), 1.75-1.68 (m, 2H), 1.67-1.56 (m, 2H); MS (ESI) m/z: 432.1 (M−H⁺).

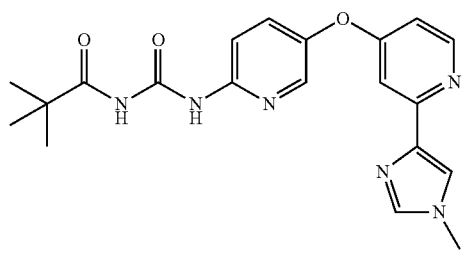 [SMILES: Cn1cnc(-c2cc(Oc3ccc(NC(=O)NC(=O)C(C)(C)C)nc3)ccn2)c1]

Example 104

A solution of 2,2,2-trimethylacetamide (0.065 g, 0.645 mmol) in DCE (2 mL) was treated with oxalyl chloride (0.056 mL, 0.645 mmol), stirred at RT for 5 min, then heated at 80° C. for 30 min. The mixture was cooled to RT, added to a mixture of Example A22 (0.115 g, 0.430 mmol) and pyridine (0.278 mL, 3.44 mmol) in dioxane (4 mL) and stirred at RT overnight. The mixture was treated with satd. NaHCO₃, extracted with EtOAc (3×) and the combined organics were dried over Na₂SO₄ and concentrated to dryness. The material was treated with MeCN and the solid collected via filtration to afford N-((5-((2-(1-methyl-1H-imidazol-4-yl)pyridin-4-yl)oxy)pyridin-2-yl)carbamoyl)pivalamide (132 mg, 78%) as a white solid. $^1$H NMR (400 MHz, DMSO-d₆): δ 11.23 (s, 1H), 10.44 (s, 1H), 8.37 (d, J=5.7 Hz, 1H), 8.28 (d, J=2.9 Hz, 1H), 8.10 (d, J=9.0 Hz, 1H), 7.77 (dd, J=9.0, 2.9 Hz, 1H), 7.68 (d, J=1.3 Hz, 1H), 7.60 (d, J=1.3 Hz, 1H), 7.24 (d, J=2.6 Hz, 1H), 6.81 (dd, J=5.6, 2.6 Hz, 1H), 3.67 (s, 3H), 1.21 (s, 9H); MS (ESI) m/z: 395.2 (M+H⁺).

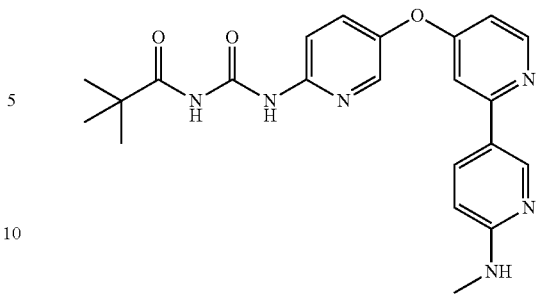

Example 105

A solution of Example A1 (0.380 g, 1.510 mmol) and 6-(methylamino)-3-pyridinylboronic (0.252 g, 1.661 mmol) in dioxane (8 mL) was sparged with Ar, treated with a solution of K₂CO₃ (0.417 g, 3.02 mmol) in water (2 mL) and heated at 90° C. for 16 h. The mixture was cooled to RT, treated with water and extracted with EtOAc (2×). The combined organics were washed with brine, dried over Na₂SO₄, concentrated to dryness and purified via silica gel chromatography (MeOH/DCM) to afford N-methyl-4-((6-nitropyridin-3-yl)oxy)-[2,3'-bipyridin]-6'-amine (300 mg, 61%) as an orange amorphous solid. $^1$H NMR (400 MHz, DMSO-d₆): δ 8.73 (d, J=2.5 Hz, 1H), 8.58 (d, J=2.8 Hz, 1H), 8.55 (d, J=5.6 Hz, 1H), 8.39 (d, J=8.9 Hz, 1H), 8.06 (dd, J=8.8, 2.5 Hz, 1H), 7.96 (dd, J=8.9, 2.9 Hz, 1H), 7.61 (d, J=2.3 Hz, 1H), 7.00 (dd, J=5.6, 2.3 Hz, 1H), 6.87 (q, J=5.2 Hz, 1H), 6.48 (d, J=8.8 Hz, 1H), 2.80 (d, J=4.7 Hz, 3H); MS (ESI) m/z: 324.1 (M+H⁺).

A mixture of BOC-anhydride (0.215 mL, 0.928 mmol), N-methyl-4-((6-nitropyridin-3-yl)oxy)-[2,3'-bipyridin]-6'-amine (0.3 g, 0.928 mmol) and DMAP (5 mg) in THF (10 mL) was stirred at RT for 3 days. The mixture was concentrated to dryness and purified via silica gel chromatography (EtOAc/Hex) to afford tert-butyl methyl(4-((6-nitropyridin-3-yl)oxy)-[2,3'-bipyridin]-6'-yl)carbamate (260 mg, 66%) as a white solid. MS (ESI) m/z: 424.1 (M+H⁺).

A solution of tert-butyl methyl(4-((6-nitropyridin-3-yl)oxy)-[2,3'-bipyridin]-6'-yl)carbamate (0.26 g, 0.614 mmol) in EtOAc (10 mL) was treated with 10% Pd/C (50% wet, 6.53 mg, 0.061 mmol) and hydrogenated (1 atm) for 16 h. The solids were removed via filtration through diatomaceous earth, washed with EtOAc and the filtrate concentrated to dryness to afford tert-butyl (4-((6-aminopyridin-3-yl)oxy)-[2,3'-bipyridin]-6'-yl)(methyl)carbamate (210 mg, 87%) as a white amorphous solid. $^1$H NMR (400 MHz, DMSO-d₆): δ 8.99 (d, J=2.5 Hz, 1H), 8.49 (d, J=5.7 Hz, 1H), 8.34 (dd, J=8.8, 2.5 Hz, 1H), 7.84 (d, J=2.9 Hz, 1H), 7.75 (d, J=8.8 Hz, 1H), 7.55 (d, J=2.4 Hz, 1H), 7.31 (dd, J=8.9, 3.0 Hz, 1H), 6.75 (dd, J=5.7, 2.4 Hz, 1H), 6.52 (d, J=8.9 Hz, 1H), 6.03 (s, 2H), 3.33 (s, 3H), 1.47 (s, 9H); MS (ESI) m/z: 394.2 (M+H⁺).

A solution of 2,2,2-trimethylacetamide (0.062 g, 0.610 mmol) in DCE (3 mL) was treated with oxalyl chloride (0.080 mL, 0.915 mmol), stirred at RT for 1 h, then heated at 75° C. for 3 h. The mixture was cooled to RT, treated with a solution of tert-butyl (4-((6-aminopyridin-3-yl)oxy)-[2,3'-bipyridin]-6'-yl)(methyl)carbamate (0.12 g, 0.305 mmol) and TEA (0.170 mL, 1.220 mmol) in DCM (3 mL) and stirred at RT for 2 h. The mixture was treated with brine, extracted with DCM (2×) and the combined organics were washed with brine, dried over Na₂SO₄, concentrated to dryness and purified via silica gel chromatography (EtOAc/Hex) to afford tert-butyl methyl(4-((6-(3-pivaloylureido)pyridin-3-yl)oxy)-[2,3'-bipyridin]-6'-yl)carbamate (100 mg, 63%) as a white amorphous solid. $^1$H NMR (400 MHz, DMSO-$d_6$): δ 11.23 (s, 1H), 10.44 (s, 1H), 9.02 (d, J=2.5 Hz, 1H), 8.55 (d, J=5.7 Hz, 1H), 8.37 (dd, J=8.8, 2.5 Hz, 1H), 8.30 (d, J=2.9 Hz, 1H), 8.10 (d, J=9.0 Hz, 1H), 7.77-7.76 (m, 2H), 7.65 (d, J=2.4 Hz, 1H), 6.89 (dd, J=5.7, 2.4 Hz, 1H), 3.33 (s, 3H), 1.47 (s, 9H), 1.21 (s, 9H); MS (ESI) m/z: 521.3 (M+H$^+$).

A mixture of tert-butyl methyl(4-((6-(3-pivaloylureido)pyridin-3-yl)oxy)-[2,3'-bipyridin]-6'-yl)carbamate (0.1 g, 0.192 mmol) and TFA (0.148 mL, 1.921 mmol) in DCM (4 mL) was stirred at RT for 7 h, then concentrated to dryness. The residue was treated with satd. NaHCO$_3$, extracted with EtOAc (2×) and the combined organics were washed with brine, dried over Na$_2$SO$_4$ and concentrated to dryness. The material was treated with 30% EtOAc/Hex, sonicated and the resulting solid collected via filtration to afford N-((5-((6'-(methylamino)-[2,3'-bipyridin]-4-yl)oxy)pyridin-2-yl)carbamoyl)pivalamide (61 mg, 76%) as a white solid. $^1$H NMR (400 MHz, DMSO-$d_6$): δ 11.21 (s, 1H), 10.42 (s, 1H), 8.69 (d, J=2.4 Hz, 1H), 8.44 (d, J=5.7 Hz, 1H), 8.27 (d, J=2.9 Hz, 1H), 8.09 (d, J=9.0 Hz, 1H), 8.02 (dd, J=8.8, 2.5 Hz, 1H), 7.75 (dd, J=9.0, 2.9 Hz, 1H), 7.39 (d, J=2.4 Hz, 1H), 6.83 (q, J=5.0 Hz, 1H), 6.73 (dd, J=5.7, 2.4 Hz, 1H), 6.48 (d, J=8.8 Hz, 1H), 2.80 (d, J=4.7 Hz, 3H), 1.21 (s, 9H); MS (ESI) m/z: 421.2 (M+H$^+$).

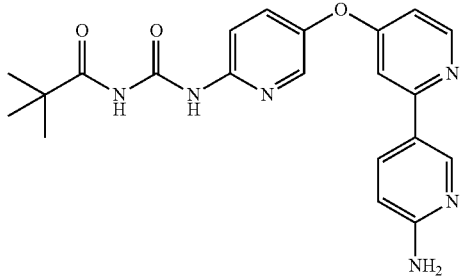 [SMILES: CC(C)(C)C(=O)NC(=O)Nc1ccc(Oc2ccnc(-c3ccc(N)nc3)c2)cn1]

Example 106

A solution of Example A1 (0.525 g, 2.086 mmol) and 5-(4,4,5,5-tetramethyl-1,3,2-dioxaborolan-2-yl)pyridin-2-amine (0.551 g, 2.504 mmol) in dioxane (16 mL) was sparged with Ar, treated with a solution of K$_2$CO$_3$ (0.577 g, 4.17 mmol) in water (4 mL) and heated at 90° C. for 1 h. The mixture was cooled to RT, treated with water and extracted with EtOAc (3×). The combined organics were washed with brine, dried over Na$_2$SO$_4$ and concentrated to dryness. The material was treated with 60% EtOAc/Hex, sonicated and the resulting solid collected via filtration to afford 4-((6-nitropyridin-3-yl)oxy)-[2,3'-bipyridin]-6'-amine (580 mg, 90%) as a dark orange solid. $^1$H NMR (400 MHz, DMSO-$d_6$): δ 8.66 (d, J=2.5 Hz, 1H), 8.58 (d, J=2.8 Hz, 1H), 8.55 (d, J=5.6 Hz, 1H), 8.40 (dd, J=8.9, 0.5 Hz, 1H), 8.06 (dd, J=8.7, 2.5 Hz, 1H), 7.96 (dd, J=8.9, 2.8 Hz, 1H), 7.61 (d, J=2.3 Hz, 1H), 7.02 (dd, J=5.6, 2.3 Hz, 1H), 6.48 (dd, J=8.7, 0.7 Hz, 1H), 6.32 (s, 2H); MS (ESI) m/z: 310.1 (M+H$^+$).

A solution of 4-((6-nitropyridin-3-yl)oxy)-[2,3'-bipyridin]-6'-amine (0.58 g, 1.875 mmol), BOC-anhydride (0.653 mL, 2.81 mmol) and DMAP (10 mg) in THF (20 mL) was stirred at RT for 2 days, treated with additional BOC-anhydride (15 eq.) and stirred at RT for 6 h. The mixture was concentrated to dryness and purified via silica gel chromatography (EtOAc/Hex) to afford 6'-(bis(tert-butoxycarbonyl)amino)-4-((6-nitropyridin-3-yl)oxy)-[2,3'-bipyridine](630 mg, 66%) as a white solid. MS (ESI) m/z: 510.2 (M+H$^+$).

A solution of 6'-(bis(tert-butoxycarbonyl)amino)-4-((6-nitropyridin-3-yl)oxy)-[2,3'-bipyridine](0.600 g, 1.178 mmol) in EtOAc (15 mL) and MeOH (5 mL) was treated with 10% Pd/C (50% wet, 0.125 g, 1.178 mmol) and hydrogenated (1 atm) for 16 h. The solids were removed via filtration through diatomaceous earth, washed with EtOAc and the filtrate concentrated to dryness to afford 6'-(bis(tert-butoxycarbonyl)amino)-4-((6-aminopyridin-3-yl)oxy)-[2,3'-bipyridine](0.55 g, 97%) as a white amorphous solid. $^1$H NMR (400 MHz, DMSO-$d_6$): δ 9.06 (d, J=2.5 Hz, 1H), 8.53 (d, J=5.7 Hz, 1H), 8.46 (dd, J=8.5, 2.5 Hz, 1H), 7.84 (d, J=3.0 Hz, 1H), 7.63 (d, J=2.4 Hz, 1H), 7.48 (d, J=8.0 Hz, 1H), 7.32 (dd, J=8.9, 3.0 Hz, 1H), 6.79 (dd, J=5.7, 2.4 Hz, 1H), 6.53 (d, J=8.9 Hz, 1H), 6.03 (s, 2H), 1.40 (s, 18H); MS (ESI) m/z: 480.2 (M+H$^+$).

A solution of 2,2,2-trimethylacetamide (0.084 g, 0.834 mmol) in DCE (3 mL) was treated with oxalyl chloride (0.073 mL, 0.834 mmol), stirred at RT for 1 h, then heated at 75° C. for 3 h. The mixture was cooled to RT, treated with a solution of 6'-(bis(tert-butoxycarbonyl)amino)-4-((6-aminopyridin-3-yl)oxy)-[2,3'-bipyridine](0.2 g, 0.417 mmol) and TEA (0.174 mL, 1.251 mmol) in DCM (3 mL) and stirred at RT for 2 h. The mixture was treated with brine, extracted with DCM (2×) and the combined organics were washed with brine, dried over Na$_2$SO$_4$ and concentrated to dryness to afford N-((5-((6'-(bis(tert-butoxycarbonyl)amino)-[2,3'-bipyridin]-4-yl)oxy)pyridin-2-yl)carbamoyl)pivalamide (230 mg, 91%) as a white amorphous solid. $^1$H NMR (400 MHz, DMSO-$d_6$): δ 11.22 (s, 1H), 10.45 (br s, 1H), 9.08 (d, J=2.5 Hz, 1H), 8.58 (d, J=5.7 Hz, 1H), 8.49 (dd, J=8.5, 2.5 Hz, 1H), 8.30 (d, J=2.9 Hz, 1H), 8.10 (d, J=9.0 Hz, 1H), 7.78 (dd, J=9.0, 2.9 Hz, 1H), 7.73 (d, J=2.4 Hz, 1H), 7.48 (d, J=8.4 Hz, 1H), 6.94 (dd, J=5.7, 2.4 Hz, 1H), 1.40 (s, 18H), 1.21 (s, 9H); MS (ESI) m/z: 607.3 (M+H$^+$).

A mixture of N-((5-((6'-(bis(tert-butoxycarbonyl)amino)-[2,3'-bipyridin]-4-yl)oxy)pyridin-2-yl)carbamoyl)pivalamide (0.23 g, 0.379 mmol) and TFA (0.44 mL, 5.7 mmol) in DCM (4 mL) was stirred at RT for 16 h. The mixture was concentrated to dryness, treated with satd. NaHCO$_3$ and extracted with EtOAc (2×). The combined organics were washed with brine, dried over Na$_2$SO$_4$, concentrated to dryness and purified via silica gel chromatography (MeOH/DCM) to afford N-((5-((6'-amino-[2,3'-bipyridin]-4-yl)oxy)pyridin-2-yl)carbamoyl)pivalamide (125 mg, 81%) as a white solid. $^1$H NMR (400 MHz, DMSO-$d_6$): δ 11.21 (s, 1H), 10.45 (br s, 1H), 8.62 (d, J=2.5 Hz, 1H), 8.44 (d, J=5.7 Hz, 1H), 8.27 (d, J=2.9 Hz, 1H), 8.09 (d, J=9.0 Hz, 1H), 8.01 (dd, J=8.7, 2.5 Hz, 1H), 7.74 (dd, J=9.0, 2.9 Hz, 1H), 7.38 (d, J=2.4 Hz, 1H), 6.74 (dd, J=5.7, 2.4 Hz, 1H), 6.47 (d, J=8.7 Hz, 1H), 6.27 (d, J=4.7 Hz, 2H), 1.21 (s, 9H); MS (ESI) m/z: 407.2 (M+H$^+$).

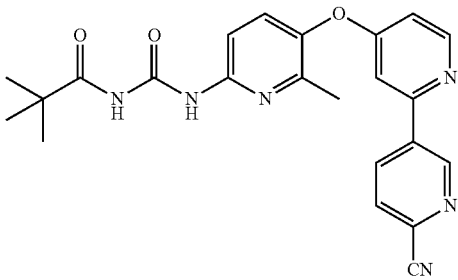 [SMILES: Cc1nc(NC(=O)NC(=O)C(C)(C)C)ccc1Oc1ccnc(-c2ccc(C#N)nc2)c1]

Example 107

A solution of 2,2,2-trimethylacetamide (0.080 g, 0.791 mmol) in DCE (4 mL) was treated with oxalyl chloride (0.069 mL, 0.791 mmol), stirred at RT for 1 h, then heated at 75° C. for 3 h. The mixture was cooled to RT, treated with a solution of Example A23 (0.12 g, 0.396 mmol) and TEA (0.165 mL, 1.187 mmol) in THF (3 mL) and stirred at RT for 2 h. The mixture was treated with brine, extracted with EtOAc (2×) and the combined organics were washed with brine, dried over Na$_2$SO$_4$ and concentrated to dryness. The material was suspended in 3:1 MeCN/H$_2$O, sonicated and the solid collected via filtration and dried to afford N-((5-((6'-cyano-[2,3'-bipyridin]-4-yl)oxy)-6-methylpyridin-2-yl)carbamoyl)pivalamide (98 mg, 58%) as an off-white solid. $^1$H NMR (400 MHz, DMSO-d$_6$): δ 11.16 (s, 1H), 10.40 (br s, 1H), 9.41 (d, J=2.2 Hz, 1H), 8.64 (dd, J=8.2, 2.3 Hz, 1H), 8.60 (d, J=5.7 Hz, 1H), 8.13 (dd, J=8.2, 0.8 Hz, 1H), 7.92 (br d, J=8.8 Hz, 1H), 7.80 (d, J=2.4 Hz, 1H), 7.67 (d, J=8.8 Hz, 1H), 6.91 (dd, J=5.7, 2.4 Hz, 1H), 2.28 (s, 3H), 1.21 (s, 9H); MS (ESI) m/z: 431.2 (M+H$^+$).

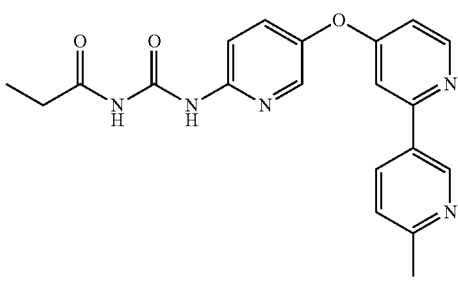 [SMILES: CCC(=O)NC(=O)Nc1ccc(Oc2ccnc(-c3ccc(C)nc3)c2)cn1]

Example 108

A solution of propionamide (0.047 g, 0.647 mmol) in DCE (2 mL) was treated with oxalyl chloride (0.057 mL, 0.647 mmol), stirred at RT for 5 min, then warmed to 80° C. for 0.5 h. The solution was cooled to RT, added to a mixture of Example A15 (0.12 g, 0.431 mmol) and pyridine (0.279 mL, 3.45 mmol) in dioxane (4 mL) and stirred at RT for 3 h. The mixture was treated with satd. NaHCO$_3$, extracted with EtOAc (3×) and the combined organics were dried over Na$_2$SO$_4$, concentrated to dryness and purified via silica gel chromatography (MeOH/EtOAc). The material was suspended in MeCN and the solid collected via filtration to afford N-((5-(((6'-methyl-[2,3'-bipyridin]-4-yl)oxy)pyridin-2-yl)carbamoyl)propionamide (58 mg, 36%) as a white solid. $^1$H NMR (400 MHz, DMSO-d$_6$): δ 11.07 (s, 1H), 10.82 (s, 1H), 9.10 (d, J=2.35 Hz, 1H), 8.55 (d, J=5.66 Hz, 1H), 8.30-8.26 (m, 2H), 8.09 (d, J=9.03 Hz, 1H), 7.76 (dd, J=9.03, 2.93 Hz, 1H), 7.64 (d, J=2.39 Hz, 1H), 7.34 (d, J=8.16 Hz, 1H), 6.89 (dd, J=5.67, 2.39 Hz, 1H), 2.50 (s, 3H), 2.41 (q, J=7.48 Hz, 2H), 1.05 (t, J=7.48 Hz, 3H); MS (ESI) m/z: 378.2 (M+H$^+$).

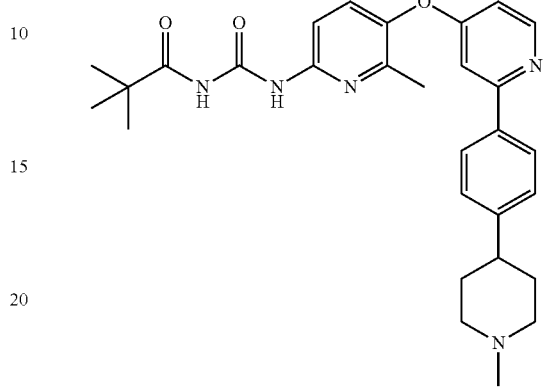

Example 109

A solution of 2,2,2-trimethylacetamide (0.041 g, 0.401 mmol) in DCE (2 mL) was treated with oxalyl chloride (0.035 mL, 0.401 mmol), stirred at RT for 5 min, then warmed to 80° C. for 0.5 h. The solution was cooled to RT, added to a mixture of Example A24 (0.10 g, 0.267 mmol) and pyridine (0.173 mL, 2.136 mmol) in dioxane (4 mL), treated with DIEA (0.2 mL, 1.145 mmol) and stirred at RT for 3 h. The mixture was treated with satd. NaHCO$_3$, extracted with EtOAc (3×) and the combined organics were washed with 1M NaOH, then brine, dried over Na$_2$SO$_4$ and concentrated to dryness. The material was treated with MeCN and the solid was collected via filtration and dried to afford N-((6-methyl-5-((2-(4-(1-methylpiperidin-4-yl)phenyl)pyridin-4-yl)oxy)pyridin-2-yl)carbamoyl)pivalamide (57 mg, 43%) as a white solid. $^1$H NMR (400 MHz, DMSO-d$_6$): δ 11.16 (s, 1H), 10.41 (s, 1H), 8.50 (d, J=5.7 Hz, 1H), 7.96-7.90 (m, 3H), 7.66 (d, J=8.8 Hz, 1H), 7.40 (d, J=2.4 Hz, 1H), 7.32 (d, J=8.2 Hz, 2H), 6.77 (dd, J=5.6, 2.4 Hz, 1H), 2.89 (br d, J=10.8 Hz, 2H), 2.53-2.43 (m, 1H), 2.27 (s, 3H), 2.22 (s, 3H), 2.02 (br s, 2H), 1.77-1.61 (m, 4H), 1.21 (s, 9H); MS (ESI) m/z: 502.3 (M+H$^+$).

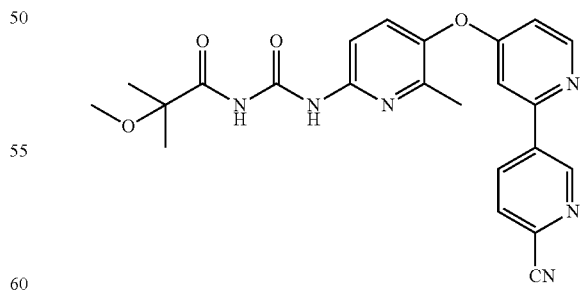

Example 110

A mixture of Example A23 (0.12 g, 0.396 mmol), Example B16 (0.119 g, 0.593 mmol) and 1-methylpyrrolidine (0.034 g, 0.396 mmol) in THF (4 mL) was heated at 55° C. for 6 h, then cooled to RT and concentrated to dryness. The residue was purified via silica gel chromatography (MeOH/DCM), then re-purified via reverse-phase silica gel chromatography (MeCN/H₂O with 0.1% TFA). The combined fractions were neutralized with satd. NaHCO₃, extracted with EtOAc (2×) and the combined organics were washed with brine, dried over Na₂SO₄ and concentrated to dryness to afford N-((5-((6'-cyano-[2,3'-bipyridin]-4-yl)oxy)-6-methylpyridin-2-yl)carbamoyl)-2-methoxy-2-methylpropanamide (98 mg, 56%) as a white solid. ¹H NMR (400 MHz, DMSO-d₆): δ 10.78 (br s, 1H), 10.15 (br s, 1H), 9.41 (dd, J=2.2, 0.8 Hz, 1H), 8.66 (dd, J=8.2, 2.2 Hz, 1H), 8.61 (d, J=5.7 Hz, 1H), 8.14 (dd, J=8.2, 0.8 Hz, 1H), 7.88 (br s, 1H), 7.81 (d, J=2.4 Hz, 1H), 7.68 (d, J=8.8 Hz, 1H), 6.91 (dd, J=5.7, 2.4 Hz, 1H), 3.20 (s, 3H), 2.29 (s, 3H), 1.35 (s, 6H); MS (ESI) m/z: 447.2 (M+H⁺).

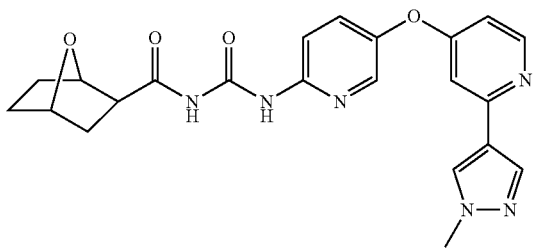 [SMILES: Cn1cc(-c2cc(Oc3ccc(NC(=O)NC(=O)C4CC5CCC4O5)nc3)ccn2)cn1]

Example 111

A solution of Example B22 (0.300 g, 2.110 mmol) in DCM (10 mL) was treated with oxalyl chloride (0.260 g, 2.048 mmol) followed by catalytic DMF and stirred at RT for 2 h. The mixture was treated with silver cyanate (0.500 g, 3.34 mmol), stirred at RT for 1 h, treated with Example A2 (0.267 g, 1.000 mmol) and pyridine (0.024 g, 0.300 mmol) and stirred at RT overnight. The solids were removed via filtration, washed with DCM and the filtrate concentrated to dryness and purified via silica gel chromatography (EtOAc/THF) to afford N-((5-((2-(1-methyl-1H-pyrazol-4-yl)pyridin-4-yl)oxy)pyridin-2-yl)carbamoyl)-7-oxabicyclo[2.2.1]heptane-2-carboxamide (155 mg, 35%) as an off-white solid. ¹H NMR (400 MHz, DMSO-d₆): δ 10.97 (s, 1H), 10.88 (s, 1H), 8.37 (d, J=5.7 Hz, 1H), 8.26-8.25 (m, 2H), 8.09 (d, J=9.0 Hz, 1H), 7.97 (s, 1H), 7.73 (dd, J=9.0, 2.9 Hz, 1H), 7.23 (d, J=2.4 Hz, 1H), 6.71 (dd, J=5.7, 2.4 Hz, 1H), 4.65 (d, J=4.6 Hz, 1H), 4.58 (m, 1H), 3.84 (s, 3H), 2.80 (m, 1H), 2.03-1.99 (m, 1H), 1.64-1.49 (m, 4H), 1.48-1.42 (m, 1H); MS (ESI) m/z: 435.2 (M+H⁺).

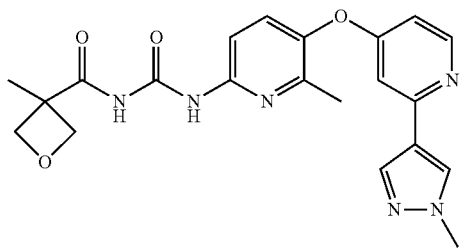

Example 112

A solution of 3-methyloxetane carboxylic acid (0.400 g, 3.44 mmol) in DCM (10 mL) was treated with oxalyl chloride (0.400 g, 3.15 mmol) followed by catalytic DMF and stirred at RT for 0.5 h. The mixture was treated with silver cyanate (0.600 g, 4.00 mmol), stirred at RT for 10 minutes, treated with Example A6 (0.200 g, 0.711 mmol) and pyridine (0.056 g, 0.711 mmol) and stirred at RT. The solids were removed via filtration, washed with DCM and the filtrate concentrated to dryness and purified via silica gel chromatography to provide 3-methyl-N-((6-methyl-5-((2-(1-methyl-1H-pyrazol-4-yl)pyridin-4-yl)oxy)pyridin-2-yl)carbamoyl)oxetane-3-carboxamide (53 mg, 16%) as a white solid. MS (ESI) m/z: 423.2 (M+H⁺).

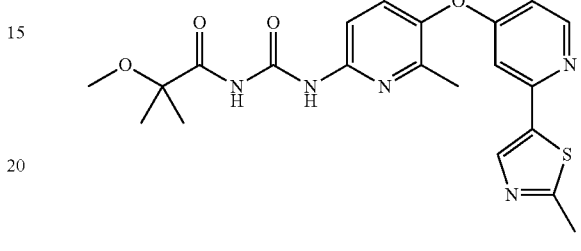

Example 113

A solution of Example B16 (0.135 g, 0.670 mmol) and Example A20 (0.1 g, 0.335 mmol) in dioxane (2 mL) was treated with 1-methylpyrrolidine (0.070 mL, 0.670 mmol) and heated at 80° C. overnight. The mixture was cooled to RT, treated with satd. NaHCO₃ and extracted with EtOAc (4×). The combined organics were washed with water, then brine, dried over Na₂SO₄, concentrated to dryness and purified via silica gel chromatography (EtOAc/Hex). The material was treated with MeCN, sonicated for 10 min, and the resulting solid was collected via filtration to afford 2-methoxy-2-methyl-N-((6-methyl-5-((2-(2-methylthiazol-5-yl)pyridin-4-yl)oxy)pyridin-2-yl)carbamoyl)propanamide (127 mg, 86%) as a white solid. ¹H NMR (400 MHz, DMSO-d₆): δ 10.78 (s, 1H), 10.15 (s, 1H), 8.39 (d, J=5.8 Hz, 1H), 8.32 (s, 1H), 7.87 (m, 1H), 7.66 (d, J=8.8 Hz, 1H), 7.56 (d, J=2.4 Hz, 1H), 6.72 (dd, J=5.8, 2.4 Hz, 1H), 3.20 (s, 3H), 2.65 (s, 3H), 2.28 (s, 3H), 1.35 (s, 6H); MS (ESI) m/z: 442.2 (M+H⁺).

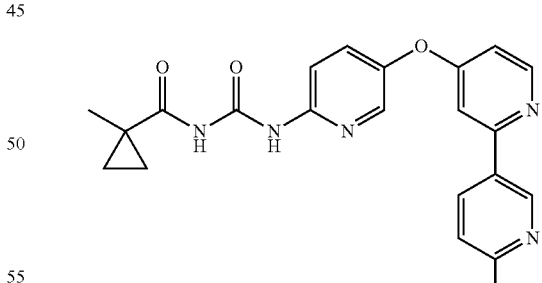

Example 114

A solution of Example B20 (0.158 g, 0.862 mmol) and Example A15 (0.12 g, 0.431 mmol) in dioxane (4 mL) was treated with 1-methylpyrrolidine (0.090 mL, 0.862 mmol) and heated at 80° C. overnight. The mixture was cooled to RT, treated with satd. NaHCO₃ and extracted with EtOAc (4×). The combined organics were washed with water, then brine, dried over Na₂SO₄, concentrated to dryness and purified via silica gel chromatography (EtOAc/Hex). The material was treated with MeCN, sonicated and the resulting solid collected via filtration and dried to afford 1-methyl-N-((5-((6'-methyl-[2,3'-bipyridin]-4-yl)oxy)pyridin-2-yl)carbamoyl) cyclopropanecarboxamide (83 mg, 48%) as a white solid. $^1$H NMR (400 MHz, DMSO-$d_6$): δ 11.25 (br s, 1H), 10.13 (br s, 1H), 9.10 (d, J=2.3 Hz, 1H), 8.55 (d, J=5.7 Hz, 1H), 8.29-8.27 (m, 2H), 8.10-8.06 (m, 1H), 7.77 (dd, J=9.0, 2.9 Hz, 1H), 7.64 (d, J=2.4 Hz, 1H), 7.34 (d, J=8.2 Hz, 1H), 6.89 (dd, J=5.7, 2.4 Hz, 1H), 2.50 (s, 3H), 1.36 (s, 3H), 1.22-1.20 (m, 2H), 0.77-0.75 (m, 2H); MS (ESI) m/z: 404.2 (M+H$^+$).

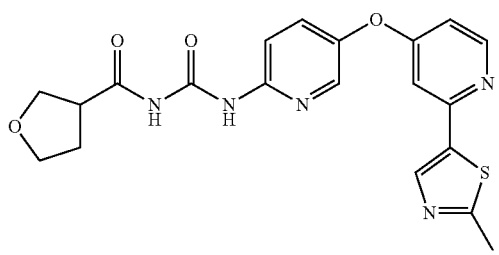 [SMILES: Cc1ncc(-c2cc(Oc3ccc(NC(=O)NC(=O)C4CCOC4)nc3)ccn2)s1]

Example 115

A solution of tetrahydrofuran-3-carboxylic acid (0.123 g, 1.055 mmol) in DCM (5 mL) was treated with oxalyl chloride (0.092 mL, 1.055 mmol) and catalytic DMF (1 drop), stirred at RT for 2 h, then concentrated to dryness. The residue was treated with DCM (5 mL) and silver cyanate (0.158 g, 1.055 mmol), stirred at RT for 2 h, treated with Example A13 (0.15 g, 0.528 mmol) and stirred at RT overnight. The solid was removed via filtration, washed with DCM and the filtrate was concentrated to dryness and purified via silica gel chromatography (MeOH/DCM). The material was re-purified via reverse-phase silica gel chromatography (MeCN/H$_2$O with 0.1% TFA); combined fractions were neutralized with NaHCO$_3$, extracted with EtOAc (2×) and the combined organics were washed with brine, dried over Na$_2$SO$_4$ and concentrated to dryness to afford N-((5-((2-(2-methylthiazol-5-yl)pyridin-4-yl)oxy)pyridin-2-yl)carbamoyl)tetrahydrofuran-3-carboxamide (25 mg, 11%) as a white solid. $^1$H NMR (400 MHz, DMSO-$d_6$): δ 11.00 (br s, 2H), 8.41 (d, J=5.8 Hz, 1H), 8.33 (s, 1H), 8.29 (d, J=2.9 Hz, 1H), 8.10 (d, J=9.0 Hz, 1H), 7.76 (dd, J=9.0, 2.9 Hz, 1H), 7.61 (d, J=2.4 Hz, 1H), 6.83 (dd, J=5.8, 2.4 Hz, 1H), 3.87 (t, J=8.3 Hz, 1H), 3.79-3.74 (m, 2H), 3.70-3.64 (m, 1H), 3.24 (m, 1H), 2.66 (s, 3H), 2.10-2.05 (m, 2H); MS (ESI) m/z: 426.1 (M+H$^+$).

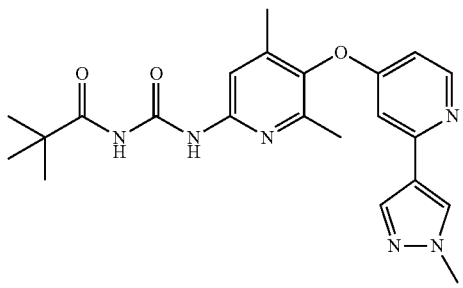 [SMILES: Cc1cc(NC(=O)NC(=O)C(C)(C)C)nc(C)c1Oc1ccnc(-c2cnn(C)c2)c1]

Example 116

A solution of 2,2,2-trimethylacetamide (51 mg, 0.508 mmol) in DCE (2 mL) was treated with oxalyl chloride (64 mg, 0.508 mmol), stirred at RT for 5 min, then warmed to 80° C. for 45 min. The mix was cooled to RT, added to a solution of diisopropylethylamine (188 mg, 1.456 mmol) and Example A25 (100 mg, 0.339 mmol) in dioxane (4 mL) and stirred at RT for 3 h. The mixture was treated with EtOAc, washed successively with satd. NaHCO$_3$, 1N NaOH and brine, dried over Na$_2$SO$_4$ and concentrated to dryness. The material was treated with MeCN, sonicated, and the resulting solid was collected via filtration and dried to afford N-((4,6-dimethyl-5-((2-(1-methyl-1H-pyrazol-4-yl)pyridin-4-yl)oxy)pyridin-2-yl)carbamoyl)pivalamide (91 mg, 68%) as a white solid. $^1$H NMR (400 MHz, DMSO-$d_6$): δ 11.11 (s, 1H), 10.39 (br s, 1H), 8.33 (d, J=5.7 Hz, 1H), 8.25 (s, 1H), 7.96 (s, 1H), 7.83 (s, 1H), 7.12 (d, J=2.4 Hz, 1H), 6.52 (dd, J=5.7, 2.4 Hz, 1H), 3.84 (s, 3H), 2.18 (s, 3H), 2.11 (s, 3H), 1.21 (s, 9H); MS (ESI) m/z: 423.2 (M+H$^+$).

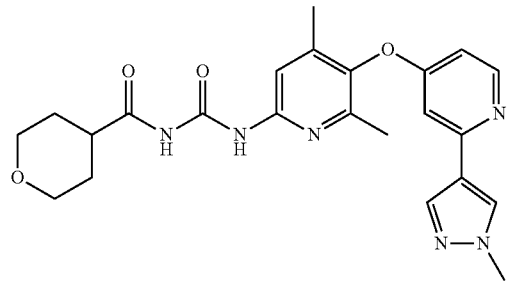 [SMILES: Cc1cc(NC(=O)NC(=O)C2CCOCC2)nc(C)c1Oc1ccnc(-c2cnn(C)c2)c1]

Example 117

A mixture of Example B5 (66 mg, 0.508 mmol) in DCE (2 mL) was treated with oxalyl chloride (64 mg, 0.508 mmol), stirred at RT for 5 min, then warmed to 80° C. for 45 min. The mixture was cooled to RT, added to a solution of DIEA (188 mg, 1.456 mmol) and Example A25 (100 mg, 0.339 mmol) in dioxane (4 mL) and stirred at RT for 3 h. The mixture was diluted with EtOAc, washed successively with satd. NaHCO$_3$, 1N NaOH and brine, dried over Na$_2$SO$_4$, concentrated to dryness and purified via reverse-phase silica gel chromatography (MeCN/H$_2$O with 0.1% TFA). The pure fractions were partially evaporated under reduced pressure and the aqueous residue was neutralized with satd. NaHCO$_3$ and extracted with EtOAc (3×). The combined organics were washed with brine, dried over Na$_2$SO$_4$ and concentrated to dryness to afford N-((4,6-dimethyl-5-((2-(1-methyl-1H-pyrazol-4-yl)pyridin-4-yl)oxy)pyridin-2-yl)carbamoyl)tetrahydro-2H-pyran-4-carboxamide (29 mg, 19%) as a white solid. $^1$H NMR (400 MHz, DMSO-$d_6$): δ 10.95 (s, 1H), 10.86 (s, 1H), 8.33 (d, J=5.7 Hz, 1H), 8.25 (s, 1H), 7.95 (s, 1H), 7.84 (s, 1H), 7.11 (d, J=2.4 Hz, 1H), 6.51 (dd, J=5.7, 2.5 Hz, 1H), 3.90-3.85 (m, 2H), 3.84 (s, 3H), 3.30-3.27 (m, 2H), 2.73-2.65 (m, 1H), 2.18 (s, 3H), 2.10 (s, 3H), 1.74-1.68 (m, 2H), 1.65-1.55 (m, 2H); MS (ESI) m/z: 451.2 (M+H$^+$).

145

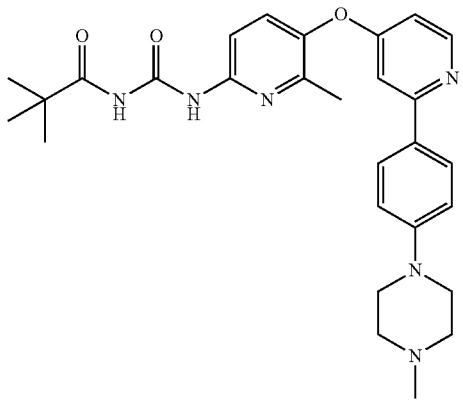 [SMILES: Cc1nc(NC(=O)NC(=O)C(C)(C)C)ccc1Oc1ccnc(-c2ccc(N3CCN(C)CC3)cc2)c1]

Example 118

A mixture of Example A4 (0.676 g, 2.55 mmol), 1-methyl-4-(4-(4,4,5,5-tetramethyl-1,3,2-dioxaborolan-2-yl)phenyl)piperazine (1 g, 3.31 mmol), Pd(PPh$_3$)$_4$ (0.147 g, 0.127 mmol) and K$_2$CO$_3$ (1.055 g, 7.64 mmol) in dioxane (8 mL) and water (2 mL) was sparged with Ar, heated at 90° C. overnight, then cooled to RT. The mixture was treated with brine, extracted with EtOAc (3×) and the combined organics were dried over Na$_2$SO$_4$, concentrated to dryness and purified via silica gel chromatography (MeOH/DCM) to afford 1-methyl-4-(4-(4-((2-methyl-6-nitropyridin-3-yl)oxy)pyridin-2-yl)phenyl)piperazine (333 mg, 32%). $^1$H NMR (400 MHz, DMSO-d$_6$): δ 8.55 (d, J=5.6 Hz, 1H), 8.22 (d, J=8.7 Hz, 1H), 7.95 (d, J=8.8 Hz, 2H), 7.81 (d, J=8.7 Hz, 1H), 7.58 (d, J=2.3 Hz, 1H), 6.98 (d, J=8.8 Hz, 2H), 6.94 (dd, J=5.6, 2.3 Hz, 1H), 3.21 (m, 4H), 2.52 (s, 3H), 2.43 (m, 4H), 2.21 (s, 3H); MS (ESI) m/z: 406.2 (M+H$^+$).

A solution of 1-methyl-4-(4-(4-((2-methyl-6-nitropyridin-3-yl)oxy)pyridin-2-yl)phenyl)piperazine (0.333 g, 0.821 mmol) in MeOH (20 mL) was treated with 10% Pd/C (50% wet, 0.089 g, 0.082 mmol) and hydrogenated (1 atm) overnight. The solids were removed via filtration through diatomaceous earth, washed with MeOH and the filtrate concentrated to dryness to afford 6-methyl-5-((2-(4-(4-methylpiperazin-1-yl)phenyl)pyridin-4-yl)oxy)pyridin-2-amine (247 mg, 80%). $^1$H NMR (400 MHz, DMSO-d$_6$): δ 8.38 (d, J=5.7 Hz, 1H), 7.85 (d, J=8.8 Hz, 2H), 7.21-7.20 (m, 2H), 6.98 (d, J=8.8 Hz, 2H), 6.57 (dd, J=5.6, 2.4 Hz, 1H), 6.35 (d, J=8.7 Hz, 1H), 5.94 (s, 2H), 3.20 (t, J=4.7 Hz, 4H), 2.45 (s, 4H), 2.22 (s, 3H), 2.07 (s, 3H); MS (ESI) m/z: 376.2 (M+H$^+$).

A solution of 2,2,2-trimethylacetamide (0.040 g, 0.400 mmol) in DCE (2 mL) was treated with oxalyl chloride (0.035 mL, 0.400 mmol), stirred at RT for 5 min, then warmed to 80° C. for 0.5 h. The solution was cooled to RT, added to a mixture of 6-methyl-5-((2-(4-(4-methylpiperazin-1-yl)phenyl)pyridin-4-yl)oxy)pyridin-2-amine (0.10 g, 0.266 mmol) and DIEA (0.2 mL, 1.145 mmol) in dioxane (4 mL) and stirred at RT for 3 h. The mixture was treated with satd. NaHCO$_3$, extracted with EtOAc (3×) and the combined organics were washed with 1N NaOH, then brine, dried over Na$_2$SO$_4$ and concentrated to dryness. The material was treated with MeCN, and the resulting solid was collected via filtration and dried to afford N-((6-methyl-5-((2-(4-(4-methylpiperazin-1-yl)phenyl)pyridin-4-yl)oxy)pyridin-2-yl)carbamoyl)pivalamide (75 mg, 56%) as a white solid. $^1$H NMR (400 MHz, DMSO-d$_6$): δ 11.16 (br s, 1H), 10.40 (br s, 1H), 8.43 (d, J=5.6 Hz, 1H), 7.94-7.87 (m, 3H), 7.65 (d, J=8.8 Hz, 1H), 7.33 (d, J=2.4 Hz, 1H), 6.97 (d, J=8.8 Hz, 2H), 6.65 (dd, J=5.6, 2.4 Hz, 1H), 3.21 (t, J=4.6 Hz, 4H), 2.44 (br s, 4H), 2.27 (s, 3H), 2.21 (s, 3H), 1.21 (s, 9H); MS (ESI) m/z: 503.3 (M+H$^+$).

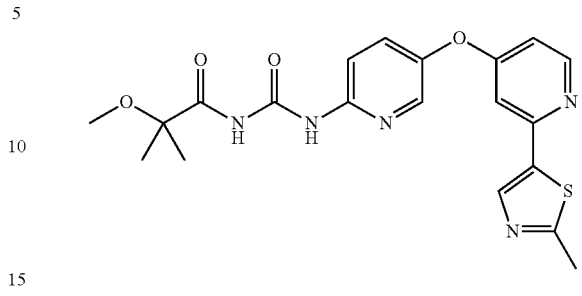

Example 119

A solution of Example B16 (0.142 g, 0.703 mmol) and Example A13 (0.1 g, 0.352 mmol) in dioxane (2 mL) was treated with 1-methylpyrrolidine (0.073 mL, 0.703 mmol) and heated at 80° C. for 3 h. The mixture was cooled to RT, treated with satd. NaHCO$_3$ and extracted with EtOAc (4×). The combined organics were washed with water, then brine, dried over Na$_2$SO$_4$, concentrated to dryness and purified via silica gel chromatography (EtOAc/DCM) to afford 2-methoxy-2-methyl-N-((5-((2-(2-methylthiazol-5-yl)pyridin-4-yl)oxy)pyridin-2-yl)carbamoyl)propanamide (104 mg, 69%) as a white solid. $^1$H NMR (400 MHz, DMSO-d$_6$): δ 10.82 (br s, 1H), 10.23 (br s, 1H), 8.41 (d, J=5.8 Hz, 1H), 8.32 (s, 1H), 8.28 (d, J=3.0 Hz, 1H), 8.03 (br s, 1H), 7.76 (dd, J=9.0, 2.9 Hz, 1H), 7.60 (d, J=2.4 Hz, 1H), 6.82 (dd, J=5.8, 2.4 Hz, 1H), 3.20 (s, 3H), 2.65 (s, 3H), 1.35 (s, 6H); MS (ESI) m/z: 428.2 (M+H$^+$).

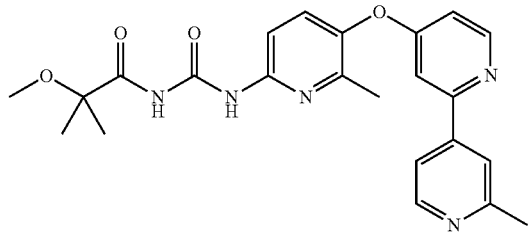

Example 120

A suspension of Example A11 (0.1 g, 0.342 mmol) and Example B16 (0.25 g, 1.242 mmol) in dioxane (2 mL) was treated with pyridine (0.15 mL, 1.855 mmol) and heated at 45° C. overnight. The mixture was treated with satd. NaHCO$_3$, extracted with EtOAc (4×) and the combined organics were dried over MgSO$_4$, concentrated to dryness and purified via silica gel chromatography (MeOH/DCM). The material was treated with Et$_2$O, the solid removed via filtration, the filtrate concentrated to dryness and purified via reverse-phase chromatography (MeCN/H$_2$O with 0.1% TFA). Combined fractions were neutralized with satd. NaHCO$_3$ and extracted with DCM (4×). The combined organics were dried over MgSO$_4$, concentrated to dryness and further purified via silica gel chromatography (MeOH/DCM) to afford 2-methoxy-2-methyl-N-((6-methyl-5-((2'-methyl-[2,4'-bipyridin]-4-yl)oxy)pyridin-2-yl)carbamoyl)propanamide (40 mg, 26%) as a white solid. $^1$H NMR (400 MHz, DMSO-d$_6$): δ 10.78 (s, 1H), 10.15 (s, 1H), 8.57 (d, J=5.6 Hz, 1H), 8.52 (d, J=5.3 Hz, 1H), 7.94-7.82 (m, 2H), 7.80 (d, J=5.4 Hz, 1H), 7.70-7.64 (m, 2H), 6.88 (dd, J=5.6, 2.4 Hz, 1H), 3.20 (s, 3H), 2.53 (s, 3H), 2.29 (s, 3H), 1.35 (s, 6H); MS (ESI) m/z: 436.2 (M+H$^+$).

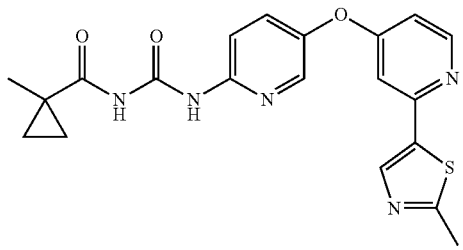

Example 121

A mixture of Example A13 (150 mg, 0.528 mmol), 1-methylpyrrolidine (135 mg, 1.583 mmol) and Example B20 (213 mg, 1.161 mmol) in dioxane (3 mL) was heated at 80° C. under Ar for 20 h, then cooled to RT. The mixture was concentrated to dryness and purified via reverse-phase silica gel chromatography (MeCN/H$_2$O with 0.1% TFA). The fractions were partially concentrated under reduced pressure, the aqueous residue treated with satd. NaHCO$_3$ and the resulting solid collected via filtration and dried to afford 1-methyl-N-((5-((2-(2-methylthiazol-5-yl)pyridin-4-yl)oxy)pyridin-2-yl)carbamoyl)cyclopropanecarboxamide (123 mg, 56%). $^1$H NMR (400 MHz, DMSO-d$_6$): δ 11.30 (s, 1H), 10.14 (br s, 1H), 8.40 (d, J=5.8 Hz, 1H), 8.32 (s, 1H), 8.26 (d, J=2.9 Hz, 1H), 8.09-8.04 (m, 1H), 7.74 (dd, J=9.0, 2.9 Hz, 1H), 7.60 (d, J=2.4 Hz, 1H), 6.81 (dd, J=5.7, 2.4 Hz, 1H), 2.65 (s, 3H), 1.34 (s, 3H), 1.20-1.18 (m, 2H), 0.73-0.72 (m, 2H); MS (ESI) m/z: 410.1 (M+H$^+$).

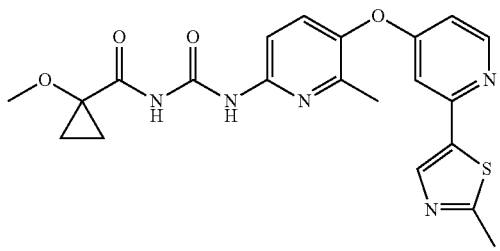

Example 122

A suspension of Example B18 (0.107 g, 0.537 mmol) and Example A20 (0.080 g, 0.268 mmol) in dioxane (1.5 mL) was treated with 1-methylpyrrolidine (0.023 g, 0.268 mmol), heated at 80° C. overnight, treated with additional Example B18 (0.050 g, 0.251 mmol) and 1-methylpyrrolidine (0.02 mL) and heated at 80° C. overnight again. The mixture was cooled to RT, treated with satd. NaHCO$_3$, extracted with DCM (4×) and the combined organics were dried over MgSO$_4$, concentrated to dryness and purified via silica gel chromatography (MeOH/DCM). The resulting oil was treated with MeOH and the solid collected via filtration to afford 1-methoxy-N-((6-methyl-5-((2-(2-methylthiazol-5-yl)pyridin-4-yl)oxy)pyridin-2-yl)carbamoyl)cyclopropanecarboxamide (33 mg, 26%) as a white solid. $^1$H NMR (400

MHz, acetone-d$_6$): δ 11.01 (s, 1H), 9.38 (s, 1H), 8.41 (d, J=5.7 Hz, 1H), 8.19 (s, 1H), 8.05-8.01 (m, 1H), 7.62 (d, J=8.8 Hz, 1H), 7.44 (d, J=2.4 Hz, 1H), 6.76 (dd, J=5.7, 2.4 Hz, 1H), 3.47 (s, 3H), 2.67 (s, 3H), 2.32 (s, 3H), 1.34-1.33 (m, 2H), 1.25-1.24 (m, 2H); MS (ESI) m/z: 440.2 (M+H$^+$).

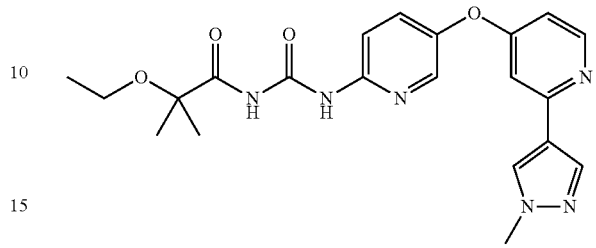

Example 123

A solution of Example B21 (0.35 g, 1.626 mmol) and Example A2 (0.15 g, 0.561 mmol) in dioxane (2.8 mL) was treated with 1-methylpyrrolidine (0.15 mL, 1.427 mmol), heated at 80° C. for 4 h, then cooled to RT. The mixture was treated with satd. NaHCO$_3$, extracted with DCM (4×) and the combined organics were dried over Na$_2$SO$_4$, concentrated to dryness and purified via silica gel chromatography (MeOH/DCM). The material was re-purified via silica gel chromatography (EtOAc/Hex, MeOH/EtOAc) to afford 2-ethoxy-2-methyl-N-((5-((2-(1-methyl-1H-pyrazol-4-yl)pyridin-4-yl)oxy)pyridin-2-yl)carbamoyl)propanamide (77 mg, 31%) as a white solid. $^1$H NMR (400 MHz, DMSO-d$_6$): δ 10.84 (br s, 1H), 10.11 (br m, 1H), 8.37 (d, J=5.7 Hz, 1H), 8.25 (s, 2H), 8.02 (br m, 1H), 7.96 (s, 1H), 7.75 (dd, J=9.0, 2.9 Hz, 1H), 7.22 (d, J=2.4 Hz, 1H), 6.70 (dd, J=5.7, 2.4 Hz, 1H), 3.84 (s, 3H), 3.40 (q, J=7.0 Hz, 2H), 1.36 (s, 6H), 1.16 (t, J=7.0 Hz, 3H); MS (ESI) m/z: 425.2 (M+H$^+$).

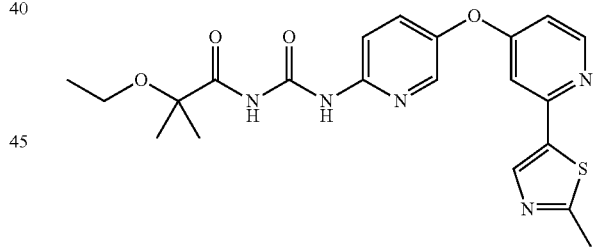

Example 124

A solution of Example B21 (0.35 g, 1.626 mmol) and Example A13 (0.15 g, 0.528 mmol) in dioxane (2.6 mL) was treated with 1-methylpyrrolidine (0.15 mL, 1.427 mmol), heated at 80° C. overnight, then cooled to RT. The mixture was treated with satd. NaHCO$_3$, extracted with DCM (4×) and the combined organics were dried over Na$_2$SO$_4$, concentrated to dryness and purified via silica gel chromatography (MeOH/DCM). The material was re-purified via silica gel chromatography (EtOAc/Hex) to afford 2-ethoxy-2-methyl-N-((5-((2-(2-methylthiazol-5-yl)pyridin-4-yl)oxy)pyridin-2-yl)carbamoyl)propanamide (122 mg, 51%) as a white solid. $^1$H NMR (400 MHz, DMSO-d$_6$): δ 10.85 (s, 1H), 10.12 (very br s, 1H), 8.41 (d, J=5.8 Hz, 1H), 8.32 (s, 1H), 8.27 (d, J=2.8 Hz, 1H), 8.03 (br m, 1H), 7.77 (dd, J=9.0, 2.9 Hz, 1H), 7.60

(d, J=2.4 Hz, 1H), 7.03 (br m, 1H), 6.82 (dd, J=5.8, 2.4 Hz, 1H), 3.40 (q, J=7.0 Hz, 2H), 2.65 (s, 3H), 1.36 (s, 6H), 1.16 (t, J=7.0 Hz, 3H); MS (ESI) m/z: 442.2 (M+H⁺).

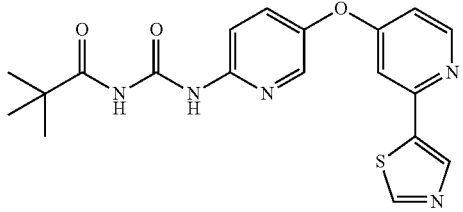 [SMILES: CC(C)(C)C(=O)NC(=O)Nc1ccc(Oc2ccnc(-c3cncs3)c2)cn1]

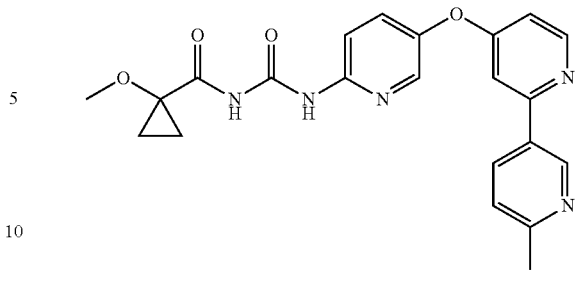

Example 125

A solution of Example A1 (0.3 g, 1.192 mmol) in toluene (10 mL) was sparged with Ar, treated with 5-(tributylstannyl) thiazole (0.446 g, 1.192 mmol), Pd(PPh₃)₄ (0.138 g, 0.119 mmol) and heated at 110° C. for 16 h. The mixture was cooled to RT, treated with EtOAc and 10% aq. KF solution (30 mL) and stirred for 1 h. The solids were removed via filtration through diatomaceous earth, and the layers of the filtrate were separated. The aqueous layer was extracted with additional EtOAc (1×) and the combined organics were washed with brine, dried over Na₂SO₄, concentrated to dryness and purified via silica gel chromatography (EtOAc/Hex) to afford 5-(4-((6-nitropyridin-3-yl)oxy)pyridin-2-yl)thiazole (180 mg, 50%) as a pale orange solid. ¹H NMR (400 MHz, DMSO-d₆): δ 9.16 (s, 1H), 8.64-8.63 (m, 2H), 8.57 (d, J=5.7 Hz, 1H), 8.43 (d, J=8.9 Hz, 1H), 8.04 (dd, J=8.9, 2.8 Hz, 1H), 7.89 (d, J=2.4 Hz, 1H), 7.15 (dd, J=5.7, 2.4 Hz, 1H); MS (ESI) m/z: 301.1 (M+H⁺).

A solution of 5-(4-((6-nitropyridin-3-yl)oxy)pyridin-2-yl) thiazole (0.18 g, 0.599 mmol) in EtOAc (10 mL) and MeOH (3 mL) was treated with 10% Pd/C (50% wet, 0.064 g, 0.060 mmol) and hydrogenated (1 atm) for 16 h. The solids were removed via filtration through diatomaceous earth, washed with EtOAc and the filtrate was concentrated to dryness to afford 5-((2-(thiazol-5-yl)pyridin-4-yl)oxy)pyridin-2-amine (150 mg, 74%). MS (ESI) m/z: 271.1 (M+H⁺).

A solution of 2,2,2-trimethylacetamide (0.090 g, 0.888 mmol) in DCE (3 mL) was treated with oxalyl chloride (0.078 mL, 0.888 mmol), stirred at RT for 1 h, then heated at 75° C. for 2 h. The mixture was cooled to RT, treated with a solution of 5-((2-(thiazol-5-yl)pyridin-4-yl)oxy)pyridin-2-amine (0.12 g, 0.444 mmol) and TEA (0.186 mL, 1.332 mmol) in THF (5 mL) and stirred at RT for 1 h. The mixture was treated with water, extracted with DCM (2×) and the combined organics were washed with brine, dried over Na₂SO₄, concentrated to dryness and purified via silica gel chromatography (MeOH/EtOAc) to afford N-((5-((2-(thiazol-5-yl)pyridin-4-yl)oxy)pyridin-2-yl)carbamoyl)pivalamide (67 mg, 38%) as a white solid. ¹H NMR (400 MHz, DMSO-d₆): δ 11.23 (s, 1H), 10.44 (s, 1H), 9.13 (s, 1H), 8.61 (s, 1H), 8.44 (d, J=5.8 Hz, 1H), 8.29 (d, J=2.9 Hz, 1H), 8.10 (d, J=9.0 Hz, 1H), 7.77 (dd, J=9.0, 2.9 Hz, 1H), 7.70 (d, J=2.4 Hz, 1H), 6.86 (dd, J=5.8, 2.4 Hz, 1H), 1.21 (s, 9H); MS (ESI) m/z: 398.1 (M+H⁺).

Example 126

A mixture of Example A15 (80 mg, 0.287 mmol) and 1-methylpyrrolidine (73 mg, 0.862 mmol) in dioxane (2 mL) was treated with a solution of the Example B18 in dioxane (100 mg/mL, 126 mg, 0.632 mmol) and heated at 80° C. overnight. Additional Example B18 (200 mg) was added and the mixture heated at 80° C. for 24 h. The mixture was cooled to RT, treated with EtOAc, washed with satd. NaHCO₃, then brine, dried over Na₂SO₄, concentrated to dryness and purified via silica gel chromatography (MeOH/EtOAc) to afford 1-methoxy-N-((5-((6'-methyl-[2,3'-bipyridin]-4-yl)oxy)pyridin-2-yl)carbamoyl)cyclopropanecarboxamide (33 mg, 26%) as a white solid. ¹H NMR (400 MHz, DMSO-d₆): δ: δ 10.87 (br m, 1H), 10.44 (very br m, 1H), 9.10 (d, J=2.4 Hz, 1H), 8.55 (d, J=5.7 Hz, 1H), 8.30-8.26 (m, 2H), 8.14-7.95 (br m, 1H), 7.78 (dd, J=9.0, 2.9 Hz, 1H), 7.64 (d, J=2.4 Hz, 1H), 7.34 (d, J=8.2 Hz, 1H), 6.90 (dd, J=5.7, 2.4 Hz, 1H), 3.32 (s, 3H), 2.50 (s, 3H), 1.23 (s, 4H); MS (ESI) m/z: 420.2 (M+H⁺).

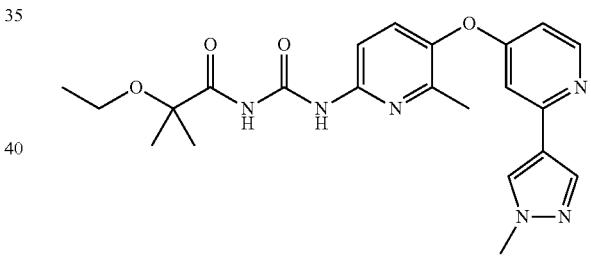

Example 127

A solution of Example B21 (0.35 g, 1.626 mmol) and Example A6 (0.15 g, 0.533 mmol) in dioxane (2.7 mL) was treated with 1-methylpyrrolidine (0.15 mL, 1.427 mmol), heated at 80° C. for 3 h, then cooled to RT. The mixture was treated with satd. NaHCO₃, extracted with DCM (4×) and the combined organics were dried over Na₂SO₄, concentrated to dryness and purified via silica gel chromatography (MeOH/DCM). The material was re-purified via silica gel chromatography (EtOAc/Hex, MeOH/EtOAc) then by reverse-phase silica gel chromatography (MeCN/H₂O with 0.1% TFA). The oure fractions were partially concentrated under reduced pressure and the aqueous residue was neutralized with satd. NaHCO₃. The resulting solid was collected via filtration and dried to afford 2-ethoxy-2-methyl-N-((6-methyl-5-((2-(1-methyl-1H-pyrazol-4-yl)pyridin-4-yl)oxy)pyridin-2-yl)carbamoyl)propanamide (114 mg, 46%) as a white solid. ¹H NMR (400 MHz, DMSO-d₆): δ 10.95 (s, 1H), 10.07 (s, 1H), 8.35 (d, J=5.7 Hz, 1H), 8.25 (s, 1H), 8.15-7.75 (m, 2H), 7.60 (d, J=8.6 Hz, 1H), 7.15 (d, J=2.4 Hz, 1H), 6.60 (dd, J=5.7, 2.4

Hz, 1H), 3.84 (s, 3H), 3.39 (q, J=7.0 Hz, 2H), 2.26 (s, 3H), 1.34 (s, 6H), 1.13 (t, J=6.9 Hz, 3H); MS (ESI) m/z: 439.2 (M+H⁺).

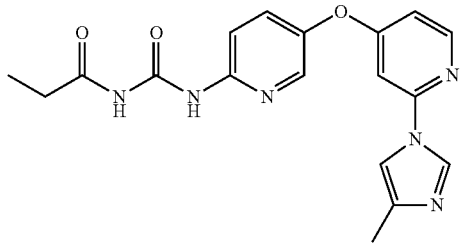 [SMILES: CCC(=O)NC(=O)Nc1ccc(Oc2ccnc(-n3cnc(C)c3)c2)cn1]

Example 128

A suspension of propionamide (0.029 g, 0.393 mmol) in DCE (2 mL) was treated with oxalyl chloride (0.034 mL, 0.393 mmol), stirred at RT, then heated at 80° C. for 2.5 h. The mixture was cooled to RT, added drop-wise to a solution of Example A21 (0.070 g, 0.262 mmol) and pyridine (0.042 mL, 0.524 mmol) in THF (2 mL) and stirred at RT overnight. The mixture was treated with satd. NaHCO₃, extracted with EtOAc (2×) and the combined organics were washed with brine, dried over Na₂SO₄ and concentrated to dryness. The material was treated with EtOAc and the solid was collected via filtration to afford N-((5-((2-(4-methyl-1H-imidazol-1-yl)pyridin-4-yl)oxy)pyridin-2-yl)carbamoyl)propionamide (36 mg, 36%) as a tan solid. ¹H NMR (400 MHz, DMSO-d₆): δ 11.09 (s, 1H), 10.84 (s, 1H), 8.40 (d, J=1.4 Hz, 1H), 8.34 (d, J=5.8 Hz, 1H), 8.30 (d, J=2.9 Hz, 1H), 8.10 (d, J=9.0 Hz, 1H), 7.77 (dd, J=9.0, 2.9 Hz, 1H), 7.65 (m, 1H), 7.40 (d, J=2.2 Hz, 1H), 6.85 (dd, J=5.8, 2.2 Hz, 1H), 2.42 (q, J=7.5 Hz, 2H), 2.14 (d, J=1.0 Hz, 3H), 1.06 (t, J=7.5 Hz, 3H); MS (ESI) m/z: 367.2 (M+H⁺).

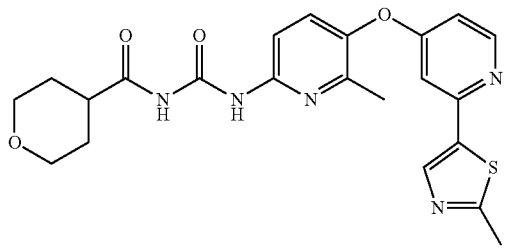 [SMILES: Cc1ncc(-c2cc(Oc3ccc(NC(=O)NC(=O)C4CCOCC4)nc3C)ccn2)s1]

Example 129

A suspension of Example B5 (0.032 g, 0.249 mmol) in DCE (2.1 mL) was treated drop-wise with oxalyl chloride (0.022 mL, 0.249 mmol), stirred at RT for 0.5 h, then heated at 80° C. for 1 h. The mixture was cooled to RT, treated with a solution of pyridine (0.101 mL, 1.247 mmol) and Example A20 (0.062 g, 0.208 mmol) in THF (2.1 mL) and stirred at RT overnight. The mixture was treated with satd. NaHCO₃, extracted with DCM (5×) and the combined organics were dried over Na₂SO₄, concentrated to dryness and purified via silica gel chromatography (MeOH/DCM). The material was treated with MeCN and the resulting solid was collected via filtration and dried to afford N-((6-methyl-5-((2-(2-methylthiazol-5-yl)pyridin-4-yl)oxy)pyridin-2-yl)carbamoyl)tetrahydro-2H-pyran-4-carboxamide (17 mg, 16%) as a white solid. ¹H NMR (400 MHz, DMSO-d₆): δ 11.01 (s, 1H); 10.87 (s, 1H), 8.39 (d, J=5.8 Hz, 1H), 8.32 (s, 1H), 7.91 (d, J=8.8 Hz, 1H), 7.64 (d, J=8.8 Hz, 1H), 7.55 (d, J=2.4 Hz, 1H), 6.71 (dd, J=5.8, 2.4 Hz, 1H), 3.88 (m, 2H), 3.36-3.28 (m, 2H), 2.73-2.67 (m, 1H), 2.65 (s, 3H), 2.26 (s, 3H), 1.68-1.66 (m, 4H); MS (ESI) m/z: 454.2 (M+H⁺).

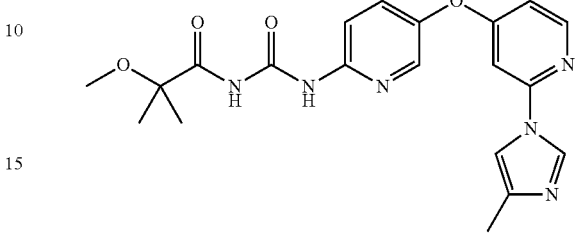

Example 130

A mixture of Example B16 (2.258 g, 11.22 mmol), Example A21 (2.0 g, 7.48 mmol) and 1-methylpyrrolidine (0.255 g, 2.99 mmol) in THF (40 mL) was heated at 60° C. for 16 h. The mixture was cooled to RT and partitioned with EtOAc (100 mL) and sat. aqueous NaHCO₃ solution. The aqueous layer was separated and extracted with EtOAc (50 mL). The combined organics were washed with brine, dried over Na₂SO₄, evaporated to dryness, and purified via silica gel chromatography (MeOH/EtOAc). The purified residue was treated with 30% EtOAc-hexanes (15 mL) and sonicated for few minutes. The suspended solids were collected by filtration and dried in vacuo to afford 2-methoxy-2-methyl-N-((5-((2-(4-methyl-1H-imidazol-1-yl)pyridin-4-yl)oxy)pyridin-2-yl)carbamoyl)propanamide (1.65 g, 54%) as a white powder. ¹H NMR (400 MHz, DMSO-d₆): δ 10.83 (s, 1H), 10.26 (s, 1H), 8.40 (d, J=1.4 Hz, 1H), 8.34 (d, J=5.8 Hz, 1H), 8.30 (d, J=3.0 Hz, 1H), 8.04 (br s, 1H), 7.79 (dd, J=9.0, 2.9 Hz, 1H), 7.65 (t, J=1.3 Hz, 1H), 7.39 (d, J=2.2 Hz, 1H), 6.85 (dd, J=5.8, 2.2 Hz, 1H), 3.21 (s, 3H), 2.14 (d, J=1.0 Hz, 3H), 1.36 (s, 6H); MS (ESI) m/z: 411.2 (M+H⁺).

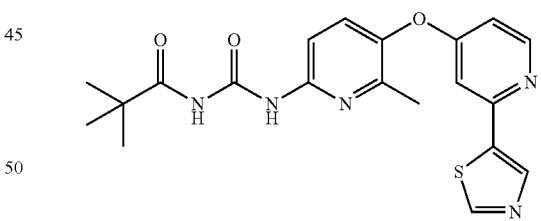

Example 131

A solution of Example A4 (0.35 g, 1.318 mmol) in toluene (8 mL) was sparged with Ar, treated with 5-(tributylstannyl)thiazole (0.493 g, 1.318 mmol) and Pd(PPh₃)₄ (0.152 g, 0.132 mmol), heated at 110° C. for 16 h, then cooled to RT. The mixture was treated with EtOAc and 10% aq. KF solution, stirred for 1 h and the solids were removed via filtration through diatomaceous earth. The layers of the filtrate were separated, the aqueous layer extracted with additional EtOAc (1×) and the combined organics were washed with brine, dried over Na₂SO₄, concentrated to dryness and purified via silica gel chromatography (MeOH/DCM) to afford 5-(4-((2- methyl-6-nitropyridin-3-yl)oxy)pyridin-2-yl)thiazole (270 mg, 65%) as a pale orange solid. ¹H NMR (400 MHz, DMSO-d₆): δ 9.14 (s, 1H), 8.62 (s, 1H), 8.53 (d, J=5.7 Hz, 1H), 8.24 (d, J=8.7 Hz, 1H), 7.90 (d, J=8.7 Hz, 1H), 7.81 (d, J=2.4 Hz, 1H), 7.06 (dd, J=5.7, 2.4 Hz, 1H), 2.51 (s, 3H); MS (ESI) m/z: 315.1 (M+H⁺).

A solution of 5-(4-((2-methyl-6-nitropyridin-3-yl)oxy)pyridin-2-yl)thiazole (0.34 g, 1.082 mmol) in THF (10 mL) and MeOH (10 mL) was treated with NH₄Cl (2.314 g, 43.3 mmol) followed by zinc powder (1.061 g, 16.23 mmol) and stirred at RT for 24 h. The solids were removed via filtration through diatomaceous earth, washed well with MeOH and the filtrate concentrated to dryness. The residue was treated with water, extracted with EtOAc (3×) and the combined organics were washed with brine, dried over Na₂SO₄ and concentrated to dryness. The material was suspended in 30% EtOAc/Hex, sonicated and the solid collected via filtration and dried to afford 6-methyl-5-((2-(thiazol-5-yl)pyridin-4-yl)oxy)pyridin-2-amine (220 mg, 72%) as an off-white solid. ¹H NMR (400 MHz, DMSO-d₆): δ 9.12 (s, 1H), 8.58 (s, 1H), 8.37 (d, J=5.8 Hz, 1H), 7.59 (d, J=2.4 Hz, 1H), 7.20 (d, J=8.7 Hz, 1H), 6.61 (dd, J=5.8, 2.4 Hz, 1H), 6.35 (d, J=8.7 Hz, 1H), 5.97 (s, 2H), 2.08 (s, 3H); MS (ESI) m/z: 285.1 (M+H⁺).

A solution of 2,2,2-trimethylacetamide (0.071 g, 0.703 mmol) in DCE (3 mL) was treated with oxalyl chloride (0.062 mL, 0.703 mmol), stirred at RT for 1 h, then heated at 75° C. for 2 h. The mixture was cooled to RT, treated with a solution of 6-methyl-5-((2-(thiazol-5-yl)pyridin-4-yl)oxy)pyridin-2-amine (0.1 g, 0.352 mmol) and TEA (0.146 mL, 1.055 mmol) in THF (3 mL) and stirred at RT for 1 h. The mixture was treated with water, extracted with DCM (2×) and the combined organics were washed with brine, dried over Na₂SO₄, concentrated to dryness and purified via silica gel chromatography (MeOH/EtOAc) to afford N-((6-methyl-5-((2-(thiazol-5-yl)pyridin-4-yl)oxy)pyridin-2-yl)carbamoyl)pivalamide (122 mg, 84%) as a white solid. ¹H NMR (400 MHz, DMSO-d₆): δ 11.17 (s, 1H), 10.45 (br s, 1H), 9.13 (s, 1H), 8.61 (s, 1H), 8.42 (d, J=5.8 Hz, 1H), 7.92 (s, 1H), 7.66-7.65 (m, 2H), 6.75 (dd, J=5.8, 2.4 Hz, 1H), 2.27 (s, 3H), 1.21 (s, 9H); MS (ESI) m/z: 412.2 (M+H⁺).

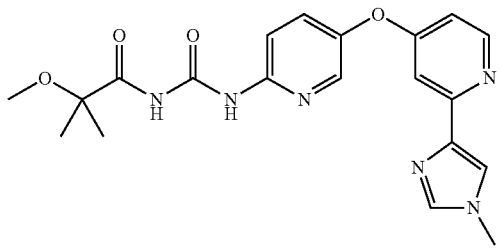

Example 132

A solution of Example B16 (0.151 g, 0.748 mmol) and Example A22 (0.1 g, 0.374 mmol) in dioxane (2 mL) was treated with 1-methylpyrrolidine (0.078 mL, 0.748 mmol), heated at 80° C. overnight then cooled to RT. The mixture was treated with 1N NaOH, extracted with EtOAc (4×) and the combined organics were washed with 1N NaOH, then brine, dried over Na₂SO₄, concentrated to dryness and purified via silica gel chromatography (MeOH/DCM) to afford 2-methoxy-2-methyl-N-((5-((2-(1-methyl-1H-imidazol-4-yl)pyridin-4-yl)oxy)pyridin-2-yl)carbamoyl)propanamide (72 mg, 47%) as a white solid. ¹H NMR (400 MHz, DMSO-d₆): δ 10.80 (br s, 1H), 9.98 (br s, 1H), 8.37 (d, J=5.7 Hz, 1H), 8.28 (d, J=2.9 Hz, 1H), 8.02 (m, 1H), 7.77 (dd, J=9.0, 2.9 Hz, 1H), 7.68 (d, J=1.3 Hz, 1H), 7.60 (d, J=1.3 Hz, 1H), 7.24 (d, J=2.6 Hz, 1H), 6.81 (dd, J=5.6, 2.6 Hz, 1H), 3.67 (s, 3H), 3.21 (s, 3H), 1.36 (s, 6H); MS (ESI) m/z: 411.2 (M+H⁺).

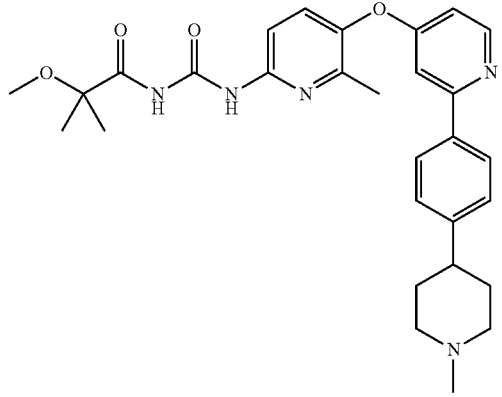 [SMILES: COC(C)(C)C(=O)NC(=O)Nc1ccc(Oc2ccnc(-c3ccc(C4CCN(C)CC4)cc3)c2)c(C)n1]

Example 133

A solution of Example B16 (0.129 g, 0.641 mmol) and Example A24 (0.12 g, 0.320 mmol) in dioxane (4 mL) was treated with 1-methylpyrrolidine (0.067 mL, 0.641 mmol) and heated at 80° C. overnight. Additional Example B16 (0.04 g) was added, the mixture heated for 4 h, then cooled to RT, treated with 1N NaOH and extracted with EtOAc (4×). The combined organics were washed with 1N NaOH, then brine, dried over Na₂SO₄, concentrated to dryness and purified via silica gel chromatography (MeOH/DCM) to afford 2-methoxy-2-methyl-N-((6-methyl-5-((2-(4-(1-methylpiperidin-4-yl)phenyl)pyridin-4-yl)oxy)pyridin-2-yl)carbamoyl)propanamide (99 mg, 60%). ¹H NMR (400 MHz, DMSO-d₆): δ 10.77 (s, 1H), 10.13 (s, 1H), 8.50 (d, J=5.7 Hz, 1H), 7.94 (d, J=8.2 Hz, 2H), 7.86 (br m, 1H), 7.67 (d, J=8.8 Hz, 1H), 7.41 (d, J=2.4 Hz, 1H), 7.32 (d, J=8.2 Hz, 2H), 6.77 (dd, J=5.7, 2.4 Hz, 1H), 3.20 (s, 3H), 2.86 (m, 2H), 2.53-2.43 (m, 1H), 2.28 (s, 3H), 2.18 (s, 3H), 1.99-1.92 (m, 2H), 1.77-1.60 (m, 4H), 1.35 (s, 6H); MS (ESI) m/z: 518.3 (M+H⁺).

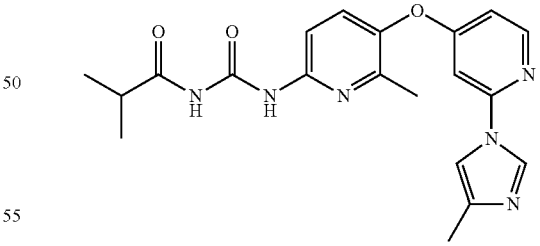

Example 134

A solution of isobutyryl chloride (0.150 g, 1.408 mmol) in DCM (10 mL) was treated with silver cyanate (0.300 g, 2.002 mmol), stirred at RT for 1 h, treated with Example A26 (0.150 g, 0.533 mmol) and catalytic pyridine and stirred at RT for 1 h. The solids were removed via filtration, washed with DCM and THF and the filtrate concentrated to dryness and purified via silica gel chromatography (EtOAc/DCM) to afford N-((6- methyl-5-((2-(4-methyl-1H-imidazol-1-yl)pyridin-4-yl)oxy)pyridin-2-yl)carbamoyl)isobutyramide (126 mg, 59%). $^1$H NMR (400 MHz, DMSO-d$_6$): δ 11.06 (s, 1H), 10.84 (s, 1H), 8.39 (d, J=1.3 Hz, 1H), 8.32 (d, J=5.8 Hz, 1H), 7.92 (d, J=8.8 Hz, 1H), 7.66-7.63 (m, 2H), 7.33 (d, J=2.2 Hz, 1H), 6.60 (dd, J=5.8, 2.2 Hz, 1H), 2.67 (m, 1H), 2.26 (s, 3H), 2.13 (d, J=1.0 Hz, 3H), 1.09 (d, J=6.8 Hz, 6H); MS (ESI) m/z: 395.2 (M+H$^+$).

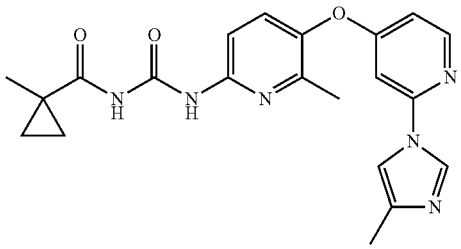 [SMILES: Cc1cn(-c2cc(Oc3ccc(NC(=O)NC(=O)C4(C)CC4)nc3C)ccn2)cn1]

Example 135

A solution of 1-methylcyclopropane carboxylic acid (0.150 g, 1.498 mmol) in DCM (10 mL) was treated with oxalyl chloride (0.170 g, 1.339 mmol) followed by catalytic DMF and stirred at RT for 1 h. The mixture was treated with silver cyanate (0.300 g, 2.002 mmol), stirred at RT for 1 h, treated with Example A26 (0.150 g, 0.533 mmol) and stirred at RT for an additional 1 h. The solids were removed via filtration, washed with DCM and THF and the filtrate was concentrated to dryness and purified via silica gel chromatography (EtOAc/DCM) to afford 1-methyl-N-((6-methyl-5-((2-(4-methyl-1H-imidazol-1-yl)pyridin-4-yl)oxy)pyridin-2-yl)carbamoyl)cyclopropanecarboxamide (32 mg, 15%). $^1$H NMR (400 MHz, DMSO-d$_6$): δ 11.20 (br s, 1H), 10.07 (br s, 1H), 8.38 (d, J=1.4 Hz, 1H), 8.31 (d, J=5.8 Hz, 1H), 7.89 (br m, 1H), 7.68-7.64 (m, 2H), 7.33 (d, J=2.2 Hz, 1H), 6.76 (dd, J=5.8, 2.2 Hz, 1H), 2.26 (s, 3H), 2.13 (d, J=1.0 Hz, 3H), 1.36 (s, 3H), 1.23-1.20 (m, 2H), 0.78-0.76 (m, 2H); MS (ESI) m/z: 407.2 (M+H$^+$).

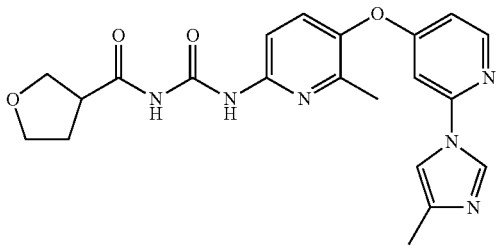 [SMILES: Cc1cn(-c2cc(Oc3ccc(NC(=O)NC(=O)C4CCOC4)nc3C)ccn2)cn1]

Example 136

A solution of tetrahydrofuran-3-carboxylic acid (0.150 g, 1.292 mmol) in DCM (10 mL) was treated with oxalyl chloride (0.250 g, 1.970 mmol) followed by catalytic DMF, stirred at RT for 1 h, then concentrated to dryness. The residue was dissolved in DCM (10 mL), treated with silver cyanate (0.300 g, 2.002 mmol), stirred at RT for 1 h, treated with Example A26 (0.150 g, 0.533 mmol) and catalytic pyridine and stirred at RT for an additional 1 h. The solids were removed via filtration, washed with DCM and THF and the filtrate was concentrated to dryness and purified via silica gel chromatography (EtOAc/DCM) to afford N-((6-methyl-5-((2-(4-methyl-1H-imidazol-1-yl)pyridin-4-yl)oxy)pyridin-2-yl)carbamoyl)tetrahydrofuran-3-carboxamide (75 mg, 33%). $^1$H NMR (400 MHz, DMSO-d$_6$): δ 10.96 (s, 1H), 10.94 (s, 1H), 8.39 (d, J=1.3 Hz, 1H), 8.31 (d, J=5.8 Hz, 1H), 7.91 (d, J=8.8 Hz, 1H), 7.67-7.63 (m, 2H), 7.33 (d, J=2.2 Hz, 1H), 6.75 (dd, J=5.8, 2.2 Hz, 1H), 3.88 (t, J=8.3 Hz, 1H), 3.79-3.73 (m, 2H), 3.70-3.65 (m, 1H), 3.23 (m, 1H), 2.26 (s, 3H), 2.13 (d, J=1.0 Hz, 3H), 2.10-2.04 (m, 2H); MS (ESI) m/z: 423.2 (M+H$^+$).

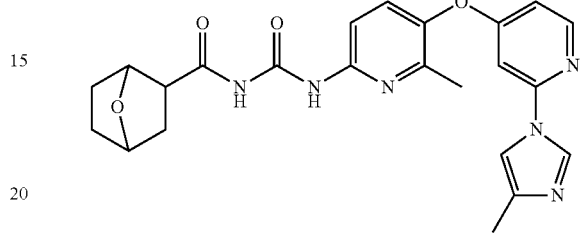

Example 137

A solution of Example B22 (0.150 g, 1.055 mmol) in DCM (10 mL) was treated with oxalyl chloride (0.200 g, 1.576 mmol) followed by catalytic DMF, stirred at RT for 1 h, then concentrated to dryness. The residue was dissolved in DCM (10 mL), treated with silver cyanate (0.300 g, 2.002 mmol), stirred at RT for 1 h, treated with Example A26 (0.150 g, 0.533 mmol) and catalytic pyridine and stirred at RT for an additional 1 h. The solids were removed via filtration, washed with DCM and THF and the filtrate was concentrated to dryness and purified via silica gel chromatography (EtOAc/DCM) to afford exo-N-((6-methyl-5-((2-(4-methyl-1H-imidazol-1-yl)pyridin-4-yl)oxy)pyridin-2-yl)carbamoyl)-7-oxabicyclo[2.2.1]heptane-2-carboxamide (74 mg, 31%). $^1$H NMR (400 MHz, DMSO-d$_6$): δ 10.92 (s, 1H), 10.87 (s, 1H), 8.39 (d, J=1.3 Hz, 1H), 8.31 (d, J=5.8 Hz, 1H), 7.92 (d, J=8.8 Hz, 1H), 7.67-7.63 (m, 2H), 7.33 (d, J=2.2 Hz, 1H), 6.75 (dd, J=5.8, 2.2 Hz, 1H), 4.64 (d, J=4.6 Hz, 1H), 4.58 (t, J=4.7 Hz, 1H), 2.80 (dd, J=8.8, 5.0 Hz, 1H), 2.26 (s, 3H), 2.13 (d, J=1.0 Hz, 3H), 2.06 (m, 1H), 1.64-1.43 (m, 5H); MS (ESI) m/z: 449.2 (M+H$^+$).

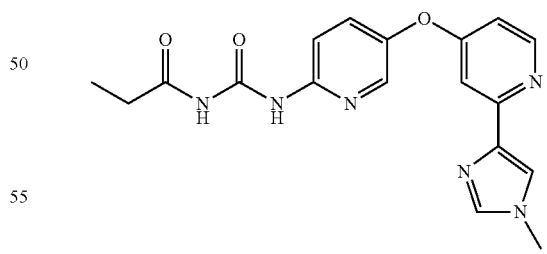

Example 138

A solution of propionamide (0.047 g, 0.645 mmol) in DCE (2 mL) was treated with oxalyl chloride (0.056 mL, 0.645 mmol), stirred at RT for 5 min, then heated at 80° C. for 0.5 h. The mixture cooled to RT, added to a mixture of Example A22 (0.115 g, 0.430 mmol) and pyridine (0.278 mL, 3.44 mmol) in dioxane (4 mL) and stirred at RT overnight. The mixture was treated with 1N NaOH, extracted with EtOAc (4×) and DCM (2×) and the combined organics were washed with 1N NaOH, then brine, dried over Na$_2$SO$_4$ and concentrated to dryness. The material was treated with MeCN and the resulting solid was collected via filtration to afford N-((5-((2-(1-methyl-1H-imidazol-4-yl)pyridin-4-yl)oxy)pyridin-2-yl)carbamoyl) propionamide (90 mg, 57%). $^1$H NMR (400 MHz, DMSO-d$_6$): δ 11.07 (s, 1H), 10.83 (s, 1H), 8.37 (d, J=5.6 Hz, 1H), 8.28 (d, J=2.9 Hz, 1H), 8.10 (d, J=9.0 Hz, 1H), 7.76 (dd, J=9.0, 2.9 Hz, 1H), 7.68 (d, J=1.3 Hz, 1H), 7.60 (m, 1H), 7.24 (d, J=2.6 Hz, 1H), 6.81 (dd, J=5.7, 2.6 Hz, 1H), 3.67 (s, 3H), 2.41 (q, J=7.5 Hz, 2H), 1.05 (t, J=7.5 Hz, 3H); MS (ESI) m/z: 367.2 (M+H$^+$).

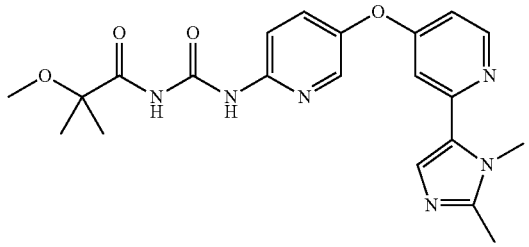

Example 139

A mixture of 1,2-dimethyl-5-(tributylstannyl)imidazole (0.25 g, 0.649 mmol), Example A1 (0.163 g, 0.649 mmol) and Pd(PPh$_3$)$_4$ (0.038 g, 0.032 mmol) in toluene (6.5 mL) was sparged with Ar and heated at 110° C. overnight. The mixture was cooled to RT, treated with EtOAc and 10% aq KF and stirred for 1 h. The solids were removed via filtration through diatomaceous earth, the filtrate extracted with EtOAc (3×) and the combined organics were washed with 10% aq KF, then brine, dried over Na$_2$SO$_4$, concentrated to dryness and purified via silica gel chromatography (MeOH/DCM) to afford 2-(1,2-dimethyl-1H-imidazol-5-yl)-4-((6-nitropyridin-3-yl)oxy)pyridine (80 mg, 40%). $^1$H NMR (400 MHz, DMSO-d$_6$): δ 8.58-8.57 (m, 2H), 8.40 (d, J=8.9 Hz, 1H), 7.98 (dd, J=8.9, 2.8 Hz, 1H), 7.47 (d, J=2.4 Hz, 1H), 7.37 (s, 1H), 7.04 (dd, J=5.7, 2.4 Hz, 1H), 3.86 (s, 3H), 2.34 (s, 3H); MS (ESI) m/z: 312.1 (M+H$^+$).

A solution of 2-(1,2-dimethyl-1H-imidazol-5-yl)-4-((6-nitropyridin-3-yl)oxy)pyridine (0.08 g, 0.257 mmol) in MeOH (20 mL) was treated with 10% Pd/C (50% w/w water, 2.73 mg, 0.001 mmol) and hydrogenated (1 atm) overnight. The solids were removed via filtration through diatomaceous earth, washed with warm MeOH and the filtrate concentrated to dryness to afford 5-((2-(1,2-dimethyl-1H-imidazol-5-yl)pyridin-4-yl)oxy)pyridin-2-amine (50 mg, 69%). $^1$H NMR (400 MHz, DMSO-d$_6$): δ 8.41 (d, J=5.8 Hz, 1H), 7.81 (d, J=2.9 Hz, 1H), 7.29 (dd, J=8.9, 3.0 Hz, 1H), 7.23 (s, 1H), 7.13 (d, J=2.4 Hz, 1H), 6.66 (dd, J=5.7, 2.5 Hz, 1H), 6.51 (d, J=8.9 Hz, 1H), 6.02 (s, 2H), 3.80 (s, 3H), 2.32 (s, 3H); MS (ESI) m/z: 282.1 (M+H$^+$).

A solution of Example B16 (0.072 g, 0.355 mmol) and 5-((2-(1,2-dimethyl-1H-imidazol-5-yl)pyridin-4-yl)oxy)pyridin-2-amine (0.05 g, 0.178 mmol) in dioxane (2 mL) was treated with 1-methylpyrrolidine (0.037 mL, 0.355 mmol) and heated at 80° C. overnight. Additional Example B16 (0.040 g) was added. The mixture was heated at 80° C. for 4 h, then cooled to RT, treated with satd. NaHCO$_3$ and extracted with EtOAc (3×). The combined organics were washed with water, then brine, dried over Na$_2$SO$_4$, concentrated to dryness and purified via silica gel chromatography (MeOH/DCM) to afford N-((5-((2-(1,2-dimethyl-1H-imidazol-5-yl)pyridin-4-yl)oxy)pyridin-2-yl)carbamoyl)-2-methoxy-2-methylpropanamide (28 mg, 37%). $^1$H NMR (400 MHz, DMSO-d$_6$): δ 10.81 (br s, 1H), 10.20 (br s, 1H), 8.46 (d, J=5.8 Hz, 1H), 8.27 (d, J=2.9 Hz, 1H), 8.02 (br s, 1H), 7.76 (dd, J=9.0, 2.9 Hz, 1H), 7.29 (s, 1H), 7.24 (d, J=2.4 Hz, 1H), 6.77 (dd, J=5.7, 2.5 Hz, 1H), 3.82 (s, 3H), 3.21 (s, 3H), 2.33 (s, 3H), 1.35 (s, 6H); MS (ESI) m/z: 425.2 (M+H$^+$).

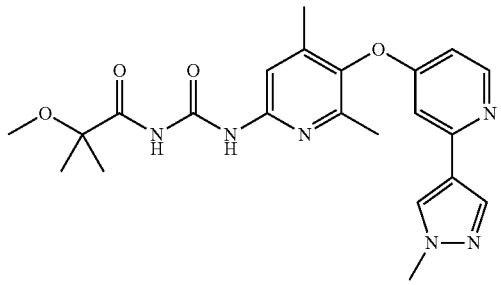 [SMILES: COC(C)(C)C(=O)NC(=O)Nc1cc(C)c(Oc2ccnc(-c3cnn(C)c3)c2)c(C)n1]

Example 140

A mixture of Example A25 (100 mg, 0.339 mmol), N-methylpyrrolidine (29 mg, 0.339 mmol) and Example B16 (0.150 g, 0.745 mmol) in dioxane (2 mL) was heated at 80° C. overnight. The mixture was cooled to RT, diluted with EtOAc, washed with satd. NaHCO$_3$, then brine, dried over Na$_2$SO$_4$, concentrated to dryness and purified via silica gel chromatography (EtOAc/Hex) to afford N-((4,6-dimethyl-5-((2-(1-methyl-1H-pyrazol-4-yl)pyridin-4-yl)oxy)pyridin-2-yl)carbamoyl)-2-methoxy-2-methylpropanamide (82 mg, 53%). $^1$H NMR (400 MHz, DMSO-d$_6$): δ 10.70 (br s, 1H), 10.06 (br s, 1H), 8.34 (d, J=5.7 Hz, 1H), 8.25 (s, 1H), 7.96 (s, 1H), 7.88-7.72 (br m, 1H), 7.13 (d, J=2.4 Hz, 1H), 6.53 (dd, J=5.7, 2.4 Hz, 1H), 3.84 (s, 3H), 3.20 (s, 3H), 2.21 (s, 3H), 2.10 (s, 3H), 1.35 (s, 6H); MS (ESI) m/z: 439.2 (M+H$^+$).

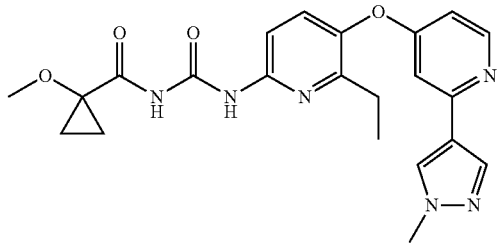 [SMILES: CCc1nc(NC(=O)NC(=O)C2(OC)CC2)ccc1Oc1ccnc(-c2cnn(C)c2)c1]

Example 141

A mixture of Example A17 (100 mg, 0.339 mmol), N-methylpyrrolidine (29 mg, 0.339 mmol) and Example B18 (148 mg, 0.745 mmol) in dioxane (2 mL) was heated at 80° C. overnight. The mixture was cooled to RT, treated with EtOAc, washed with satd. NaHCO$_3$, then brine, dried over Na$_2$SO$_4$, concentrated to dryness and purified via silica gel chromatography (EtOAc/Hex) to afford N-((6-ethyl-5-((2-(1-methyl-1H-pyrazol-4-yl)pyridin-4-yl)oxy)pyridin-2-yl)carbamoyl)-1-methoxycyclopropanecarboxamide (51 mg, 33%). $^1$H NMR (400 MHz, DMSO-d$_6$): δ 10.88 (br s, 1H), 10.39 (br s, 1H), 8.35 (d, J=5.7 Hz, 1H), 8.25 (s, 1H), 7.96 (s, 1H), 7.94-7.84 (br m, 1H), 7.63 (d, J=8.8 Hz, 1H), 7.18 (d, J=2.4 Hz, 1H), 6.61 (dd, J=5.7, 2.4 Hz, 1H), 3.84 (s, 3H), 3.30 (s, 3H), 2.59 (q, J=7.5 Hz, 2H), 1.24 (m, 4H), 1.12 (t, J=7.5 Hz, 3H); MS (ESI) m/z: 437.2 (M+H$^+$).

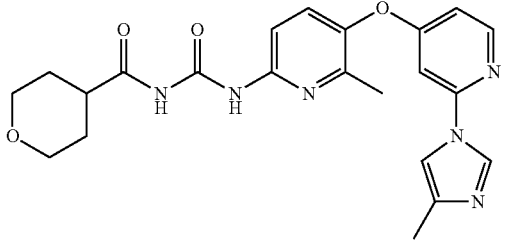 [SMILES: Cc1cn(-c2cc(Oc3ccc(NC(=O)NC(=O)C4CCOCC4)nc3C)ccn2)cn1]

Example 142

A solution of tetrahydropyran-4-carboxylic acid (0.150 g, 1.153 mmol) in DCM (10 mL) was treated with oxalyl chloride (0.200 g, 1.576 mmol) followed by catalytic DMF, stirred at RT for 1 h, then concentrated to dryness. The residue was dissolved in DCM (10 mL), treated with silver cyanate (0.300 g, 2.002 mmol), stirred at RT for 1 h, treated with Example A26 (0.150 g, 0.533 mmol) and catalytic pyridine and stirred for an additional 1 h. The solids were removed via filtration, washed with DCM and THF and the filtrate concentrated to dryness and purified via silica gel chromatography (MeOH/DCM). The material was treated with MeCN and the resulting solid collected via filtration to afford N-((6-methyl-5-((2-(4-methyl-1H-imidazol-1-yl)pyridin-4-yl)oxy)pyridin-2-yl)carbamoyl)tetrahydro-2H-pyran-4-carboxamide (84 mg, 35%). $^1$H NMR (400 MHz, DMSO-d$_6$): δ 11.02 (s, 1H), 10.87 (s, 1H), 8.66 (d, J=1.4 Hz, 1H), 8.37 (d, J=5.8 Hz, 1H), 7.92 (d, J=8.8 Hz, 1H), 7.84 (s, 1H), 7.66 (d, J=8.8 Hz, 1H), 7.36 (d, J=2.2 Hz, 1H), 6.86 (dd, J=5.8, 2.2 Hz, 1H), 3.88 (m, 2H), 3.30 (m, 2H), 2.69 (m, 1H), 2.27 (s, 3H), 2.21 (d, J=1.0 Hz, 3H), 1.72 (m, 2H), 1.61 (m, 2H); MS (ESI) m/z: 437.2 (M+H$^+$).

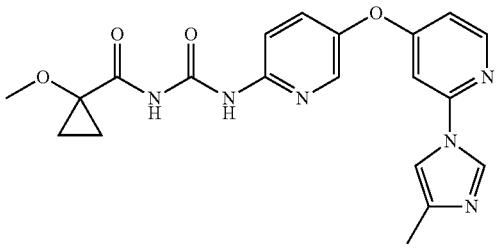 [SMILES: COC1(C(=O)NC(=O)Nc2ccc(Oc3ccnc(-n4cnc(C)c4)c3)cn2)CC1]

Example 143

A mixture of Example B18 (0.174 g, 0.875 mmol), Example A21 (0.15 g, 0.438 mmol) and 1-methylpyrrolidine (0.1 mL, 0.962 mmol) in dioxane (5 mL) was heated at 70° C. overnight. The mixture was cooled to RT, treated with satd. NaHCO$_3$, extracted with EtOAc (3×) and the combined organics were dried over Na$_2$SO$_4$, concentrated to dryness and purified via silica gel chromatography (MeOH/DCM). The material was further purified via reverse-phase silica gel chromatography (MeCN/H$_2$O with 0.1% TFA). Combined fractions were treated with satd. NaHCO$_3$, extracted with EtOAc (2×) and the combined organics were dried over Na$_2$SO$_4$ and concentrated to dryness to afford 1-methoxy-N-((5-((2-(4-methyl-1H-imidazol-1-yl)pyridin-4-yl)oxy)pyridin-2-yl)carbamoyl)cyclopropanecarboxamide (35 mg, 20%). $^1$H NMR (400 MHz, DMSO-d$_6$): δ 10.87 (br s, 1H), 10.44 (br s, 1H), 8.41 (s, 1H), 8.34 (d, J=5.8 Hz, 1H), 8.30 (d, J=3.0 Hz, 1H), 8.06 (br s, 1H), 7.79 (dd, J=9.0, 2.9 Hz, 1H), 7.65 (s, 1H), 7.40 (d, J=2.2 Hz, 1H), 6.85 (dd, J=5.8, 2.2 Hz, 1H), 3.32 (s, 3H), 2.14 (d, J=1.0 Hz, 3H), 1.24 (br s, 4H); MS (ESI) m/z: 409.2 (M+H$^+$).

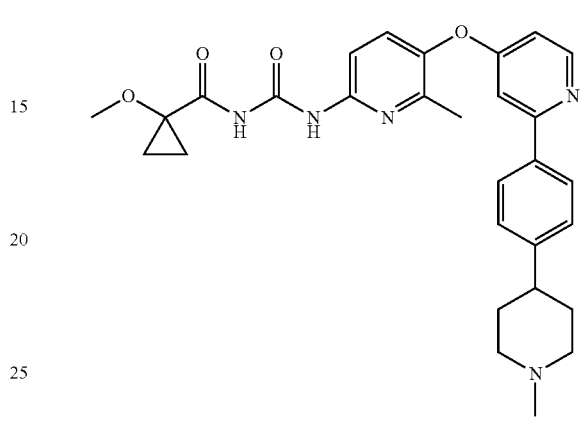

Example 144

A mixture of Example B18 (0.106 g, 0.534 mmol), Example A24 (0.10 g, 0.267 mmol) and 1-methylpyrrolidine (0.056 mL, 0.534 mmol) in dioxane (4 mL) was heated at 80° C. overnight. The mixture was cooled to RT, treated with 1N NaOH, extracted with EtOAc (3×) and the combined organics were washed with 1N NaOH, then brine, dried over Na$_2$SO$_4$, concentrated to dryness and purified via silica gel chromatography (MeOH/DCM/NH$_4$OH). The material was further purified via reverse-phase silica gel chromatography (MeCN/H$_2$O with 0.1% TFA). Pure fractions were partially concentrated under reduced pressure and the resulting aqueous residue was treated with 1N NaOH, extracted with EtOAc (3×) and the combined organics were dried over Na$_2$SO$_4$ and concentrated to dryness to afford 1-methoxy-N-((6-methyl-5-((2-(4-(1-methylpiperidin-4-yl)phenyl)pyridin-4-yl)oxy)pyridin-2-yl)carbamoyl)cyclopropanecarboxamide (35 mg, 25%). $^1$H NMR (400 MHz, DMSO-d$_6$): δ 10.87 (br s, 1H), 10.41 (br s, 1H), 8.50 (d, J=5.6 Hz, 1H), 8.01-7.86 (m, 3H), 7.67 (d, J=8.8 Hz, 1H), 7.41 (d, J=2.4 Hz, 1H), 7.32 (d, J=8.2 Hz, 2H), 6.77 (dd, J=5.6, 2.4 Hz, 1H), 3.30 (s, 3H), 2.89-2.83 (m, 2H), 2.50-2.48 (m, 1H), 2.28 (s, 3H), 2.18 (s, 3H), 2.01-1.91 (m, 2H), 1.77-1.59 (m, 4H), 1.23 (br s, 4H); MS (ESI) m/z: 516.3 (M+H$^+$).

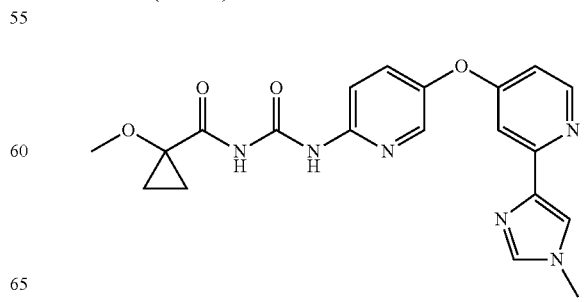

Example 145

A mixture of Example B18 (0.149 g, 0.748 mmol), Example A22 (0.1 g, 0.374 mmol) and 1-methylpyrrolidine (0.078 mL, 0.748 mmol) in dioxane (2 mL) was heated at 80° C. overnight. The mixture was cooled to RT, treated with 1N NaOH, extracted with EtOAc (3×) and the combined organics were washed with 1N NaOH, then brine, dried over $Na_2SO_4$, concentrated to dryness and purified via silica gel chromatography (MeOH/DCM/$NH_4OH$) to afford 1-methoxy-N-((5-((2-(1-methyl-1H-imidazol-4-yl)pyridin-4-yl)oxy)pyridin-2-yl)carbamoyl)cyclopropanecarboxamide (95 mg, 62%). $^1$H NMR (400 MHz, DMSO-$d_6$): δ 10.86 (br s, 1H), 10.01 (br s, 1H), 8.37 (d, J=5.7 Hz, 1H), 8.28 (d, J=2.9 Hz, 1H), 8.03 (br s, 1H), 7.78 (dd, J=9.0, 2.9 Hz, 1H), 7.68 (d, J=1.3 Hz, 1H), 7.60 (s, 1H), 7.24 (d, J=2.6 Hz, 1H), 6.81 (dd, J=5.7, 2.6 Hz, 1H), 3.67 (s, 3H), 3.32 (s, 3H), 1.23 (br s, 4H); MS (ESI) m/z: 409.2 (M+H$^+$).

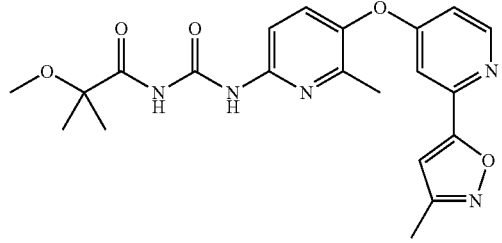 [SMILES: COC(C)(C)C(=O)NC(=O)Nc1ccc(Oc2ccnc(-c3cc(C)no3)c2)c(C)n1]

Example 146

A mixture of Example B16 (0.100 g, 0.496 mmol), Example A7 (0.07 g, 0.248 mmol) and DBU (3.74 µL, 0.025 mmol) in dioxane (3 mL) was heated at 65° C. for 16 h, concentrated to dryness and purified via reverse-phase silica gel chromatography (MeCN/$H_2O$ with 0.1% TFA). Pure fractions were combined and treated with satd. NaHCO$_3$, extracted with EtOAc (2×) and the combined organics were washed with brine, dried over $Na_2SO_4$ and concentrated to dryness to afford 2-methoxy-2-methyl-N-((6-methyl-5-((2-(3-methylisoxazol-5-yl)pyridin-4-yl)oxy)pyridin-2-yl)carbamoyl)propanamide (58 mg, 55%). $^1$H NMR (400 MHz, DMSO-$d_6$): δ 10.79 (br s, 1H), 10.15 (br s, 1H), 8.56 (d, J=5.7 Hz, 1H), 7.88 (br s, 1H), 7.70 (d, J=8.7 Hz, 1H), 7.35 (d, J=2.5 Hz, 1H), 6.98-6.97 (m, 2H), 3.20 (s, 3H), 2.28 (s, 3H), 2.27 (s, 3H), 1.35 (s, 6H); MS (ESI) m/z: 426.2 (M+H$^+$).

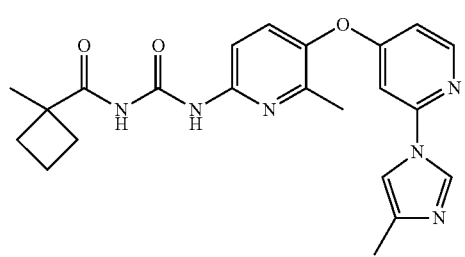 [SMILES: Cc1cn(-c2cc(Oc3ccc(NC(=O)NC(=O)C4(C)CCC4)nc3C)ccn2)cn1]

Example 147

A solution of Example B19 (0.600 g, 5.26 mmol) in DCM (20 mL) was treated with oxalyl chloride (0.600 g, 4.73 mmol) followed by catalytic DMF and stirred at RT for 1 h. The mixture was treated with silver cyanate (1.200 g, 8.01 mmol), stirred at RT for 2 h, treated with Example A26 (0.200 g, 0.711 mmol) and catalytic pyridine (1 drop) and stirred at RT overnight. The solids were removed via filtration, washed with DCM and THF and the filtrate concentrated to dryness and purified via silica gel chromatography (EtOAc/DCM) to afford 1-methyl-N-((6-methyl-5-((2-(4-methyl-1H-imidazol-1-yl)pyridin-4-yl)oxy)pyridin-2-yl)carbamoyl)cyclobutanecarboxamide (64 mg, 21%). $^1$H NMR (400 MHz, DMSO-$d_6$): δ 11.13 (s, 1H), 10.57 (s, 1H), 8.65 (d, J=1.4 Hz, 1H), 8.37 (d, J=5.8 Hz, 1H), 7.93 (d, J=8.8 Hz, 1H), 7.83 (s, 1H), 7.67 (d, J=8.8 Hz, 1H), 7.37 (d, J=2.2 Hz, 1H), 6.85 (dd, J=5.8, 2.2 Hz, 1H), 2.39 (m, 2H), 2.27 (s, 3H), 2.20 (br s, 3H), 1.88 (m, 3H), 1.69 (m, 1H), 1.43 (s, 3H); MS (ESI) m/z: 421.2 (M+H$^+$).

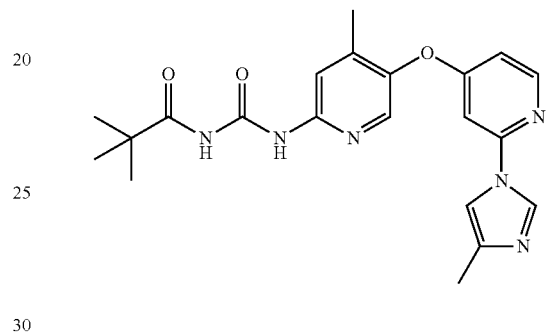

Example 148

A solution of 2,2,2-trimethylacetamide (0.041 g, 0.403 mmol) in DCE (2 mL) was treated with oxalyl chloride (0.035 mL, 0.403 mmol), stirred at RT for 1 h, then heated at 75° C. for 3 h. The mixture was cooled to RT, treated with a solution of Example A27 (0.081 g, 0.202 mmol) and TEA (0.084 mL, 0.605 mmol) in DCM (3 mL) and stirred at RT for 1 h. The mixture was treated with water, extracted with DCM (2×) and the combined organics were washed with brine, dried over $Na_2SO_4$, concentrated to dryness and purified via silica gel chromatography (MeOH/EtOAc) to afford N-((4-methyl-5-((2-(4-methyl-1H-imidazol-1-yl)pyridin-4-yl)oxy)pyridin-2-yl)carbamoyl)pivalamide (31 mg, 37%). $^1$H NMR (400 MHz, DMSO-$d_6$): δ 11.19 (s, 1H), 10.43 (s, 1H), 8.39 (d, J=1.4 Hz, 1H), 8.31 (d, J=5.8 Hz, 1H), 8.17 (s, 1H), 8.02 (s, 1H), 7.64 (s, 1H), 7.33 (d, J=2.2 Hz, 1H), 6.74 (dd, J=5.8, 2.2 Hz, 1H), 2.17 (s, 3H), 2.13 (s, 3H), 1.21 (s, 9H); MS (ESI) m/z: 409.2 (M+H$^+$).

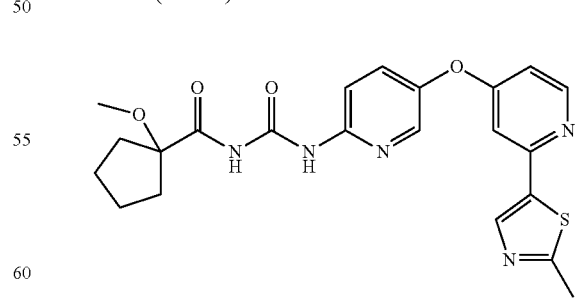

Example 149

A mixture of Example B23 (0.190 g, 0.835 mmol), Example A13 (0.095 g, 0.334 mmol) and DBU (10.07 µL, 0.067 mmol) in dioxane (4 mL) was heated at 60° C. for 16 h, concentrated to dryness and purified via reverse-phase silica gel chromatography (MeCN/H₂O with 0.1% TFA). The combined fractions were treated with satd. NaHCO₃, extracted with EtOAc (2×) and the combined organics were washed with brine, dried over Na₂SO₄ and concentrated to dryness to afford 1-methoxy-N-((5-((2-(2-methylthiazol-5-yl)pyridin-4-yl)oxy)pyridin-2-yl)carbamoyl)cyclopentanecarboxamide (73 mg, 48%). ¹H NMR (400 MHz, DMSO-d₆): δ 10.85 (br s, 1H), 10.39 (br s, 1H), 8.41 (d, J=5.8 Hz, 1H), 8.32 (s, 1H), 8.28 (d, J=3.0 Hz, 1H), 8.03 (br s, 1H), 7.77 (dd, J=9.0, 2.9 Hz, 1H), 7.60 (d, J=2.4 Hz, 1H), 6.82 (dd, J=5.8, 2.4 Hz, 1H), 3.15 (s, 3H), 2.65 (s, 3H), 1.92 (d, J=6.9 Hz, 4H), 1.68-1.66 (m, 4H); MS (ESI) m/z: 454.2 (M+H⁺).

RT for 3 h. The mixture was cooled to RT, treated with EtOAc, washed with satd. NaHCO₃, then brine, dried over Na₂SO₄, concentrated to dryness and purified via silica gel chromatography (MeOH/EtOAc). The material was further purified via reverse-phase chromatography (MeCN/H₂O with 0.1% TFA); the organics were removed under reduced pressure and the aqueous residue was treated with satd. NaHCO₃ and allowed to stand at RT. The resulting solid was collected via filtration, washed with water and dried to afford N-((5-((2-(2-methyloxazol-5-yl)pyridin-4-yl)oxy)pyridin-2-yl)carbamoyl)pivalamide (67 mg, 45%). ¹H NMR (400 MHz, DMSO-d₆): δ 11.24 (s, 1H), 10.45 (s, 1H), 8.48 (d, J=5.7 Hz, 1H), 8.30 (d, J=2.9 Hz, 1H), 8.11 (d, J=9.0 Hz, 1H), 7.78 (d, J=9.1 Hz, 1H), 7.64 (s, 1H), 7.17 (s, 1H), 6.92 (d, J=5.6 Hz, 1H), 2.46 (s, 3H), 1.21 (s, 9H); MS (ESI) m/z: 396.2 (M+H⁺).

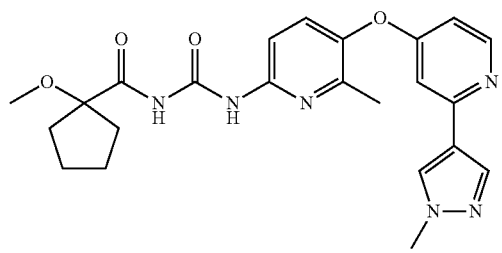 [SMILES: COC1(C(=O)NC(=O)Nc2ccc(Oc3ccnc(-c4cnn(C)c4)c3)c(C)n2)CCCC1]

Example 150

A mixture of Example B23 (0.202 g, 0.889 mmol), Example A6 (0.1 g, 0.355 mmol) and DBU (10.72 µL, 0.071 mmol) in dioxane (3 mL) was heated at 70° C. for 4 h, concentrated to dryness and purified via reverse-phase chromatography (MeCN/H₂O with 0.1% TFA). The combined fractions were treated with satd. NaHCO₃, extracted with EtOAc (2×) and the combined organics were washed with brine, dried over Na₂SO₄ and concentrated to dryness to afford 1-methoxy-N-((6-methyl-5-((2-(1-methyl-1H-pyrazol-4-yl)pyridin-4-yl)oxy)pyridin-2-yl)carbamoyl)cyclopentanecarboxamide (85 mg, 53%). ¹H NMR (400 MHz, DMSO-d₆): δ 10.90 (br s, 1H), 10.30 (br s, 1H), 8.35 (d, J=5.7 Hz, 1H), 8.25 (s, 1H), 7.96 (s, 1H), 7.86 (br s, 1H), 7.64 (d, J=8.8 Hz, 1H), 7.17 (d, J=2.4 Hz, 1H), 6.61 (dd, J=5.7, 2.4 Hz, 1H), 3.84 (s, 3H), 3.14 (s, 3H), 2.27 (s, 3H), 1.97-1.88 (m, 4H), 1.66 (s, 4H); MS (ESI) m/z: 451.2 (M+H⁺).

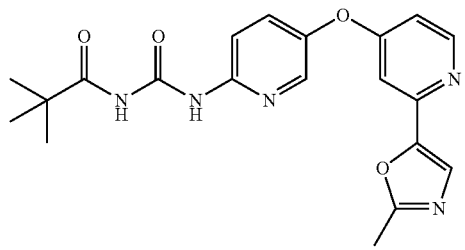 [SMILES: Cc1ncc(-c2cc(Oc3ccc(NC(=O)NC(=O)C(C)(C)C)nc3)ccn2)o1]

Example 151

A solution of 2,2,2-trimethylacetamide (57 mg, 0.559 mmol) in DCE (2 mL) was treated with oxalyl chloride (71 mg, 0.559 mmol), stirred at RT for 5 min, then warmed to 80° C. for 45 min. The mixture was cooled to RT, added drop-wise to a solution of DIEA (207 mg, 1.603 mmol) and Example A28 (100 mg, 0.373 mmol) in dioxane (4 mL) and stirred at

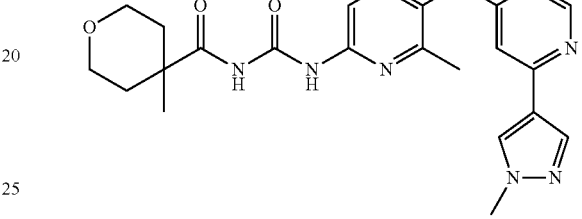

Example 152

A mixture of Example B24 (3.44 g, 24.0 mmol) in DCE (60 mL) was treated with oxalyl chloride (3.05 g, 24.0 mmol), stirred at RT for 5 min, then heated at 80° C. for 45 min. The mixture was cooled to RT, added drop-wise to a solution of DIEA (9.30 g, 72 mmol) and Example A6 (4.50 g, 16.0 mmol) in dioxane (90 mL) and stirred at RT overnight. The mixture was diluted with EtOAc (100 mL), washed with satd. NaHCO₃ (100 mL), then brine (100 mL), dried over Na₂SO₄, and concentrated to dryness. The resultant foam was treated with MeCN (75 mL) and was sonicated for 10 min. The slurry was diluted with MeCN (25 mL), and the solids were collected by filtration, washed with MeCN (2×15 mL), and dried in vacuo. The solid was finely ground (mortor and pestle) and then triturated with MeCN (75 mL), collected by filtration, washed with MeCN (2×30 mL) and dried at 80° C. under vacuum to provide 4-methyl-N-((6-methyl-5-((2-(1-methyl-1H-pyrazol-4-yl)pyridin-4-yl)oxy)pyridin-2-yl)carbamoyl)tetrahydro-2H-pyran-4-carboxamide (4.74 g, 64%). ¹H NMR (400 MHz, DMSO-d₆): δ 11.15 (s, 1H), 10.53 (br s, 1H), 8.35 (d, J=5.7 Hz, 1H), 8.25 (s, 1H), 7.96 (s, 1H), 7.94-7.89 (br m, 1H), 7.63 (d, J=8.8 Hz, 1H), 7.16 (d, J=2.4 Hz, 1H), 6.61 (dd, J=5.7, 2.4 Hz, 1H), 3.84 (s, 3H), 3.66 (m, 2H), 3.44 (m, 2H), 2.26 (s, 3H), 2.05 (m, 2H), 1.49 (m, 2H), 1.27 (s, 3H); MS (ESI) m/z: 451.2 (M+H⁺).

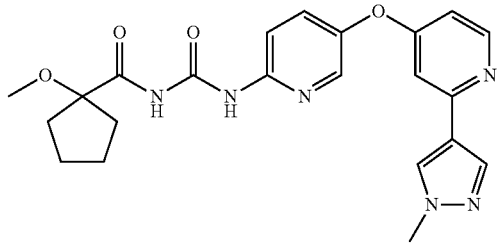 [SMILES: COC1(C(=O)NC(=O)Nc2ccc(Oc3ccnc(-c4cnn(C)c4)c3)cn2)CCCC1]

Example 153

A mixture of Example B23 (0.213 g, 0.935 mmol), Example A2 (0.1 g, 0.374 mmol) and DBU (0.011 g, 0.075 mmol) in dioxane (4 mL) was heated at 70° C. for 4 h, cooled to RT, concentrated to dryness and purified via reverse-phase chromatography (MeCN/H$_2$O with 0.1% TFA). Combined fractions were treated with satd. NaHCO$_3$, extracted with EtOAc (2×) and the combined organics were washed with brine, dried over Na$_2$SO$_4$ and concentrated to dryness to afford 1-methoxy-N-((5-((2-(1-methyl-1H-pyrazol-4-yl)pyridin-4-yl)oxy)pyridin-2-yl)carbamoyl)cyclopentanecarboxamide (90 mg, 55%). $^1$H NMR (400 MHz, DMSO-d$_6$): δ 10.84 (s, 1H), 10.38 (br s, 1H), 8.37 (d, J=5.7 Hz, 1H), 8.26-8.25 (m, 2H), 8.03 (br s, 1H), 7.96 (s, 1H), 7.74 (dd, J=9.0, 2.9 Hz, 1H), 7.23 (d, J=2.4 Hz, 1H), 6.70 (dd, J=5.7, 2.4 Hz, 1H), 3.84 (s, 3H), 3.15 (s, 3H), 1.92 (d, J=6.9 Hz, 4H), 1.67-1.65 (m, 4H); MS (ESI) m/z: 437.2 (M+H$^+$).

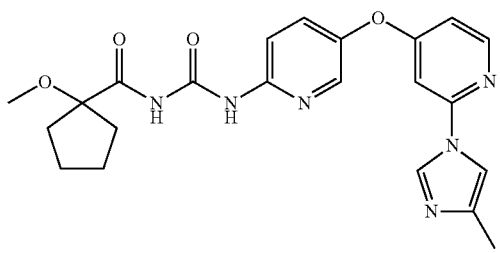

Example 154

A mixture of Example B23 (0.213 g, 0.935 mmol), Example A21 (0.1 g, 0.374 mmol) and DBU (0.011 g, 0.075 mmol) in dioxane (4 mL) was heated at 65° C. for 20 h, cooled to RT, concentrated to dryness and purified via reverse-phase chromatography (MeCN/H$_2$O with 0.1% TFA). Combined fractions were treated with satd. NaHCO$_3$, extracted with EtOAc (2×) and the combined organics were washed with brine, dried over Na$_2$SO$_4$ and concentrated to dryness to afford 1-methoxy-N-((5-((2-(4-methyl-1H-imidazol-1-yl)pyridin-4-yl)oxy)pyridin-2-yl)carbamoyl)cyclopentanecarboxamide (128 mg, 78%). $^1$H NMR (400 MHz, DMSO-d$_6$): δ 10.85 (s, 1H), 10.39 (br s, 1H), 8.40 (d, J=1.3 Hz, 1H), 8.34 (d, J=5.8 Hz, 1H), 8.30 (d, J=3.0 Hz, 1H), 8.04 (br s, 1H), 7.78 (dd, J=9.0, 2.9 Hz, 1H), 7.64 (s, 1H), 7.39 (d, J=2.2 Hz, 1H), 6.84 (dd, J=5.8, 2.2 Hz, 1H), 3.15 (s, 3H), 2.13 (d, J=1.0 Hz, 3H), 1.93 (m, 4H), 1.66 (m, 4H); MS (ESI) m/z: 437.2 (M+H$^+$).

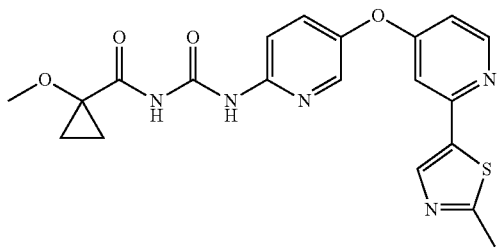

Example 155

A mixture of Example B18 (0.210 g, 1.055 mmol), Example A13 (0.150 g, 0.528 mmol), and N-methylpyrrolidine (0.027 mL, 0.264 mmol) in dioxane (5 mL) was heated at 80° C. overnight, cooled to RT, concentrated to dryness and purified via silica gel chromatography (MeOH/EtOAc). The material was treated with MeCN, sonicated and the resulting solid was collected via filtration and dried to afford 1-methoxy-N-((5-((2-(2-methylthiazol-5-yl)pyridin-4-yl)oxy)pyridin-2-yl)carbamoyl)cyclopropanecarboxamide (80 mg, 36%). $^1$H NMR (400 MHz, DMSO-d$_6$): δ 10.88 (br s, 1H), 10.44 (br s, 1H), 8.41 (d, J=5.8 Hz, 1H), 8.33 (s, 1H), 8.28 (d, J=3.0 Hz, 1H), 8.04 (br s, 1H), 7.77 (dd, J=9.0, 2.9 Hz, 1H), 7.60 (d, J=2.4 Hz, 1H), 6.82 (dd, J=5.8, 2.4 Hz, 1H), 3.31 (s, 3H), 2.65 (s, 3H), 1.23 (s, 4H); MS (ESI) m/z: 426.1 (M+H$^+$).

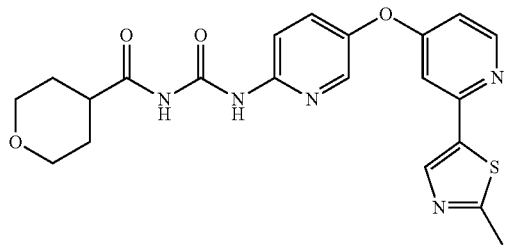 [SMILES: Cc1ncc(-c2cc(Oc3ccc(NC(=O)NC(=O)C4CCOCC4)nc3)ccn2)s1]

Example 156

A suspension of Example B5 (0.596 g, 4.61 mmol) in dioxane (15 mL) was treated with oxalyl chloride (0.820 mL, 9.69 mmol), stirred at RT for 10 min, then heated to 80° C. for 4 h. The mixture was cooled to RT, concentrated to dryness, treated with Example A13 (0.200 g, 0.703 mmol), pyridine (0.120 mL, 1.481 mmol) and THF (5 mL) and stirred at RT overnight. The mixture was concentrated to dryness, the residue suspended in MeCN and sonicated, and the resulting solid was collected via filtration, suspended in water, stirred for 15 min, then again collected via filtration. The solid was treated with MTBE, stirred for 1 h and then collected via filtration to afford N-((5-((2-(2-methylthiazol-5-yl)pyridin-4-yl)oxy)pyridin-2-yl)carbamoyl)tetrahydro-2H-pyran-4-carboxamide (110 mg, 33%). $^1$H NMR (400 MHz, DMSO-d$_6$): δ 11.06 (s, 1H), 10.89 (s, 1H), 8.41 (d, J=5.6 Hz, 1H), 8.32 (s, 1H), 8.28 (d, J=2.9 Hz, 1H), 8.09 (d, J=9.0 Hz, 1H), 7.75 (dd, J=9.0, 2.9 Hz, 1H), 7.60 (d, J=2.4 Hz, 1H), 6.82 (dd, J=5.8, 2.4 Hz, 1H), 3.88 (m, 2H), 3.34-3.25 (m, 3H), 2.65 (s, 3H), 1.72 (m, 2H), 1.62-1.59 (m, 2H); MS (ESI) m/z: 440.2 (M+H$^+$).

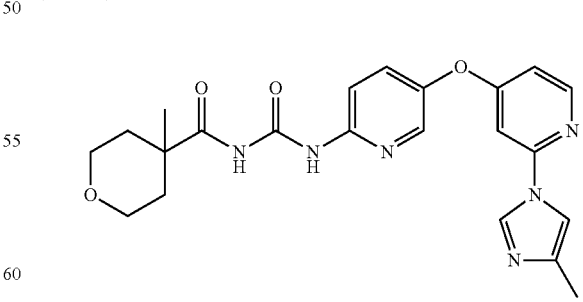

Example 157

A mixture of Example B24 (80 mg, 0.561 mmol) in DCE (2 mL) was treated with oxalyl chloride (71 mg, 0.561 mmol), stirred at RT for 5 min, then warmed to 80° C. for 45 min. The mixture was cooled to RT, added drop-wise to a solution of DIEA (208 mg, 1.609 mmol) and Example A21 (100 mg, 0.374 mmol) in dioxane (4 mL) and stirred at RT overnight. The mixture was treated with EtOAc, washed with satd. NaHCO₃, then brine, dried over Na₂SO₄, concentrated to dryness and purified via reverse-phase silica gel chromatography (MeCN/H₂O with 0.1% TFA). The pure fractions were partially concentrated under reduced pressure and the aqueous residue treated with satd. NaHCO₃. The resulting solid was collected via filtration and dried to afford 4-methyl-N-((5-((2-(4-methyl-1H-imidazol-1-yl)pyridin-4-yl)oxy)pyridin-2-yl)carbamoyl)tetrahydro-2H-pyran-4-carboxamide (53 mg, 31%). ¹H NMR (400 MHz, DMSO-d₆): δ 11.22 (s, 1H), 10.56 (s, 1H), 8.39 (d, J=1.4 Hz, 1H), 8.34 (d, J=5.8 Hz, 1H), 8.31 (d, J=2.9 Hz, 1H), 8.10 (d, J=9.0 Hz, 1H), 7.78 (dd, J=9.0, 3.0 Hz, 1H), 7.64 (s, 1H), 7.38 (d, J=2.2 Hz, 1H), 6.84 (dd, J=5.8, 2.2 Hz, 1H), 3.68-3.61 (m, 2H), 3.44 (m, 2H), 2.13 (s, 3H), 2.04 (m, 2H), 1.50 (m, 2H), 1.27 (s, 3H); MS (ESI) m/z: 437.2 (M+H⁺).

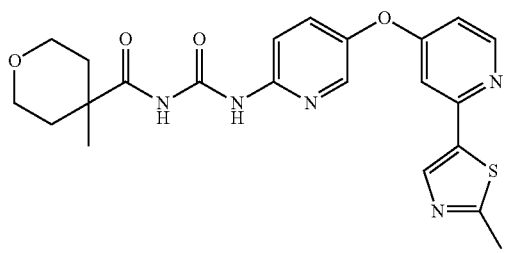 [SMILES: Cc1ncc(-c2cc(Oc3ccc(NC(=O)NC(=O)C4(C)CCOCC4)nc3)ccn2)s1]

Example 158

A mixture of Example B24 (76 mg, 0.528 mmol) in DCE (2 mL) was treated with oxalyl chloride (67 mg, 0.528 mmol), stirred at RT for 5 min, then warmed to 80° C. for 45 min. The mixture was cooled to RT, added drop-wise to a solution of DIEA (195 mg, 1.512 mmol) and Example A13 (100 mg, 0.352 mmol) in dioxane (4 mL) and stirred at RT overnight. The mixture was treated with EtOAc, washed with satd. NaHCO₃, then brine, dried over Na₂SO₄, concentrated to dryness and purified via reverse-phase silica gel chromatography (MeCN/H₂O with 0.1% TFA). The combined purified fractions were partially concentrated under reduced pressure, the aqueous residue was treated with satd. NaHCO₃ and the resulting solid collected via filtration and dried to afford 4-methyl-N-((5-((2-(2-methylthiazol-5-yl)pyridin-4-yl)oxy)pyridin-2-yl)carbamoyl)tetrahydro-2H-pyran-4-carboxamide (102 mg, 63%). ¹H NMR (400 MHz, DMSO-d₆): δ 11.22 (s, 1H), 10.57-10.54 (br s, 1H), 8.41 (d, J=5.8 Hz, 1H), 8.32 (s, 1H), 8.29 (d, J=2.9 Hz, 1H), 8.10 (d, J=9.0 Hz, 1H), 7.77 (dd, J=9.0, 2.9 Hz, 1H), 7.60 (d, J=2.4 Hz, 1H), 6.82 (dd, J=5.8, 2.4 Hz, 1H), 3.65 (m, 2H), 3.44 (m, 2H), 2.65 (s, 3H), 2.08-2.04 (m, 2H), 1.50 (m, 2H), 1.27 (s, 3H); MS (ESI) m/z: 454.2 (M+H⁺).

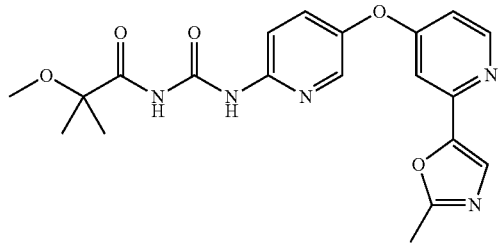 [SMILES: COC(C)(C)C(=O)NC(=O)Nc1ccc(Oc2ccnc(-c3cnc(C)o3)c2)cn1]

Example 159

A mixture of Example B16 (0.100 g, 0.497 mmol), Example A28 (61 mg, 0.226 mmol) and N-methylpyrrolidine (19 mg, 0.226 mmol) in dioxane (2 mL) was heated at 80° C. overnight. The mixture was cooled to RT, treated with EtOAc, washed with satd. NaHCO₃, then brine, dried over Na₂SO₄, concentrated to dryness and purified via reverse-phase silica gel chromatography (MeCN/H₂O with 0.1% TFA). The combined purified fractions were partially concentrated under reduced pressure and the aqueous residue was treated with satd. NaHCO₃ and extracted with EtOAc (3×). The combined organics were washed with brine, dried over Na₂SO₄ and concentrated to dryness to afford 2-methoxy-2-methyl-N-((5-((2-(2-methyloxazol-5-yl)pyridin-4-yl)oxy)pyridin-2-yl)carbamoyl)propanamide (22 mg, 22%). ¹H NMR (400 MHz, DMSO-d₆): δ 10.84 (s, 1H), 10.31 (br s, 1H), 8.48 (d, J=5.7 Hz, 1H), 8.30-8.29 (m, 1H), 8.03 (br s, 1H), 7.79 (dd, J=9.0, 2.9 Hz, 1H), 7.64 (s, 1H), 7.17 (d, J=2.4 Hz, 1H), 6.92 (dd, J=5.7, 2.5 Hz, 1H), 3.21 (s, 3H), 2.46 (s, 3H), 1.35 (s, 6H); MS (ESI) m/z: 412.2 (M+H⁺).

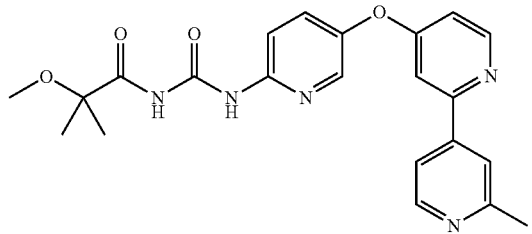

Example 160

A solution of Example B16 (0.108 g, 0.539 mmol) and Example A16 (0.1 g, 0.359 mmol) in dioxane (2 mL) was treated with a solution of 1-methylpyrrolidine (0.05 mL, 0.476 mmol) in pyridine (0.2 mL, 2.473 mmol), heated at 60° C. overnight, then at 80° C. for 4 h. The mixture was cooled to RT, treated with 50% satd. NaHCO₃, and extracted with EtOAc (4×). The combined organics were dried over MgSO₄, concentrated to dryness and purified via silica gel chromatography (MeOH/DCM). The material was treated with Hex, sonicated and the resulting solid was collected via filtration to afford 2-methoxy-2-methyl-N-((5-((2'-methyl-[2,4'-bipyridin]-4-yl)oxy)pyridin-2-yl)carbamoyl)propanamide (87 mg, 57%). ¹H NMR (400 MHz, DMSO-d₆): δ 10.82 (br s, 1H), 10.21 (br s, 1H), 8.60 (d, J=5.6 Hz, 1H), 8.53 (d, J=5.2 Hz, 1H), 8.30 (d, J=2.9 Hz, 1H), 8.03 (br s, 1H), 7.90 (s, 1H), 7.79-7.78 (m, 2H), 7.71 (d, J=2.4 Hz, 1H), 6.99 (dd, J=5.6, 2.4 Hz, 1H), 3.21 (s, 3H), 2.53 (s, 3H), 1.36 (s, 6H); MS (ESI) m/z: 422.2 (M+H⁺).

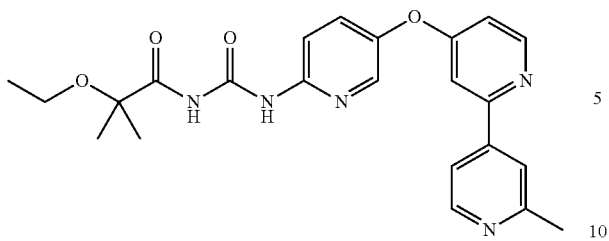

Example 161

A solution of Example B21 (0.290 g, 1.347 mmol) and Example A16 (0.25 g, 0.898 mmol) in dioxane (5 mL) was treated with a solution of 1-methylpyrrolidine (0.15 mL, 1.427 mmol) in pyridine (0.5 mL, 6.18 mmol), heated at 60° C. overnight, then 80° C. for 4 h. The mixture was cooled to RT, treated with 50% satd. NaHCO$_3$, extracted with EtOAc (4×) and the combined organics were dried over MgSO$_4$, concentrated to dryness and purified via silica gel chromatography (MeOH/DCM). The material was dissolved in MTBE, treated with an equal volume of Hex, placed in the freezer for 2 days and the resulting solid collected via filtration to afford 2-ethoxy-2-methyl-N-((5-((2'-methyl-[2,4'-bipyridin]-4-yl)oxy)pyridin-2-yl)carbamoyl)propanamide (41 mg, 10%). $^1$H NMR (400 MHz, acetone-d$_6$): δ 10.99 (br s, 1H), 9.15 (br s, 1H), 8.62 (d, J=5.6 Hz, 1H), 8.54 (d, J=5.2 Hz, 1H), 8.28 (d, J=2.9 Hz, 1H), 8.21 (d, J=9.0 Hz, 1H), 7.90 (s, 1H), 7.80-7.78 (m, 1H), 7.75 (dd, J=9.0, 2.9 Hz, 1H), 7.64 (d, J=2.4 Hz, 1H), 7.01 (dd, J=5.6, 2.4 Hz, 1H), 3.60 (q, J=7.0 Hz, 2H), 2.55 (s, 3H), 1.49 (s, 6H), 1.27 (t, J=7.0 Hz, 3H); MS (ESI) m/z: 436.2 (M+H$^+$).

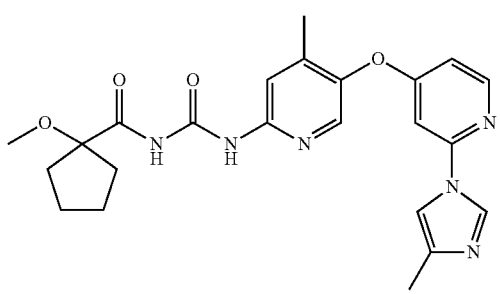 [SMILES: COC1(C(=O)NC(=O)Nc2cc(C)c(Oc3ccnc(-n4cnc(C)c4)c3)cn2)CCCC1]

Example 162

A mixture of Example B23 (0.121 g, 0.533 mmol), Example A27 (0.075 g, 0.267 mmol) and DBU (4.02 µL, 0.027 mmol) in dioxane (3 mL) was heated at 55° C. overnight, concentrated to dryness and purified via reverse-phase silica gel chromatography (MeCN/H$_2$O with 0.1% TFA). Combined fractions were treated with satd. NaHCO$_3$, extracted with EtOAc (2×) and the combined organics were washed with brine, dried over Na$_2$SO$_4$ and concentrated to dryness to afford 1-methoxy-N-((4-methyl-5-((2-(4-methyl-1H-imidazol-1-yl)pyridin-4-yl)oxy)pyridin-2-yl)carbamoyl)cyclopentanecarboxamide (36 mg, 30%). $^1$H NMR (400 MHz, DMSO-d$_6$): δ 10.78 (s, 1H), 10.38 (s, 1H), 8.39 (d, J=1.3 Hz, 1H), 8.31 (d, J=5.8 Hz, 1H), 8.17 (s, 1H), 7.96 (s, 1H), 7.64 (s, 1H), 7.32 (d, J=2.2 Hz, 1H), 6.75 (dd, J=5.8, 2.2 Hz, 1H), 3.15 (s, 3H), 2.17 (s, 3H), 2.13 (d, J=1.0 Hz, 3H), 1.95-1.91 (m, 4H), 1.68-1.64 (m, 4H); MS (ESI) m/z: 451.2 (M+H$^+$).

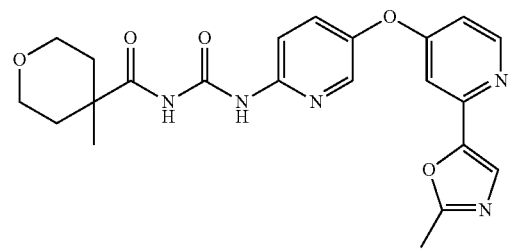 [SMILES: Cc1ncc(-c2cc(Oc3ccc(NC(=O)NC(=O)C4(C)CCOCC4)nc3)ccn2)o1]

Example 163

A mixture of Example B24 (72 mg, 0.503 mmol) in DCE (2 mL) was treated with oxalyl chloride (64 mg, 0.503 mmol), stirred at RT for 5 min, then heated at 80° C. for 45 min. The mixture was cooled to RT, added drop-wise to a solution of DIEA (186 mg, 1.443 mmol) and Example A28 (90 mg, 0.335 mmol) in dioxane (2 mL) and stirred at RT for 4 h. The mixture was diluted with EtOAc, washed with satd. NaHCO$_3$, then brine, dried over Na$_2$SO$_4$, concentrated to dryness and purified via reverse-phase silca gel chromatography (MeCN/H$_2$O with 0.1% TFA). The combined purified fractions were partially concentrated under reduced pressure and the aqueous residue was treated with satd. NaHCO$_3$ and extracted with EtOAc (2×). The combined organics were washed with brine, dried over Na$_2$SO$_4$ and concentrated to dryness to afford 4-methyl-N-((5-((2-(2-methyloxazol-5-yl)pyridin-4-yl)oxy)pyridin-2-yl)carbamoyl)tetrahydro-2H-pyran-4-carboxamide (55 mg, 38%). $^1$H NMR (400 MHz, DMSO-d$_6$): δ 11.24 (s, 1H), 10.57 (s, 1H), 8.50 (d, J=5.7 Hz, 1H), 8.31 (d, J=2.9 Hz, 1H), 8.13 (d, J=9.0 Hz, 1H), 7.80 (dd, J=9.0, 2.9 Hz, 1H), 7.65 (s, 1H), 7.18 (d, J=2. Hz, 1H), 6.93 (dd, J=5.7, 2.5 Hz, 1H), 3.67-3.62 (m, 2H), 3.48-3.41 (m, 2H), 2.47 (s, 3H), 2.07-2.02 (m, 2H), 1.54-1.46 (m, 2H), 1.28 (s, 3H); MS (ESI) m/z: 438.2 (M+H$^+$).

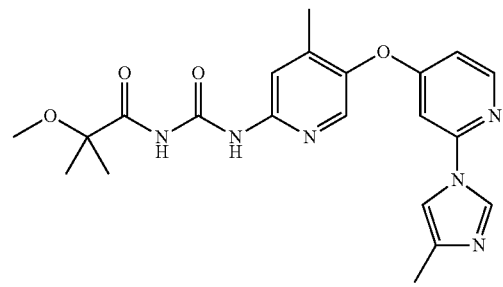 [SMILES: COC(C)(C)C(=O)NC(=O)Nc1cc(C)c(Oc2ccnc(-n3cnc(C)c3)c2)cn1]

Example 164

A mixture of Example B16 (0.114 g, 0.569 mmol), Example A27 (0.08 g, 0.284 mmol) and DBU (4.29 µL, 0.028 mmol) in dioxane (4 mL) was heated at 60° C. for 4 h, cooled to RT, concentrated to dryness and purified via reverse-phase silica gel chromatography (MeCN/H$_2$O with 0.1% TFA). Combined fractions were treated with satd. NaHCO$_3$, extracted with EtOAc (2×) and the combined organics were washed with brine, dried over Na$_2$SO$_4$ and concentrated to dryness to afford 2-methoxy-2-methyl-N-((4-methyl-5-((2-(4-methyl-1H-imidazol-1-yl)pyridin-4-yl)oxy)pyridin-2-yl)carbamoyl)propanamide (83 mg, 69%). $^1$H NMR (400 MHz, DMSO-d$_6$): δ 10.76 (s, 1H), 10.20 (very br s, 1H), 8.39 (d, J=1.4 Hz, 1H), 8.31 (d, J=5.8 Hz, 1H), 8.17 (s, 1H), 7.94 (br s, 1H), 7.63 (t, J=1.3 Hz, 1H), 7.32 (d, J=2.2 Hz, 1H), 6.75 (dd, J=5.8, 2.2 Hz, 1H), 3.21 (s, 3H), 2.17 (s, 3H), 2.13 (d, J=1.0 Hz, 3H), 1.35 (s, 6H); MS (ESI) m/z: 425.2 (M+H⁺).

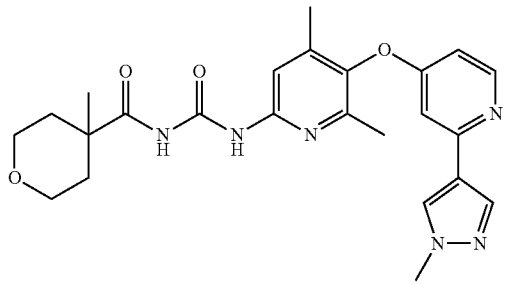 [SMILES: Cc1cc(NC(=O)NC(=O)C2(C)CCOCC2)nc(C)c1Oc1ccnc(-c2cnn(C)c2)c1]

Example 165

A solution of Example B24 (49 mg, 0.343 mmol) in DCE (1 mL) was treated with oxalyl chloride (47 mg, 0.370 mmol), heated at 80° C. for 45 min, then cooled to RT, treated with a solution of Example A25 (78 mg, 0.264 mmol) and TEA (107 mg, 1.056 mmol) in THF (3 mL) and stirred at RT overnight. The mixture was diluted with EtOAc, washed with satd. NaHCO₃, then brine, dried over Na₂SO₄, concentrated to dryness and purified via reverse-phase silica gel chromatography (MeCN/H₂O with 0.1% TFA). The organics were removed under reduced pressure and the aqueous residue was treated with satd. NaHCO₃, allowed to stand at RT and the resulting solid collected via filtration to afford N-((4,6-dimethyl-5-((2-(1-methyl-1H-pyrazol-4-yl)pyridin-4-yl)oxy) pyridin-2-yl)carbamoyl)-4-methyltetrahydro-2H-pyran-4-carboxamide (21 mg, 17%). ¹H NMR (400 MHz, DMSO-d₆): δ 11.15 (s, 1H), 10.51 (br s, 1H), 8.33 (d, J=5.7 Hz, 1H), 8.25 (s, 1H), 7.96 (s, 1H), 7.85 (br s, 1H), 7.11 (d, J=2.4 Hz, 1H), 6.52 (dd, J=5.7, 2.5 Hz, 1H), 3.84 (s, 3H), 3.68-3.62 (m, 2H), 3.46-3.39 (m, 2H), 2.18 (s, 3H), 2.11 (s, 3H), 2.05 (m, 2H), 1.52-1.44 (m, 2H), 1.26 (s, 3H); MS (ESI) m/z: 465.3 (M+H⁺).

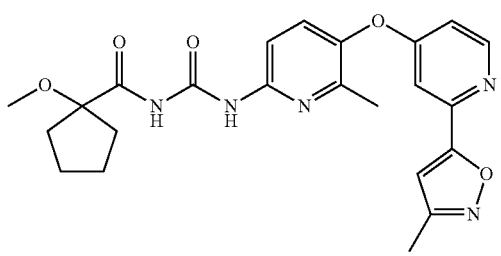 [SMILES: COC1(C(=O)NC(=O)Nc2ccc(Oc3ccnc(-c4cc(C)no4)c3)c(C)n2)CCCC1]

Example 166

A mixture of Example B23 (0.091 g, 0.399 mmol), Example A7 (0.045 g, 0.159 mmol) and N-methylpyrrolidine (4.07 mg, 0.048 mmol) in THF (3 mL) was heated at 55° C. for 24 h, concentrated to dryness and purified via reverse-phase silica gel chromatography (MeCN/H₂O with 0.1% TFA). The combined fractions were treated with satd. NaHCO₃, extracted with EtOAc (2×) and the combined organics were washed with brine, dried over Na₂SO₄ and concentrated to dryness to afford 1-methoxy-N-((6-methyl-5-((2-(3-methylisoxazol-5-yl)pyridin-4-yl)oxy)pyridin-2-yl)carbamoyl)cyclopentanecarboxamide (40 mg, 56%). ¹H NMR (400 MHz, DMSO-d₆): δ 10.81 (br s, 1H), 10.33 (br s, 1H), 8.56 (d, J=5.7 Hz, 1H), 7.89 (br s, 1H), 7.70 (d, J=8.8 Hz, 1H), 7.35 (d, J=2.5 Hz, 1H), 6.99-6.96 (m, 2H), 3.14 (s, 3H), 2.28 (s, 3H), 2.27 (s, 3H), 1.95-1.90 (m, 4H), 1.68-1.63 (m, 4H); MS (ESI) m/z: 452.2 (M+H⁺).

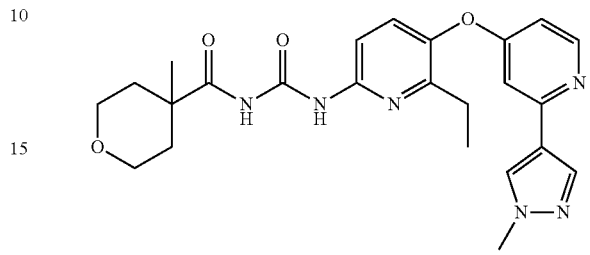

Example 167

A solution of Example B24 (79 mg, 0.550 mmol) in DCE (2 mL) was treated with oxalyl chloride (75 mg, 0.593 mmol), heated at 80° C. for 45 min, then cooled to RT, treated with a solution of Example A17 (125 mg, 0.423 mmol) and TEA (171 mg, 1.693 mmol) in THF (4 mL) and stirred at RT for 3 h. The mixture was diluted with EtOAc, washed with satd. NaHCO₃, then brine, dried over Na₂SO₄, concentrated to dryness and purified via reverse-phase silica gel chromatography (MeCN/H₂O with 0.1% TFA). The combined fractions were partially concentrated under reduced pressure and the aqueous residue was treated with satd. NaHCO₃ and extracted with EtOAc (2×). The combined organics were washed with brine, dried over Na₂SO₄ and concentrated to dryness to afford N-((6-ethyl-5-((2-(1-methyl-1H-pyrazol-4-yl)pyridin-4-yl)oxy)pyridin-2-yl)carbamoyl)-4-methyltetrahydro-2H-pyran-4-carboxamide (63 mg, 31%). ¹H NMR (400 MHz, DMSO-d₆): δ 11.18 (s, 1H), 10.52 (br s, 1H), 8.36 (d, J=5.7 Hz, 1H), 8.26 (s, 1H), 7.96 (s, 1H), 7.93 (br d, J=8.6 Hz, 1H), 7.65 (d, J=8.8 Hz, 1H), 7.18 (d, J=2.4 Hz, 1H), 6.62 (dd, J=5.7, 2.4 Hz, 1H), 3.84 (s, 3H), 3.68-3.62 (m, 2H), 3.48-3.40 (m, 2H), 2.60 (q, J=7.5 Hz, 2H), 2.08-2.02 (m, 2H), 1.54-1.46 (m, 2H), 1.27 (s, 3H), 1.14 (t, J=7.5 Hz, 3H); MS (ESI) m/z: 465.3 (M+H⁺).

Example 168

Using a procedure analogous to Example 166, Example B23 (0.13 g, 0.575 mmol), Example A11 (0.08 g, 0.29 mmol) and 1-methylpyrrolidine (0.012 g, 0.14 mmol) were combined in THF (3 mL) to afford 1-methoxy-N-((5-((2'-methyl-[2,4'-bipyridin]-4-yl)oxy)pyridin-2-yl)carbamoyl)cyclopentanecarboxamide (60 mg, 47%). ¹H NMR (400 MHz, DMSO-d$_6$): δ 10.86 (s, 1H), 10.36 (br s, 1H), 8.60 (d, J=5.6 Hz, 1H), 8.52 (d, J=5.2 Hz, 1H), 8.30 (d, J=2.9 Hz, 1H), 8.03 (br s, 1H), 7.90 (s, 1H), 7.80-7.78 (m, 2H), 7.71 (d, J=2.3 Hz, 1H), 6.98 (dd, J=5.6, 2.3 Hz, 1H), 3.15 (s, 3H), 2.53 (s, 3H), 1.94-1.92 (m, 4H), 1.67-1.65 (m, 4H); MS (ESI) m/z: 448.2 (M+H$^+$).

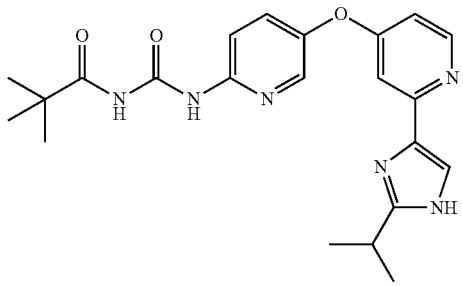 [SMILES: CC(C)c1nc(-c2cc(Oc3ccc(NC(=O)NC(=O)C(C)(C)C)nc3)ccn2)c[nH]1]

Example 169

A −78° C. solution of 2,2,2-trimethylacetamide (1 g, 9.89 mmol) in THF (20 mL) was treated drop-wise with lithium bis(trimethylsilyl)amide (1.0N in THF, 11.86 mL, 11.86 mmol), stirred for 30 min, treated drop-wise with a solution of isopropenyl chloroformate (1.43 g, 11.86 mmol) in THF (5 mL), warmed to RT and stirred for 1 h. The mixture was treated with satd. NaHCO$_3$, extracted with EtOAc (2×) and the combined organics were washed with satd. NH$_4$Cl, then brine, dried over Na$_2$SO$_4$ and concentrated to dryness to afford prop-1-en-2-yl pivaloylcarbamate (1.94 g, 106%) which was used without further purification.

A mixture of Example A29 (150 mg, 0.508 mmol), N-methylpyrrolidine (86 mg, 1.016 mmol) and prop-1-en-2-yl pivaloylcarbamate (282 mL, 1.524 mmol) in dioxane (5 mL) was heated at 80° C. for 4 days. The mixture was cooled to RT, diluted with EtOAc, washed with satd. NaHCO$_3$, then brine, dried over Na$_2$SO$_4$, concentrated to dryness and purified via reverse-phase silica gel chromatography (MeCN/H$_2$O with 0.1% TFA). The fractions were concentrated under reduced pressure, the aqueous residue was neutralized with satd. NaHCO$_3$ and the resulting precipitate was collected via filtration to afford N-((5-((2-(2-isopropyl-1H-imidazol-4-yl)pyridin-4-yl)oxy)pyridin-2-yl)carbamoyl)pivalamide (24 mg, 11%). $^1$H NMR (400 MHz, DMSO-d$_6$): δ 11.95 (s, 1H), 11.24 (s, 1H), 10.44 (br s, 1H), 8.36 (d, J=5.6 Hz, 1H), 8.28 (m, 1H), 8.10 (br d, J=8.9 Hz, 1H), 7.75 (dd, J=8.9, 3.3 Hz, 1H), 7.55 (s, 1H), 7.25 (d, J=2.5 Hz, 1H), 6.76 (dd, J=5.7, 2.6 Hz, 1H), 2.94 (m, 1H), 2.06 (s, 6H), 1.21 (s, 9H). MS (ESI) m/z: 423.2 (M+H$^+$).

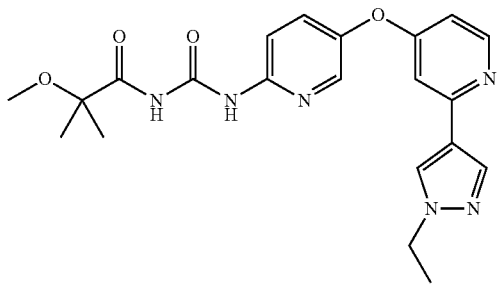 [SMILES: CCn1cc(-c2cc(Oc3ccc(NC(=O)NC(=O)C(C)(C)OC)nc3)ccn2)cn1]

Example 170

A mixture of Example C5 (0.12 g, 0.33 mmol), 1-ethyl-4-(4,4,5,5-tetramethyl-1,3,2-dioxaborolan-2-yl)-1H-pyrazole (80 mg, 0.36 mmol) and K$_2$CO$_3$ (0.14 g, 0.99 mmol) in dioxane (4 mL) and H$_2$O (1 mL) was sparged with Ar, treated with Pd(PPh$_3$)$_4$ (0.040 g, 0.034 mmol), sparged again with Ar and heated at 90° C. overnight. The mixture was cooled to RT, treated with satd. NaHCO$_3$, extracted with EtOAc (3×) and the combined organics were dried over Na$_2$SO$_4$, concentrated to dryness and purified via silica gel chromatography (MeOH/DCM) to obtain N-((5-((2-(1-ethyl-1H-pyrazol-4-yl)pyridin-4-yl)oxy)pyridin-2-yl)carbamoyl)-2-methoxy-2-methylpropanamide (40 mg, 28%). $^1$H NMR (400 MHz, DMSO-d$_6$): δ 10.82 (s, 1H), 10.20 (br s, 1H), 8.38 (d, J=5.7 Hz, 1H), 8.31 (s, 1H), 8.27 (d, J=2.9 Hz, 1H), 8.02 (br s, 1H), 7.98 (s, 1H), 7.75 (dd, J=9.0, 2.9 Hz, 1H), 7.24 (d, J=2.4 Hz, 1H), 6.71 (dd, J=5.7, 2.4 Hz, 1H), 4.14 (q, J=7.3 Hz, 2H), 3.21 (s, 3H), 1.37 (t, J=7.3 Hz, 3H), 1.36 (s, 6H); MS (ESI) m/z: 425.2 (M+H$^+$).

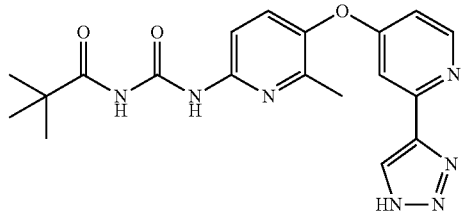 [SMILES: Cc1nc(NC(=O)NC(=O)C(C)(C)C)ccc1Oc1ccnc(-c2c[nH]nn2)c1]

Example 171

A solution of 2,2,2-trimethylacetamide (0.052 g, 0.517 mmol) in DCE (3 mL) was treated with oxalyl chloride (0.027 mL, 0.314 mmol), stirred at RT for 1 h, then heated at 75° C. for 2 h and cooled to RT. To this mixture was added a solution of Example A30 (0.12 g, 0.314 mmol), TEA (0.044 mL, 0.314 mmol) in DCM (3 mL) and the resultant mixture was stirred at RT for 1 h. The mixture was diluted with water (30 mL) and DCM (20 mL). The aqueous layer was separated and extracted with DCM (20 mL). The combined organics were washed with brine, dried (Na$_2$SO$_4$) and concentrated to afford (4-(4-((2-methyl-6-(3-pivaloylureido)pyridin-3-yl)oxy)pyridin-2-yl)-1H-1,2,3-triazol-1-yl)methyl pivalate (0.16 g, 100%) as a colorless foam that was used without further purification. MS (ESI) m/z: 510.3 (M+H$^+$).

A solution of (4-(4-((2-Methyl-6-(3-pivaloylureido)pyridin-3-yl)oxy)pyridin-2-yl)-1H-1,2,3-triazol-1-yl)methyl pivalate (0.16 g, 0.314 mmol) and TEA (0.175 mL, 1.256 mmol) in MeOH (5 mL) was stirred at 40° C. for ~40 h. The solvent was evaporated to dryness and the residue was purified by silica gel chromatography (MeOH/DCM), and lyophilized from MeCN/H$_2$O to afford N-((5-((2-(1H-1,2,3-triazol-4-yl)pyridin-4-yl)oxy)-6-methylpyridin-2-yl)carbamoyl)pivalamide (62 mg, 50%) as a white solid. $^1$H NMR (400 MHz, DMSO-d$_6$): δ 11.18 (s, 1H), 10.40 (br s, 1H), 8.49 (d, J=5.9 Hz, 1H), 8.23 (br s, 1H), 7.93 (br s, 1H), 7.70 (d, J=8.8 Hz, 1H), 7.35 (br s, 1H), 6.90 (d, J=5.5 Hz, 1H), 2.26 (s, 3H), 1.21 (s, 9H); MS (ESI) m/z: 396.2 (M+H$^+$).

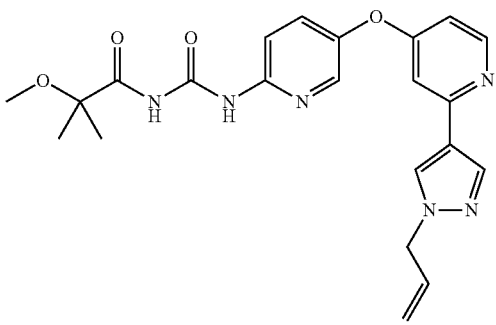 [SMILES: C=CCn1cc(-c2cc(Oc3ccc(NC(=O)NC(=O)C(C)(C)OC)nc3)ccn2)cn1]

Example 172

A mixture of Example C5 (0.12 g, 0.33 mmol), 1-allyl-4-(4,4,5,5-tetramethyl-1,3,2-dioxaborolan-2-yl)-1H-pyrazole (0.085 g, 0.36 mmol) and K$_2$CO$_3$ (0.14 g, 0.99 mmol) in dioxane (4 mL) and H$_2$O (1 mL) was sparged with Ar, treated with Pd(PPh$_3$)$_4$ (0.040 g, 0.034 mmol), sparged again with Ar and heated at 90° C. overnight. The mixture was cooled to RT, treated with satd. NaHCO$_3$, extracted with EtOAc (3×) and the combined organics were dried over Na$_2$SO$_4$, concentrated to dryness and purified via reverse phase silica gel chromatography (MeCN/H$_2$O (0.1% TFA)) to obtain N-((5-((2-(1-allyl-1H-pyrazol-4-yl)pyridin-4-yl)oxy)pyridin-2-yl)carbamoyl)-2-methoxy-2-methylpropanamide (22 mg, 14.6%). $^1$H NMR (400 MHz, DMSO-d$_6$): δ 10.83 (s, 1H), 10.21 (br s, 1H), 8.41 (d, J=5.8 Hz, 1H), 8.33 (s, 1H), 8.28 (d, J=2.9 Hz, 1H), 8.05 (s, 1H), 8.03 (br s, 1H), 7.76 (dd, J=9.0, 2.9 Hz, 1H), 7.31 (d, J=2.4 Hz, 1H), 6.77 (d, J=5.7 Hz, 1H), 6.02 (m, 1H), 5.21 (m, 1H), 5.13 (m, 1H), 4.77 (d, J=5.8 Hz, 2H), 3.21 (s, 3H), 1.36 (s, 6H); MS (ESI) m/z: 437.2 (M+H$^+$).

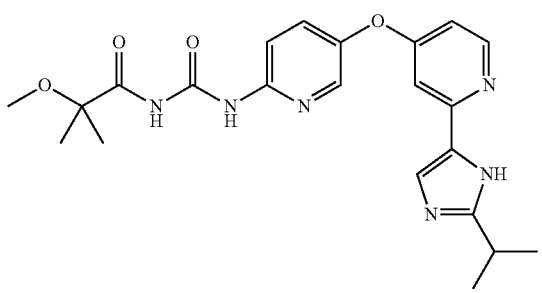 [SMILES: COC(C)(C)C(=O)NC(=O)Nc1ccc(Oc2ccnc(-c3cnc(C(C)C)[nH]3)c2)cn1]

Example 173

A mixture of Example A29 (358 mg, 1.212 mmol), N-methylpyrrolidine (206 mg, 2.424 mmol) and Example B16 (859 mg, 1.524 mmol) in dioxane (5 mL) was heated to 80° C. for 24 h, diluted with EtOAc (40 mL) and washed successively with satd NaHCO$_3$ solution (40 mL) and brine (40 mL). The organic phase was separated, dried (Na$_2$SO$_4$), evaporated at reduced pressure, and purified by reverse phase silica gel chromatography (MeCN/H$_2$O (0.1% TFA)). The purified aqueous fractions were combined and treated with saturated NaHCO$_3$ (5 mL). The resultant mixture was sonicated for 10 min. The off-white precipitate was collected by filtration and dried in vacuo at 80° C. overnight to provide N-((5-((2-(2-isopropyl-1H-imidazol-5-yl)pyridin-4-yl)oxy)pyridin-2-yl)carbamoyl)-2-methoxy-2-methylpropanamide (203 mg, 38%). $^1$H NMR (400 MHz, DMSO-d$_6$): δ 11.96 (s, 1H), 10.82 (s, 1H), 10.23 (v br s, 1H), 8.35 (d, J=5.7 Hz, 1H), 8.28 (d, J=2.8 Hz, 1H), 8.08-7.96 (m, 1H), 7.76 (m, 1H), 7.55 (s, 1H), 7.24 (d, J=2.5 Hz, 1H), 6.76 (m, 1H), 3.21 (s, 3H), 2.94 (m, 1H), 1.35 (s, 6H), 1.21 (m, 6H); MS (ESI) m/z: 439.2 (M+H$^+$).

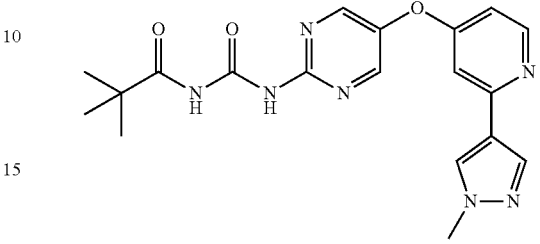

Example 174

A mixture of 2,2,2-trimethylacetamide (76 mg, 0.755 mmol) in DCE (2 mL) was treated drop-wise with oxalyl chloride (96 mg, 0.755 mmol) and the resultant mixture was stirred at RT for 5 min and at 80° C. for 45 min. The mixture was cooled to RT and added dropwise to a solution of DIEA (293 mg, 2.264 mmol) and Example A31 (135 mg, 0.503 mmol) in dioxane (3 mL). The mixture was stirred at RT for 18 h, diluted with EtOAc (40 mL), and washed successively with satd NaHCO$_3$ (40 mL) and brine (40 mL). The organic phase was separated, dried (Na$_2$SO$_4$) and evaporated at reduced pressure. The residual foam was purified by reverse phase silica gel chromatography (MeCN/H$_2$O (0.1% TFA)). The purified aqueous fractions were combined, partially concentrated and treated with saturated NaHCO$_3$ (5 mL). The resultant milky suspension was extracted with EtOAc (3×25 mL). The combined extracts were washed with brine (25 mL), dried over Na$_2$SO$_4$, and evaporated at reduced pressure to give a white solid. The solid was triturated with MTBE (10 mL), collected by filtration, washed with MTBE (2×2 mL) and dried under vacuum at 80° C. to provide N-((5-((2-(1-methyl-1H-pyrazol-4-yl)pyridin-4-yl)oxy)pyrimidin-2-yl)carbamoyl)pivalamide (115 mg, 57%). $^1$H NMR (400 MHz, DMSO-d$_6$): δ 11.24 (s, 1H), 10.96 (s, 1H), 8.72 (s, 2H), 8.39 (d, J=5.7 Hz, 1H), 8.28 (s, 1H), 7.99 (s, 1H), 7.28 (d, J=2.5 Hz, 1H), 6.84 (dd, J=5.7, 2.5 Hz, 1H), 3.84 (s, 3H), 1.21 (s, 9H); MS (ESI) m/z: 396.2 (M+H$^+$).

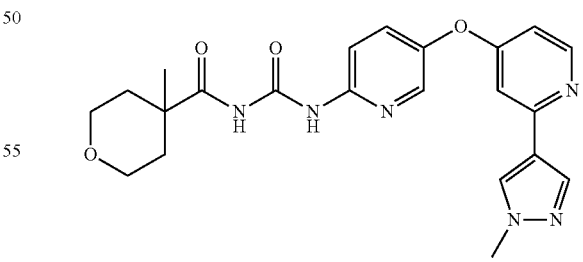

Example 175

A solution of Example B24 (161 mg, 1.122 mmol) in DCE (2 mL) was treated drop-wise with oxalyl chloride (142 mg, 1.122 mmol) and the resultant mixture was stirred at RT for 5 min and at 80° C. for 45 min. The mixture was cooled to RT, added dropwise to a solution of DIEA (435 mg, 3.37 mmol) and Example A2 (200 mg, 0.748 mmol) in dioxane (4 mL), and stirred at RT for 18 h. EtOAc (30 mL) and satd. NaHCO$_3$ (20 mL) were added. The organic phase was separated, washed with brine (20 mL), dried over Na$_2$SO$_4$ and evaporated at reduced pressure. The residual foam was purified by reverse phase silica gel chromatography (MeCN/H$_2$O (0.1% TFA)). The purified aqueous fractions were combined, concentrated and treated with saturated NaHCO$_3$ (5 mL). The resultant milky suspension was extracted with EtOAc (2×30 mL). The combined extracts were washed with brine (30 mL), dried over Na$_2$SO$_4$, and evaporated at reduced pressure to give a oily foam. The foam was dissolved in MeCN (3 mL), diluted with water (5 mL), frozen and lyophilized to provide 4-methyl-N-((5-((2-(1-methyl-1H-pyrazol-4-yl)pyridin-4-yl)oxy)pyridin-2-yl)carbamoyl)tetrahydro-2H-pyran-4-carboxamide (154 mg, 46%) as a white solid. $^1$H NMR (400 MHz, DMSO-d$_6$): δ 11.21 (s, 1H), 10.55 (s, 1H), 8.38 (d, J=5.7 Hz, 1H), 8.27 (d, J=2.9 Hz, 1H), 8.26 (s, 1H), 8.09 (d, J=9.0 Hz, 1H), 7.96 (s, 1H), 7.74 (dd, J=9.0, 2.9 Hz, 1H), 7.22 (d, J=2.4 Hz, 1H), 6.70 (dd, J=5.7, 2.4 Hz, 1H), 3.84 (s, 3H), 3.68-3.62 (m, 2H), 3.44 (m, 2H), 2.04 (m, 2H), 1.50 (m, 2H), 1.27 (s, 3H); MS (ESI) m/z: 437.2 (M+H$^+$).

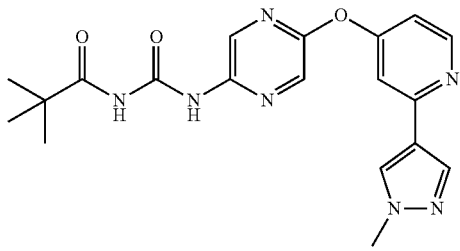 [SMILES: Cn1cc(-c2cc(Oc3cnc(NC(=O)NC(=O)C(C)(C)C)cn3)ccn2)cn1]

Example 176

A mixture of 2,2,2-trimethylacetamide 0.068 g, 0.67 mmol) in DCE (3 mL) was treated with oxalyl chloride (0.117 mL, 1.342 mmol), stirred at 70° C. for 16 h, and concentrated to dryness. A solution of Example A32 (0.09 g, 0.335 mmol) and TEA (0.140 mL, 1.006 mmol) in DCM (3 mL) was added and the mixture was stirred at RT for 1 h. The solvent was evaporated to dryness. The residue was sequentially purified by reverse phase silica gel chromatography (MeCN/H$_2$O (0.1% TFA)), and then again purified by silica gel chromatography (MeOH/DCM), and was lyophilized from MeCN/water to provide N-((5-((2-(1-methyl-1H-pyrazol-4-yl)pyridin-4-yl)oxy)pyrazin-2-yl)carbamoyl)pivalamide (38 mg. 29%) as a white solid. $^1$H NMR (400 MHz, DMSO-d$_6$): δ 11.27 (s, 1H), 10.56 (s, 1H), 8.90 (d, J=1.4 Hz, 1H), 8.45 (d, J=5.7 Hz, 1H), 8.42 (d, J=1.4 Hz, 1H), 8.28 (s, 1H), 7.99 (s, 1H), 7.44 (d, J=2.3 Hz, 1H), 6.96 (d, J=5.6 Hz, 1H), 3.85 (s, 3H), 1.21 (s, 9H).

The following assays demonstrate that certain compounds of Formula I inhibit kinase activity of c-FMS kinase, c-KIT kinase, or PDGFRβ kinase in enzymatic assays and also inhibit the activity of c-FMS kinase in M-NFS-60 and THP-1 cell lines. In vivo evaluations of certain compounds of Formula I also demonstrate inhibition of c-FMS in a pharmcodynamic model. Further demonstration of activity may be demonstrated in a peritibial implant model, a U-251 or GL-261 glioma model, or in a MDA-MB-231 breast cancer xenograft model.

uFMS Kinase (Seq. ID No. 1) Assay

Activity of unphosphorylated c-FMS kinase (uFMS, Seq. ID no. 1) was determined by following the production of ADP from the FMS kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 μL) contained FMS (purchased from Millipore) (10 nM), polyE4Y (1 mg/mL), MgCl$_2$ (10 mM), pyruvate kinase (4 units), lactate dehydrogenase (0.7 units), phosphoenol pyruvate (1 mM), NADH (0.28 mM) and ATP (500 μM) in 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on Synergy 2 plate reader. The reaction rate was calculated using the 3 to 4 h time frame. Percent inhibition was obtained by comparison of reaction rate with that of a control (i.e. in the absence of test compound). IC$_{50}$ values were calculated from a series of percent inhibition values determined at a range of inhibitor concentrations using software routines as implemented in the GraphPad Prism software package.

```
uFMS Kinase sequence (Y538-end) used for screening
                                          (Seq. ID No. 1)
YKYKQKPKYQ  VRWKIIESYE  GNSYTFIDPT  QLPYNEKWEF

PRNNLQFGKT  LGAGAFGKVV  EATAFGLGKE  DAVLKVAVKM

LKSTAHADEK  EALMSELKIM  SHLGQHENIV  NLLGACTHGG

PVLVITEYCC  YGDLLNFLRR  KAEAMLGPSL  SPGQDPEGGV

DYKNIHLEKK  YVRRDSGFSS  QGVDTYVEMR  PVSTSSNDSF

SEQDLDKEDG  RPLELRDLLH  FSSQVAQGMA  FLASKNCIHR

DVAARNVLLT  NGHVAKIGDF  GLARDIMNDS  NYIVKGNARL

PVKWMAPESI  FDCVYTVQSD  VWSYGILLWE  IFSLGLNPYP

GILVNSKFYK  LVKDGYQMAQ  PAFAPKNIYS  IMQACWALEP

THRPTFQQIC  SFLQEQAQED  RRERDYTNLP  SSSRSGGSGS

SSSELEEESS  SEHLTCCEQG  DIAQPLLQPN  NYQFC
``` uKit kinase (Seq. ID No. 2) Assay

Activity of unphosphorylated c-KIT kinase (uKIT, Seq. ID no. 2) was determined by following the production of ADP from the KIT kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 μl) contained unphosphorylated KIT (12 nM), polyE4Y (1 mg/mL), MgCl$_2$ (10 mM), pyruvate kinase (4 units), lactate dehydrogenase (0.7 units), phosphoenol pyruvate (1 mM), and NADH (0.28 mM) and ATP (2000 μM) in 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on Synergy 2 plate reader (BioTech). Reaction rates around 3 to 4 h time frame were used to calculate % inhibitions, from which IC$_{50}$ values were generated.

uKit with N-terminal GST fusion used for screening
(Seq ID No. 2)

```
LGYWKIKGLV QPTRLLLEYL EEKYEEHLYE RDEGDKWRNK

KFELGLEFPN LPYYIDGDVK LTQSMAIIRY IADKHNMLGG

CPKERAEISM LEGAVDIRYG VSRIAYSKDF ETLKVDFLSK

LPEMLKMFED RLCHKTYLNG DHVTHPDFML YDALDVVLYM

DPMCLDAFPK LVCFKKRIEA IPQIDKYLKS SKYIWPLQGW

QATFGGGDHP PKSDLVPRHN QTSLYKKAGS AAAVLEENLY

FQGTYKYLQK PMYEVQWKVV EEINGNNYVY IDPTQLPYDH

KWEFPRNRLS FGKTLGAGAF GKVVEATAYG LIKSDAAMTV

AVKMLKPSAH LTEREALMSE LKVLSYLGNH MNIVNLLGAC

TIGGPTLVIT EYCCYGDLLN FLRRKRDSFI CSKQEDHAEA

ALYKNLLHSK ESSCSDSTNE YMDMKPGVSY VVPTKADKRR

SVRIGSYIER DVTPAIMEDD ELALDLEDLL SFSYQVAKGM

AFLASKNCIH RDLAARNILL THGRITKICD FGLARDIKND

SNYVVKGNAR LPVKWMAPES IFNCVYTFESD VWSYGIFLWE

LFSLGSSPYP GMPVDSKFYK MIKEGFRMLS PEHAPAEMYD

IMKTCWDADP LKRPTFKQIV QLIEKQISES TNHIYSNLAN

CSPNRQKPVV DHSVRINSVG STASSSQPLL VHDDV
```

Unphosphorylated PDGFRβ (uPDGFRβ) Kinase (Seq. ID No. 3) Assay

Activity of unphosphorylated PDGFRβ kinase (uPDGFRβ, Seq. ID No. 3) was determined by following the production of ADP from the kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophotometrically. The reaction mixture (100 µL) contained PDGFRβ (DeCode, 15.7 nM), polyE4Y (2.5 mg/mL), $MgCl_2$ (10 mM), pyruvate kinase (4 units), lactate dehydrogenase (0.7 units), phosphoenol pyruvate (1 mM) and NADH (0.28 mM) and ATP (500 µM) in a 90 mM Tris buffer containing 0.2% octyl-glucoside and 1% DMSO, at pH 7.5. The inhibition reaction was started by mixing serial diluted test compound with the above reaction mixture. The absorption at 340 nm was monitored continuously for 4 h at 30° C. on a Polarstar Optima or Synergy 2 plate reader. The reaction rate was calculated using the 1.5 to 2.5 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

uPDGFRβ Kinase Sequence (residues 557-1106) used for screening
(Seq ID No. 3)

```
QKKPRYEIRW KVIESVSSDG HEYIYVDPMQ LPYDSTWELP

RDQLVLGRTL GSGAFGQVVE ATAHGLSHSQ ATMKVAVKML

KSTARSSEKQ ALMSELKIMS HLGPHLNVVN LLGACTKGGP

IYIITEYCRY GDLVDYLHRN KHTFLQHHSD KRRPPSAELY

SNALPVGLPL PSHVSLTGE SDGGYMDMSK DESVDYVPML

DMKGDVKYAD IESSNYMAPY DNYVPSAPER TCRATLINES

PVLSYMDLVG FSYQVANGME FLASKNCVHR DLAARNVLIC

EGKLVKICDF GLARDIMRDS NYISKGSTFL PLKWMAPESI

FNSLYTTLSD VWSFGILLWE IFTLGGTPYP ELPMNEQFYN

AIKRGYRMAQ PAHASDEIYE IMQKCWEEKF EIRPPFSQLV

LLLERLLGEG YKKKYQQVDE EFLRSDHPAI LRSQARLPGF

HGLRSPLDTS SVLYTAVQPN EGDNDYIIPL PDPKPEVADE

GPLEGSPSLA SSTLNEVNTS STISCDSPLE PQDEPEPEPQ

LELQVEPEPE LEQLPDSGCP APRAEAEDSF L
```

Using the enzymatic protocols described above, compounds of Formula I were shown to be inhibitors in assays measuring the kinase activity of uFMS kinase, uKIT kinase, or uPDGFRβ kinase, as indicated below in Table 1.

TABLE 1

Activity of Compounds of Formula Ia in Enyzmatic Assays of c-FMS kinase, c-KIT kinase, or PDGFRβ kinase.

| Example | uFMS | uKIT | uPDGFRb |
|---|---|---|---|
| 1 | ++++ | NT | +++ |
| 2 | ++++ | ++++ | +++ |
| 3 | ++++ | ++++ | ++++ |
| 4 | ++++ | ++ | ++ |
| 5 | ++++ | NT | +++ |
| 6 | ++++ | + | + |
| 7 | +++ | + | + |
| 8 | +++ | NT | + |
| 9 | ++++ | +++ | ++ |
| 10 | ++++ | + | + |
| 11 | ++++ | ++++ | +++ |
| 12 | ++++ | +++ | ++ |
| 13 | ++++ | ++++ | +++ |
| 14 | ++++ | NT | ++ |
| 15 | +++ | NT | + |
| 16 | ++++ | +++ | +++ |
| 17 | +++ | ++ | + |
| 18 | ++++ | ++ | ++ |
| 19 | ++++ | +++ | +++ |
| 20 | +++ | NT | + |
| 21 | +++ | NT | + |
| 22 | ++++ | +++ | ++ |
| 23 | ++++ | + | + |
| 24 | ++++ | ++ | + |
| 25 | +++ | NT | + |
| 26 | ++++ | ++ | ++ |
| 27 | + | + | + |
| 28 | ++ | + | + |
| 29 | +++ | + | + |
| 30 | ++ | + | + |
| 31 | ++++ | ++++ | ++++ |
| 32 | ++++ | ++++ | +++ |
| 33 | ++++ | ++ | +++ |
| 34 | ++++ | ++ | ++ |
| 35 | ++++ | ++ | +++ |
| 36 | ++++ | ++ | ++ |
| 37 | ++++ | +++ | +++ |
| 38 | ++++ | +++ | ++++ |
| 39 | ++++ | + | + |
| 40 | ++++ | ++ | ++ |
| 41 | ++++ | + | + |
| 42 | ++++ | ++ | ++ |
| 43 | ++++ | +++ | ++ |
| 44 | ++++ | + | + |
| 45 | ++++ | +++ | +++ |
| 46 | ++++ | +++ | ++ |

TABLE 1-continued

Activity of Compounds of Formula Ia in Enyzmatic Assays of c-FMS kinase, c-KIT kinase, or PDGFRβ kinase.

| Example | uFMS | uKIT | uPDGFRb |
|---|---|---|---|
| 47 | ++++ | ++++ | +++ |
| 48 | ++++ | ++++ | NT |
| 49 | +++ | + | + |
| 50 | ++ | + | NT |
| 51 | ++++ | ++ | + |
| 52 | ++++ | ++ | + |
| 53 | +++ | ++ | + |
| 54 | ++++ | ++ | + |
| 55 | ++++ | + | + |
| 56 | ++++ | + | + |
| 57 | ++++ | + | + |
| 58 | ++++ | + | + |
| 59 | +++ | ++ | NT |
| 60 | ++++ | + | + |
| 61 | ++++ | + | + |
| 62 | ++++ | ++++ | ++++ |
| 63 | ++++ | ++ | ++ |
| 64 | ++++ | ++++ | +++ |
| 65 | ++++ | ++++ | ++ |
| 66 | ++++ | ++ | + |
| 67 | ++++ | ++++ | +++ |
| 68 | ++++ | ++ | ++ |
| 69 | ++++ | ++ | ++ |
| 70 | ++++ | + | ++ |
| 71 | ++++ | + | + |
| 72 | ++++ | + | ++ |
| 73 | ++++ | + | ++ |
| 74 | ++++ | ++++ | +++ |
| 75 | ++++ | ++ | ++ |
| 76 | ++++ | + | + |
| 77 | ++++ | ++ | + |
| 78 | ++++ | ++ | + |
| 79 | +++ | + | + |
| 80 | ++++ | ++ | NT |
| 81 | +++ | + | + |
| 82 | ++ | + | + |
| 83 | ++++ | + | + |
| 84 | ++++ | ++ | ++ |
| 85 | +++ | + | + |
| 86 | ++++ | + | + |
| 87 | ++++ | ++ | ++ |
| 88 | ++++ | +++ | ++ |
| 89 | +++ | + | + |
| 90 | +++ | + | + |
| 91 | ++++ | +++ | ++ |
| 92 | ++++ | ++ | ++ |
| 93 | +++ | + | + |
| 94 | ++++ | + | + |
| 95 | +++ | + | + |
| 96 | +++ | + | + |
| 97 | +++ | ++ | + |
| 98 | ++ | + | + |
| 99 | ++++ | + | ++ |
| 100 | ++++ | +++ | + |
| 101 | ++++ | ++ | ++++ |
| 102 | ++++ | ++ | ++ |
| 103 | +++ | + | ++ |
| 104 | ++++ | + | + |
| 105 | ++++ | ++ | ++ |
| 106 | ++++ | ++ | + |
| 107 | +++ | + | + |
| 108 | +++ | + | + |
| 109 | ++++ | ++ | ++ |
| 110 | +++ | + | + |
| 111 | ++++ | ++ | NT |
| 112 | ++++ | ++ | NT |
| 113 | ++++ | + | + |
| 114 | ++++ | +++ | NT |
| 115 | +++ | + | NT |
| 116 | ++++ | +++ | +++ |
| 117 | ++++ | +++ | ++ |
| 118 | ++++ | +++ | ++ |
| 119 | ++++ | ++ | + |
| 120 | ++++ | + | + |
| 121 | ++++ | ++ | NT |
| 122 | +++ | + | NT |
| 123 | ++++ | ++ | ++ |
| 124 | ++++ | + | + |
| 125 | ++++ | + | + |
| 126 | ++++ | ++ | +++ |
| 127 | ++++ | ++ | ++ |
| 128 | ++ | + | NT |
| 129 | +++ | + | NT |
| 130 | +++ | + | + |
| 131 | ++++ | + | + |
| 132 | ++++ | + | ++ |
| 133 | ++++ | +++ | NT |
| 134 | +++ | + | + |
| 135 | +++ | + | + |
| 136 | ++ | + | + |
| 137 | +++ | + | + |
| 138 | ++ | + | + |
| 139 | ++ | + | + |
| 140 | ++++ | +++ | ++ |
| 141 | +++ | + | + |
| 142 | +++ | ++ | NT |
| 143 | +++ | ++ | NT |
| 144 | ++++ | ++ | NT |
| 145 | +++ | + | + |
| 146 | ++++ | + | ++ |
| 147 | ++++ | + | + |
| 148 | ++++ | +++ | + |
| 149 | ++++ | ++ | ++ |
| 150 | ++++ | +++ | ++ |
| 151 | ++++ | + | + |
| 152 | ++++ | + | + |
| 153 | ++++ | +++ | +++ |
| 154 | ++++ | + | ++ |
| 155 | ++++ | ++ | + |
| 156 | +++ | ++ | + |
| 157 | +++ | ++ | ++ |
| 158 | +++ | + | ++ |
| 159 | +++ | + | + |
| 160 | ++++ | + | + |
| 161 | ++++ | + | + |
| 162 | ++++ | +++ | ++ |
| 163 | +++ | ++ | + |
| 164 | ++++ | + | + |
| 165 | ++++ | ++ | +++ |
| 166 | ++++ | ++ | ++ |
| 167 | +++ | + | + |
| 168 | ++++ | ++ | ++ |
| 169 | ++++ | + | + |
| 170 | ++++ | ++ | + |
| 171 | ++++ | + | + |
| 172 | ++++ | ++ | + |
| 173 | +++ | + | + |
| 174 | +++ | ++ | + |
| 175 | ++++ | ++ | ++ |
| 176 | +++ | + | + |

NT: Not Tested; +: $IC_{50} > 1$ uM; ++: $0.1$ uM $< IC_{50} \leq 1$ uM; +++: $0.01$ uM $< IC_{50} \leq 0.1$ uM; ++++: $IC_{50} \leq 0.01$ uM M-NFS-60 Cell Culture M-NFS-60 cells (catalog #CRL-1838) were obtained from the American Type Culture Collection (ATCC, Manassas, Va.). Briefly, cells were grown in suspension in RPMI 1640 medium supplemented with 10% characterized fetal bovine serum (Invitrogen, Carlsbad, Calif.), 0.05 mM 2-mercaptoethanol, and 20 ng/mL mouse recombinant macrophage colony stimulating factor (M-CSF) at 37° C., 5% $CO_2$, and 95% humidity. Cells were allowed to expand until reaching saturation at which point they were subcultured or harvested for assay use.

M-NFS-6 Cell Proliferation Assay

A serial dilution of test compound was dispensed into a 384-well black clear bottom plate (Corning, Corning, N.Y.).

Two thousand five hundred cells were added per well in 50 μL complete growth medium. Plates were incubated for 67 h at 37° C., 5% $CO_2$, and 95% humidity. At the end of the incubation period 10 μL of a 440 μM solution of resazurin (Sigma, St. Louis, Mo.) in PBS was added to each well and incubated for an additional 5 h at 37° C., 5% $CO_2$, and 95% humidity. Plates were read on a Synergy2 reader (Biotek, Winooski, Vt.) using an excitation of 540 nM and an emission of 600 nM. $IC_{50}$ values were calculated from a series of percent inhibition values determined at a range of inhibitor concentrations using software routines as implemented in the GraphPad Prism software package.

THP-1 Cell Culture

THP-1 cells (catalog #TIB-202) were obtained from the ATCC. Briefly, cells were grown in RPMI 1640 supplemented with 10% characterized fetal bovine serum, 1% sodium pyruvate, 1% Penicillin-Streptomycin-Glutamine (PSG) and 55 uM 2-mercaptoethanol (Invitrogen, Carlsbad, Calif.) at 37 degrees Celsius, 5% $CO_2$, 95% humidity. Cells were allowed to expand until reaching 70-95% confluency at which point they were subcultured or harvested for assay use.

Phospho-FMS ELISA Assay

A serial dilution of test compound was diluted 1:100 in assay medium (RPMI 1640 supplemented with 10% characterized fetal bovine serum) in a 96 well black clear bottom plate (Corning, Corning, N.Y.). In a separate 96 well black clear bottom plate, one hundred and fifty thousand THP-1 cells were added per well in 100 μL in assay medium. Fifty microliters of diluted compound was then added to the cells. Plates were incubated for 4 hours at 37 degrees Celsius, 5% $CO_2$, 95% humidity. At the end of the incubation period, cells were stimulated with 50 μL of a 100 nM solution of recombinant human M-CSF (catalog #216-MC, R & D Systems, Minneapolis, Minn.) in assay medium and the plate was incubated for 5 minutes at 37 degrees Celsius, 5% $CO_2$, 95% humidity. Lysates were prepared and used to perform the phospho-FMS ELISA as described by the manufacturer (catalog #DYC3268, R & D Systems, Minneapolis, Minn.). GraphPad Prism was used to calculate $IC_{50}$ values obtained from data generated from the ELISA assay.

Osteoclast Tartrate-Resistant Acid Phosphatase Assay

A serial dilution of test compound was dispensed into a 384-well black clear bottom plate (Nalge Nunc International, Rochester, N.Y.). Compound was diluted by the addition of DMEM media supplemented with 10% characterized fetal bovine serum (Invitrogen, Carlsbad, Calif.). Diluted compound was transferred to a 384-well black clear bottom plate. Two-thousand five hundred osteoclast precursors (Lonza, Walkersville, Md.) were added per well in growth media containing Receptor Activator of Nuclear Factor Kappa-beta ligand (RANKL) and M-CSF (R&D Systems, Minneapolis, Minn.). Plates were incubated for 7-14 days at 37 degrees Celsius, 5% $CO_2$, and 95% humidity to allow differentiation of osteoclast precursors. At the end of the incubation period, 10 μL of supernatant from each well was transferred to a clear 384-well plate. Tartrate-resistant acid phosphatase activity in the supernatant samples was determined using an acid phosphatase assay kit (Sigma, St. Louis, Mo.). Absorbance was measured at 550 nm using a plate reader. Data was analyzed using Prism software (Graphpad, San Diego, Calif.) to calculate $IC_{50}$ values.

The compounds of formula I were demonstrated to be functional inhibitors in one or more of the cellular assays described above, as indicated in Table 2.

TABLE 2

Inhibitory effects of compounds of formula I versus M-NFS-60, THP-1 and Osteoclast Cells

| Example | M-NFS-60 cell proliferation | Osteoclast assay | pFMS inhibition in THP-1 cells |
|---|---|---|---|
| 1 | ++++ | ++++ | ++++ |
| 2 | ++++ | ++++ | ++++ |
| 3 | ++++ | ++++ | ++++ |
| 4 | ++++ | ++++ | +++ |
| 5 | ++++ | ++++ | NT |
| 6 | +++ | ++++ | ++++ |
| 7 | ++ | +++ | +++ |
| 8 | +++ | +++ | +++ |
| 9 | ++++ | ++++ | ++++ |
| 10 | +++ | ++++ | ++++ |
| 11 | ++++ | ++++ | +++ |
| 12 | ++++ | ++++ | +++ |
| 13 | ++++ | ++++ | ++++ |
| 14 | ++++ | +++ | NT |
| 15 | +++ | +++ | +++ |
| 16 | ++++ | ++++ | ++++ |
| 17 | +++ | +++ | +++ |
| 18 | ++++ | ++++ | ++++ |
| 19 | ++++ | ++++ | ++++ |
| 20 | + | NT | NT |
| 21 | ++ | NT | NT |
| 22 | +++ | ++++ | NT |
| 23 | +++ | ++++ | ++++ |
| 24 | +++ | ++++ | ++++ |
| 25 | ++ | NT | NT |
| 26 | ++++ | ++++ | +++ |
| 27 | + | NT | NT |
| 28 | + | NT | NT |
| 29 | ++ | NT | NT |
| 30 | + | NT | NT |
| 31 | ++++ | ++++ | +++ |
| 32 | +++ | ++++ | ++++ |
| 33 | +++ | ++++ | +++ |
| 34 | +++ | ++++ | +++ |
| 35 | +++ | +++ | +++ |
| 36 | +++ | +++ | +++ |
| 37 | +++ | ++ | NT |
| 38 | +++ | +++ | +++ |
| 39 | +++ | +++ | +++ |
| 40 | +++ | ++++ | ++++ |
| 41 | +++ | ++++ | ++++ |
| 42 | +++ | ++++ | ++++ |
| 43 | +++ | +++ | +++ |
| 44 | +++ | ++++ | ++++ |
| 45 | +++ | ++++ | ++++ |
| 46 | +++ | NT | NT |
| 47 | +++ | +++ | +++ |
| 48 | +++ | +++ | ++++ |
| 49 | + | ++ | ++ |
| 50 | + | NT | NT |
| 51 | +++ | ++++ | ++++ |
| 52 | ++++ | ++++ | ++++ |
| 53 | +++ | ++++ | ++++ |
| 54 | ++++ | ++++ | ++++ |
| 55 | ++++ | ++++ | +++ |
| 56 | ++++ | +++ | ++++ |
| 57 | +++ | ++++ | ++++ |
| 58 | +++ | ++++ | +++ |
| 59 | +++ | NT | NT |
| 60 | +++ | +++ | ++++ |
| 61 | +++ | ++++ | ++++ |
| 62 | ++++ | ++++ | NT |
| 63 | ++++ | ++++ | NT |
| 64 | ++++ | +++ | NT |
| 65 | ++++ | ++++ | NT |
| 66 | +++ | ++++ | ++++ |
| 67 | ++++ | ++++ | NT |
| 68 | +++ | ++++ | NT |
| 69 | ++++ | +++ | +++ |
| 70 | +++ | ++++ | +++ |
| 71 | +++ | ++++ | +++ |
| 72 | +++ | ++++ | ++++ |
| 73 | +++ | ++++ | ++++ |
| 74 | ++++ | +++ | NT |

TABLE 2-continued

Inhibitory effects of compounds of formula I versus M-NFS-60, THP-1 and Osteoclast Cells

| Example | M-NFS-60 cell proliferation | Osteoclast assay | pFMS inhibition in THP-1 cells |
|---|---|---|---|
| 75 | ++++ | ++++ | ++++ |
| 76 | +++ | +++ | ++++ |
| 77 | ++++ | ++++ | ++++ |
| 78 | ++++ | ++++ | ++++ |
| 79 | +++ | ++++ | ++++ |
| 80 | ++++ | +++ | ++++ |
| 81 | +++ | +++ | +++ |
| 82 | + | ++ | NT |
| 83 | +++ | +++ | ++ |
| 84 | ++++ | ++++ | ++++ |
| 85 | ++ | +++ | NT |
| 86 | ++++ | +++ | ++++ |
| 87 | ++++ | ++++ | NT |
| 88 | ++++ | ++++ | NT |
| 89 | +++ | +++ | NT |
| 90 | + | +++ | NT |
| 91 | ++++ | ++++ | ++++ |
| 92 | ++++ | ++++ | ++++ |
| 93 | +++ | ++++ | ++++ |
| 94 | +++ | +++ | NT |
| 95 | ++ | +++ | NT |
| 96 | + | ++ | NT |
| 97 | +++ | +++ | +++ |
| 98 | + | ++ | NT |
| 99 | +++ | +++ | ++++ |
| 100 | +++ | ++++ | NT |
| 101 | ++++ | +++ | NT |
| 102 | ++++ | +++ | NT |
| 103 | +++ | +++ | ++++ |
| 104 | ++++ | ++++ | ++++ |
| 105 | +++ | ++++ | NT |
| 106 | ++++ | ++++ | NT |
| 107 | ++ | +++ | +++ |
| 108 | + | +++ | NT |
| 109 | ++++ | +++ | NT |
| 110 | ++ | +++ | NT |
| 111 | ++++ | ++++ | NT |
| 112 | ++ | +++ | NT |
| 113 | +++ | ++++ | +++ |
| 114 | +++ | ++++ | NT |
| 115 | ++ | +++ | NT |
| 116 | +++ | +++ | NT |
| 117 | +++ | +++ | NT |
| 118 | +++ | +++ | NT |
| 119 | +++ | +++ | +++ |
| 120 | +++ | +++ | +++ |
| 121 | +++ | ++++ | NT |
| 122 | ++ | +++ | NT |
| 123 | +++ | ++++ | +++ |
| 124 | +++ | +++ | +++ |
| 125 | ++ | ++++ | +++ |
| 126 | +++ | ++++ | +++ |
| 127 | +++ | ++++ | +++ |
| 128 | + | ++ | NT |
| 129 | ++ | +++ | NT |
| 130 | +++ | +++ | ++++ |
| 131 | +++ | +++ | ++++ |
| 132 | +++ | ++++ | ++++ |
| 133 | ++++ | +++ | NT |
| 134 | ++ | +++ | NT |
| 135 | +++ | ++++ | +++ |
| 136 | ++ | ++ | NT |
| 137 | ++ | +++ | NT |
| 138 | ++ | +++ | NT |
| 139 | ++ | +++ | NT |
| 140 | ++++ | +++ | ++++ |
| 141 | ++ | +++ | NT |
| 142 | ++ | +++ | NT |
| 143 | ++ | +++ | NT |
| 144 | ++++ | ++++ | NT |
| 145 | ++++ | ++++ | ++++ |
| 146 | ++++ | +++ | +++ |
| 147 | +++ | +++ | NT |
| 148 | ++++ | +++ | NT |
| 149 | +++ | +++ | NT |
| 150 | ++++ | +++ | NT |
| 151 | ++++ | ++++ | ++++ |
| 152 | ++++ | +++ | +++ |
| 153 | ++++ | ++++ | NT |
| 154 | +++ | +++ | +++ |
| 155 | +++ | +++ | NT |
| 156 | ++ | +++ | NT |
| 157 | ++ | +++ | NT |
| 158 | +++ | +++ | +++ |
| 159 | +++ | +++ | ++++ |
| 160 | ++++ | +++ | ++++ |
| 161 | +++ | +++ | +++ |
| 162 | ++++ | +++ | NT |
| 163 | +++ | +++ | NT |
| 164 | ++++ | +++ | ++++ |
| 165 | +++ | +++ | +++ |
| 166 | +++ | +++ | NT |
| 167 | ++ | ++ | +++ |
| 168 | +++ | +++ | NT |
| 169 | +++ | +++ | ++++ |
| 170 | ++++ | ++++ | +++ |
| 171 | +++ | +++ | +++ |
| 172 | +++ | ++++ | ++++ |
| 173 | +++ | +++ | ++++ |
| 174 | +++ | +++ | +++ |
| 175 | +++ | +++ | +++ |
| 176 | + | +++ | +++ |

NT: Not Tested; +: $IC_{50} > 1$ uM; ++: $0.1$ uM $< IC_{50} \leq 1$ uM; +++: $0.01$ uM $< IC_{50} \leq 0.1$ uM; ++++: $IC_{50} \leq 0.01$ uM Analysis of cFOS mRNA Production in a c-FMS Mouse Spleen Pharmacodynamic Model To examine the in vivo modulation of FMS activity by compounds of formula I, spleen samples from female DBA/1 mice were collected and analyzed for M-CSF stimulated production of cFOS mRNA. Briefly, six to seven week old female Taconic DBA/1BO J Born Tac mice were treated with a single oral dose (by gavage) of either vehicle or compound. Plasma and spleen samples were collected from four mice at each timepoint 2, 4, 6, 8, 12, 18, and 24 hours after dosing. Fifteen minutes prior to euthanasia, all mice were injected IV with 1 µg (100 µL fixed volume) of M-CSF. M-CSF, Recombinant Mouse Macrophage Colony Stimulating Factor (36.4 kDa homodimer, ≥98% purity) was obtained from Gibco. All procedures carried out in this experiment were conducted in compliance with all the laws, regulations and guidelines of the National Institutes of Health (NIH). cFOS mRNA levels in spleen extracts were determined using a quantitative reverse transcriptase PCR kit from Life Technologies. Plasma levels of FMS inhibitors were determined by mass spectrometer analysis. The degree of FMS inhibition was correlative to the amount of decrease observed in cFOS mRNA levels in the spleen samples of treated animals compared to vehicle.

In this model, Examples 6, 10, 55, 99, 120, 123, 130, 152, and 160 afforded ≥50% inhibition of cFOS mRNA levels out to 8 h post 30 mg/kg dose.

PC-3 Peritibial Implant Model of Cancer Bone Metastasis

To evaluate in vivo anti-cancer activity of compounds of Formula I, the PC-3 M-luc peritibial injection model of bone invasiveness model is employed. Briefly, PC-3 M-luc cells are obtained from Xenogen Corporation (Caliper Life Sciences) and expanded using MEM media modified with L-Glutamine (Cell Gro® #10-045-CV) supplemented with 10% fetal bovine serum, 1% penicillin-streptomycin-glutamine, 1% non-essential amino acids, and 1% MEM vitamins in 5% $CO_2$ atmosphere at 37° C. Six to 7 week old male nude mice (Crl:NU-Foxn1nu) are obtained from Charles River Laboratories. Test mice are implanted peritibially on Day 0 with $1×10^6$ cells/mouse (0.1 mL) using an insulin syringe with a fixed 28-gauge needle. The needle is inserted at the ankle between the tibia and fibula until the bevel of the needle reaches approximately half way between the knee and ankle. Treatments begin on Day 0. Animals are dosed by oral gavage twice daily for the study duration. All procedures carried out in this experiment are conducted in compliance with all the laws, regulations and guidelines of the National Institutes of Health (NIH). When the primary tumor reaches approximately 800 mg in size, ex-vivo micro-CT is performed on the tumor bearing fixed hind limb samples using a GE RS150 small animal micro-CT scanner using with the following settings:

X-ray tube voltage=70 kVp
X-ray tube current=25 mA
Exposure time=20 ms
Number of frames=500
Angle increment between frames=0.4o
Number of averages per frame=2
Acquisition method=Parker Images are then reconstructed at high resolution (100 microns; isotropic). Isosurface volume renderings are used to delineate lesions in the hind limbs. A constant threshold is used to produce consistent representation of the isosurface between different anatomical sites and samples. Lesions in the right hind limb are scored with values of 0, 1, 2, 3, or 4 based on a qualitative assessment of lesion size as defined by:

0: Normal Bone
1: Minimal lesions. Some roughening of the isosurface. Small areas of apparent bone resorption.
2: Mild. More numerous lesions. Significant roughening of the isosurface. Full thickness lesions apparent.
3: Moderate. Full thickness lesions larger and more numerous.
4: Marked. Many, large, full thickness lesions. Significant distortion of remaining structure. Marked bone loss.

U251 Intra-Cerebro-Ventricular Implant in Mice

To evaluate in vivo anti-cancer activity compounds of Formula I in combination with fractionated, localized head radiation, an orthotopic U251-luc (Luc) human glioma carcinoma model in female outbred nu/nu mice is employed. Briefly, U251 cells are obtained from the ATCC and altered to be luciferase expressing. They are grown in RPMI 1640 Media supplemented with 10% FBS and 1% PSG. The growth environment is maintained in an incubator with a 5% $CO_2$ atmosphere at 37° C. Female Harlan Nude mice (Hsd:Athymic-Nude-Fox1nu) 8-9 weeks old are used in this study. Test animals are implanted intracranially with U251-luc (Lucm-Cherry) cells. Briefly, animals are injected subcutaneously with 5 mg/kg carprofen and anesthetized using 2% isoflurane in air. The animals are then secured in a stereotaxic frame (ASIinstruments, Inc.) and a hole drilled 2 mm right lateral, 1 mm anterior to the coronal suture. The cell suspension (stored on wet ice) is mixed thoroughly and drawn up into a 50 μl syringe. The syringe needle is centered over the burr hole and lowered 3 mm into the brain and retracted 1 mm to form a "reservoir" for the deposition of the cell suspension. 10 μl of the cell suspension ($1×10^6$ cells/mouse) is then injected slowly into the brain tissue. The tumor progression is tracked with in vivo bioluminescence imaging performed using an IVIS 50 optical imaging system (Xenogen, Alameda, Calif.). Bioluminescence images are acquired at periodic intervals for tumor burden estimation. All procedures carried out in this experiment are conducted in compliance with all the laws, regulations and guidelines of the National Institutes of Health (NIH). Treatment begins when the mean brain bioluminescence signal for all groups in the experiment is ~$1.3×10^9$ photons/sec (typically 9 days post-implant). All mice receive 2Gy of radiation each day for five consecutive days from a RadSource RS-2000 irradiator. Additionally, mice receive test compound dosed by oral gavage or optionally with co-administered bevacizumab by tail vein injection. Bioluminescence images are acquired generally on days 8, 10, 14, 17, 21, 22, 24, 28 and 35 post-implant for tumor burden estimation. For each measurement, each mouse is injected subcutaneously with 150 mg/kg D-Luciferin (Promega) and imaged 10 minutes after the injection. Images are analyzed using Living Image (Xenogen, Alameda, Calif.) software. The BLI signal in the brain is calculated with a fixed area ROI to estimate the tumor burden. Average BLI signal for each group is compared to vehicle control to determine therapeutic benefit. Twenty-eight days after the first radiation treatment mice are euthanized, via over-exposure to carbon dioxide, for blood and brain collection. Whole blood is collected via terminal cardiac puncture and placed into EDTA Microtainer® tubes. Brains are excised and placed into 10% neutral buffered formalin.

GL261 Intracranial Implant Model

To evaluate the in vivo anti-cancer activity of compounds of formula I, an intracranial implant of GL261-luc2 murine glioma is employed. Briefly GL261-luc2 cells are obtained from Caliper Life Sciences, Inc and expanded in Dulbecco's Modified Eagle Media (DMEM) which is supplemented with 10% FBS and 1% PSG. The growth environment is maintained in an incubator with a 5% $CO_2$ atmosphere at 37° C. Following expansion, cells are re-suspended using serum-free media to generate a concentration of $1×10^8$ cells/mL. Six to seven week old female C57BL/6J-Tyrc-2J/J from Jackson Labs are implanted intracranially on Day 0 with GL261-luc2 cells. For aseptic surgical implantation, animals are injected subcutaneously with 5 mg/kg carprofen, anesthetized using 2% isoflurane in air. The animals are then secured in a stereotaxic frame (ASIinstruments, Inc.) and a hole is drilled 2 mm right lateral, 1 mm anterior to the coronal suture. The cell suspension (stored on wet ice) is mixed thoroughly and drawn up into a 50 μL syringe. The syringe needle is centered over the burr hole and lowered 3 mm into the brain and retracted 1 mm to form a "reservoir" for the deposition of the cell suspension. 10 μL of the cell suspension ($1×10^6$ cells/mouse) is then injected slowly into the brain tissue. The tumor progression is tracked with in vivo bioluminescence imaging performed using an IVIS 50 optical imaging system (Xenogen, Alameda, Calif.). Bioluminescence images are acquired at periodic intervals for tumor burden estimation. The quantity of emitted light from the tumor after systemic injection of D-Luciferin is expected to correlate with tumor size. Each mouse is injected intraperitoneally (IP) with 150 mg/kg D-Luciferin and imaged in the prone position 10 minutes after the injection. Medium and small binning of the CCD chip is used, and the exposure time is adjusted (10 seconds to 1 minute) to obtain at least several hundred counts from the tumors and to avoid saturation of the CCD chip. Images are analyzed using Living Image (Xenogen, Alameda, Calif.) software. Each unique signal is circled manually and labeled by group and mouse number. Treatment begins by oral gavage of test compound when the mean brain bioluminescence signal for all groups in the experiment is $280×10^6$ photons/sec. All procedures carried out in this experiment are conducted in compliance with all the laws, regulations and guidelines of the National Institutes of Health (NIH). At the end of study all mice are euthanized via over-exposure to carbon dioxide for blood and brain collection. Whole blood is collected via terminal cardiac puncture and placed into EDTA Microtainer® tubes. Brains are excised and placed into 10% neutral buffered formalin.

MDA-MB-231 Xenograft Study

To evaluate the in vivo anti-cancer activity compounds of formula I, a MDA-MB-231-luc-D3H2LN human breast carcinoma xenograft is employed. Briefly, MDA-MB-231-luc-D3H2LN cells are obtained from Xenogen and expanded in Minimal Essential Media (MEM) with EBSS which is modified with 1% L-glutamine and supplemented with 10% FBS, 1% PSG, 1% non-essential amino acids, and 1% sodium pyruvate. The growth environment is maintained in an incubator with a 5% $CO_2$ atmosphere at 37° C. Cells are harvested and re-suspended using 50% serum-free media and 50% Matrigel® to generate a stock concentration of $5 \times 10^6$ cells/mL.

Six to 7 week old female C.B-17/IcrHsd-PrkdcscidLystbg mice are injected with 200 μL of cell suspension subcutaneously, just below the right axilla. All procedures carried out in this experiment are conducted in compliance with all the laws, regulations and guidelines of the National Institutes of Health (NIH). Treatment begins when the mean tumor burden is approximately 150 mg. All mice are dosed with test compound by oral gavage. Body weights and tumor measurements are recorded three times weekly. Tumor burden (mg) is estimated from caliper measurements by the formula for the volume of a prolate ellipsoid assuming unit density as: Tumor burden (mg)=(L×W2)/2, where L and W are the respective orthogonal tumor length and width measurements (mm). The primary endpoints to evaluate efficacy is % T/C. % T/C is defined as the median tumor mass of a Treated Group divided by the median tumor mass of the Control Group×100. Ex vivo bioluminescence imaging is performed as animals exit the study, using an IVIS 50 optical imaging system (Xenogen, Alameda, Calif.). Animals are injected IP with 150 mg/kg D-Luciferin (Promega) and euthanized 10 minutes following the injection. The primary tumor is removed and snap frozen for future analysis and the mouse opened and imaged in the supine position. Large binning of the CCD chip is used, and the exposure time is adjusted (1 to 2 minutes) to obtain at least several hundred counts from the tumors and to avoid saturation of the CCD chip. Images are analyzed using Living Image (Xenogen, Alameda, Calif.) software. Each unique signal is circled manually and labeled by group and mouse number. Total BLI signal is correlative to tumor size and compared to vehicle control to determine treatment benefit.

Compounds with structures similar to certain compounds of Formula I have been previously disclosed in WO2010/051373 as inhibitors of cMET, c-KIT, KDR, c-FMS and PDGFRa/b kinases, specifically examples 44 and 56 cited within WO2010/051373. These compounds were disclosed as part of a broader genus defined by Formula If. These compounds of WO2010/051373 differ from the compounds of the instant invention (Formula I) by the presence of an aromatic "A" moiety selected from the group consisting of indanyl, tetrahydronapthyl, thienyl, phenyl, naphthyl, pyrazinyl, pyridazinyl, triazinyl, pyridinyl, and pyrimidinyl. The compounds of the instant invention have an A moiety moiety that is optionally substituted alkyl, cycloalkyl or non-aromatic heterocyclyl.

It has unexpectedly been found that compounds of the instant invention which include only non-aromatic "A" moieties frequently exhibit much greater kinase selectivity than examples 44 and 56 of WO2010/051373, especially toward c-FMS kinase. In addition to an enhanced selectivity profile unexpectedly afforded by the changing of the A-moiety in the instant invention to a non-aromatic group, the selectivity profile of many compounds of the instant invention is further enhanced toward c-FMS kinase by the discovery of additional optimal substituents at the X2 position and the W-position of Formula I.

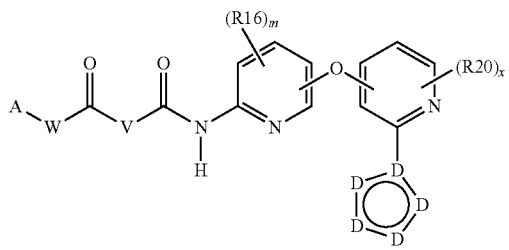

Formula If

WO2010/051373

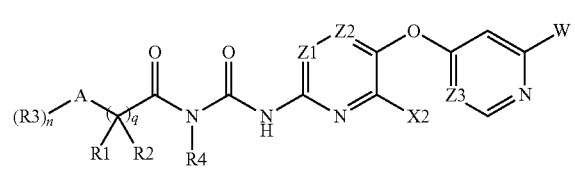

Instant Invention Formula I

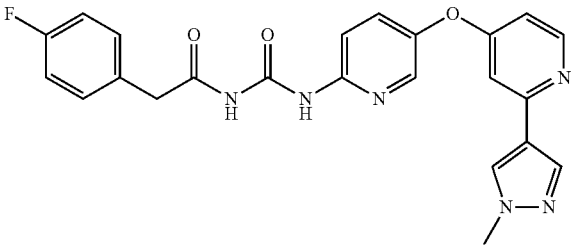

Ex 44

WO2010/051373

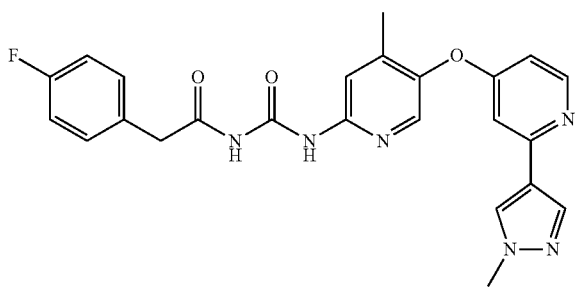

Ex 56

WO2010/051373

Comparative data for examples 44 and 56 of WO2010/051373 and representative compounds of the instant invention are illustrated in table 3 below along with chemical structures. As evidenced by entries 1 and 2 of table 3, the two examples from WO2010/051373 are potent c-FMS kinase inhibitors, but only 4.7-6.8 fold more potent against uFMS than against unphosphorylated KIT (uKIT) kinase and only 2-8 fold more potent versus uFMS than against unphosphorylated PDGFR-β (uPDGFR-β) kinase. Entry 3 of table 3 illustrates that example 4 of the instant invention improves the selectivity of uFMS over uKIT and uPDGFR to about 20-fold, compared to 4.7-8 fold for entry 1. The only difference in structure between entries 1 and 3 is the nature of the A moiety. Entries 4 and 5 of table 3 further illustrate that shorter alkyl "A" moieties unexpectedly afford even greater selectivity for FMS, being 50-260 fold more potent for uFMS versus uKIT and more than 200 fold more potent for uFMS versus uPDGFR kinase. Entries 6-7 of table 3 illustrate that placement of a non-hydrogen substituent in the X2 position of Formula I further enhances selectivity toward uFMS kinase, when compared with entries 3 and 4 respectively. This finding was not anticipated by the teaching of WO2010/051373 where the only example of Formula If with a non-hydrogen R16 moiety (example 56, table 3 entry 2) displayed nearly identical selectivity toward uKIT compared with WO2010/051373 example 44 (table 3 entry 1). Entries 8-11 of table 3 illustrate that W-moieties other than pyrazole also unexpectedly afford enhanced selectivity for uFMS kinase in the presence of certain substituents at the A- and X2 positions of Formula I. This additional novel finding could not have been anticipated from WO2010/051373 which contained only pyrazoles as working examples. Examples 3-11 further illustrate that compounds of Formula I retain high selectivity versus cMET and KDR kinase. Taken together, these results support that the compounds of the instant invention display unexpected properties as selective inhibitors of FMS kinase, in spite of their similarity to compounds of WO2010/051373.

Example 4

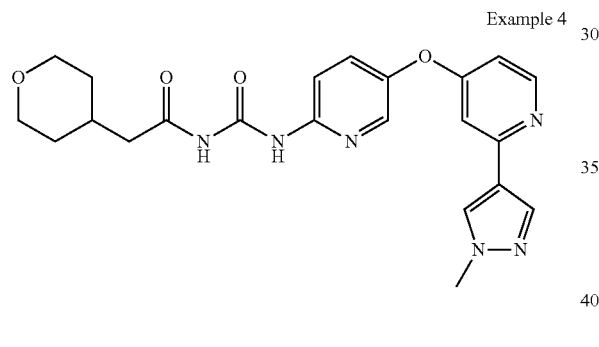

Example 24

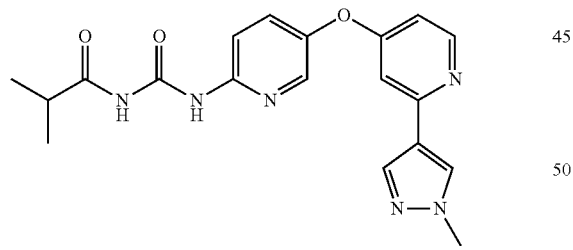

Example 55

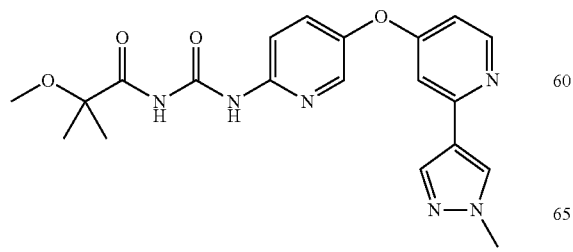

Example 8

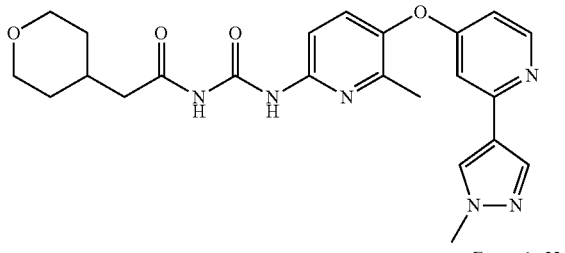

Example 23

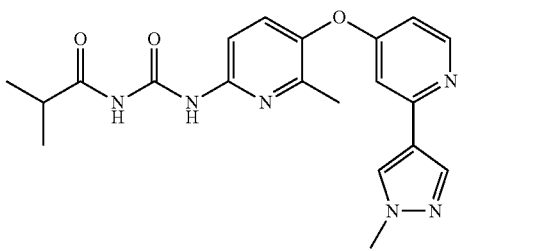

Example 56

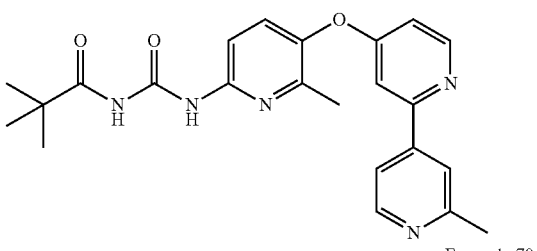

Example 70

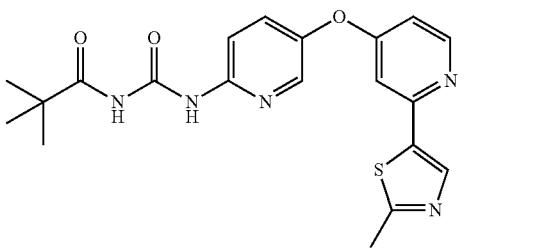

Example 99

Example 151

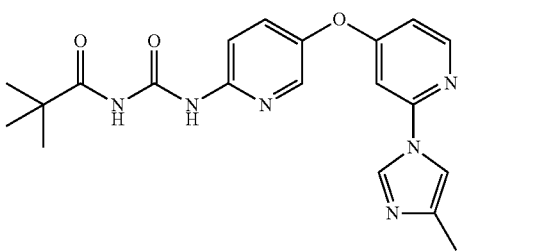

TABLE 3

| Entry | Compound | IC$_{50}$ (nM) | | | | |
|---|---|---|---|---|---|---|
| | | uFMS | uKIT | uPDGFRβ | cMET | KDR |
| 1 | WO2010/051373 Ex 44 | 3 | 14 | 24 | 558 | 2,400 |
| 2 | WO2010/051373 Ex 56 | 4 | 27 | 8 | 1,400 | 1,600 |
| 3 | Example 4 | 8 | 165 | 168 | >5,000 | >3,300 |
| 4 | Example 24 | 4 | 215 | >3,300 | NT | >3,300 |
| 5 | Example 55 | 5 | 1,300 | 1,100 | >5,000 | >3,300 |
| 6 | Example 8 | 12 | 1,700 | 1,600 | NT | >3,300 |
| 7 | Example 23 | 5 | 1,100 | >3,300 | >5,000 | >3,300 |
| 8 | Example 56 | 4 | 3,100 | 2,800 | >5,000 | >3,300 |
| 9 | Example 70 | 4 | 2,600 | 922 | >5,000 | >3,300 |
| 10 | Example 99 | 4 | 4,000 | 366 | >5,000 | >10,000 |
| 11 | Example 151 | 5 | 2,100 | 2,300 | >5,000 | >3,300 |

What is claimed is:

1. A compound of Formula I,

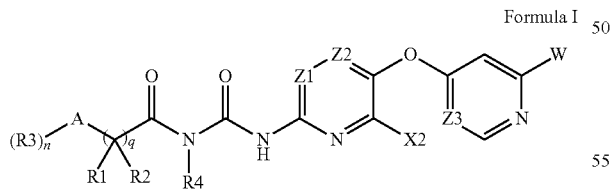

Formula I or a pharmaceutically acceptable salt, enantiomer, stereoisomer, or tautomer thereof, wherein:

A is selected from the group consisting of C1-C6 alkyl, deutero-C1-C6 alkyl wherein the alkyl chain is partially or completely deuterated, branched C3-C8 alkyl, fluoroC1-C6alkyl wherein the alkyl is fully or partially fluorinated, C3-C8carbocyclyl, C6-C12 spirobicycloalkyl, adamantyl, bicyclo[2.2.1]heptanyl, and bicyclo[2.2.2]octyl, and wherein each A moiety may be further substituted with one, two, or three R3 moieties;

W is a pyrrolyl, furanyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, triazinyl, or phenyl, and wherein each W is optionally substituted by one, two, or three R5;

each X1, X2, and X3 is individually and independently hydrogen, C1-C6 alkyl, or fluoro-C1-C6 alkyl wherein the alkyl chain is partially or completely fluorinated;

Z1 is CX3;

Z2 is CX1;

Z3 is CH;

each R1 and R2 is individually and independently H, C1-C6 alkyl, fluoroC1-C6alkyl wherein the alkyl is fully or partially fluorinated, hydroxyl, C1-C6 alkoxy, fluoroC1-C6alkoxy wherein the alkyl group is fully or partially fluorinated, or cyano;

each R3 is individually and independently H, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano;

each R4 is individually and independently hydrogen;

each R5 is individually and independently hydrogen, C1-C6 alkyl, deutero-C1-C6 alkyl wherein the alkyl chain is partially or completely deuterated, branched C3-C8 alkyl, halogen, cyano, fluoro-C1-C6 alkyl wherein the alkyl chain is partially or completely fluorinated, —(CH$_2$)$_m$—C(O)NR8(R9), —(CH$_2$)$_m$—C(O)R7, —(CH$_2$)$_m$—CN, (CH$_2$)$_m$—NR8(R9), or —(CH$_2$)$_m$—R7;

each R7 is independently and individually selected from the group consisting of

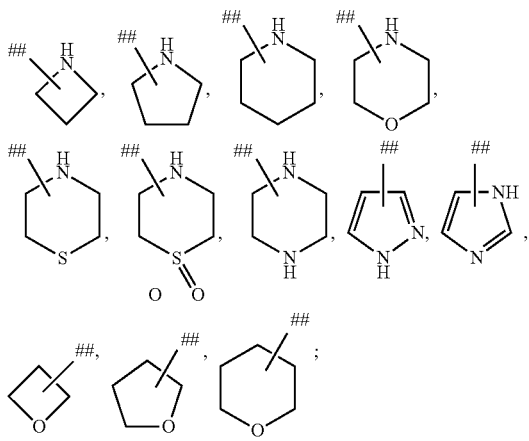

and wherein the symbol (##) is the point of attachment to R5 moieties containing a R7 moiety;

each R7 is optionally substituted with —(R10)$_p$;

each R8 and R9 is individually and independently H, C1-C6 alkyl, fluoro-C1-C6 alkyl wherein the alkyl chain is partially or completely fluorinated, or branched C3-C8 alkyl;

each R10 is C1-C6 alkyl;

each m is individually and independently 0, 1, 2, or 3;

each n is individually and independently 0, 1, 2, or 3;

each p is 0, 1, 2, or 3; and each q is 0, 1, 2, or 3.

2. The compound of claim 1, wherein W is selected from the group consisting of pyrazolyl, imidazolyl, isoxazolyl, oxazolyl, thiazolyl, triazolyl, pyridinyl, and phenyl.

3. The compound of claim 2, wherein the compound is a compound of Formula Ia,

Formula Ia

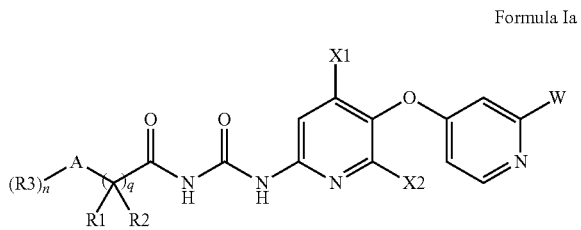

or a pharmaceutically acceptable salt, enantiomer, stereoisomer, or tautomer thereof, wherein the A moiety is selected from C1-C6 alkyl, branched C3-C8alkyl, fluoroC1-C6alkyl wherein the alkyl is fully or partially fluorinated, or C3-C8carbocyclyl.

4. The compound of claim 3, wherein W is pyrazolyl, imidazolyl, pyridinyl, phenyl, or oxazolyl, wherein each W is optionally substituted with —(R5)$_p$.

5. The compound of claim 4, wherein X1 is H and X2 is C1-C6 alkyl.

6. The compound of claim 4 wherein X1 is C1-C6 alkyl and X2 is H.

7. The compound of claim 4 wherein X1 and X2 are H.

8. The compound of claim 4, wherein the compound is a compound of Formula Ib,

Formula Ib

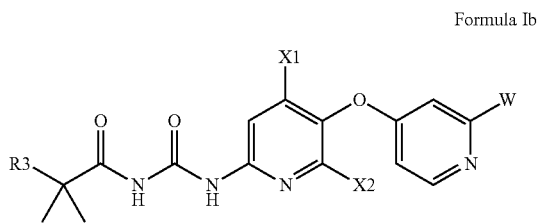

wherein R3 is C1-C6alkyl, hydrogen or C1-C6alkoxy, or a pharmaceutically acceptable salt, enantiomer, stereoisomer, or tautomer thereof.

9. The compound of claim 8, wherein X1 is H and X2 is C1-C6 alkyl.

10. The compound of claim 8 wherein X1 is C1-C6 alkyl and X2 is H.

11. The compound of claim 8 wherein X1 and X2 are H.

12. The compound of claim 4, wherein the compound is a compound of Formula Ic,

Formula Ic

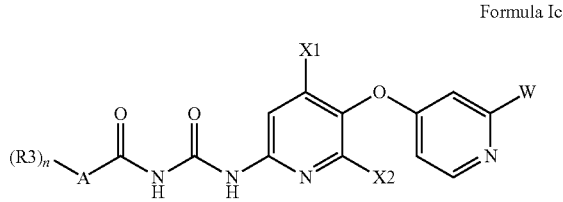

or a pharmaceutically acceptable salt, enantiomer, stereoisomer, or tautomer thereof, wherein A is C3-C8 carbocyclyl and R3 is C1-C6alkyl, hydrogen or C1-C6alkoxy.

13. The compound of claim 12, wherein X1 is H and X2 is C1-C6 alkyl.

14. The compound of claim 12 wherein X1 is C1-C6 alkyl and X2 is H.

15. The compound of claim 12 wherein X1 and X2 are H.

16. The compound of claim 1 selected from the group consisting of trans-3-fluoro-3-methyl-N-((5-((2-(1-methyl-1H-pyrazol-4-yl)pyridin-4-yl)oxy)pyridin-2-yl)carbamoyl) cyclobutanecarboxamide, 3,3-dimethyl-N-((5-((2-(1-methyl-1H-pyrazol-4-yl)pyridin-4-yl)oxy)pyridin-2-yl) carbamoyl)cyclobutanecarboxamide, N-((5-((2-(1-methyl-1H-pyrazol-4-yl)pyridin-4-yl)oxy)pyridin-2-yl)carbamoyl)-3-(1-(trifluoromethyl)cyclopropyl)propanamide, 3,3-dimethyl-N-((5-((6-(1-methyl-1H-pyrazol-4-yl)pyrimidin-4-yl)oxy)pyridin-2-yl)carbamoyl)cyclobutanecarboxamide, N-((6-methyl-5-((2-(1-methyl-1H-pyrazol-4-yl)pyridin-4- yl)oxy)pyridin-2-yl)carbamoyl)pivalamide, N-((6-methyl-5-((2-(1-methyl-1H-pyrazol-4-yl)pyridin-4-yl)oxy)pyridin-2-yl)carbamoyl)propionamide, trans-4-methyl-N-((6-methyl-5-((2-(1-methyl-1H-pyrazol-4-yl)pyridin-4-yl)oxy)pyridin-2-yl)carbamoyl)cyclohexanecarboxamide, N-((6-methyl-5-((2-(1-methyl-1H-pyrazol-4-yl)pyridin-4-yl)oxy)pyridin-2-yl)carbamoyl)-3-(1-(trifluoromethyl)cyclopropyl)propanamide, 4,4-difluoro-N-((6-methyl-5-((2-(1-methyl-1H-pyrazol-4-yl)pyridin-4-yl)oxy)pyridin-2-yl)carbamoyl)cyclohexanecarboxamide, 3,3-dimethyl-N-((6-methyl-5-((2-(1-methyl-1H-pyrazol-4-yl)pyridin-4-yl)oxy)pyridin-2-yl)carbamoyl)cyclobutanecarboxamide, 3,3-dimethyl-N-((6-methyl-5-((2-(3-methylisoxazol-5-yl)pyridin-4-yl)oxy)pyridin-2-yl)carbamoyl)cyclobutanecarboxamide, N-((6-methyl-5-((2-(1-methyl-1H-pyrazol-4-yl)pyridin-4-yl)oxy)pyridin-2-yl)carbamoyl)-3-oxocyclobutanecarboxamide, N-((6-methyl-5-((2-(1-methyl-1H-pyrazol-4-yl)pyridin-4-yl)oxy)pyridin-2-yl)carbamoyl)cyclohexanecarboxamide, N-((6-methyl-5-((2-(1-methyl-1H-pyrazol-4-yl)pyridin-4-yl)oxy)pyridin-2-yl)carbamoyl)cyclobutanecarboxamide, N-((6-methyl-5-((2-(1-methyl-1H-pyrazol-4-yl)pyridin-4-yl)oxy)pyridin-2-yl)carbamoyl)cyclopentanecarboxamide, 2-methoxy-N-((6-methyl-5-((2-(1-methyl-1H-pyrazol-4-yl)pyridin-4-yl)oxy)pyridin-2-yl)carbamoyl)acetamide, 2-methoxy-N-((5-((2-(1-methyl-1H-pyrazol-4-yl)pyridin-4-yl)oxy)pyridin-2-yl)carbamoyl)acetamide, 3,3-difluoro-N-((6-methyl-5-((2-(1-methyl-1H-pyrazol-4-yl)pyridin-4-yl)oxy)pyridin-2-yl)carbamoyl)cyclobutanecarboxamide, N-((6-methyl-5-((2-(1-methyl-1H-pyrazol-4-yl)pyridin-4-yl)oxy)pyridin-2-yl)carbamoyl)isobutyramide, N-((5-((2-(1-methyl-1H-pyrazol-4-yl)pyridin-4-yl)oxy)pyridin-2-yl)carbamoyl)isobutyramide, 4-methoxy-N-((6-methyl-5-((2-(1-methyl-1H-pyrazol-4-yl)pyridin-4-yl)oxy)pyridin-2-yl)carbamoyl)butanamide, N-((5-((2-(1-methyl-1H-pyrazol-4-yl)pyridin-4-yl)oxy)pyridin-2-yl)carbamoyl)pivalamide, 1-cyano-N-((5-((2-(1-methyl-1H-pyrazol-4-yl)pyridin-4-yl)oxy)pyridin-2-yl)carbamoyl)cyclopropanecarboxamide, 1-cyano-N-((6-methyl-5-((2-(1-methyl-1H-pyrazol-4-yl)pyridin-4-yl)oxy)pyridin-2-yl)carbamoyl)cyclopropanecarboxamide, 2-cyano-2-methyl-N-((6-methyl-5-((2-(1-methyl-1H-pyrazol-4-yl)pyridin-4-yl)oxy)pyridin-2-yl)carbamoyl)propanamide, 2-cyano-2-methyl-N-((5-((2-(1-methyl-1H-pyrazol-4-yl)pyridin-4-yl)oxy)pyridin-2-yl)carbamoyl)propanamide, N-((5-((2-(1-methyl-1H-pyrazol-4-yl)pyridin-4-yl)oxy)pyridin-2-yl)carbamoyl)spiro[3.3]heptane-2-carboxamide, N-((6-methyl-5-((2-(1-methyl-1H-pyrazol-4-yl)pyridin-4-yl)oxy)pyridin-2-yl)carbamoyl)spiro[3.3]heptane-2-carboxamide, N-((5-((2-(1-methyl-1H-pyrazol-4-yl)pyridin-4-yl)oxy)pyridin-2-yl)carbamoyl)-1-(trifluoromethyl)cyclopropanecarboxamide, N-((6-methyl-5-((2-(1-methyl-1H-pyrazol-4-yl)pyridin-4-yl)oxy)pyridin-2-yl)carbamoyl)-1-(trifluoromethyl)cyclopropanecarboxamide, 3,3,3-trifluoro-2,2-dimethyl-N-((5-((2-(1-methyl-1H-pyrazol-4-yl)pyridin-4-yl)oxy)pyridin-2-yl)carbamoyl)propanamide, 3,3,3-trifluoro-2,2-dimethyl-N-((6-methyl-5-((2-(1-methyl-1H-pyrazol-4-yl)pyridin-4-yl)oxy)pyridin-2-yl)carbamoyl)propanamide, N-((6-methyl-5-((2-(1-methyl-1H-pyrazol-4-yl)pyridin-4-yl)oxy)pyridin-2-yl)carbamoyl)adamantane-1-carboxamide, N-((5-((2-(1-methyl-1H-pyrazol-4-yl)pyridin-4-yl)oxy)pyridin-2-yl)carbamoyl)adamantane-1-carboxamide, N-((6-methyl-5-((6'-methyl-[2,3'-bipyridin]-4-yl)oxy)pyridin-2-yl)carbamoyl)pivalamide, N-((5-((2-(1-(trideuteromethyl)-1H-pyrazol-4-yl)pyridin-4-yl)oxy)pyridin-2-yl)carbamoyl)isobutyramide, N-((6-methyl-5-((2-(1-(trideuteromethyl)-1H-pyrazol-4-yl)pyridin-4-yl)oxy)pyridin-2-yl)carbamoyl)isobutyramide, N-((6-methyl-5-((2-(1-(trideuteromethyl)-1H-pyrazol-4-yl)pyridin-4-yl)oxy)pyridin-2-yl)carbamoyl)pivalamide, trans-N-((6-methyl-5-((2-(1-methyl-1H-pyrazol-4-yl)pyridin-4-yl)oxy)pyridin-2-yl)carbamoyl)-4-(trifluoromethyl)cyclohexanecarboxamide, trans-N-((5-((2-(1-methyl-1H-pyrazol-4-yl)pyridin-4-yl)oxy)pyridin-2-yl)carbamoyl)-4-(trifluoromethyl)cyclohexanecarboxamide, 2-cyclohexyl-N-((6-methyl-5-((2-(1-methyl-1H-pyrazol-4-yl)pyridin-4-yl)oxy)pyridin-2-yl)carbamoyl)acetamide, 4,4,4-trifluoro-3,3-dimethyl-N-((6-methyl-5-((2-(1-methyl-1H-pyrazol-4-yl)pyridin-4-yl)oxy)pyridin-2-yl)carbamoyl)butanamide, 4,4,4-trifluoro-3,3-dimethyl-N-((5-((2-(1-methyl-1H-pyrazol-4-yl)pyridin-4-yl)oxy)pyridin-2-yl)carbamoyl)butanamide, N-((5-((2-(1-methyl-1H-pyrazol-4-yl)pyridin-4-yl)oxy)pyridin-2-yl)carbamoyl)cyclopropanecarboxamide, 1-methyl-N-((5-((2-(1-methyl-1H-pyrazol-4-yl)pyridin-4-yl)oxy)pyridin-2-yl)carbamoyl)cyclopropanecarboxamide, N-((6-methyl-5-((2-(1-methyl-1H-pyrazol-4-yl)pyridin-4-yl)oxy)pyridin-2-yl)carbamoyl)cyclopropanecarboxamide, 1-methyl-N-((6-methyl-5-((2-(1-methyl-1H-pyrazol-4-yl)pyridin-4-yl)oxy)pyridin-2-yl)carbamoyl)cyclopropanecarboxamide, 2-methoxy-2-methyl-N-((5-((2-(1-methyl-1H-pyrazol-4-yl)pyridin-4-yl)oxy)pyridin-2-yl)carbamoyl)propanamide, N-((6-methyl-5-((2'-methyl-[2,4'-bipyridin]-4-yl)oxy)pyridin-2-yl)carbamoyl)pivalamide, 2-methoxy-2-methyl-N-((6-methyl-5-((2-(1-methyl-1H-pyrazol-4-yl)pyridin-4-yl)oxy)pyridin-2-yl)carbamoyl)propanamide, N-((6-methyl-5-((2-(1-methyl-1H-pyrazol-4-yl)pyridin-4-yl)oxy)pyridin-2-yl)carbamoyl)-4-(trifluoromethoxy)butanamide, N-((5-((2-(1-ethyl-1H-pyrazol-4-yl)pyridin-4-yl)oxy)-6-methylpyridin-2-yl)carbamoyl)pivalamide, N-((5-((2-(1-ethyl-1H-pyrazol-4-yl)pyridin-4-yl)oxy)-6-methylpyridin-2-yl)carbamoyl)isobutyramide, 2-(bicyclo[2.2.1]heptan-2-yl)-N-((5-((2-(1-methyl-1H-pyrazol-4-yl)pyridin-4-yl)oxy)pyridin-2-yl)carbamoyl)acetamide, 2,2-dimethyl-N-((5-((2-(1-methyl-1H-pyrazol-4-yl)pyridin-4-yl)oxy)pyridin-2-yl)carbamoyl)butanamide, N-((5-((2-(1-methyl-1H-pyrazol-4-yl)pyridin-4-yl)oxy)pyridin-2-yl)carbamoyl)bicyclo[2.2.1]heptane-2-carboxamide, N-((5-((2-(1-methyl-1H-pyrazol-4-yl)pyridin-4-yl)oxy)pyridin-2-yl)carbamoyl)cyclopentanecarboxamide, N-((5-((2-(1-methyl-1H-pyrazol-4-yl)pyridin-4-yl)oxy)pyridin-2-yl)carbamoyl)cyclohexanecarboxamide, 2,2-dimethyl-N-((6-methyl-5-((2-(1-methyl-1H-pyrazol-4-yl)pyridin-4-yl)oxy)pyridin-2-yl)carbamoyl)butanamide, N-((5-((2-(2-methylthiazol-5-yl)pyridin-4-yl)oxy)pyridin-2-yl)carbamoyl)pivalamide, N-((6-methyl-5-((6'-methyl-[2,3'-bipyridin]-4-yl)oxy)pyridin-2-yl)carbamoyl)isobutyramide, 2-methoxy-2-methyl-N-((5-((6'-methyl-[2,3'-bipyridin]-4-yl)oxy)pyridin-2-yl)carbamoyl)propanamide, N-((5-((6'-methyl-[2,3'-bipyridin]-4-yl)oxy)pyridin-2-yl)carbamoyl)pivalamide, N-((5-((2-(1-methyl-1H-pyrazol-4-yl)pyridin-4-yl)oxy)pyridin-2-yl)carbamoyl)bicyclo[2.2.2]octane-2-carboxamide, N-((5-((2-(4-(1-methylpiperidin-4-yl)phenyl)pyridin-4-yl)oxy)pyridin-2-yl)carbamoyl)isobutyramide, N-((6-methyl-5-((2-(3-methylisoxazol-5-yl)pyridin-4-yl)oxy)pyridin-2-yl)carbamoyl)pivalamide, 1-methoxy-N-((5-((2-(1-methyl-1H-pyrazol-4-yl)pyridin-4-yl)oxy)pyridin-2-yl)carbamoyl)cyclopropanecarboxamide, 1-methoxy-N-((6-methyl-5-((2-(1-methyl-1H-pyrazol-4-yl)pyridin-4-yl)oxy)pyridin-2-yl)carbamoyl)cyclopropanecarboxamide, N-((6-methyl-5-((2'-methyl-[2,4'-bipyridin]-4-yl)oxy)pyridin-2-yl)carbamoyl)isobutyramide, N-((5-((2'-methyl-[2,4'-bipyridin]-4-yl)oxy)pyridin-2-yl)carbamoyl)pivalamide, N-((6-ethyl-5-((2-(1-methyl-1H-pyrazol-4-yl)pyridin-4-yl)oxy)pyridin-2-yl)carbamoyl)pivalamide, N-((5-((2-(1-methyl-1H-pyrazol-4-yl)pyridin-4-yl)oxy)-6-(trifluoromethyl)pyridin-2-yl)

carbamoyl)isobutyramide, N-((4-methyl-5-((2-(1-methyl-1H-pyrazol-4-yl)pyridin-4-yl)oxy)pyridin-2-yl)carbamoyl)pivalamide, N-((6-methyl-5-((2-(2-methylthiazol-5-yl)pyridin-4-yl)oxy)pyridin-2-yl)carbamoyl)pivalamide, 1-methyl-N-((5-((2-(1-methyl-1H-pyrazol-4-yl)oxy)pyridin-2-yl)carbamoyl)cyclobutanecarboxamide, N-((4-methyl-5-((2-(1-methyl-1H-pyrazol-4-yl)pyridin-4-yl)oxy)pyridin-2-yl)carbamoyl)isobutyramide, N-((5-((2-(pyrimidin-5-yl)pyridin-4-yl)oxy)pyridin-2-yl)carbamoyl)pivalamide, 2-methoxy-2-methyl-N-((4-methyl-5-((2-(1-methyl-1H-pyrazol-4-yl)pyridin-4-yl)oxy)pyridin-2-yl)carbamoyl)propanamide, 1-methyl-N-((6-methyl-5-((2-(1-methyl-1H-pyrazol-4-yl)pyridin-4-yl)oxy)pyridin-2-yl)carbamoyl)cyclobutanecarboxamide, N-((5-((2-(oxazol-5-yl)pyridin-4-yl)oxy)pyridin-2-yl)carbamoyl)pivalamide, N-((5-((6'-(trifluoromethyl)-[2,3'-bipyridin]-4-yl)oxy)pyridin-2-yl)carbamoyl)pivalamide, N-((5-((2'-(trifluoromethyl)-[2,4'-bipyridin]-4-yl)oxy)pyridin-2-yl)carbamoyl)pivalamide, N-((6-methyl-5-((2'-morpholino-[2,4'-bipyridin]-4-yl)oxy)pyridin-2-yl)carbamoyl)isobutyramide, 2-methoxy-2-methyl-N-((6-methyl-5-((6'-methyl-[2,3'-bipyridin]-4-yl)oxy)pyridin-2-yl)carbamoyl)propanamide, N-((5-((2-(2-methylthiazol-5-yl)pyridin-4-yl)oxy)pyridin-2-yl)carbamoyl)propionamide, N-((5-((2-(4-methyl-1H-imidazol-1-yl)pyridin-4-yl)oxy)pyridin-2-yl)carbamoyl)pivalamide, N-((6-methyl-5-((6'-methyl-[2,3'-bipyridin]-4-yl)oxy)pyridin-2-yl)carbamoyl)cyclopentanecarboxamide, N-((5-((2-(1-methyl-1H-pyrazol-4-yl)pyridin-4-yl)oxy)pyridin-2-yl)carbamoyl)-1-(trifluoromethyl)cyclobutanecarboxamide, N-((6-methyl-5-((2-(1-methyl-1H-pyrazol-4-yl)pyridin-4-yl)oxy)pyridin-2-yl)carbamoyl)-1-(trifluoromethyl)cyclobutanecarboxamide, N-((5-((2-(1-methyl-1H-imidazol-4-yl)pyridin-4-yl)oxy)pyridin-2-yl)carbamoyl)pivalamide, N-((5-((6'-(methylamino)-[2,3'-bipyridin]-4-yl)oxy)pyridin-2-yl)carbamoyl)pivalamide, N-((5-((6'-amino-[2,3'-bipyridin]-4-yl)oxy)pyridin-2-yl)carbamoyl)pivalamide, N-((5-((6'-cyano-[2,3'-bipyridin]-4-yl)oxy)-6-methylpyridin-2-yl)carbamoyl)pivalamide, N-((5-((6'-methyl-[2,3'-bipyridin]-4-yl)oxy)pyridin-2-yl)carbamoyl)propionamide, N-((6-methyl-5-((2-(4-(1-methylpiperidin-4-yl)phenyl)pyridin-4-yl)oxy)pyridin-2-yl)carbamoyl)pivalamide, N-((5-((6'-cyano-[2,3'-bipyridin]-4-yl)oxy)-6-methylpyridin-2-yl)carbamoyl)-2-methoxy-2-methylpropanamide, 2-methoxy-2-methyl-N-((6-methyl-5-((2-(2-methylthiazol-5-yl)pyridin-4-yl)oxy)pyridin-2-yl)carbamoyl)propanamide, 1-methyl-N-((5-((6'-methyl-[2,3'-bipyridin]-4-yl)oxy)pyridin-2-yl)carbamoyl)cyclopropanecarboxamide, N-((4,6-dimethyl-5-((2-(1-methyl-1H-pyrazol-4-yl)pyridin-4-yl)oxy)pyridin-2-yl)carbamoyl)pivalamide, N-((6-methyl-5-((2-(4-(4-methylpiperazin-1-yl)phenyl)pyridin-4-yl)oxy)pyridin-2-yl)carbamoyl)pivalamide, 2-methoxy-2-methyl-N-((5-((2-(2-methylthiazol-5-yl)pyridin-4-yl)oxy)pyridin-2-yl)carbamoyl)propanamide, 2-methoxy-2-methyl-N-((6-methyl-5-((2'-methyl-[2,4'-bipyridin]-4-yl)oxy)pyridin-2-yl)carbamoyl)propanamide, 1-methyl-N-((5-((2-(2-methylthiazol-5-yl)pyridin-4-yl)oxy)pyridin-2-yl)carbamoyl)cyclopropanecarboxamide, 1-methoxy-N-((6-methyl-5-((2-(2-methylthiazol-5-yl)pyridin-4-yl)oxy)pyridin-2-yl)carbamoyl)cyclopropanecarboxamide, 2-ethoxy-2-methyl-N-((5-((2-(1-methyl-1H-pyrazol-4-yl)pyridin-4-yl)oxy)pyridin-2-yl)carbamoyl)propanamide, 2-ethoxy-2-methyl-N-((5-((2-(2-methylthiazol-5-yl)pyridin-4-yl)oxy)pyridin-2-yl)carbamoyl)propanamide, N-((5-((2-(thiazol-5-yl)pyridin-4-yl)oxy)pyridin-2-yl)carbamoyl)pivalamide, 1-methoxy-N-((5-((6'-methyl-[2,3'-bipyridin]-4-yl)oxy)pyridin-2-yl)carbamoyl)cyclopropanecarboxamide, 2-ethoxy-2-methyl-N-((6-methyl-5-((2-(1-methyl-1H-pyrazol-4-yl)pyridin-4-yl)oxy)pyridin-2-yl)carbamoyl)propanamide, N-((5-((2-(4-methyl-1H-imidazol-1-yl)pyridin-4-yl)oxy)pyridin-2-yl)carbamoyl)propionamide, 2-methoxy-2-methyl-N-((5-((2-(4-methyl-1H-imidazol-1-yl)pyridin-4-yl)oxy)pyridin-2-yl)carbamoyl)propanamide, N-((6-methyl-5-((2-(thiazol-5-yl)pyridin-4-yl)oxy)pyridin-2-yl)carbamoyl)pivalamide, 2-methoxy-2-methyl-N-((5-((2-(1-methyl-1H-imidazol-4-yl)pyridin-4-yl)oxy)pyridin-2-yl)carbamoyl)propanamide, 2-methoxy-2-methyl-N-((6-methyl-5-((2-(4-(1-methylpiperidin-4-yl)phenyl)pyridin-4-yl)oxy)pyridin-2-yl)carbamoyl)propanamide, N-((6-methyl-5-((2-(4-methyl-1H-imidazol-1-yl)pyridin-4-yl)oxy)pyridin-2-yl)carbamoyl)isobutyramide, 1-methyl-N-((6-methyl-5-((2-(4-methyl-1H-imidazol-1-yl)pyridin-4-yl)oxy)pyridin-2-yl)carbamoyl)cyclopropanecarboxamide, N-((5-((2-(1-methyl-1H-imidazol-4-yl)pyridin-4-yl)oxy)pyridin-2-yl)carbamoyl)propionamide, N-((5-((2-(1,2-dimethyl-1H-imidazol-5-yl)pyridin-4-yl)oxy)pyridin-2-yl)carbamoyl)-2-methoxy-2-methylpropanamide, N-((4,6-dimethyl-5-((2-(1-methyl-1H-pyrazol-4-yl)pyridin-4-yl)oxy)pyridin-2-yl)carbamoyl)-2-methoxy-2-methylpropanamide, N-((6-ethyl-5-((2-(1-methyl-1H-pyrazol-4-yl)pyridin-4-yl)oxy)pyridin-2-yl)carbamoyl)-1-methoxycyclopropanecarboxamide, 1-methoxy-N-((5-((2-(4-methyl-1H-imidazol-1-yl)pyridin-4-yl)oxy)pyridin-2-yl)carbamoyl)cyclopropanecarboxamide, 1-methoxy-N-((6-methyl-5-((2-(4-(1-methylpiperidin-4-yl)phenyl)pyridin-4-yl)oxy)pyridin-2-yl)carbamoyl)cyclopropanecarboxamide, 1-methoxy-N-((5-((2-(1-methyl-1H-imidazol-4-yl)pyridin-4-yl)oxy)pyridin-2-yl)carbamoyl)cyclopropanecarboxamide, 2-methoxy-2-methyl-N-((6-methyl-5-((2-(3-methylisoxazol-5-yl)pyridin-4-yl)oxy)pyridin-2-yl)carbamoyl)propanamide, 1-methyl-N-((6-methyl-5-((2-(4-methyl-1H-imidazol-1-yl)pyridin-4-yl)oxy)pyridin-2-yl)carbamoyl)cyclobutanecarboxamide, N-((4-methyl-5-((2-(4-methyl-1H-imidazol-1-yl)pyridin-4-yl)oxy)pyridin-2-yl)carbamoyl)pivalamide, 1-methoxy-N-((5-((2-(2-methylthiazol-5-yl)pyridin-4-yl)oxy)pyridin-2-yl)carbamoyl)cyclopentanecarboxamide, 1-methoxy-N-((6-methyl-5-((2-(1-methyl-1H-pyrazol-4-yl)pyridin-4-yl)oxy)pyridin-2-yl)carbamoyl)cyclopentanecarboxamide, N-((5-((2-(2-methyloxazol-5-yl)pyridin-4-yl)oxy)pyridin-2-yl)carbamoyl)pivalamide, 1-methoxy-N-((5-((2-(1-methyl-1H-pyrazol-4-yl)pyridin-4-yl)oxy)pyridin-2-yl)carbamoyl)cyclopentanecarboxamide, 1-methoxy-N-((5-((2-(4-methyl-1H-imidazol-1-yl)pyridin-4-yl)oxy)pyridin-2-yl)carbamoyl)cyclopentanecarboxamide, 1-methoxy-N-((5-((2-(2-methylthiazol-5-yl)pyridin-4-yl)oxy)pyridin-2-yl)carbamoyl)cyclopropanecarboxamide, 2-methoxy-2-methyl-N-((5-((2-(2-methyloxazol-5-yl)pyridin-4-yl)oxy)pyridin-2-yl)carbamoyl)propanamide, 2-methoxy-2-methyl-N-((5-((2'-methyl-[2,4'-bipyridin]-4-yl)oxy)pyridin-2-yl)carbamoyl)propanamide, 2-ethoxy-2-methyl-N-((5-((2'-methyl-[2,4'-bipyridin]-4-yl)oxy)pyridin-2-yl)carbamoyl)propanamide, 1-methoxy-N-((4-methyl-5-((2-(4-methyl-1H-imidazol-1-yl)pyridin-4-yl)oxy)pyridin-2-yl)carbamoyl)cyclopentanecarboxamide, 2-methoxy-2-methyl-N-((4-methyl-5-((2-(4-methyl-1H-imidazol-1-yl)pyridin-4-yl)oxy)pyridin-2-yl)carbamoyl)propanamide, 1-methoxy-N-((6-methyl-5-((2-(3-methylisoxazol-5-yl)pyridin-4-yl)oxy)pyridin-2-yl)carbamoyl)cyclopentanecarboxamide, 1-methoxy-N-((5-((2'-methyl-[2,4'-bipyridin]-4-yl)oxy)pyridin-2-yl)carbamoyl)cyclopentanecarboxamide, N-((5-((2-(2-isopropyl-1H-imidazol-4-yl)pyridin-4-yl)oxy)pyridin-2-yl)carbamoyl)pivalamide, N-((5-((2-(1-ethyl-1H-pyrazol-4-yl)pyridin-4-yl)oxy)pyridin-2-yl)carbamoyl)-2-methoxy-2-methylpropanamide, N-((5-((2-(1H-1,2,3-triazol-4-yl)

pyridin-4-yl)oxy)-6-methylpyridin-2-yl)carbamoyl) pivalamide, N-((5-((2-(2-isopropyl-1H-imidazol-5-yl)pyridin-4-yl)oxy)pyridin-2-yl)carbamoyl)-2-methoxy-2-methylpropanamide, N-((5-((2-(1-methyl-1H-pyrazol-4-yl)pyridin-4-yl)oxy)pyrimidin-2-yl)carbamoyl)pivalamide, N-((5-((2-(1-ethyl-2-isopropyl-1H-imidazol-5-yl)pyridin-4-yl)oxy)pyridin-2-yl)carbamoyl)pivalamide, and N-((5-((2-(1-methyl-1H-pyrazol-4-yl)pyridin-4-yl)oxy)pyrazin-2-yl)carbamoyl)pivalamide.

17. A pharmaceutical composition, comprising a compound of claim 16 and a pharmaceutically acceptable carrier.

18. The compound of claim 1 selected from the group consisting of N-((6-methyl-5-((2-(1-methyl-1H-pyrazol-4-yl)pyridin-4-yl)oxy)pyridin-2-yl)carbamoyl)pivalamide, N-((5-((2-(4-methyl-1H-imidazol-1-yl)pyridin-4-yl)oxy)pyridin-2-yl)carbamoyl)pivalamide, N-((5-((2-(1-methyl-1H-imidazol-4-yl)pyridin-4-yl)oxy)pyridin-2-yl)carbamoyl)pivalamide, and N-((5-((2-(2-methyloxazol-5-yl)pyridin-4-yl)oxy)pyridin-2-yl)carbamoyl)pivalamide.

19. A pharmaceutical composition, comprising a compound of claim 18 and a pharmaceutically acceptable carrier.

20. The compound of claim 1 selected from 2-methoxy-2-methyl-N-((5-((2-(1-methyl-1H-pyrazol-4-yl)pyridin-4-yl)oxy)pyridin-2-yl)carbamoyl)propanamide, 2-ethoxy-2-methyl-N-((5-((2-(1-methyl-1H-pyrazol-4-yl)pyridin-4-yl)oxy)pyridin-2-yl)carbamoyl)propanamide, 2-methoxy-2-methyl-N-((5-((2-(1-methyl-1H-imidazol-4-yl)pyridin-4-yl)oxy)pyridin-2-yl)carbamoyl)propanamide, 2-methoxy-2-methyl-N-((5-((2-(2-methyloxazol-5-yl)pyridin-4-yl)oxy)pyridin-2-yl)carbamoyl)propanamide, 2-methoxy-2-methyl-N-((5-((2-(4-methyl-1H-imidazol-1-yl)pyridin-4-yl)oxy)pyridin-2-yl)carbamoyl)propanamide, 2-methoxy-2-methyl-N-((6-methyl-5-((2'-methyl-[2,4'-bipyridin]-4-yl)oxy)pyridin-2-yl)carbamoyl)propanamide, 2-methoxy-2-methyl-N-((5-((2'-methyl-[2,4'-bipyridin]-4-yl)oxy)pyridin-2-yl)carbamoyl)propanamide or 2-methoxy-2-methyl-N-((4-methyl-5-((2-(4-methyl-1H-imidazol-1-yl)pyridin-4-yl)oxy)pyridin-2-yl)carbamoyl)propanamide.

21. A pharmaceutical composition, comprising a compound of claim 20 and a pharmaceutically acceptable carrier.

22. The compound of claim 1 wherein the compound is N-((5-((2-(4-methyl-1H-imidazol-1-yl)pyridin-4-yl)oxy)pyridin-2-yl)carbamoyl)pivalamide.

23. A pharmaceutical composition, comprising the compound of claim 22 and a pharmaceutically acceptable carrier.

24. The compound of claim 1 wherein the compound is compound 2-methoxy-2-methyl-N-((5-((2-(1-methyl-1H-pyrazol-4-yl)pyridin-4-yl)oxy)pyridin-2-yl)carbamoyl)propanamide.

25. A pharmaceutical composition, comprising the compound of claim 24 and a pharmaceutically acceptable carrier.

26. The compound of claim 1 wherein the compound is compound 2-ethoxy-2-methyl-N-((5-((2-(1-methyl-1H-pyrazol-4-yl)pyridin-4-yl)oxy)pyridin-2-yl)carbamoyl)propanamide.

27. A pharmaceutical composition, comprising the compound of claim 26 and a pharmaceutically acceptable carrier.

28. The compound of claim 1 wherein the compound is compound 2-methoxy-2-methyl-N-((5-((2-(1-methyl-1H-imidazol-4-yl)pyridin-4-yl)oxy)pyridin-2-yl)carbamoyl)propanamide.

29. A pharmaceutical composition, comprising the compound of claim 28 and a pharmaceutically acceptable carrier.

30. The compound of claim 1 wherein the compound is compound 2-methoxy-2-methyl-N-((5-((2-(4-methyl-1H-imidazol-1-yl)pyridin-4-yl)oxy)pyridin-2-yl)carbamoyl)propanamide.

31. A pharmaceutical composition, comprising the compound of claim 30 and a pharmaceutically acceptable carrier.

32. The compound of claim 1 wherein the compound is compound N-((5-((2-(2-methyloxazol-5-yl)pyridin-4-yl)oxy)pyridin-2-yl)carbamoyl)pivalamide.

33. A pharmaceutical composition, comprising the compound of claim 32 and a pharmaceutically acceptable carrier.

34. The compound of claim 1 wherein the compound is compound 2-methoxy-2-methyl-N-((6-methyl-5-((2'-methyl-[2,4'-bipyridin]-4-yl)oxy)pyridin-2-yl)carbamoyl)propanamide.

35. A pharmaceutical composition, comprising the compound of claim 34 and a pharmaceutically acceptable carrier.

36. The compound of claim 1 wherein the compound is compound 2-methoxy-2-methyl-N-((5-((2'-methyl-[2,4'-bipyridin]-4-yl)oxy)pyridin-2-yl)carbamoyl)propanamide.

37. A pharmaceutical composition, comprising the compound of claim 36 and a pharmaceutically acceptable carrier.

38. A pharmaceutical composition, comprising a compound of claim 1 and a pharmaceutically acceptable carrier.

39. The composition of claim 38, further comprising an additive selected from adjuvants, excipients, diluents, or stabilizers.

40. A method of treating cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia, the method comprising administering to a patient in need thereof an effective amount of a compound of claim 1.

41. A method of treating glioblastomas, breast cancers, pancreatic cancers, metastasis of primary tumor sites, or cancers that are metastatic to bone, the method comprising administering to a patient in need thereof an effective amount of a compound of claim 1.

42. The method of claim 40, wherein the compound is administered orally, parenterally, by inhalation, or subcutaneously.

43. The method of claim 41, wherein the compound is administered orally, parenterally, by inhalation, or subcutaneously.

* * * * *